(12) United States Patent
Rodriguez-Llorente et al.

(10) Patent No.: US 9,186,108 B2
(45) Date of Patent: Nov. 17, 2015

(54) METHODS AND SYSTEMS FOR DETERMINING AN ALGORITHM SETTING BASED ON A SKEW METRIC

(75) Inventors: Fernando Rodriguez-Llorente, London (GB); Pirow Engelbrecht, Royston (GB); Nicholas James Wooder, Royston (GB)

(73) Assignee: Covidien LP, Mansfield, MA (US)

( * ) Notice: Subject to any disclaimer, the term of this patent is extended or adjusted under 35 U.S.C. 154(b) by 414 days.

(21) Appl. No.: 13/609,592

(22) Filed: Sep. 11, 2012

(65) Prior Publication Data

US 2014/0073873 A1  Mar. 13, 2014

(51) Int. Cl.
| | |
|---|---|
| G06F 7/00 | (2006.01) |
| A61B 5/00 | (2006.01) |
| A61B 5/024 | (2006.01) |
| A61B 5/1455 | (2006.01) |

(52) U.S. Cl.
CPC ............ *A61B 5/7203* (2013.01); *A61B 5/7246* (2013.01); *A61B 5/02427* (2013.01); *A61B 5/14551* (2013.01); *A61B 5/7228* (2013.01)

(58) Field of Classification Search
CPC ............ A61B 5/02416; A61B 5/7221; A61B 5/7264; G06F 17/148; G06F 19/3412
See application file for complete search history.

(56) References Cited

U.S. PATENT DOCUMENTS

| | | | |
|---|---|---|---|
| 4,911,167 A | 3/1990 | Corenman et al. | |
| 4,938,228 A | 7/1990 | Righter et al. | |
| 4,955,379 A | 9/1990 | Hall | |
| 5,188,108 A | 2/1993 | Secker | |
| 5,853,364 A | 12/1998 | Baker, Jr. et al. | |
| 6,002,952 A | 12/1999 | Diab et al. | |
| 6,178,343 B1 | 1/2001 | Bindszus et al. | |
| 6,339,715 B1 | 1/2002 | Bahr et al. | |
| 6,463,311 B1 | 10/2002 | Diab | |
| 6,519,486 B1 | 2/2003 | Edgar, Jr. et al. | |
| 6,684,090 B2 | 1/2004 | Ali et al. | |
| 6,801,802 B2 | 10/2004 | Sitzman et al. | |
| 7,016,715 B2 | 3/2006 | Stetson | |
| 7,018,338 B2 | 3/2006 | Vetter et al. | |
| 7,373,194 B2 | 5/2008 | Weber et al. | |
| 7,530,955 B2 | 5/2009 | Diab et al. | |
| 7,534,212 B2 | 5/2009 | Baker, Jr. | |
| 7,740,591 B1 | 6/2010 | Starr et al. | |
| 7,922,665 B2 | 4/2011 | Baker, Jr. | |
| 8,007,441 B2 | 8/2011 | Baker, Jr. | |
| 8,285,352 B2 | 10/2012 | Addison et al. | |
| 2004/0138538 A1 | 7/2004 | Stetson | |
| 2011/0071406 A1* | 3/2011 | Addison et al. | 600/484 |

OTHER PUBLICATIONS

Bolanos, M et al. Proceedings of the 28th IEEE EMBS Annual International Conference, NYC, USA Aug. 30-Sep. 3, 2006, p. 4289-4294.*

* cited by examiner

*Primary Examiner* — Mary Zeman
(74) *Attorney, Agent, or Firm* — Shvarts & Leiz LLP

(57) ABSTRACT

A physiological monitoring system may determine physiological information, such as physiological rate information, from a physiological signal. The system may determine a skew metric based on the physiological signal. The system may determine an algorithm setting based on a reference relationship between the determined skew metric and a value indicative of a physiological rate. The algorithm setting may, for example, affect the amount of filtering applied to the physiological signal.

28 Claims, 105 Drawing Sheets

600

| FLAG TYPE | DESCRIPTION |
|---|---|
| PULSE LOST | No pulse detected |
| SENSOR OFF | No sensor detected |
| GAIN CHANGE | Change in amplifier gain and/or LED power |
| NO VALID SATURATION | Unable to calculate SpO2 value |
| INITIALIZATION | Start of algorithm, Re-start of algorithm |
| DROPOUT | Stop calculation and restart or change algorithm setting |
| MODE | Algorithm settings applied based on Mode |

$$A = \begin{bmatrix} (N-M)+1 & (N-M)+2 & \cdots & N-1 & N \\ (N-M) & (N-M)+1 & \cdots & N-2 & N-1 \\ \vdots & \vdots & \ddots & \vdots & \vdots \\ 2 & 3 & \cdots & M & M+1 \\ 1 & 2 & \cdots & M-1 & M \end{bmatrix} \leftarrow 7210$$

$$A' = \begin{bmatrix} (N-M)+1 & (N-M) & \cdots & 2 & 1 \\ (N-M)+2 & (N-M)+1 & \cdots & 3 & 2 \\ \vdots & \vdots & \ddots & \vdots & \vdots \\ N-1 & N-2 & \cdots & M & M-1 \\ N & N-1 & \cdots & M+1 & M \end{bmatrix} \leftarrow 7220$$

$$A*A' = [C_{k,j}] = \qquad \leftarrow 7230$$

$$\begin{bmatrix} C_{0,0} & C_{1,-1} & \cdots & C_{(N-M)-1,-(N-M)+1} & C_{N-M,-(N-M)} \\ C_{0,1} & C_{1,0} & \cdots & C_{(N-M)-1,-(N-M)+2} & C_{N-M,-(N-M)+1} \\ \vdots & \vdots & \ddots & \vdots & \vdots \\ C_{0,(N-M)-1} & C_{1,(N-M)-2} & \cdots & C_{(N-M)-1,0} & C_{N-M,-1} \\ C_{0,(N-M)} & C_{1,(N-M)-1} & \cdots & C_{(N-M)-1,1} & C_{N-M,0} \end{bmatrix}$$

FIG. 72

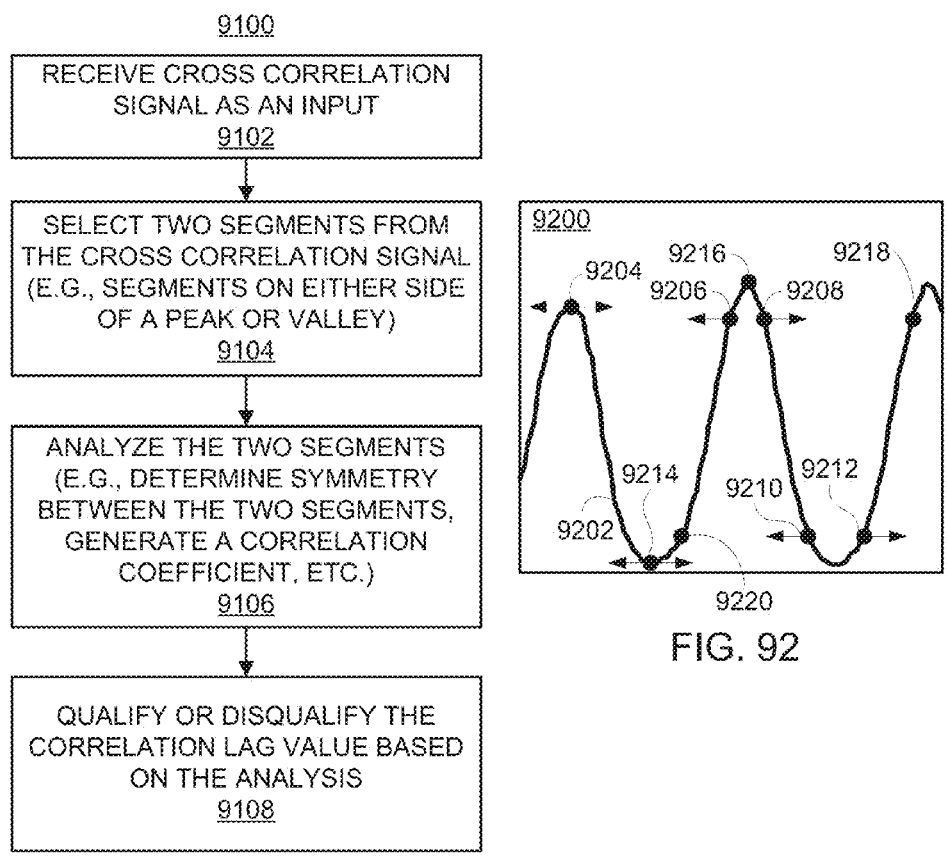
FIG. 91
FIG. 92
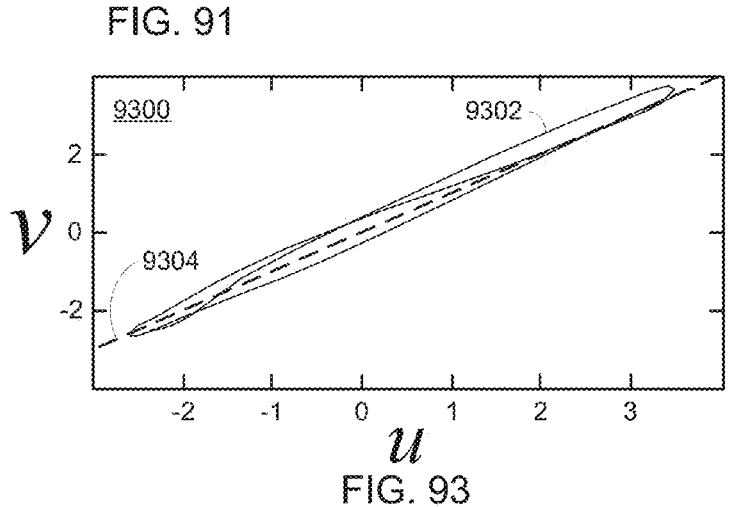
FIG. 93

METHODS AND SYSTEMS FOR DETERMINING AN ALGORITHM SETTING BASED ON A SKEW METRIC

The present disclosure relates to determining physiological information. More particularly, the present disclosure relates to determining an algorithm setting based on a skew metric.

SUMMARY

A physiological monitor may determine one or more physiological parameters such as, for example, a physiological rate based on signals received from one or more physiological sensors. The physiological monitor may analyze physiological signals (e.g., photoplethysmographic (PPG) signals) for oscillometric behavior characterized by a pulse rate, a respiration rate, or both. Physiological signals may include one or more noise components, which may include the effects of ambient light, electromagnetic radiation from powered devices (e.g., at 60 Hz or 50 HZ), subject movement, and/or other non-physiological or undesired physiological signal components. In some circumstances, the determination of a pulse rate from photoplethysmographic information may present challenges. Factors such as, for example, noise, subject movement, the shape of physiological pulses, subjects having low perfusion with small physiological pulses, and/or other factors may present challenges in determining pulse rate.

The physiological monitor in accordance with the present disclosure may include a sensor, having a detector, which may generate an intensity signal (e.g., a PPG signal) based on light attenuated by the subject. Processing equipment of the monitor, a processing module, and/or other suitable processing equipment may determine a value indicative of a physiological rate based on the intensity signal. For example, the processing equipment may determine a pulse rate based on analysis of the intensity signal.

In some embodiments, the processing equipment may use one or more operating modes to determine a physiological parameter of a subject. An operating mode may be used to determine the physiological parameter (e.g., pulse rate) based on a particular criterion. A first mode may use, for example, relatively strict criteria to determine the physiological parameter, but may not be required to post a rate as output. Another mode may implement a relatively narrow, adjustable band-pass filter on the physiological data (e.g., time series data), which is good at rejecting noise when it is tuned to the correct rate. The various modes may include qualification techniques to qualify calculated values and physiological parameters determined thereof. The qualification techniques can provide an accurate assessment of whether a calculated parameter is indicative of a physiological parameter, and can also prevent the band-pass filter from being initially tuned to noise and deviating away from the correct physiological rate. In addition, in the event that the band-pass is tuned incorrectly, the processing equipment may drop out of a current operating mode and return to an initialization mode based on qualification failure information. Accordingly, physiological parameters (e.g., pulse rate) may be reliably determined in the presence of noise.

In some embodiments, the processing equipment may determine one or more algorithm settings based on the intensity signal, and determine a value indicative of a physiological rate of the subject based on the intensity signal and based on the algorithm setting. Determining the value indicative of the physiological rate may include performing a correlation calculation such as a correlation, and/or filtering a signal (e.g., a signal derived from an intensity signal) based on the algorithm setting. The filtering may include applying a band-pass filter, a finite impulse response filter, or any other suitable filter, based on the algorithm settings. In some embodiments, the processing equipment may generate a correlation sequence based on segments of the physiological signal to determine a likely period of a periodic physiological behavior (e.g., heart rate). For example, the processing equipment may generate the correlation sequence, determine a peak in the sequence having a lag value (e.g., relative lag in sample number or time between correlated segments) indicative of a period, and then qualify the lag value based on the algorithm settings. Algorithm settings may also be used to apply signal conditioning to the physiological signal prior to processing.

In some embodiments, the processing equipment may fill a buffer with generated values when a full window of data is not available. In some embodiments, the processing equipment may determine one or more initialization values based on the physiological data, and generate a window of data based on the one or more initialization values and one or more samples of the physiological data. The initialization values may be based on random numbers, values based on noise values, a sample value, a scaled sample value (e.g., scaled by signal noise), any other values, or any combination thereof.

In some embodiments, the processing equipment manages one or more status flags such as a gain change status flag. In some embodiments, a status indicator (e.g., a gain change indicator or high noise indicator) may be received while the physiological data is being received. For example, a gain change indicator may be a change in gain in an analog amplifier. The processing equipment may set a period of time during which received values of the physiological data are not added to the window of data in response to receiving the status indicator. The period of time may be, for example, a multiple of a period associated with a physiological rate of the subject. Artifacts associated with, for example, a gain change may be mitigated by omitting that data from the buffer. In some embodiments, the processing equipment may use a window of data having values taken before and after the period of time. In some such embodiments, the processing equipment may modify some of the values in the window of data to smooth the transition between values of the physiological data received prior to receiving the status indicator and values of the physiological data received after the period of time is over.

In some embodiments, the processing equipment may determine one or more metrics based on the physiological data, which may then be used to classify the data, determine an algorithm setting, or both. In some embodiments, the algorithm setting affects the amount of filtering applied to the physiological data. In some embodiments, the processing equipment may generate a difference signal, generate a sorted difference signal (e.g., sorted by value), partition a window of data, perform any other data manipulation or calculation, or any combination thereof. In some embodiments, the processing equipment may monitor the temporal history of a metric, and adjust an algorithm setting if the metric exhibits temporal changes greater than a threshold. Some techniques for determining algorithm settings are discussed below.

In some embodiments, the processing equipment may generate a sorted difference signal, and identify two midpoints of two respected segments of the sorted difference signal. The processing equipment may determine a first offset associated with one segment (e.g., a value of the segment at a particular location), and determine a second offset associated with the other segment (e.g., a value of the segment at a particular location). In some embodiments, the processing equipment may determine a first difference between the first midpoint and the first offset, and determine a second difference between the second midpoint and the second offset. The processing equipment may determine a ratio based on the first difference and the second difference, which may be used to classify the physiological data, determine an algorithm setting, or both. In some embodiments, the algorithm setting affects the amount of filtering applied to the physiological data. In some embodiments, the first segment may include the positive values and the second segment may include the negative values of the sorted difference signal.

In some embodiments, the processing equipment may generate a difference signal based on the physiological signal. The processing equipment may determine positive areas associated with positive regions of the difference signal, and determine negative areas associated with negative regions of the difference signal. The processing equipment may then classify the physiological data, determine an algorithm setting, or both, based on area ratios of adjacent positive and negative areas of the difference signal. In some embodiments, the algorithm setting affects the amount of filtering applied to the physiological data. The area ratios may be sorted and one or more ratios may be identified. For example, the area ratios may be normalized and the processing equipment may identify approximately the twenty-fifth percentile normalized area ratio, which may be indicative of whether the data exhibits a dicrotic notch.

In some embodiments, the processing equipment may generate a sorted difference signal based on the physiological signal, and then generate a second difference signal based on the first sorted difference signal. In some embodiments, the second difference signal may be generated based on the negative values of the sorted difference signal. The processing equipment may analyze a first segment and a second segment of the second difference signal. For example, the first segment may be in the left half of the second difference signal and the second segment may be in the right half of the second difference signal. The analysis may include, for example, determining a mean value of the first segment and determining a mean value of the second segment, and then determining a ratio of the mean values.

In some embodiments, the processing equipment may determining a skew metric based on the physiological signal, and determine an algorithm setting based on a reference relationship between the determined skew metric and a value indicative of a physiological rate. The reference relationship may include, for example, a look-up table, and the processing equipment may reference the look-up table using the skew metric as an input, and determine the value indicative of physiological rate based on the look-up table. In a further example, the reference relationship may include a function, and the processing equipment may reference the function using the skew metric as an input, and determine the value indicative of physiological rate based on the function. In some embodiments, the processing equipment may determine whether to apply a filter, such as a finite impulse response filter, based on the skew metric. In some embodiments, the processing equipment may determine the central frequency of a band pass filter that may be applied to the data to be substantially equal to the value indicative of the physiological rate. In some embodiments, the processing equipment may determine the cutoff frequency of a lowpass filter or highpass filter, based on the value indicative of the physiological rate.

In some embodiments, the processing equipment may determine one or more algorithm settings, and adjust the one or more algorithm settings in response to one or more metric values. For example, the processing equipment may receive physiological data, and determine a metric value indicative of a physiological classification. The physiological classification may be based on the presence of a dicrotic notch, magnitude of a calculated physiological rate, pulse shape, any physiological classification, or any combination thereof. In some instances, subsequent to determining the algorithm setting, the processing equipment may determine a second metric value indicative of a different physiological classification than determined previously based on subsequent physiological data. The second metric value may be the same metric above having an updated value, or a different metric, which indicates the different physiological classification. The processing equipment may then determine an algorithm setting based on the different physiological classification. Accordingly, the processing equipment may update algorithm settings as changes occur in the physiological data, in the state of the rate algorithm, or both.

In some embodiments, the processing equipment may generate a sorted difference signal based on the physiological signal, and identify one or more data points at one or both ends of the sorted difference signal as being associated with noise. The processing equipment may determine a value indicative of noise based on the one or more identified data points. In some embodiments, the processing equipment may fit a line to a segment of the sorted difference signal, determine at least one threshold based on the line fit, and identify the one or more data points associated with noise as lying outside of the at least one threshold. The segment may include samples of the sorted difference signal having similar slopes. In some embodiments, the processing equipment may fit multiple lines to multiple segments of the sorted difference signal, determine multiple thresholds based on the line fits, and identify the one or more data points comprises identifying one or more data points that are outside of the at least one threshold. In some such embodiments, the processing equipment may identify the one or more data points by determining when a difference between two adjacent data points in the sorted difference signal is greater than a threshold. In some such embodiments, the processing equipment may determine the value indicative of noise based on a ratio of the number of data points associated with noise and a total number of data points in the sorted difference signal.

In some embodiments, the processing equipment may determine a value indicative of noise using multiple segments of a sorted difference signal. The processing equipment may identify a first end group of the multiple segments and a second end group of the multiple segments at opposite ends of the sorted difference signal. The processing equipment may then determine at least one threshold based on the first end group and the second end group, and identify one or more data points of one or both ends of the sorted difference signal as being associated with noise. The processing equipment may determine a number of data points at one or both ends of the sorted difference signal as being associated with noise, and determine a value indicative of noise based on the one or more data points. In some embodiments, the processing equipment may determine a ratio of the number of number of data points associated with noise and a total number of points of the physiological signal. The processing equipment may determine an algorithm setting based on the value indicative of noise.

In some embodiments, the processing equipment may generate a first sorted difference signal based on a first segment of the physiological signal, and generate a second sorted difference signal based on a second segment of the physiological signal. The processing equipment may analyze the first sorted difference signal and the second sorted difference signal, and determine a value indicative of noise based on the analysis of the first sorted difference signal and the second sorted difference signal. In some embodiments, the processing equipment may determine a first line fit having a first slope for the first sorted difference signal, determine a second line fit having a second slope for the second sorted difference signal, and determine a difference between the first slope and the second slope. In some embodiments, the processing equipment may determine a first line fit for the first sorted difference signal, determine a second line fit for the second sorted difference signal, determine a goodness of fit associated with the first line fit, and determine a goodness of fit associated with the second line fit. In some embodiments, the processing equipment may determine a goodness of fit between the first sorted difference signal and the second sorted difference signal. In some embodiments, the processing equipment may determine a value indicative of differences between the first sorted difference signal and the second sorted difference signal.

In some embodiments, the processing equipment may generate at least one sorted difference signal based on the physiological signal, analyze the at least one sorted difference signal to determine at least two values indicative of noise, and determine a value indicative of a signal-to-noise ratio based on the two or more values indicative of noise. In some embodiments, the processing equipment may use a reference of associated values indicative of noise and values indicative of signal-to-noise ratios. In some embodiments, the processing equipment may analyze the at least one sorted difference signal to determine three values indicative of noise, select the maximum value of the three values, and determine the signal-to-noise ratio based on the maximum value. In some embodiments, the processing equipment may determine a best fit line based on the at least one sorted difference signal, generate at least one threshold based on the best fit line, and determine a number of points of the sorted difference signal that exceeds the at least one threshold. At least one value of the at least two values indicative of noise may be based on the number of points. In some embodiments, the processing equipment may generate at least one second sorted difference signal based on the physiological signal, determine a first best fit line based on the sorted difference signal, determine a second best fit line based on the second sorted difference signal, and compare the first best fit line and the second best fit line to determine at least one value of the at least two values indicative of noise.

In some embodiments, the processing equipment may apply signal conditioning to received physiological data. Signal conditioning may include filtering, normalization, baseline subtraction, derivative limiting, any other suitable signal conditioning, or any combination thereof. The following discussion provides further details regarding signal conditioning techniques.

In some embodiments, the processing equipment may calculate differences based on the physiological data, identify one or more differences that exceed a threshold, and modify the physiological data based on the one or more differences. In some embodiments, the processing equipment may determine the threshold based on the differences. In some embodiments, the processing equipment may perform a standard deviation calculation based on the differences, and determine the threshold based on the standard deviation calculation. In some embodiments, one of the one or more differences may be calculated based on two adjacent values, and the physiological data may be modified by reducing a difference between the two adjacent values. Reducing the difference between the two adjacent values may include determining an offset based on the two adjacent values, and the offset may be applied to one of the two adjacent values. In some embodiments, the processing equipment may determine one or more offsets based on the one or more differences, and perform subtractions based on the one or more offsets to modify the data.

In some embodiments, the processing equipment may generate a first signal based on a stability function such as, a Lyapunov function for example, applied to the physiological signal, generate a difference signal based on the first signal, and generate a modified physiological signal based on the difference signal. The processing equipment may identify one or more points of the difference signal that exceed a threshold, and generate the modified physiological signal by modifying one or more points in the physiological signal that correspond to the one or more points of the difference signal. In some embodiments, the processing equipment may determine a standard deviation of the difference signal, and the threshold may be based on the standard deviation of the difference signal. In some embodiments, the threshold may be a predetermined value. In some embodiments, the processing equipment may modify the physiological signal by removing portions of the physiological signal associated with the one or more points of the difference signal that exceed the threshold. In some embodiments, the processing equipment may identify the one or more points of the difference signal that exceed the threshold by identifying a pair of two threshold crossings and intermediate points between the two threshold crossings of the difference signal.

In some embodiments, the processing equipment may generate a sorted difference signal based on the physiological signal, identify one or more points in the sorted difference signal that exceed a threshold, and generate a modified physiological signal based on the one or more points. In some embodiments, the processing equipment may determine the threshold based on the sorted difference signal. In some embodiments, the processing equipment may determine a line fit based on the sorted difference signal, and determine the threshold based on the line fit. In some embodiments, the processing equipment may modify the one or more points in the sorted difference signal to generate a modified sorted difference signal, and generate a modified physiological signal by reordering the modified sorted difference signal to generate a reordered signal, and integrating the reordered signal. In some embodiments, the processing equipment may modify the one or more points in the sorted difference signal to be equal to the threshold.

In some embodiments, the processing equipment may generate a positive signal based on positive values of the physiological signal and generate a negative signal based on negative values of the physiological signal. The processing equipment may filter the positive signal to generate a filtered positive signal and filter the negative signal to generate a filtered negative signal. The processing equipment may combine the filtered positive signal and the filtered negative signal to generate a combined signal, and modify the physiological signal based on the combined signal. In some embodiments, the processing equipment may generate the positive signal by extracting the positive values of the physiological signal and inserting zeros corresponding to the negative values of the physiological signal, and generate the negative signal by extracting the negative values of the physiological signal and inserting zeros corresponding to the positive values of the physiological signal. Filtering the positive signal and the negative signal may include low pass filtering the respective signals. In some embodiments, combining the filtered positive signal and the filtered negative signal may include averaging the filtered positive signal and the filtered negative signal. In some embodiments, the processing equipment may scale the combined signal prior to modifying the physiological signal based on the combined signal. Scaling the combined signal may include, for example, scaling the combined signal based on a standard deviation of the combined signal. In some embodiments, the processing equipment may modify the physiological signal by subtracting the combined signal from the physiological signal.

In some embodiments, the processing equipment may calculate absolute values based on the physiological signal, which may include positive and negative values, filter the absolute values to generate a filtered signal, and modify the physiological signal based on the filtered signal. Filtering the absolute values may include, for example, low pass filtering the absolute values. In some embodiments, the processing equipment may modify the filtered signal prior to modifying the physiological signal based on the filtered signal. In some embodiments, modifying the filtered signal may include, for example, performing a subtraction of a minimum value of the filtered signal from the filtered signal. In some embodiments, modifying the filtered signal may include, for example, adding a gain value to the filtered signal. In some embodiments, modifying the physiological signal may include, for example, dividing the physiological signal by the filtered signal.

In some embodiments, the processing equipment may determine a metric based on the physiological signal, and selectively apply, based on the metric, a digital filter to the physiological signal to generate a filtered signal based on two or more filter coefficients. The filtered signal may correspond to a weighted sum of the physiological signal and a difference signal corresponding to the physiological signal. For example, the digital filter may include a finite impulse response filter. In some embodiments, the metric may include a de-trending metric indicative of the likely magnitude of a physiological parameter, where the two or more filter coefficients may be adjusted based on the de-trending metric. The two or more coefficients may be adjusted to increase the weight of the physiological signal relative to the difference signal if the de-trending metric is below a threshold, and may be adjusted to increase the weight of the difference signal relative to the physiological signal if the de-trending metric is above a threshold. In some embodiments, the metric may be indicative of the presence of a dicrotic notch in the physiological signal. In some embodiments, the processing equipment may receive a calculated value indicative of a physiological rate of the subject, and the two or more filter coefficients may be adjustable based on a calculated value.

In some embodiments, the processing equipment may determine a value indicative of a physiological rate based on the physiological signal, determine a metric based on the physiological signal, select one or more bandpass filter settings of a bandpass filter based on the physiological rate and based on the metric, and apply the bandpass filter having the selected settings to the physiological signal to generate a filtered signal. In some embodiments, the metric may be indicative of noise in the physiological signal. The one or more bandpass filter settings may include, for example, a spectral band, and the one or more selected bandpass filter settings may include a narrow spectral band when the metric exceeds a threshold. The one or more bandpass filter settings may include, for example, a spectral band, and the one or more selected bandpass filter settings may include a wide spectral band when the metric is below a threshold. In some embodiments, the one or more bandpass filter settings may include a center frequency that corresponds to the physiological rate.

In some embodiments, the processing equipment may perform a correlation calculation to analyze periodic components of a physiological signal such as, for example, the component attributable to a physiological rate. The correlation calculation may include, for example, generating a correlation sequence, generating a correlation matrix, performing a statistical regression analysis, or a combination thereof.

In some embodiments, the processing equipment may calculate a correlation sequence corresponding to multiple lag values based on the physiological signal. For at least one lag value of the multiple lag values, the processing equipment may compare the correlation sequence value corresponding to the at least one lag value to a threshold. The threshold may be predetermined, and may vary as a function of lag. For example, the threshold may be a predetermined square root function of lag value. The processing equipment may determine whether the correlation sequence value exceeds the threshold, determine whether the correlation sequence value corresponds to a peak, and identify a particular lag value of the multiple lag values when the correlation sequence value corresponding to the particular lag value exceeds the threshold and corresponds to a peak. In some embodiments, the processing equipment may sequentially compare the correlation sequence values corresponding to multiple lag values to the threshold in ascending order of lag value until the particular lag value is identified. Calculating the correlation sequence may include, for example, calculating one value of the correlation sequence at a time, where the most current lag value of the multiple lag values is analyzed. In some embodiments, the processing equipment may determine whether the correlation sequence value corresponds to a peak by determining that correlation sequence values adjacent to the correlation sequence value and corresponding to smaller lag values are increasing with lag value, and that correlation sequence values adjacent to the correlation sequence value and corresponding to larger lag values are decreasing with lag value. In some embodiments, the processing equipment may normalize the correlation sequence values, a portion of the physiological signal, or both.

In some embodiments, the processing equipment may generate a lag matrix including multiple segments of the physiological signal. Each of the multiple segments may include the same number of samples of the physiological signal. The processing equipment may generate a correlation matrix, which includes a set of correlation values, based on the lag matrix, and identify one or more lag values based on the correlation matrix. The correlation matrix may be generated, for example, by performing a matrix multiplication of the lag matrix with a transpose of the lag matrix. In some embodiments, the processing equipment may process the correlation matrix to generate a processed correlation matrix, and identify at least one peak based on the processed correlation matrix. For example, the processing equipment may apply a matrix rotation to the correlation matrix, average correlation values along a direction of the correlation matrix to generate an array of averaged correlation values, and identify a peak in the array of the averaged correlation values. The matrix rotation may be, for example, a substantially 45 degree matrix rotation to align peak values along a row or column of the correlation matrix. In some embodiments, the processing equipment may identify one or more regions of the correlation matrix corresponding to noise, and avoid identifying a correlation lag value in those regions.

In some embodiments, the processing equipment may select a first segment and a second segment of the physiological signal comprising a plurality of values, in which the second segment is shifted in time from the first segment. The processing equipment may determine a correlation value between the first segment and the second segment, analyze the first segment and the second segment to determine a metric, and determine correlation information based on the correlation value and based on the metric. Determining the correlation information may include, for example, modifying the correlation value based on the metric. In some embodiments, the processing equipment may select multiple segments of the physiological signal each shifted in time from the first segment by a unique lag, determine multiple correlation values between the first segment and the multiple segments, and determine that the correlation value corresponds to a peak in the multiple correlation values. In some embodiments, the processing equipment may generate multiple value pairs each including a value of the first segment and a corresponding value of the second segment. The processing equipment may determine a metric based on the plurality of value pairs and a reference relationship. For example, the processing equipment may apply a transform to the value pairs to generate transformed value pairs that include a first value and a second value, and analyze the distribution across the plurality of first values of each transformed value pairs. In some embodiments, the metric may be a confidence value, and the processing equipment may generate a modified confidence value by multiplying the correlation value and the metric.

In some embodiments, the processing equipment may qualify or disqualify a calculated value such as, for example, a correlation lag value associated with a peak. One or more qualification tests may be applied to the physiological signal, or processed data arising thereof, to determine if the value is qualified or not. In some embodiments, the processing equipment may use a calculated value in determining whether the physiological signal is qualified.

In some embodiments, the processing equipment may select pairs of sample points of the physiological signal spaced by a particular spacing based on the calculated value, determine a state for each of the pairs based on a set of criteria, determine a number of state transitions based on the determined states, and qualify or disqualify the calculated value based on the number of state transitions. The set of criteria may include, for example, a relative magnitude of sample points in a pair to each other, a relative magnitude of a sample point to a product of the other sample point in a pair and a coefficient, and a sign of each sample point in a pair. In some embodiments, the processing equipment may compare the number of state transitions to one or more thresholds which may include, for example, an upper threshold and a lower threshold. The number of states from which the state may be determined may be equal to a power of two greater than or equal to 2. In some embodiments, the calculated value may be a correlation lag value corresponding to a peak, and the particular spacing is substantially one quarter of the calculated value.

In some embodiments, the processing equipment may determine a skew metric value based on the physiological signal, determine a correlation lag value corresponding to a peak in a correlation sequence, and qualifying or disqualifying the correlation lag value based on the skew metric. In some embodiments, the processing equipment may compare the skew metric and the correlation lag value to a reference set of skew metric values and correlation lag values. For example, the reference set of skew metric values and correlation lag values may be arranged in a look-up table. In a further example, the processing equipment may identify a particular skew value of the reference set that most closely matches the determined skew metric value, determine a difference value indicative of a difference between the determined correlation lag vale and the correlation lag value of the reference set corresponding to the particular skew value, and compare the difference value to a threshold. The threshold may be, for example, predetermined or based on the determined correlation lag value.

In some embodiments, the processing equipment may determine a difference value between a set of sample points and a corresponding set of sample points of the physiological signal each spaced apart by a particular spacing based on a calculated value. The processing equipment may compute a sum based on the determined difference values, and qualify or disqualify the calculated value based on the sum. Qualifying or disqualifying the calculated value may include, for example, comparing the sum to a threshold. In some embodiments, the processing equipment may determine an absolute value of the difference between each sample point and corresponding sample point. In some embodiments, the calculated value may be indicative of a period associated with the physiological rate, and the particular spacing between corresponding sample points may be substantially equal to the period.

In some embodiments, the processing equipment may generate value pairs each including a first sample point of the physiological signal and a second point of the physiological signal spaced apart by a particular spacing based on a calculated value. The processing equipment may determine a best fit linear relationship based on the plurality of value pairs, determine at least one statistical metric based on the linear relationship and the value pairs, and qualify or disqualify the calculated value based on the at least one statistical metric. In some embodiments, the statistical metric may include a standard error between the value pairs and the linear relationship, as well as a slope of the linear relationship. In some embodiments, qualifying or disqualifying the calculated value may include determining a value indicative of the probability, relative to a predetermined probability distribution function, of the at least one statistical metric being outside of a set of bounding values. In some embodiments, the processing equipment may determine at least one additional spacing other than the particular spacing. For each of the at least one additional spacing, the processing equipment may generate value pairs each including a first sample point and a second point of the physiological signal spaced apart by the respective spacing, determine a best fit linear relationship based on the respective plurality of value pairs, and determine at least one statistical metric based on the respective linear relationship and the respective plurality of value pairs. The processing equipment may determine a value indicative of the probability, relative to a predetermined probability distribution function, of the respective at least one statistical metric being outside of the set of bounding values, and calculate a sum based on the values indicative of the probability of the respective at least one statistical metric being outside of the set of bounding values for the at least one additional lag value and the value indicative of the probability of the at least one statistical metric being outside of the set of bounding values for the particular spacing. Qualifying or disqualifying the calculated value may be, for example, based on the sum. In some embodiments, determining the probability of the statistical metric being outside of the set of bounding values may include using a reference look-up table comprising a set of probability values.

In some embodiments, the processing equipment may generate four sorted difference signals based on four respective segments of the physiological signal. The processing equipment may analyze first and second sorted difference signals to determine at least one first metric, analyze third and fourth sorted difference signals to determine at least one second metric, and qualify or disqualify a calculated value based on the at least one first metric and the at least one second metric.

A calculated value, for example, indicative of a period associated with a physiological rate may be received. In some embodiments, the third segment may be a subset of the first segment corresponding to the period associated with the physiological rate, and the fourth segment may be a subset of the second segment corresponding to the period associated with the physiological rate. The at least one first metric may include, for example, a correlation coefficient between the first segment and the second segment based on a set of value pairs including a value of the first sorted difference signal and a corresponding value of the second sorted difference signal, a value indicative of slope based on a set of value pairs including a value of the first sorted difference signal and a corresponding value of the second sorted difference signal, a value indicative of a curve length of the first sorted difference signal, a value indicative of a curve length of the second sorted difference signal, a value of the first sorted difference signal corresponding to a terminal end of the first sorted difference signal, a value of the second sorted difference signal corresponding to a terminal end of the second sorted difference signal, and a combination thereof. In some embodiments, the at least one first metric may include at least two metrics, and the processing equipment may qualify or disqualify the calculated value by comparing a first metric of the at least two metrics to a second metric of the at least two metrics. In some embodiments, qualifying or disqualifying the calculated value may include comparing the at least one first metric to a threshold. In some embodiments, qualifying or disqualifying the calculated value may include comparing the at least one first metric to the at least one second metric.

In some embodiments, the processing equipment may determine a correlation lag value corresponding to a peak in a correlation sequence, determine a correlation value at a second lag value equal to a fraction of the correlation lag value, and qualify or disqualify the correlation lag value based on the correlation value at the second lag value. The second lag value may be, for example, equal to substantially one half of the correlation lag value. In some embodiments, qualifying or disqualifying the correlation lag value may include comparing the correlation value at the second lag value to a threshold. In some embodiments, qualifying or disqualifying the correlation lag value may include comparing the correlation value at the second lag value to the correlation sequence value at the correlation lag value.

In some embodiments, the processing equipment may determine a first value indicative of a baseline of the physiological signal, determine a second value indicative of a deviation of the physiological signal from the baseline, and qualify or disqualify a calculated value based on the first value and the second value. The first value may be, for example, selected from a median value of the physiological signal, an average of the physiological signal, a coefficient corresponding to a best fit curve of the physiological signal, and a combination thereof. The second value may be, for example, selected from a standard deviation value based on the physiological signal, a standard error between the physiological signal and the first value, a root mean square value based on the physiological signal, and a combination thereof. In some embodiments, the processing equipment may perform signal conditioning on the physiological signal based on the calculated value to generate a conditioned signal, and the second value may be indicative of a deviation of the conditioned signal from the baseline. In some embodiments, qualifying or disqualifying the calculated value may be based on a ratio of the second value to the first value. For example, the ratio may be multiplied by a coefficient and compared to a threshold to determine whether to qualify or disqualify the calculated value. In some embodiments, the processing equipment may qualify or disqualify the calculated value based on comparing a metric derived from the first and second values to a history of metric values calculated at respective previous times.

In some embodiments, the processing equipment may generate a first sorted difference signal based on a first segment of the physiological signal having a size corresponding to a period associated with a potential physiological rate of a subject, generate a second sorted difference signal based on a second segment of the physiological signal having a size corresponding to a fraction of the period, and generate a third difference signal based on a third segment of the physiological signal having a size corresponding to a multiple of the period. The processing equipment may analyze the first, second, and third sorted difference signals, and qualify or disqualify a calculated value based on the analysis. The period may be, for example, derived from the calculated value. In some embodiments, qualifying or disqualifying the calculated value may include comparing at least two of the first, second, third sorted difference signals to each other. In some embodiments, the processing equipment may compare at least one of the first, second, and third sorted difference signals to a reference distribution. For example the processing equipment may use a look-up table to determine one or more reference values, and qualify or disqualify the calculated value based on the one or more reference values. In some embodiments, the processing equipment may identify the second segment by determining a standard deviation value for each of a plurality of different segments within the physiological signal, having respective sizes corresponding to the fraction of the period, and identifying the segment having the maximum standard deviation value of the plurality of standard deviation values. In some embodiments, qualifying or disqualifying the calculated value may include determining whether the calculated value is likely a harmonic of an actual period associated with a physiological rate of the subject based on analyzing the first, second, and third sorted difference signals.

In some embodiments, the processing equipment may determine a value indicative of noise in the physiological signal, adjust at least one criterion for qualifying or disqualifying a calculated value based on the value indicative of noise, and qualify or disqualify the calculated value based on the at least one adjusted criterion. Adjusting the at least one criterion may include, for example, loosening the criterion when the value indicative of noise exceeds a threshold. In a further example, adjusting the at least one criterion may include tightening the criterion when the value indicative of noise is below a threshold. In a further example, adjusting the at least one criterion may include adjusting a type of the criterion. In some embodiments, the at least one criterion may include a threshold, and the processing equipment may qualify or disqualify the calculated value by determining a metric based on the physiological signal, and comparing the metric to the threshold.

In some embodiments, the processing equipment may filter a physiological signal based on an adjustable filter to generate a filtered physiological signal, and perform calculations over time based on the filtered physiological signal to determine values indicative of a physiological parameter. The adjustable filter may be, for example, adjusted based on the values indicative of the physiological parameter. Some of the calculations performed over time are qualified, while some are disqualified. The processing equipment may determine a metric based on the physiological signal, where the metric is used to determine whether to output a value based on one or more previously calculated values when a current calculation is disqualified. The processing equipment may output a value based on one or more previously calculated values when a current calculation is disqualified and a criterion based on the metric is satisfied. Performing the calculations over time may include, for example, determining a sequence of correlation lag values. The processing equipment may maintain a counter that adjusts a counter value based on whether calculations are qualified or disqualified and the criterion may be further based on the counter value. In some embodiments, the metric may be a noise metric based on the physiological signal, and the processing equipment may maintain a counter that augments a counter value when a calculation is disqualified, determine a threshold based on the noise metric, and output the value based on one or more previously calculated values value of the physiological parameter based on a comparison of the counter value to the threshold. In some embodiments, the threshold increases when the noise metric increases. In some embodiments, the filter may include a bandpass filter having at least one adjustable setting, and the processing equipment may adjust the at least one setting based on the metric.

BRIEF DESCRIPTION OF THE FIGURES

The above and other features of the present disclosure, its nature and various advantages will be more apparent upon consideration of the following detailed description, taken in conjunction with the accompanying drawings in which:

FIG. 72 is a diagram showing an illustrative lag matrix and correlation matrix, in accordance with some embodiments of the present disclosure;

FIG. 91 is a flow diagram of illustrative steps for qualifying or disqualifying a value that may be indicative of a physiological rate based on an analysis of two segments of a cross-correlation output, in accordance with some embodiments of the present disclosure;

FIG. 92 is a plot of an illustrative cross-correlation output, showing several reference points for selecting two segments and generating a symmetry curve, in accordance with some embodiments of the present disclosure;

FIG. 93 is a plot of an illustrative symmetry curve generated using two segments of a cross-correlation, in accordance with some embodiments of the present disclosure;

FIG. 119 is a flow diagram of illustrative steps for qualifying or disqualifying a value that may be indicative of a physiological rate based on a p-value, in accordance with some embodiments of the present disclosure;

FIG. 120 is a flow diagram of illustrative steps for qualifying or disqualifying a value that may be indicative of a physiological rate based on a maximum and minimum of a correlation sequence, in accordance with some embodiments of the present disclosure;

FIG. 121 is a flow diagram of illustrative steps for adjusting qualification or disqualification criteria based on noise, in accordance with some embodiments of the present disclosure;

FIG. 122 is a flow diagram of illustrative steps for adjusting a qualification or disqualification criterion based on a value indicative of a physiological rate, in accordance with some embodiments of the present disclosure;

FIG. 123A is a flow diagram of illustrative steps for combining qualification tests, in accordance with some embodiments of the present disclosure;

FIG. 123B is a block diagram of an illustrative neural network that may receive a combination of inputs, in accordance with some embodiments of the present disclosure;

FIG. 124 is a flow diagram of illustrative steps for combining qualification tests, in accordance with some embodiments of the present disclosure;

FIG. 125 is a flow diagram of illustrative steps for analyzing qualification metrics based on scaled templates of different lengths, in accordance with some embodiments of the present disclosure;

FIG. 126 is a flow diagram of illustrative steps for selecting one or more templates, and analyzing qualification metrics based on scaled templates, in accordance with some embodiments of the present disclosure;

FIG. 127 is a flow diagram of illustrative steps for managing posting a value indicative of a physiological parameter, in accordance with some embodiments of the present disclosure;

FIG. 128 is a flow diagram of illustrative modes of a rate algorithm, in accordance with some embodiments of the present disclosure;

FIG. 129 is a flow diagram of illustrative steps for calculating and posting a physiological rate, in accordance with some embodiments of the present disclosure;

Figure 130:
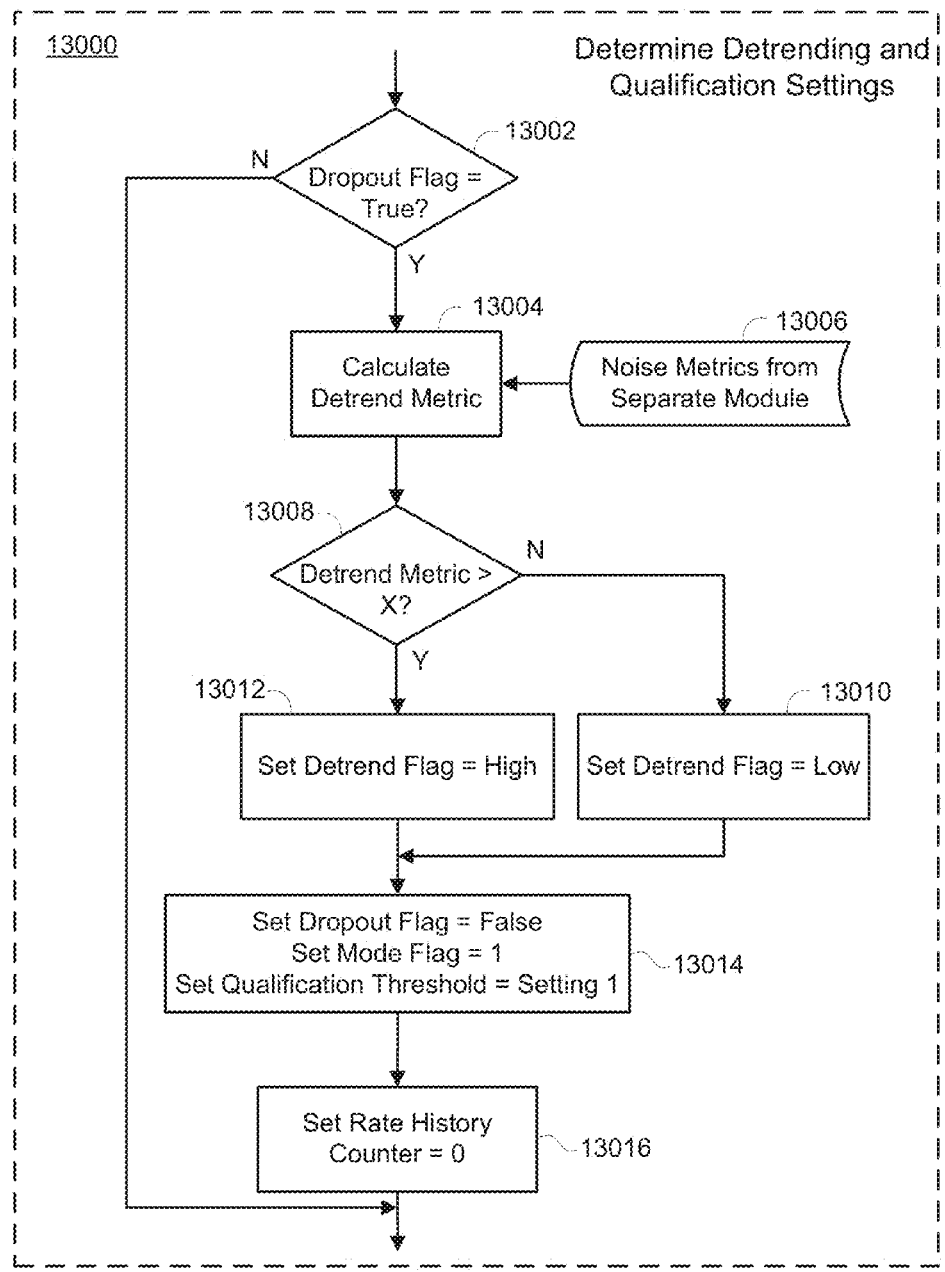
Figures 131, 132:
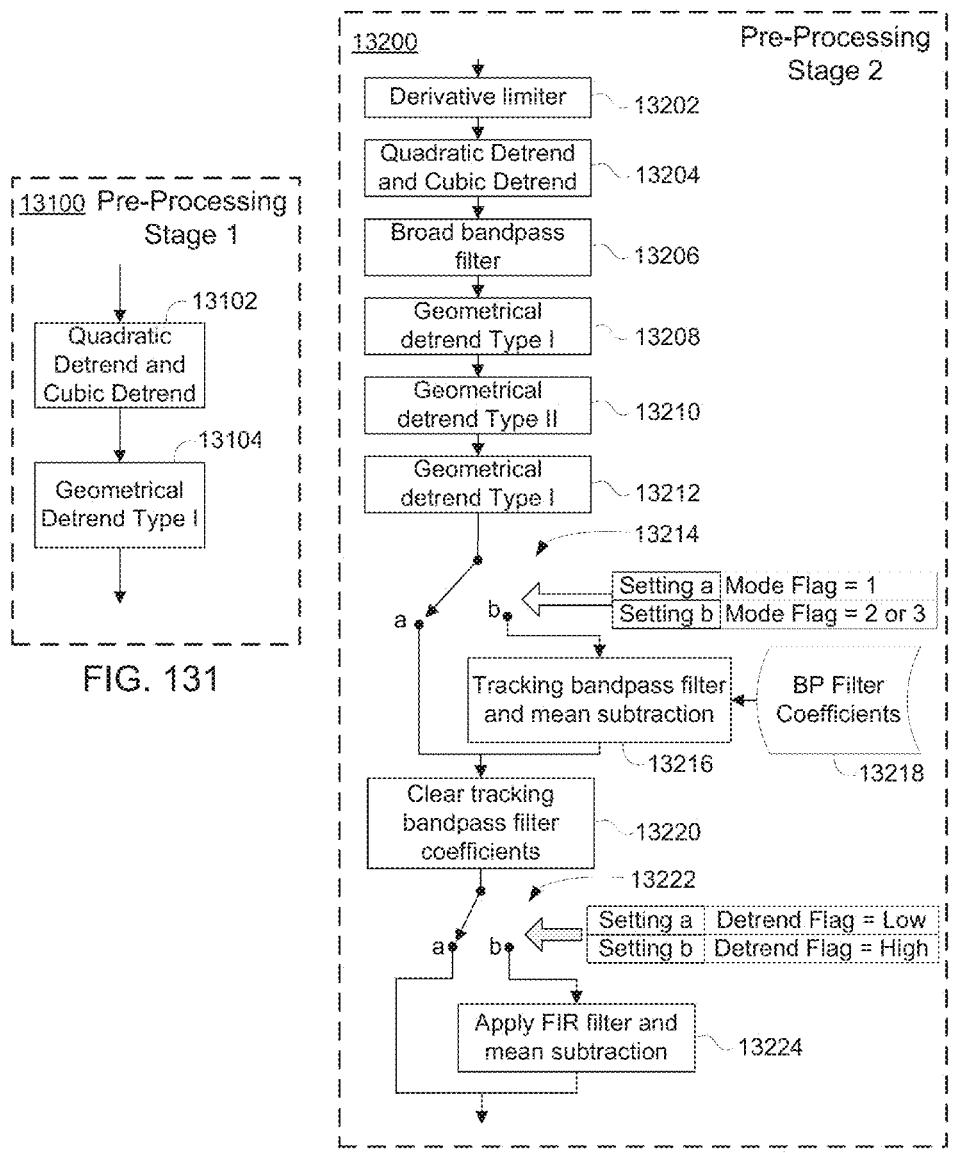
Figure 133:
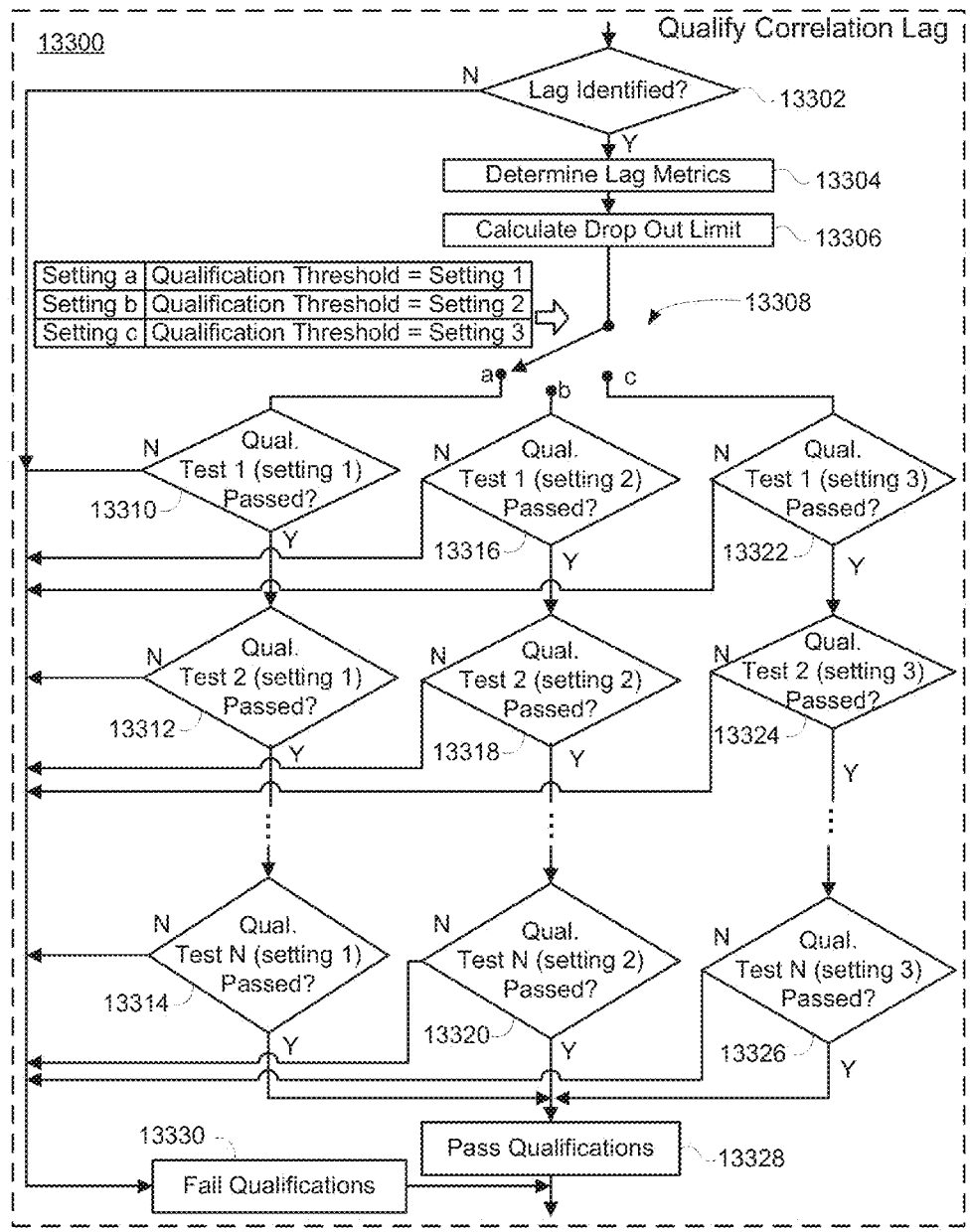
Figure 134:
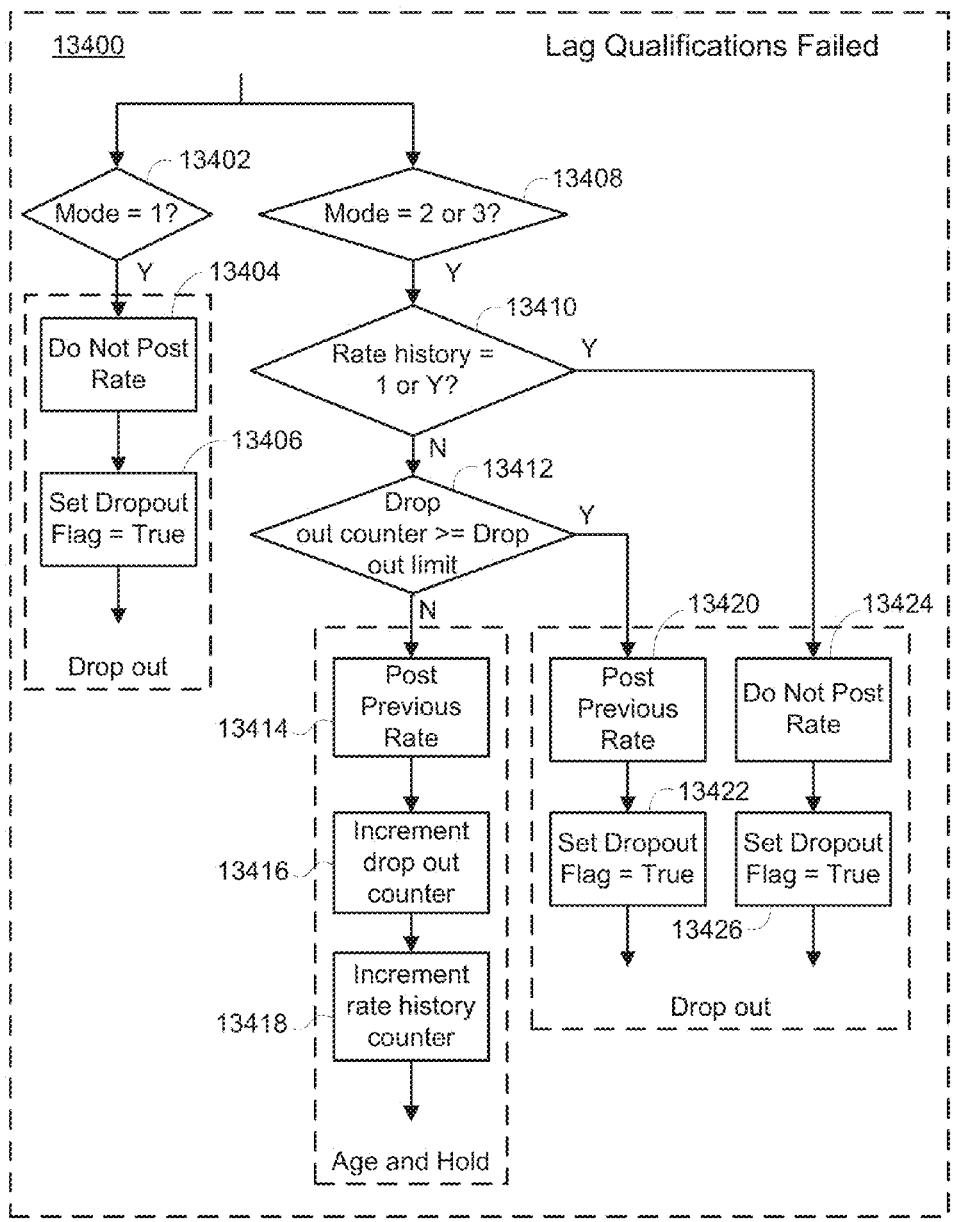
Figure 135:
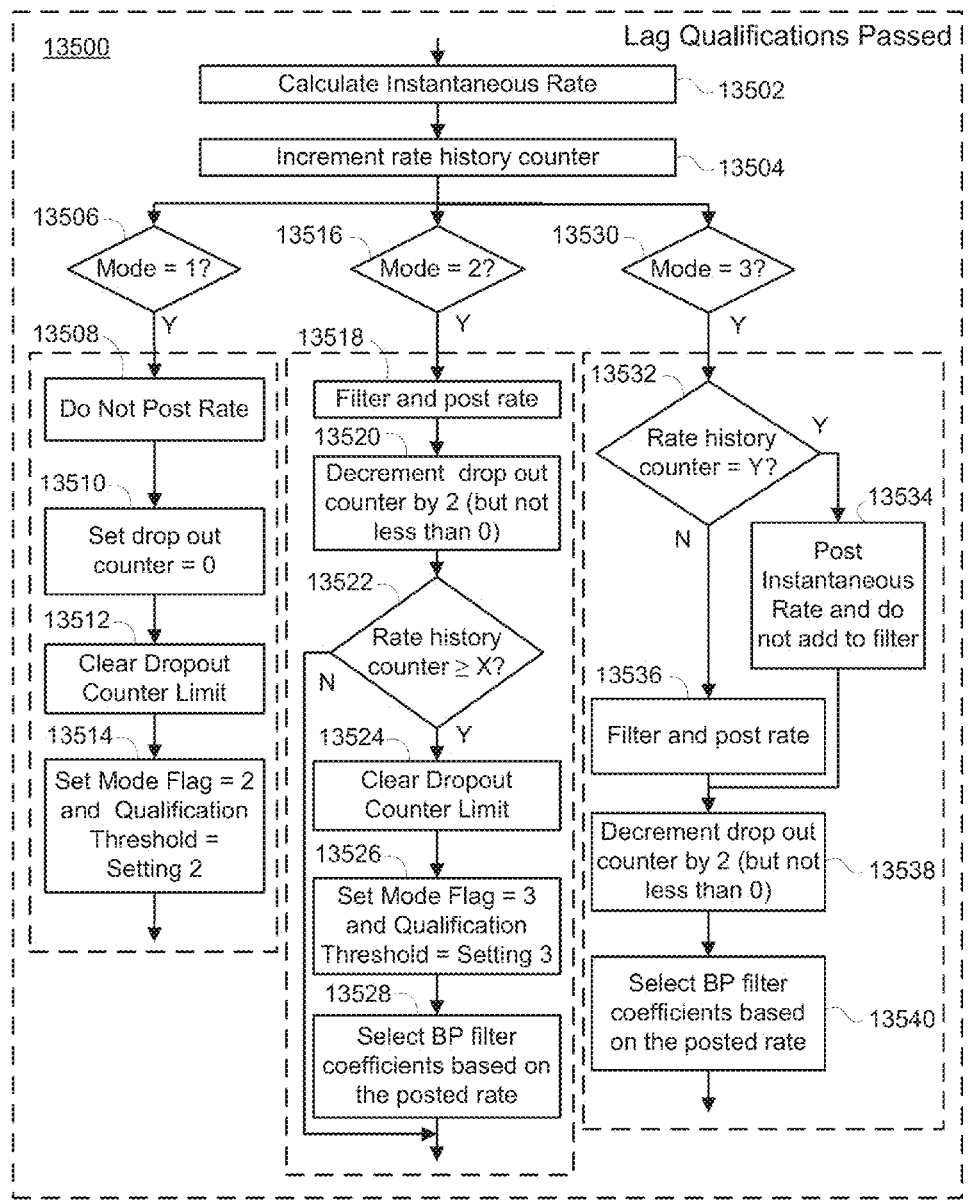
Figure 136:
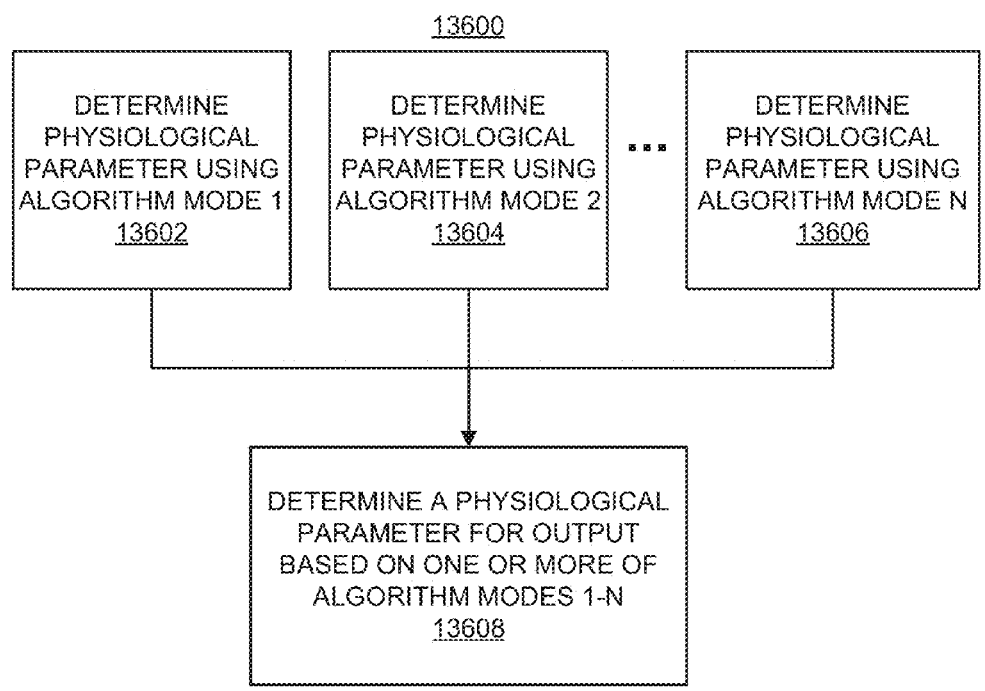

FIG. 130 is a flow diagram of illustrative steps for determining de-trending settings and qualification settings, in accordance with some embodiments of the present disclosure;

FIG. 131 is a flow diagram of illustrative steps for pre-processing physiological data, in accordance with some embodiments of the present disclosure;

FIG. 132 is a flow diagram of illustrative steps for further pre-processing physiological data, in accordance with some embodiments of the present disclosure;

FIG. 133 is a flow diagram of illustrative steps for qualifying or disqualifying a correlation lag value, in accordance with some embodiments of the present disclosure;

FIG. 134 is a flow diagram of illustrative steps for managing algorithm settings when a correlation lag value is disqualified, in accordance with some embodiments of the present disclosure;

FIG. 135 is a flow diagram of illustrative steps for managing algorithm settings when a correlation lag value is qualified, in accordance with some embodiments of the present disclosure; and FIG. 136 is a flow diagram of illustrative steps for determining a physiological parameter using more than one algorithm mode in parallel, in accordance with some embodiments of the present disclosure.

DETAILED DESCRIPTION OF THE FIGURES

The present disclosure is directed towards determining physiological information including physiological rate information. A physiological monitor may determine one or more physiological parameters such as, for example, pulse rate, respiration rate, blood oxygen saturation, blood pressure, or any other suitable parameters, based on one or more signals received from one or more sensors. For example, a physiological monitor may analyze a photoplethysmographic (PPG) signal for oscillometric behavior associated with a pulse rate, a respiration rate, or both. Physiological signals may include desired and undesired signal components. For example, physiological signals may include one or more noise components, which may include the effects of ambient light, electromagnetic radiation from powered devices (e.g., at 50 Hz or 60 Hz), subject movement, any other non-physiological signal component or undesired physiological signal component, or any combination thereof.

In some circumstances, the determination of a pulse rate from PPG information may present challenges. Typical pulse rates range from about 20 to 300 BM for human subjects. For example, the pulse rate of a neonate may be relatively high (e.g., 130-180 BPM) compared to that of a resting adult (e.g., 50-80 BPM). Various sources of noise may obscure the pulse rate. For example, motion artifacts from subject movement may occur over time scales similar to those of the pulse rate of the subject (e.g., on the order of 1 Hertz). Subject movement can prove especially troublesome in measuring pulse rates of neonates, who tend to exhibit significant movement at times during measurements. Significant movement can cause the noise component of the PPG signal to be larger and in some cases significantly larger than the desired physiological pulse component.

Other factors may also present challenges in determining pulse rate. For example, the shape of physiological pulses can vary significantly not only between subjects, but also over time for subjects. Moreover, certain pulse shapes in particular may make it difficult to determine the correct pulse rate. As an example, deep dicrotic notches may cause a single pulse to appear similar to two consecutive pulses and thus it may cause the determined pulse rate to be double the actual rate. Low perfusion is another factor that can present challenges. A subject with low perfusion typically has low-amplitude physiological pulses and therefore PPG signals derived from such subjects may be more susceptible to noise than PPG signals derived from other subjects.

A physiological signal, a signal derived thereof, or a metric derived thereof may be analyzed to determine whether the physiological signal is indicative of a desired physiological activity. Varying levels of rigor, types of qualifications, types of de-trending, or other processing characteristics may be used during the analysis, based on characteristics of the signal or one or more derived metrics. For example, signals exhibiting relatively large amounts of noise may be analyzed differently than signals exhibiting relatively less noise. In a further example, PPG signals exhibiting a dicrotic notch may be analyzed differently than PPG signals exhibiting no dicrotic notch.

The present disclosure discloses techniques for reliably determining rate information from a physiological signal and in particular to determining pulse rate from photoplethysmographic information. The present disclosure also discloses techniques for determining noise information from a physiological signal. The present disclosure also discloses techniques for conditioning physiological signals. The present disclosure also discloses techniques for qualifying physiological information. While the disclosed techniques are described in some embodiments as being implemented in the context of oximeters, it will be understood that any suitable processing device may be used in accordance with the present disclosure.

An oximeter is a medical device that may determine the oxygen saturation of the blood. One common type of oximeter is a pulse oximeter, which may indirectly measure the oxygen saturation of a subject's blood (as opposed to measuring oxygen saturation directly by analyzing a blood sample taken from the subject). Pulse oximeters may be included in physiological monitoring systems that measure and display various blood flow characteristics including, but not limited to, the oxygen saturation of hemoglobin in arterial blood. Such physiological monitoring systems may also measure and display additional physiological parameters, such as a subject's pulse rate, respiration rate, and blood pressure.

An oximeter may include a light sensor that is placed at a site on a subject, typically a fingertip, toe, forehead or earlobe, or in the case of a neonate, across a foot. The oximeter may use a light source to pass light through blood perfused tissue and photoelectrically sense the transmission of the light in the tissue. In addition, locations which are not typically understood to be optimal for pulse oximetry may be used in some embodiments. For example, additional suitable sensor locations include, without limitation, the neck to monitor carotid artery pulsatile flow, the wrist to monitor radial artery pulsatile flow, the inside of a subject's thigh to monitor femoral artery pulsatile flow, the ankle to monitor tibial artery pulsatile flow, and around or in front of the ear. Suitable sensors for these locations may include sensors for sensing attenuated light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as a photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda, t) = I_0(\lambda) \exp(-(s\beta_0(\lambda) + (1-s)\beta_r(\lambda))l(t)). \quad (1)$$

where:
$\lambda$=wavelength;
t=time;
I=intensity of light detected;
$I_0$=intensity of light transmitted;
s=oxygen saturation;
$\beta_0, \beta_r$=absorption coefficients (e.g., empirically derived); and
l(t)=a combination of concentration and path length from emitter to detector as a function of time.

In some embodiments, a physiological system may measure light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield:

$$\log I = \log I_0 - (s\beta_0 + (1-s)\beta_r)l(t)). \quad (2)$$

2. Eq. 2 is then differentiated with respect to time to yield the following:

$$\frac{d\log I}{dt} = -(s\beta_0 + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with the following:

$$\frac{d\log I(\lambda_R)/dt}{d\log I(\lambda_{IR})/dt} = \frac{-(s\beta_0(\lambda_R) + (1-s)\beta_r(\lambda_R))}{-(s\beta_0(\lambda_{IR}) + (1-s)\beta_r(\lambda_{IR}))}. \quad (4)$$

4. Solving for s yields the following:

$$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_0(\lambda_{IR}) - \beta_r(\lambda_{IR})) - \frac{d\log I(\lambda_{IR})}{dt}(\beta_0(\lambda_R) - \beta_r(\lambda_R))}. \quad (5)$$

5. Note that, in discrete time, the following approximation can be made:

$$\frac{d\log I(\lambda, t)}{dt} \cong \log I(\lambda, t_2) - \log I(\lambda, t_1). \quad (6)$$

6. Rewriting Eq. 6 yields the following:

$$\frac{d\log I(\lambda, t)}{dt} \cong \log\left(\frac{I(\lambda, t_2)}{I(\lambda, t_1)}\right). \quad (7)$$

7. Thus, Eq. 4 can be expressed as follows:

$$\frac{\frac{d\log I(\lambda_R)}{dt}}{\frac{d\log I(\lambda_{IR}, t)}{dt}} \cong \frac{\log\left(\frac{I(\lambda_R, t_1)}{I(\lambda_R, t_2)}\right)}{\log\left(\frac{I(\lambda_{IR}, t_1)}{I(\lambda_{IR}, t_2)}\right)} = R, \quad (8)$$

where R represents the "ratio of ratios."

8. Solving Eq. 4 for s using the relationship of Eq. 5 yields:

$$s = \frac{\beta_r(\lambda_R) - R\beta_r(\lambda_{IR})}{R(\beta_0(\lambda_{IR}) - \beta_r(\lambda_{IR})) - \beta_0(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the following relationship:

$$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR}, t)}{dt}} \cong \frac{\frac{I(\lambda_R, t_2) - I(\lambda_R, t_1)}{I(\lambda_R, t_1)}}{\frac{I(\lambda_{IR}, t_2) - I(\lambda_{IR}, t_1)}{I(\lambda_{IR}, t_1)}}$$
$$= \frac{(I(\lambda_R, t_2) - I(\lambda_R, t_1))I(\lambda_{IR}, t_1)}{(I(\lambda_{IR}, t_2) - I(\lambda_{IR}, t_1))I(\lambda_R, t_1)}$$
$$= R,$$

which defines a cluster of points whose slope of y versus x will give R when $$x = (I(\lambda_{IR}, t_2) - I(\lambda_{IR}, t_1))I(\lambda_R, t_1), \quad (12)$$

and $$y = (I(\lambda_R, t_2) - I(\lambda_R, t_1))I(\lambda_{IR}, t_1). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

Pulse rate can be determined from the IR light signal, the Red light signal, any other suitable wavelength light signal, or a combination of light signals.

Figure 1:
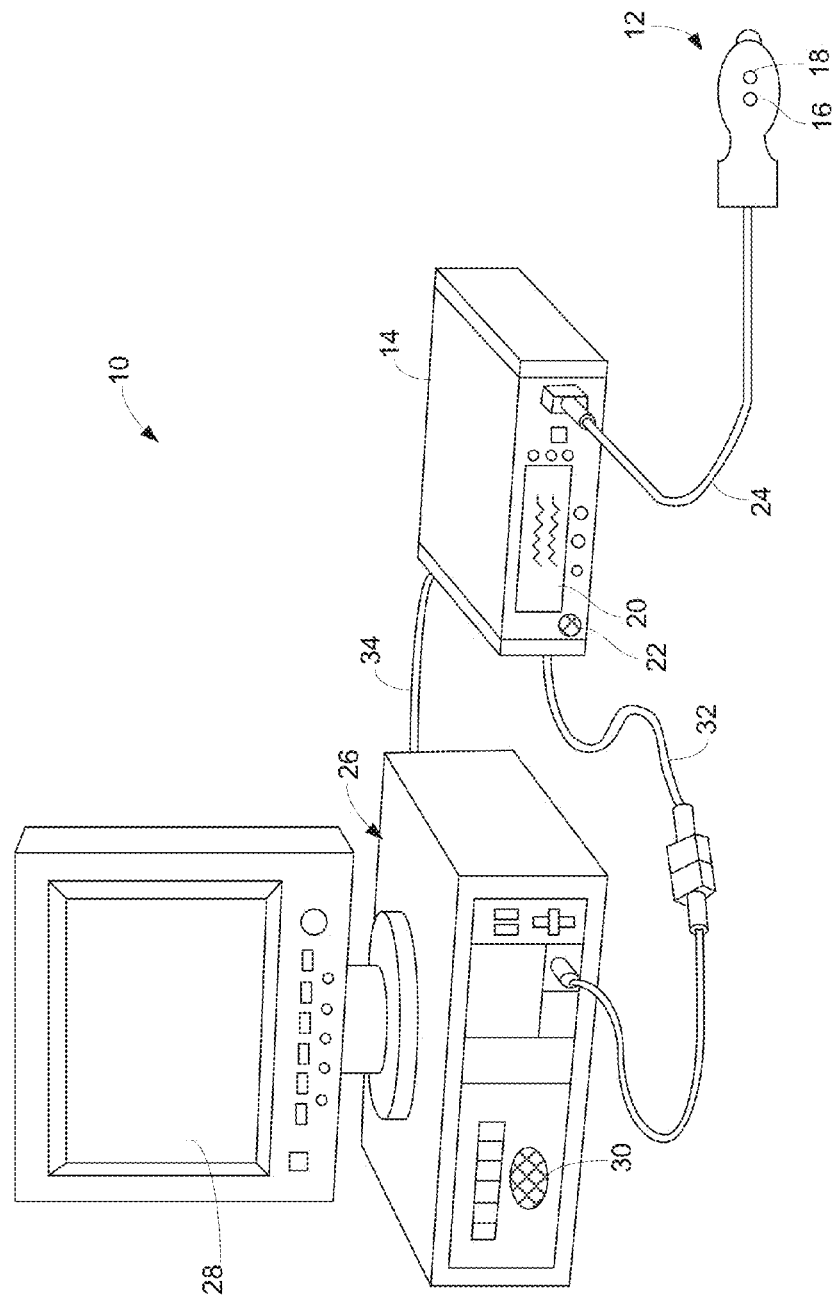
FIG. 1 shows an illustrative physiological monitoring system, in accordance with some embodiments of the present disclosure.

FIG. 1 is a perspective view of an embodiment of a physiological monitoring system 10, which may be used to implement a rate algorithm, for example. System 10 may include sensor unit 12 and monitor 14. In some embodiments, sensor unit 12 may be part of an oximeter. Sensor unit 12 may include an emitter 16 for emitting light at one or more wavelengths into a subject's tissue. A detector 18 may also be provided in sensor 12 for detecting the light originally from emitter 16 that emanates from the subject's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) which may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a subject's forehead, while a second sensor unit may be positioned at a subject's fingertip.

Sensor units may each detect any signal that carries information about a subject's physiological state, such as arterial line measurements or the pulsatile force exerted on the walls of an artery using, for example, oscillometric methods with a piezoelectric transducer. According to another embodiment, system 10 may include a plurality of sensors forming a sensor array in lieu of either or both of the sensor units. Each of the sensors of a sensor array may be a complementary metal oxide semiconductor (CMOS) sensor. Alternatively, each sensor of an array may be a charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. In some embodiments, each pixel may have a photodetector and an active amplifier. In some embodiments, a group of pixels may share an amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is attenuated by the tissue and transmitted to detector 18, such as in a sensor designed to obtain pulse oximetry data from a subject's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood pressure, blood oxygen saturation) based on data relating to light emission and detection received from one or more sensor units such as sensor unit 12. In an alternative embodiment, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a subject's physiological parameters are not within a predefined normal range. In some embodiments, the monitor 14 includes a blood pressure monitor. In some embodiments, the system 10 includes a stand-alone blood pressure monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24.

In the illustrated embodiment, system 10 includes a multi-parameter physiological monitor 26. The monitor 26 may include a cathode ray tube display, a flat panel display (as shown by display 28) such as a liquid crystal display (LCD) or a plasma display, or may include any other type of monitor now known or later developed. Multi-parameter physiological monitor 26 may be configured to calculate physiological parameters and to provide a display 28 for information from monitor 14 and from other medical monitoring devices or systems (not shown). For example, multi-parameter physiological monitor 26 may be configured to display pulse rate information from monitor 14, an estimate of a subject's blood oxygen saturation generated by monitor 14 (referred to as an "$SpO_2$" measurement), and blood pressure from monitor 14 on display 28. Multi-parameter physiological monitor 26 may include a speaker 30.

Monitor 14 may be communicatively coupled to multi-parameter physiological monitor 26 via a cable 32 or 34 that is coupled to a sensor input port or a digital communications port, respectively and/or may communicate wirelessly (not shown). In addition, monitor 14 and/or multi-parameter physiological monitor 26 may be coupled to a network to enable the sharing of information with servers or other workstations (not shown). Monitor 14 and/or multi-parameter physiological monitor 26 may be powered by a battery (not shown) or by a conventional power source such as a wall outlet. In some embodiments, monitor 14, monitor 26, or both, may include one or more communications ports (not shown in FIG. 1) such as, for example, universal serial bus (USB) ports, ethernet ports, WIFI transmitters/receivers, RS232 ports, any other suitable communications ports, or any combination thereof. In some embodiments, monitor 14, monitor 26, or both, may include memory (not shown in FIG. 1) such as, for example, a hard disk, flash memory (e.g., a multimedia card (MMC), a Secure Digital (SD) card), read only memory, any other suitable memory, any suitable communications ports for communicating with memory (e.g., a USB port for excepting flash memory drives, an Ethernet port for communicating with a remote server), or any combination thereof.

Figure 2:
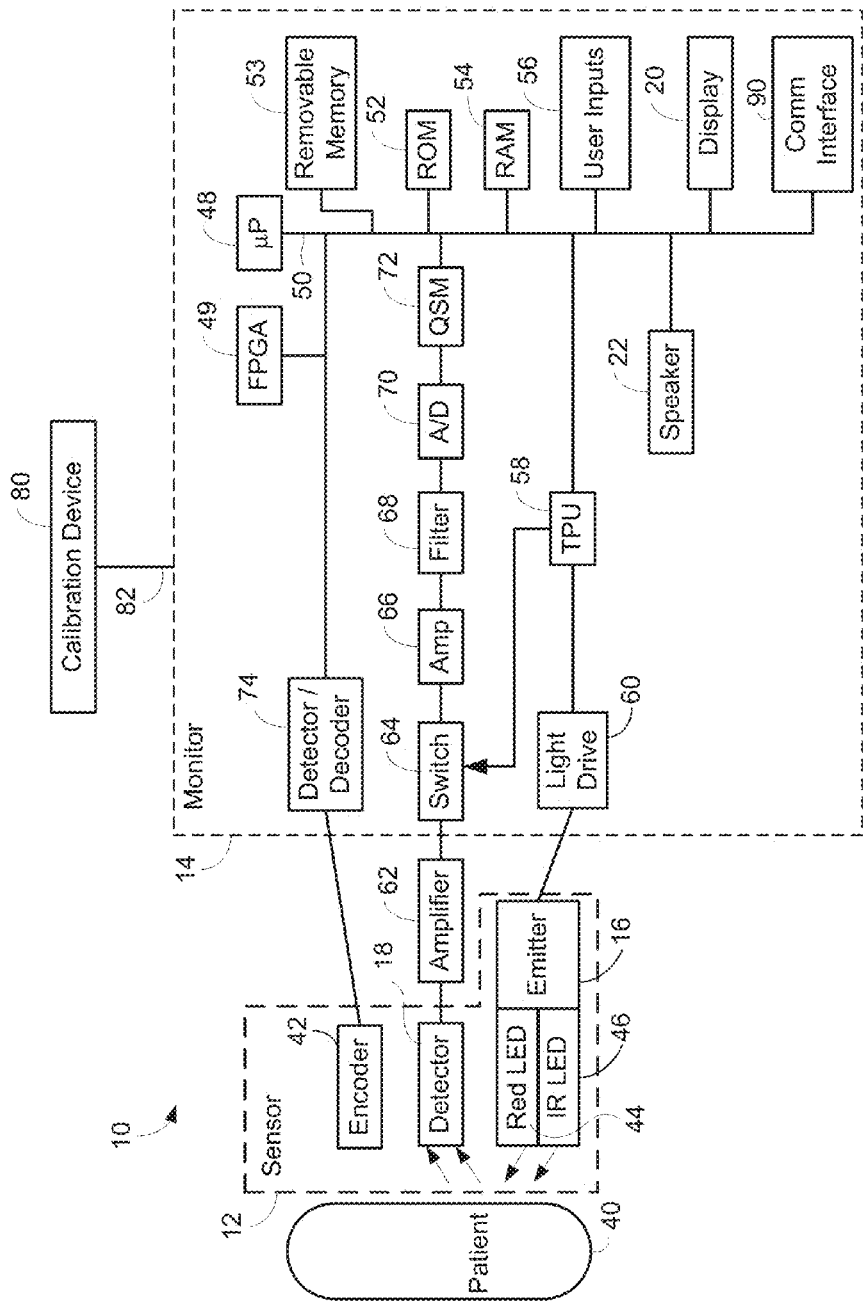
FIG. 2 is a block diagram of the illustrative physiological monitoring system of FIG. 1, which may be coupled to a subject, in accordance with some embodiments of the present disclosure.

FIG. 2 is a block diagram of a physiological monitoring system, such as physiological monitoring system 10 of FIG. 1, which may be coupled to a subject 40 in accordance with some embodiments. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a subject's tissue 40. Hence, emitter 16 may include a Red light emitting light source such as Red light emitting diode (LED) 44 and an IR light emitting light source such as IR LED 46 for emitting light into the subject's tissue 40 at the wavelengths used to calculate the subject's physiological parameters. In some embodiments, the Red wavelength may be between about 600 nm and about 700 nm, and the IR wavelength may be between about 800 nm and about 1000 nm. In some embodiments, in which a sensor array is used in place of a single sensor, each sensor may be configured to emit a single wavelength. For example, a first sensor emits only a Red light while a second emits only an IR light. In another example, the wavelengths of light used are selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16, the hemoglobin absorption profile, or both.

In some embodiments, detector 18 may be configured to detect the intensity of light at the Red and IR wavelengths. Alternatively, each sensor in the array may be configured to detect intensity at a single wavelength. In operation, light may enter detector 18 after being attenuated (e.g., absorbed, scattered) by the subject's tissue 40. Detector 18 may convert the intensity of the received light into an electrical signal. The light intensity is related to the absorption and/or reflection of light in the tissue 40. That is, when more light at a certain wavelength is absorbed or reflected, less or more light of that wavelength is received from the tissue by the detector 18. After converting the received light to an electrical signal, detector 18 may send the signal to monitor 14, where physiological parameters may be calculated based on the absorption of the Red and IR wavelengths in the subject's tissue 40.

In some embodiments, encoder 42 may contain information about sensor 12, such as sensor type (e.g., whether the sensor is intended for placement on a forehead or digit), the wavelengths of light emitted by emitter 16, power requirements or limitations of emitter 16, or other suitable information. This information may be used by monitor 14 to select appropriate algorithms, lookup tables and/or calibration coefficients stored in monitor 14 for calculating the subject's physiological parameters.

In some embodiments, encoder 42 may contain information specific to subject 40, such as, for example, the subject's age, weight, and diagnosis. Information regarding a subject's characteristics may allow monitor 14 to determine, for example, subject-specific threshold ranges in which the subject's physiological parameter measurements should fall and to enable or disable additional physiological parameter algorithms. This information may also be used to select and provide coefficients for equations from which, for example, pulse rate, blood pressure, and other measurements may be determined based on the signal or signals received at sensor unit 12. For example, some pulse oximetry sensors rely on equations to relate an area under a portion of a PPG signal corresponding to a physiological pulse to determine blood pressure. These equations may contain coefficients that depend upon a subject's physiological characteristics as stored in encoder 42. Encoder 42 may, for instance, be a coded resistor which stores values corresponding to the type of sensor unit 12 or the type of each sensor in the sensor array, the wavelengths of light emitted by emitter 16 on each sensor of the sensor array, and/or the subject's characteristics. In some embodiments, encoder 42 may include a memory on which one or more of the following information may be stored for communication to monitor 14: the type of the sensor unit 12; the wavelengths of light emitted by emitter 16; the particular wavelength each sensor in the sensor array is monitoring; a signal threshold for each sensor in the sensor array; any other suitable information; or any combination thereof. In some embodiments, encoder 42 may include an identifying component such as, for example, a radio-frequency identification (RFID) tag that may be read by decoder 74.

In some embodiments, signals from detector 18 and encoder 42 may be transmitted to monitor 14. In the embodiment shown, monitor 14 may include a general-purpose microprocessor 48, FPGA 49, or both, connected to an internal bus 50. In some embodiments, monitor 14 may include one or more microprocessors, digital signal processors (DSPs), or both. Microprocessor 48 may be adapted to execute software, which may include an operating system and one or more applications, as part of performing the functions described herein. Also connected to bus 50 may be a read-only memory (ROM) 52, a random access memory (RAM) 54, removable memory 53, user inputs 56, display 20, and speaker 22.

RAM 54, ROM 52, and removable memory 53 are illustrated by way of example (e.g., communications interface 90, flash memory, digital logic array, field programmable gate array (FPGA), or any other suitable memory), and not limitation. Any suitable computer-readable media may be used in the system for data storage. Computer-readable media are capable of storing information that can be interpreted by microprocessor 48, FPGA 49, or both. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, writable and non-writable, and removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. In some embodiments, microprocessor 48, FPGA 49, or both, may de-multiplex the signal from detector 18 using de-multiplexing techniques such as time-division, frequency-division, code division, or any other suitable de-multiplexing technique. In some embodiments, microprocessor 48, FPGA 49, or both, may perform the functions of TPU 58 using suitable timing signals and multiplexing/de-multiplexing algorithms, and accordingly TPU 58 need not be included. The received signal from detector 18 may be passed through amplifier 66, low pass filter 68, and analog-to-digital converter 70. The digital data may then be stored in a queued serial module (QSM) 72 (or buffer such as a first in first out (FIFO) buffer) for later downloading to RAM 54 as QSM 72 fills up. A window of data may be selected from the data stored in the buffer for further processing. In some embodiments, there may be multiple separate parallel paths having components equivalent to amplifier 62, switching circuit 64, amplifier 66, filter 68, and/or A/D converter 70 for multiple light wavelengths or spectra received. In some embodiments, a filter (e.g., an analog filter) may be included (not shown) between amplifier 62 and switching circuit 64.

In an embodiment, microprocessor 48 may determine the subject's physiological parameters, such as pulse rate, $SpO_2$, and/or blood pressure, using various algorithms and/or look-up tables based on the value of the received signals and/or data corresponding to the light received by detector 18. Signals corresponding to information about subject 40, and particularly about the intensity of attenuated light emanating from a subject's tissue over time, may be transmitted from encoder 42 to decoder 74. These signals may include, for example, encoded information relating to subject characteristics. Decoder 74 may translate these signals to enable the microprocessor to determine the thresholds based on algorithms or look-up tables stored in ROM 52. In some embodiments, user inputs 56 may be used enter information, select one or more options, provide a response, input settings, any other suitable inputting function, or any combination thereof. User inputs 56 may be used to enter information about the subject, such as age, weight, height, diagnosis, medications, treatments, and so forth. In some embodiments, display 20 may exhibit a list of values which may generally apply to the subject, such as, for example, age ranges or medication families, which the user may select using user inputs 56.

Calibration device 80, which may be powered by monitor 14 via a coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system). Calibration device 80 may be coupled to one or more components of monitor 14 to calibrate monitor 14.

Communications ("Comm") interface 90 may include any suitable hardware, software, or both, which may allow physiological monitoring system 10 (e.g., monitor 14, monitor 26) to communicate with electronic circuitry, a device, a network, or any combinations thereof. Communications interface 90 may include one or more receivers, transmitters, transceivers, antennas, plug-in connectors, ports, communications buses, communications protocols, device identification protocols, any other suitable hardware or software, or any combination thereof. Communications interface 90 may be configured to allow wired communication (e.g., using USB, RS-232 or other standards), wireless communication (e.g., using WiFi, IR, WiMax, BLUETOOTH, UWB, or other standards), or both. For example, communications interface 90 may be configured using a universal serial bus (USB) protocol (e.g., USB 1.0, USB 2.0, USB 3.0), and may be configured to couple to other devices (e.g., remote memory devices storing templates) using a four-pin USB standard Type-A connector (e.g., plug and/or socket) and cable. In a further example, communications interface 90 may be configured to access a database server, which may contain a template database. In some embodiments, communications interface 90 may include an internal bus such as, for example, one or more slots for insertion of expansion cards (e.g., to expand the capabilities of monitor 14, monitor 26, or both).

As described above, the optical signal attenuated by the tissue can be degraded by noise, among other sources, and an electrical signal derived thereof can also be degraded by noise. One source of noise is ambient light that reaches the light detector. Another source of noise in an intensity signal is electromagnetic coupling from other electronic instruments. Movement of the subject also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from subject movement) can degrade a sensor signal relied upon by a care provider, without the care provider's awareness. This is especially true if the monitoring of the subject is remote, the motion is too small to be observed, or the care provider is watching the instrument or other parts of the subject, and not the sensor site. Analog and/or digital processing of sensor signals (e.g., PPG signals) may involve operations that reduce the amount of noise present in the signals or otherwise identify noise components in order to prevent them from affecting measurements of physiological parameters derived from the sensor signals.

It will be understood that the present disclosure is applicable to any suitable signal and that PPG signals are used merely for illustrative purposes. Those skilled in the art will recognize that the present disclosure has wide applicability to other signals including, but not limited to, other biosignals (e.g., electrocardiograms, electroencephalograms, electrogastrograms, electromyograms, pulse rate signals, pathological signals, ultrasound signals, any other suitable biosignals), or any combination thereof.

Figure 3:
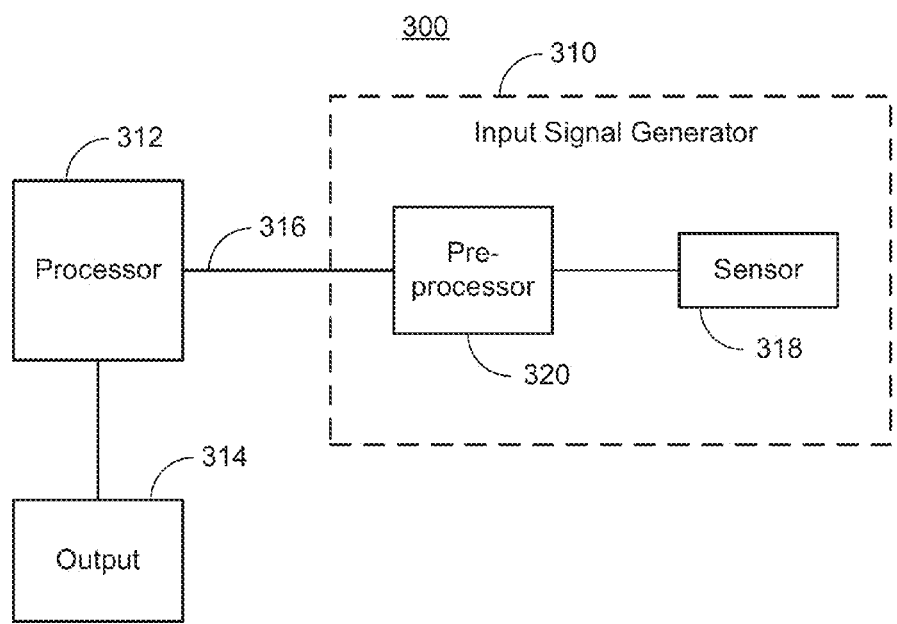
FIG. 3 is an illustrative signal processing system in accordance with some embodiments of the present disclosure.

FIG. 3 is an illustrative signal processing system 300 in accordance with some embodiments that may implement the signal processing techniques described herein. In some embodiments, signal processing system 300 may be included in a physiological monitoring system (e.g., physiological monitoring system 10 of FIGS. 1-2). In the illustrated embodiment, input signal generator 310 generates an input signal 316. As illustrated, input signal generator 310 may include pre-processor 320 coupled to sensor 318, which may provide input signal 316. In some embodiments, input signal 316 may include one or more intensity signals based on a detector output. In some embodiments, pre-processor 320 may be an oximeter and input signal 316 may be a PPG signal. In an embodiment, pre-processor 320 may be any suitable signal processing device and input signal 316 may include PPG signals and one or more other physiological signals, such as an electrocardiogram (ECG) signal. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing operations to the signal generated by sensor 318. For example, pre-processor 320 may apply a pre-determined set of processing operations to the signal provided by sensor 318 to produce input signal 316 that can be appropriately interpreted by processor 312, such as performing A/D conversion. In some embodiments, A/D conversion may be performed by processor 312. Pre-processor 320 may also perform any of the following operations on the signal provided by sensor 318: reshaping the signal for transmission, multiplexing the signal, modulating the signal onto carrier signals, compressing the signal, encoding the signal, and filtering the signal. In some embodiments, pre-processor 320 may include a current-to-voltage converter (e.g., to convert a photocurrent into a voltage), an amplifier, a filter, and A/D converter, a de-multiplexer, any other suitable pre-processing components, or any combination thereof.

In some embodiments, signal 316 may include PPG signals corresponding to one or more light frequencies, such as an IR PPG signal and a Red PPG signal. In some embodiments, signal 316 may include signals measured at one or more sites on a subject's body, for example, a subject's finger, toe, ear, arm, or any other body site. In some embodiments, signal 316 may include multiple types of signals (e.g., one or more of an ECG signal, an EEG signal, an acoustic signal, an optical signal, a signal representing a blood pressure, and a signal representing a heart rate). Signal 316 may be any suitable biosignal or any other suitable signal.

In some embodiments, signal 316 may be coupled to processor 312. Processor 312 may be any suitable software, firmware, hardware, or combination thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, include an assembly of analog electronic components. Processor 312 may calculate physiological information. For example, processor 312 may compute one or more of a pulse rate, respiration rate, blood pressure, oxygen saturation, or any other suitable physiological parameter. Processor 312 may perform any suitable signal processing of signal 316 to filter signal 316, such as any suitable band-pass filtering, adaptive filtering, closed-loop filtering, any of the filtering disclosed herein, any other suitable filtering, and/or any combination thereof. Processor 312 may also receive input signals from additional sources (not shown). For example, processor 312 may receive an input signal containing information about treatments provided to the subject. Additional input signals may be used by processor 312 in any of the calculations or operations it performs in accordance with processing system 300.

In some embodiments, all or some of pre-processor 320, processor 312, or both, may be referred to collectively as processing equipment. In some embodiments, any of the processing components and/or circuits, or portions thereof, of FIGS. 1-3 may be referred to collectively as processing equipment. For example, processing equipment may be configured to amplify, filter, sample and digitize input signal 316 (e.g., using an analog to digital converter), and calculate physiological information from the digitized signal. Accordingly, system 300 may be used to implement a rate algorithm. In some embodiments, all or some of the components of the processing equipment may referred to as a processing module.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store fiducial information or initialization information corresponding to physiological monitoring. In some embodiments, processor 312 may store physiological measurements or previously received data from signal 316 in a memory device for later retrieval. In some embodiments, processor 312 may store calculated values, such as a pulse rate, a blood pressure, a blood oxygen saturation, a fiducial point location or characteristic, an initialization parameter, or any other calculated values, in a memory device for later retrieval.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as part of sensor unit 12 (of FIGS. 1 and 2) and monitor 14 (of FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the subject (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous subject monitoring solution. In some embodiments, a wireless transceiver (not shown) may also be included in system 300 to enable wireless communication with other components of system 10. For example, pre-processor 320 may output signal 316 over BLUETOOTH, 802.11, WiFi, WiMax, cable, satellite, Infrared, or any other suitable transmission scheme. In some embodiments, a wireless transmission scheme may be used between any communicating components of system 300. In some embodiments, system 300 may include one or more communicatively coupled modules configured to perform particular tasks. In some embodiments, system 300 may be included as a module communicatively coupled to one or more other modules.

Pre-processor 320 or processor 312 may determine rate based on a periodicity within physiological signal 316 (e.g., a PPG signal) that is associated with a subject's pulse rate using one or more processing techniques. For ease of illustration, the following rate determination techniques will be described as performed by processor 312, but any suitable processing device (e.g., pre-processor 320, microprocessor 48, any other suitable components of system 10 and/or system 300, or any combination thereof) may be used to implement any of the techniques described herein.

Figure 4:
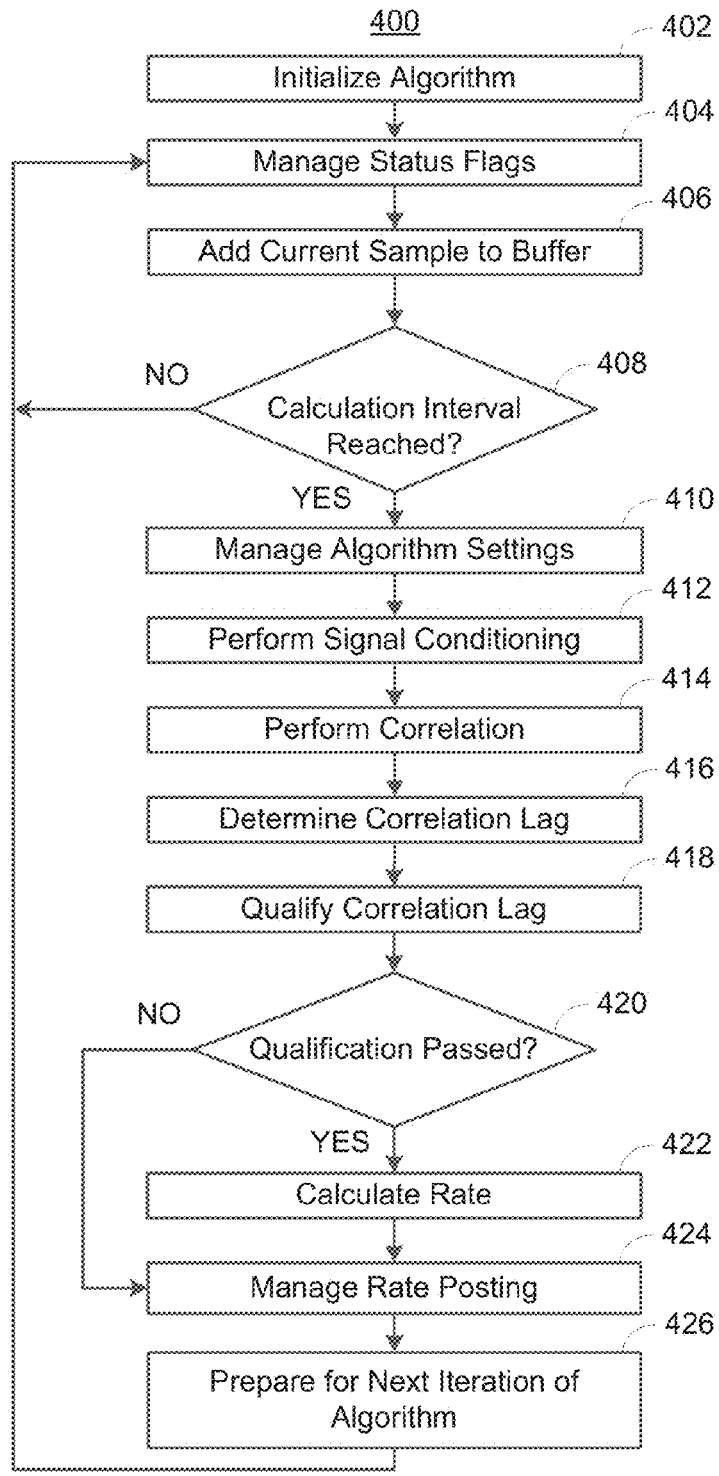
FIG. 4 is a flow diagram of illustrative steps for determining physiological information of a subject, in accordance with some embodiments of the present disclosure.

Physiological information such as pulse rate may be determined based on signals received from a physiological sensor. FIG. 4 is a flow diagram 400 of illustrative steps for determining physiological information of a subject, in accordance with some embodiments of the present disclosure. In accordance with flow diagram 400, an algorithm may be used to condition and analyze a window of data buffered from a physiological signal, and by determine a physiological rate when one or more qualification tests are passed. One or more settings of the algorithm may be managed using, for example, a mode selection that may be used to define the signal conditioning, qualification, and rate posting management. The illustrative steps of flow diagram 400, or suitable portions thereof, will be referred to as the "rate algorithm" herein.

The steps of flow diagram 400, and all subsequent flow diagrams of this disclosure, may be performed using the physiological monitoring system 10 of FIGS. 1-2, system 300 of FIG. 3, any other suitable system, or any combination thereof. For example, in some embodiments, the steps may be performed by a particular central processing unit (CPU) of physiological monitoring system 10 (e.g., including microprocessor 48, bus 50, and any or all components coupled to bus 50). In a further example (not shown), physiological monitoring system 10 may be a modular system, including one or more functional modules (i.e., software, hardware, or a combination of both) configured to perform particular tasks or portions of tasks thereof. Any suitable arrangement of physiological monitoring system 10, any other suitable system, or any combination thereof, may be used in accordance with the present disclosure. For illustrative purposes, the flow diagrams of the present disclosure will be discussed in reference to processing equipment, which may include physiological monitoring system 10, system 300 of FIG. 3, any other suitable system, any suitable components thereof, or any combination thereof.

Step 402 may include processing equipment initializing the algorithm for determining physiological information. In some embodiments, step 402 may include beginning to fill the buffer with physiological data from the physiological signal. In some embodiments, step 402 may include initializing one or more status flags or other algorithm settings.

Step 404 may include processing equipment managing one or more status flags. In some embodiments, the processing equipment may initialize one or more status flags, determine whether to change the value of one or more status flags, change the value of one or more status flags, update one or more status flags, receive information regarding one or more status flags, perform any other status flag management functions, or any combination thereof. Status flags may include a pulse lost flag, a sensor off flag, a gain change flag, a no valid saturation flag, an initialization flag, a dropout flag, a mode flag, any other suitable status flag, or any combination thereof. Status flags may assume any suitable indicator value such as, for example, a number (e.g., one or zero, or a positive integer), a letter (e.g., A, B, C), a text string (e.g., "pulse detected" or "pulse not detected"), any other suitable indicator, or any combination thereof. For example, the processing equipment may determine that no sensor is detected, and accordingly may set the value of a sensor lost flag to one. If the processing equipment subsequently detects the sensor, the processing equipment may set the value of the sensor off flag to zero.

Step 406 may include processing equipment adding a current sample from the physiological signal to a memory buffer (a "buffer" such as QSM 72 of system 10). In some embodiments the current sample may replace a sample previously stored in the buffer, replace a place-holder value in the buffer (e.g., a padding zero), add to a set of other stored values, or otherwise be stored in the memory buffer. In some embodiments, the processing equipment may add the current sample to the buffer, and if the buffer is not filled, the processing equipment may add one or more placeholder values to the buffer. For example, in some embodiments, the processing equipment may pad the buffer with zeros so the buffer does not have a reduced number of samples. In a further example, the processing equipment may pad the buffer with initialization values such as suitably scaled random values so the buffer does not have a reduced number of samples.

Step 408 may include processing equipment determining whether a calculation interval has been reached. In some embodiments, the calculation interval may include a predetermined number of samples, or corresponding time interval (e.g., 1 second corresponding to 57 samples at a sampling rate of 57 Hz). For example, when the buffer has been filled with a particular number of samples from the physiological signal, the calculation interval may be reached and the algorithm may accordingly proceed to step 410. In some embodiments, the processing equipment may determine the elapsed time since the last rate calculation, or determine the number of additional samples added to the buffer since the last rate calculation, and then determine whether to proceed to step 410, or repeat steps 404 and 406 before proceeding to step 410.

Step 410 may include processing equipment managing one or more algorithm settings. In some embodiments, algorithm settings may include an operating mode, a flag setting, a threshold setting, a posting setting, a filter setting, any other suitable setting, or any combination thereof. In some embodiments, step 410 may include determining a signal classification, determining a signal metric such as a de-trend metric or noise metric, performing any other classification or determination that may be used to affect the rate algorithm processing, or any combination thereof. For example, the processing equipment may manage the algorithm settings based on the value of a mode flag.

Step 412 may include processing equipment performing signal conditioning on the window of data stored in the buffer. Signal conditioning may include applying a filter (e.g., a low pass, high pass, band pass, notch, or any other suitable analog or digital filter), amplifying, performing an operation on the received signal (e.g., taking a derivative, averaging), applying a derivative limiter, performing normalization, performing a geometrical de-trending (e.g., of any suitable type), applying a finite impulse response (FIR) filter, performing any other suitable signal conditioning, or any combination thereof. For example, in some embodiments, step 406 may include removing a DC offset, removing low frequency components, removing high frequency components, performing a mean subtraction or other baseline subtraction, performing any other suitable signal conditioning, or any combination thereof. In a further example, step 406 may include smoothing the received physiological signal (e.g., using a moving average or other smoothing technique). In some embodiments, the type of signal conditioning performed at step 412 may depend on one or more algorithm settings (e.g., managed at step 410).

Step 414 may include processing equipment performing a correlation using the conditioned data of step 412. The correlation may include an autocorrelation, partial autocorrelation, cross-correlation, any other suitable correlation, or any combination thereof. In some embodiments, the correlation may include a discrete correlation, as shown in Eq. 14:

$$A_{xx}(j) = \sum_{n=0}^{N-1} x_n x_{n-j} \quad (14)$$

in which a discrete correlation coefficient $A_{xx}$ may be computed for N samples $x_n$ for a range of lag values indexed by j, respectively. The correlation output may include a sequence of points, and may be referred to as a correlation sequence. The term autocorrelation, as used herein, shall also refer to a partial autocorrelation. For example, the term autocorrelation may be used to describe a correlation between segments of a given window of data, whether or not the segments share any data points. Accordingly, as used herein, the term autocorrelation may be used to describe a correlation between segments of a window of data sharing zero points, all points, or some points. The term cross-correlation, as used herein, shall refer to a correlation between two sets of data points not included in the same window of data. In some embodiments, the first portion of data, the second portion of data, or both, may be padded with zeros (e.g., at either or both ends of the portion) to equate the lengths of the first and second portions to aid in performing an autocorrelation.

In some embodiments, the correlation of step 414 may include correlating a first segment of the window of data with a second segment of the window of data. The first and second segments may be exclusive of one another, may share one or more samples, or may be selected by any other suitable partition of the window of data. For example, referencing a six second window, the most recent three seconds of data may be correlated with the entire six seconds of data to produce a correlation sequence. In a further example, referencing a six second window, the most recent three seconds of data may be correlated with the previous three seconds of data, so that the segments do not overlap. In some embodiments, there may be a time gap between the first and second segments. For example, the most recent one second of data may be correlated with previous data not immediately preceding the one second of data.

The correlation output of step 414 may include a sequence of data points, indexed by lag values, and may exhibit one or more peaks, troughs, or both. Peaks may be associated with relatively high correlation, zeros may be associated with relatively low correlation, and troughs may be associated with relatively high anti-correlation. Lag values corresponding to peaks may indicate time intervals corresponding to a period of a physiological pulse rate, or a multiple thereof (e.g., when the subject's pulse rate is relatively constant).

Step 416 may include processing equipment determining a correlation lag based on the correlation output of step 414. In some embodiments, the processing equipment may identify one or more peaks of the correlation output of step 414, and accordingly determine one or more lag values associated with each of the one or more peaks. For example, in some embodiments, the processing equipment may generate one or more thresholds, and may determine the correlation lag corresponding to any threshold crossings. In a further example, the processing equipment may identify a maximum value in the correlation output, and determine the lag corresponding to the maximum. The correlation lag may be determined in units of sample point shifts (e.g., a lag of 10 points), time interval (e.g., a lag of 1 second), any other suitable lag units, or any combination thereof.

Step 418 may include processing equipment qualifying a determined correlation lag of step 416 by applying one or more qualification tests. Step 418 may include calculating one or more qualification metrics indicative of an estimated quality of the determined correlation lag value. For example, one or more correlation lag values may be determined at step 416, using any suitable technique of the present disclosure. Some illustrative techniques of step 418, referred to as "Qualification Techniques", will be described in further detail herein during the discussion of FIGS. 86-126 of the present disclosure.

Step 420 may include processing equipment determining whether the one or more qualification tests of step 418 have passed. If the correlation lag value of step 416 is determined to be qualified, then the processing equipment may proceed to calculate a rate at step 422. If the correlation lag value of step 416 is determined to be disqualified (e.g., exhibit a low confidence value), then the processing equipment may skip step 422 and proceed directly to step 424 to manage rate posting. In some embodiments, if the correlation lag value of step 416 is determined to be disqualified, then the processing equipment may update one or more counters (e.g., a dropout counter) and/or one or more status flags (e.g., a Dropout Status Flag) at step 404. In some embodiments, the processing equipment may determine whether one or more qualification tests have passed based on a qualification metric, a threshold value, a look-up table, any other suitable information, or any combination thereof.

In some situations, the processing equipment may not be able to determine a lag in step 416. For example, when there is a large amount of noise in the physiological signal, there may not be a peak in the correlation that exceeds the threshold. When a lag is not determined, the processing equipment may treat it as though the lag qualifications failed and proceed to step 424 to manage rate posting.

Step 422 may include processing equipment calculating a physiological rate. In some embodiments, the processing equipment may determine a physiological rate by identifying the correlation lag value and determining the rate having a characteristic period equal to the correlation lag value.

Step 424 may include processing equipment managing posting of the calculated rate of step 422. In some embodiments, the processing equipment may filter the calculated rate, and may output the filtered rate for display (e.g., on display 20 of physiological monitoring system 10) at step 424. For example, step 424 may include low pass filtering of the calculated rate to limit the rate of change of the outputted rate to physiological ranges. In a further example, step 424 may include applying an infinite impulse response (IIR) filter to the calculated rate of step 422. In a further example, step 424 may include applying a finite impulse response (FIR) filter to the calculated rate of step 422. In some embodiments, step 424 may include storing the filtered rate values in memory such as, for example, RAM 54 or other suitable memory of physiological monitoring system 10. If the qualification was not passed at step 420, the processing equipment may continue to post the previous rate, or no rate, at step 424.

Step 426 may include processing equipment preparing for a subsequent iteration of the algorithm. In some embodiments, step 426 may include adjusting one or more algorithm settings, setting one or more status flags, or both.

In an illustrative example, the processing equipment may implement the techniques of flow diagram 400 using three operating modes, which may be designated using a Mode Status Flag. During startup, or in the event of a dropout, the rate algorithm may operate in Mode 1. While in Mode 1, the processing equipment may perform rate calculations, yet may not post a rate at all. However, Mode 1 operation may include relatively strict qualification criteria to prevent noise tracking. When a particular number of lags have been qualified, the rate algorithm may set the Mode Status Flag to Mode 2, and begin posting rates. If calculated rates are disqualified, the rate algorithm may return to Mode 1, while if a sufficient number of calculated rates are qualified, the rate algorithm may proceed to Mode 3 and apply a bandpass filter to the physiological data.

Further details and implementations of the present disclosure, including further details and implementations of flow diagram 400, are discussed below.

Figure 5:
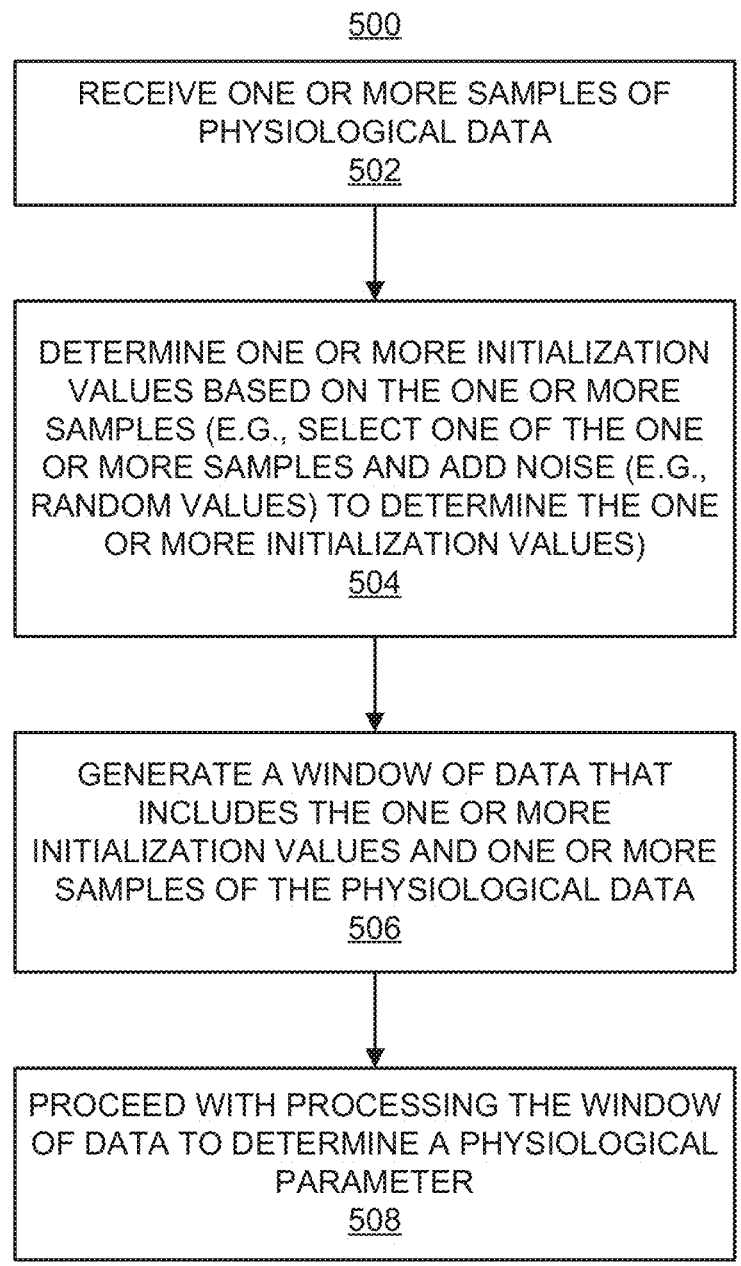
FIG. 5 is a flow diagram of illustrative steps for initializing a technique for determining physiological information, in accordance with some embodiments of the present disclosure.

FIG. 5 is a flow diagram 500 of illustrative steps for initializing a technique for determining physiological information, in accordance with some embodiments of the present disclosure. Initialization techniques may be desired in circumstances where a limited amount of physiological data may be available and/or desired (e.g., during the start of data collection). In some embodiments, Initialization allows system 300 or system 10 to start processing a physiological signal before an entire buffer (e.g., 6 or 7 seconds of data) is obtained from the physiological signal. An entire buffer of physiological data (e.g., 6 seconds in this example, although an entire buffer may be any suitable length), for example, is typically only needed to accurately determine rates down to 20 BPM. At 20 BPM, a 6 second buffer will include 2 periods worth of data. Since most rates are 50 BPM or higher, it is possible for system 300 or system 10 to begin processing physiological data before 6 seconds of data have been obtained and still accurately determine rate. In some embodiments, a fixed buffer size may be used and this may not require any modification of the algorithm. For example, Initialization may allow subsequent processing such as, for example, a correlation calculation to be performed without adjusting a template size. In a further example, a 3 second window of data may still be used in the correlation calculation, and the portions of the window not yet filled with physiological data may be filled with initialization data (e.g., noise). The initialization data may be expected to roughly cancel out. The illustrative techniques may be performed as part of steps 402, 404, 406, 408, any other suitable processing steps of flow diagram 400 or other suitable steps, or any combination thereof. In some embodiments, Initialization may be only used once and the initialization values may work their way out of the buffer as new physiological data is received. In some embodiments, Initialization may be used until sufficient physiological data is received to fill the buffer, and then the algorithm may perform steps 404-426 as needed, without repeating step 402. In some embodiments, Initialization (e.g., step 402 of flow diagram 400 and as described by the illustrative technique of flow diagram 500) may be followed by step 410. In some embodiments, an Initialization Flag may be set to one when sufficient samples of physiological data are not available, indicating that initialization techniques are to used (e.g., as described in the context of flow diagram 500).

Step 502 may include the processing equipment receiving one or more samples of physiological data, derived from a physiological signal. Step 502 may include pre-processing (e.g., using pre-processor 320) the output of a physiological sensor, and then storing a window of the processed data in any suitable memory or buffer (e.g., QSM 72 of system 10), for further processing by the processing equipment. In some embodiments, the window of data may be recalled from data stored in memory (e.g., RAM 54 of FIG. 2 or other suitable memory) for subsequent processing. The number of samples of physiological data received during Initialization may be relatively smaller than the preferred buffer size of physiological data during normal operation.

Step 504 may include processing equipment determining one or more initialization values based on the one or more received samples. Step 506 may include processing equipment generating a window of data that includes the one or more initialization values, the one or more received samples of physiological samples, or any suitable combination thereof. Initialization values may be used to fill the buffer when sufficient physiological data is not available (e.g., allowing a fixed buffer size to be used regardless of the amount of physiological data available). In some embodiments, the one or more initialization values may be generated by adding random values (e.g., noise) to the one or more received samples. For example, if a single sample of physiological data is available, the remaining buffer may be filled with samples generated by adding random values, scaled and shifted according to the received sample. As shown in the following Eq. 15a:

$$[\text{values}] = \text{sample} * (1 + K([\text{RAND}] - 0.5)) \quad (15a)$$

an array of N initialization values [values] may be generated by generating an array of N random numbers [RAND] between zero and one, subtraction 0.5 to set the expected mean to zero, scaling by a factor K (e.g., such as 0.01 or other suitable number), and adding to the received sample. Note that the subtraction of 0.5 may cause some initialization values to be greater than the value of the received sample, and some initialization values to be less than the value of the received sample. In a further example, where multiple samples of physiological data are received, Eq. 15a may be used, with the sample value replaced by an average value (or other suitable representative value derived from the multiple samples), and the factor K replaced with a standard deviation (or other variation metric derived from the multiple samples). In a further example, where multiple samples of physiological data are received, initialization values may be generated using Eq. 15a for each of the received samples, in which the sample value and the factor K are taken from one or more received samples and used to generate one or more initialization values. In some embodiments, the random numbers may be generated in real-time or may be predetermined random numbers to minimize unpredictability. In a further example, the processing equipment may apply Eq. 15b:

$$[\text{values}] = V * (1 + C * N) \quad (15b)$$

to generate one or more initialization values [values] from a value V based on at least one sample (e.g., a sample value, a sample value average), a coefficient C, and a noise value N (e.g., a standard deviation value derived from a physiological signal, a noise metric). Any suitable technique may be used to fill the remaining buffer with determined initialization values based on one or more received samples of physiological data. The portion of the buffer filled with random numbers may roughly cancel or may have a relatively small impact during subsequent correlation calculations.

Step 508 may include the processing equipment proceeding with processing the window of data of step 506. In some embodiments, the window of data of step 506 may be analyzed using any of the techniques of steps 410-426 of flow diagram 400 of FIG. 4. For example, the window of data, which may include one or more initialization values, may be conditioned (e.g., using any suitable Signal Conditioning Technique).

In an illustrative example, the algorithm may require at least a second of physiological data to determine a physiological rate, and accordingly the first second's worth of data may be used to determine how to fill the remaining portion of the buffer with initialization values. Referencing a six second buffer, once the first second of physiological data is obtained during Initialization, the processing equipment may fill the buffer with the one second of physiological data and five seconds of initialization values. For example, one or more suitable properties of the first second of data (e.g., average, standard deviation, maximum, minimum) may be used to determine initialization values for the remaining portion of the buffer. The algorithm may proceed to step 404 (e.g., where the status flags may set to skip step 406), and then to steps 410-426, until another second of physiological data is available. As more physiological data becomes available, it may displace the initialization values from the buffer, until the buffer is filled completely with physiological data and no initialization values. In some embodiments, Initialization is completed after the initialization values are determined based on a first portion of the physiological data. In some embodiments, Initialization continues until the buffer is completed filled with physiological data. For example, the processing equipment may perform steps 404-426 and then obtain additional physiological data and determine updated initialization values based on the additional data. Once the buffer is completely filled with physiological data, the processing equipment may perform steps 404-426 without performing another Initialization at step 402. In any of the embodiments, suitable steps of the algorithm of flow diagram 400 may be performed multiple times during Initialization, until a full window of physiological data is available to fill the buffer. For example, a rate may be calculated at step 422 each second while the buffer is partially filled with initialization values.

In some embodiments, the algorithm may use a relatively smaller buffer during startup. For example, the algorithm may use a buffer size of 4 seconds during startup rather than six seconds. Further, the algorithm may use a template size of 2 seconds to generate an correlation sequence at step 414. In some embodiments, the algorithm may, for example, transition to a six second buffer after the first rate has posted. Some such techniques, described as Fast Start are described below. Fast Start may be used in circumstances where a reduced-size window of data may be available and/or desired. In some embodiments, Fast Start allows system 300 or system 10 to start processing a physiological signal before an entire buffer (e.g., 6 or 7 seconds of data) is obtained. Fast Start may be especially useful during start-up, and/or start of data collection. An entire buffer of data (e.g., 6 seconds in this example, although an entire buffer may be any suitable length), for example, is typically only needed to accurately compute rates down to 20 BPM. Since most rates are 60 BPM or higher, the rate algorithm can begin determining information sooner. Fast start parameters may include buffer sizes of a physiological signal, templates sizes, an increment of increase in buffer size and/or template size, a time and/or available buffer size to end Fast Start, correlation analysis parameters, signal conditioning parameters, qualification parameters, any other suitable parameters, or any combination thereof. For example, the processing equipment may determine a starting buffer and correlation template size (e.g., a two second buffer and a one second template). In a further example, the processing equipment may determine how to increment the buffer and template size as more data is available and/or desired (e.g., increase the buffer size by one second for each calculation with the correlation template being a fixed proportion of the buffer). In a further example, the processing equipment may determine that when a six second buffer of data is available, the rate algorithm may transition out of Fast Start mode and begin normal operation. In a further example, the processing equipment may determine signal conditioning parameters such as curve fit subtraction parameters. In some embodiments, the processing equipment may determine whether to operate in Fast Start mode.

Figures 6, 7:
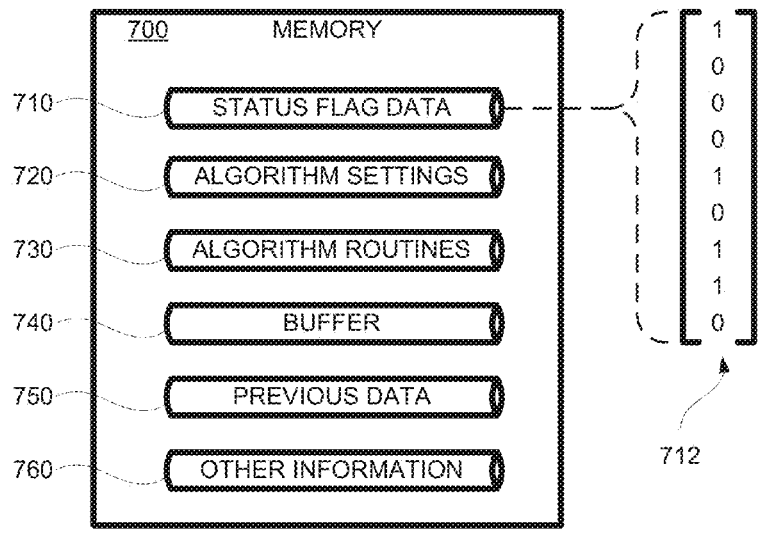
FIG. 6 is a table of illustrative status flags, in accordance with some embodiments of the present disclosure.
FIG. 7 is a block diagram of illustrative memory including rate algorithm information, in accordance with some embodiments of the present disclosure.

FIG. 6 is a table 600 of illustrative status flags, in accordance with some embodiments of the present disclosure. Status flags may include a pulse lost flag, a sensor lost flag, a gain change flag, a no valid saturation flag, an initialization flag, a dropout flag, a mode flag, any other suitable status flag, or any combination thereof. Status flags may assume any suitable indicator value such as, for example, a number (e.g., one or zero, or a positive integer), a letter (e.g., A, B, C), a text string (e.g., "pulse detected" or "pulse not detected"), any other suitable indicator, or any combination thereof. The rate algorithm may use status flags, for example, to aid in determining or otherwise managing algorithm settings. FIG. 7 is a block diagram of illustrative memory 700 including rate algorithm information, in accordance with some embodiments of the present disclosure. Memory 700 may store status flag data 710, algorithm settings 720, algorithm routines 730, buffer 740, physiological data 750, any other suitable information 760, or any combination thereof. In the illustrated embodiment, status flag data 710 includes status flag data structure 712, which includes an array of flag indicators (e.g., numerical values, letters, text strings), although any other suitable data structure, or any combination thereof may be used in accordance with the present disclosure. Any suitable number of status flags may be stored in memory, and accordingly, the processing equipment may update any of the status flags as desired. Algorithm settings 720 may include threshold values, switch settings, parameter values, any other suitable settings, or any combination thereof. Algorithm routines 730 may include sets of computer readable instructions, executable functions, any other computer code, or any combination thereof. Buffer 740 may include a current interval of physiological data from a physiological signal, an interval of sequentially calculated values, any other suitable set or sets of values, or any combination thereof. Previous data 750 may include historical physiological data, historical calculated values, any other suitable information determined or received previously, or any combination thereof. Other information 760 may include references such as look-up tables, databases, any other suitable information that may be used by the rate algorithm, or any combination thereof.

In some embodiments, a Pulse Lost Status Flag and/or Sensor Off Status Flag may be used. If either of these flags are received, the rate algorithm may be stopped (e.g., rate calculation may stop), although data may continue to be added to the buffer, optionally. The algorithm may be restarted when a flag is received indicating that either or both of these flags have been cleared. In some embodiments, the processing equipment may set a Pulse Lost Status Flag based on a calculated rate (e.g., the rate is outside of an expected physiological range), a signal conditioning metric (e.g., a determined noise metric based on the physiological signal), a result of a Qualification test (e.g., a disqualified rate), an output of a separate module configured to detect when the pulse is lost, any other suitable information, or any combination thereof.

In some embodiments, a Gain Change Status Flag may be used. When a gain change occurs, an artifact may be introduced into the physiological signal. The artifact may include, for example, a baseline change, damped oscillations that dissipate out after a few seconds, or other features. For example, during servoing, when LED power and/or amplifier gain settings are adjusted, the physiological signal may exhibit gain changes. The rate algorithm may continue to add the data to the buffer, but not calculate a rate for a predetermined time interval (or corresponding sample interval). For example, the rate algorithm may be paused until the artifact has passed through the buffer (e.g., displaced by physiological data received after the artifact). In a further example, the buffer may be reinitialized once the artifact is over (e.g., using any suitable Initialization Technique), and the baseline has settled. In a further example, the rate algorithm may freeze the buffer until the artifact is over and then continue filling the buffer. To minimize potential discontinuities in the data, the rate algorithm may smooth or filter the signal from before and after the artifact, freeze the buffer for a period of time that is an integer multiple of the period of a previously calculated rate, perform any other suitable processing to minimize the potential discontinuities, or perform any combination thereof.

In some embodiments, a No Valid Saturation Status Flag may be used. In some circumstances, where an oxygen saturation module is not able to calculate a valid oxygen saturation value, the processing equipment may set the No Valid Saturation Status Flag. In some embodiments, during these flagged conditions, the rate algorithm may continue unaffected. However, the No Valid Saturation Status Flag may indicate that the rate is wrong (e.g., when rate information feeds into a saturation calculation for filtering or any other purpose). In some embodiments, the rate algorithm may be reinitialized (e.g., using any suitable Initialization Technique), or may perform other suitable checks (e.g., using any suitable Qualification Technique) to confirm the correct rate is being calculated. In some embodiments, rate may continue to be calculated during a No Valid Saturation Status Flag, but not posted.

In some embodiments, an Initialization Status Flag may be used. In some embodiments, the processing equipment may set the Initialization Status Flag during startup of the rate algorithm. For example, as the buffer is filled with physiological data, the Initialization Status Flag may be set. In a further example, the processing equipment may set the Initialization Status Flag prior to a rate calculation being performed. In some embodiments, the rate algorithm may set the Initialization Status Flag if the Dropout Status Flag is set. In some embodiments, the rate algorithm may release the Initialization Status Flag when a rate has been calculated, qualified, or both.

In some embodiments, a Dropout Status Flag may be used. In some embodiments, the processing equipment may set the Dropout Status Flag when one or more calculated rates are disqualified. The rate algorithm may use the Dropout Status Flag, for example, to prevent locking on to noise in the physiological signal. When the Dropout Status Flag is set, the rate algorithm may clear all buffers and settings, and transition to a particular Mode.

In some embodiments, a Mode Status Flag may be used. In some embodiments, the processing equipment may set the Mode Status Flag depending upon which mode the rate algorithm is currently operating in, or is to operate in. The rate algorithm may, for example, change the Mode Status Flag value based on any other suitable flag value, based on whether a calculated rate is qualified or disqualified, based on a history of qualifications or disqualifications, based on predetermined time intervals, based on any other suitable criterion, or based on any combination thereof.

Figure 8:
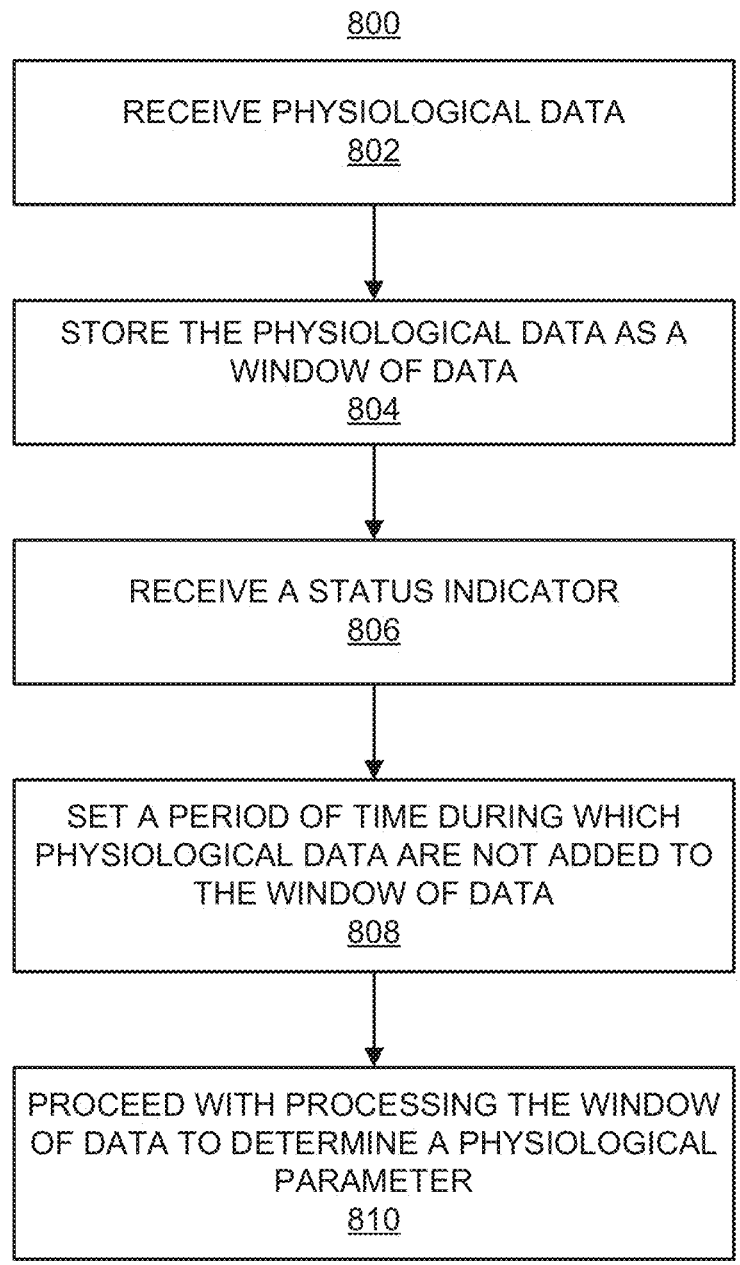
FIG. 8 is a flow diagram of illustrative steps for managing a status indicator, in accordance with some embodiments of the present disclosure.

FIG. 8 is a flow diagram 800 of illustrative steps for managing a status indicator, in accordance with some embodiments of the present disclosure.

Step 802 may include the processing equipment receiving physiological data, derived from a physiological signal. Step 802 may include pre-processing (e.g., using pre-processor 320) the output of a physiological sensor, and then, at step 804, storing a window of the physiological data in any suitable memory or buffer (e.g., QSM 72 of system 10), for further processing by the processing equipment. In some embodiments, the window of data may be recalled from data stored in memory (e.g., RAM 54 of FIG. 2 or other suitable memory) for subsequent processing.

Step 806 may include the processing equipment receiving or generating a status indicator. In some embodiments, for example, the status indicator may be a gain change indicator or Gain Change flag, set based on hardware gain changes. For example, a gain change indicator may be set by the processing equipment based on a controlled change in amplification (e.g., switching from 1× gain to 4× gain) of the photodetector signal, a change in LED power (e.g., an increase or decrease in supplied current to a RED and/or IR LED), or both. In some embodiments, the status indicator may be a Pulse Lost or Sensor Off status indicator. For example, if a PPG sensor becomes unplugged or otherwise inoperative, a Sensor Off status indicator may be set. The status indicator may include any suitable numerical value, letter, text string, symbol, or any combination thereof.

Step 808 may include the processing equipment setting a period of time during which physiological data are not added to the window of data. In some embodiments, physiological data may be added to the window of data, but rate is not calculated for a predetermined time interval (e.g., number of seconds, number of samples). For example, in response to a status indicator, the processing equipment may cease from rate calculation for a time interval equal to or greater than the length of the buffer, to allow any large signal changes to substantially pass through the buffer. In some embodiments, the buffer may be re-initialized after a status indicator (e.g., an initialization flag is activated), and the algorithm may proceed with a partial buffer similar to start-up. In some embodiments, the portion of data corresponding to a transient change due to, for example, a gain change or sensor off condition, may be excluded from the window of data. For example, the buffer may be frozen (i.e., no new data is added) until the transient change artifact has passed, and the physiological data before and after the artifact may be joined (e.g., concatenated). Smoothing or other suitable processing techniques may be applied in some such instances.

Step 810 may include the processing equipment proceeding with processing the window of data of step 804 to determine a physiological parameter. In some embodiments, after the status indicator has been received and the processing equipment has omitted physiological data corresponding to the gain change artifact, the processing equipment may perform a Rate Calculation.

Figure 9:
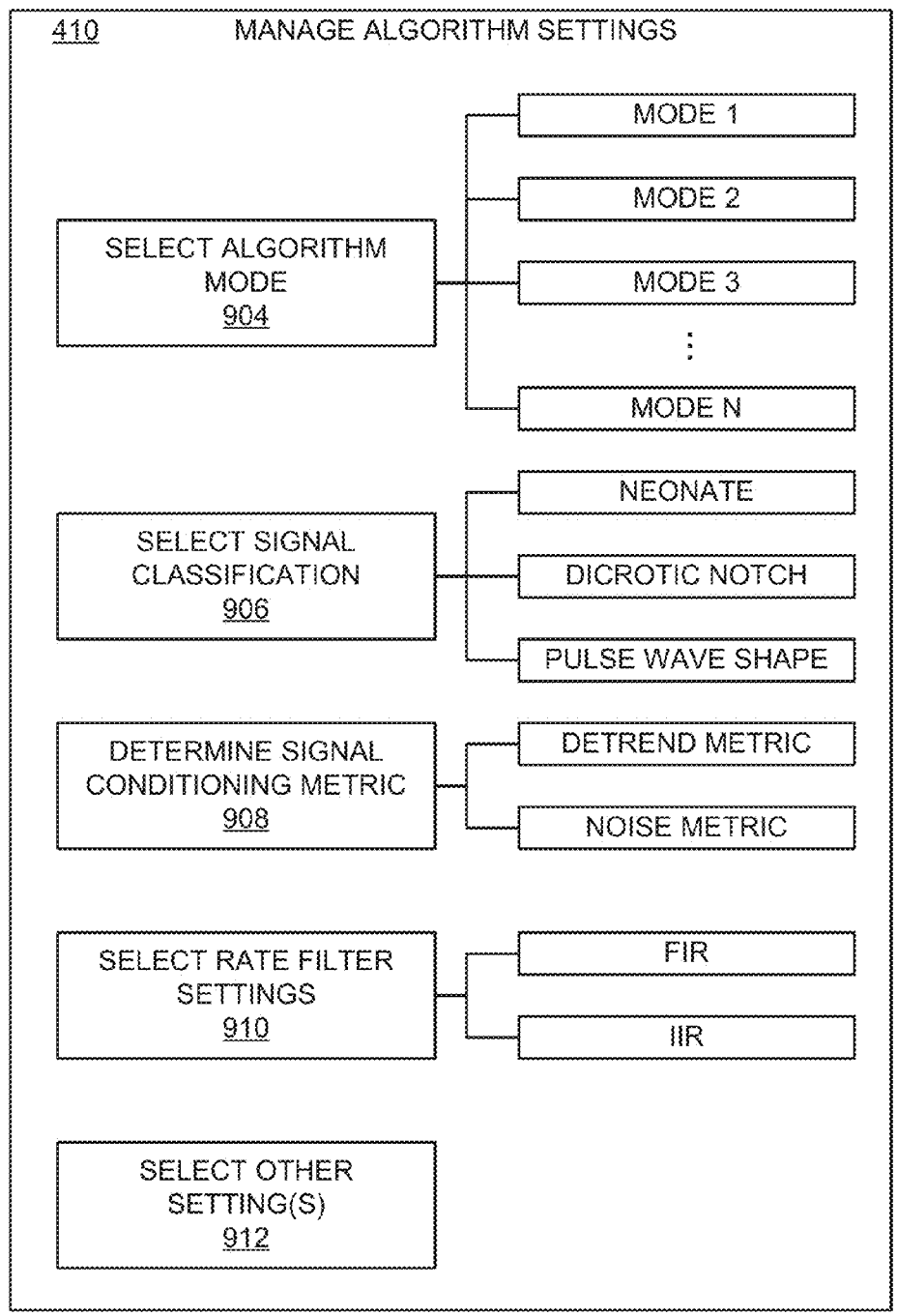
FIG. 9 is a block diagram of illustrative techniques for managing algorithm settings, in accordance with some embodiments of the present disclosure.

FIG. 9 is a block diagram of illustrative techniques for managing algorithm settings, in accordance with some embodiments of the present disclosure. The techniques may be implemented as part of manage algorithm settings step 410 of FIG. 4. The techniques may include selecting an algorithm mode 904, selecting a signal classification 906, determining a signal conditioning metric 908, selecting rate filter settings 910, selecting other settings 912, or any combination thereof. Selecting an algorithm mode 904 may include selecting the mode from multiple modes based on one or more status flags, or other information. For example, upon startup, the processing equipment may select Mode 1. After one or more lags have been qualified, the processing equipment may select Mode 2. If, for example, the rate algorithm wants to turn on a bandpass filter, which may be indicative of higher confidence in the rate calculation, the processing equipment may transition to Mode 3. This is merely illustrative. Any suitable number of modes and mode transitions may be used. Selecting a signal classification 906 may include selecting a signal classification from multiple classifications. For example, classifications may be based on subject age (e.g., neonate, adult), presence of a dicrotic notch, pulse wave shape, any other suitable classifications, or any combination thereof. The signal classification may be selected based on user input, one or more determined metrics, any other suitable information, or any combination thereof. Determining a signal conditioning metric 908 may include determining a de-trend metric, a noise metric, any other suitable signal metric, or any combination thereof. In some embodiments, the processing equipment may determine a signal conditioning metric to apply de-trending, reduce noise, reduce artifacts, reject a window of data, or other signal conditioning function. Selecting rate filter settings 910 may include selecting a type of rate filter, a filter parameter or coefficient value, any other rate filter type or rate filter setting, or any combination thereof. For example, the processing equipment may select a low pass filter, a high pass filter, a band pass filter, a finite impulse response (FIR) filter, an infinite impulse response (IIR filter), any other suitable filter type, or any combination thereof. Further, the processing equipment may select the amount of filtering that may be applied to physiological data. For example, the processing equipment may select a FIR filter to filter the posted rate value, and a corresponding set of filter coefficients (e.g., to weight the previous input values for generating an output value). Selecting other settings 912 may include selecting threshold values, count threshold values (e.g., for activating a Dropout status flag), posting settings (e.g., whether to post rate values or not), qualification tests, any other suitable settings, or any combination thereof.

Figure 10:
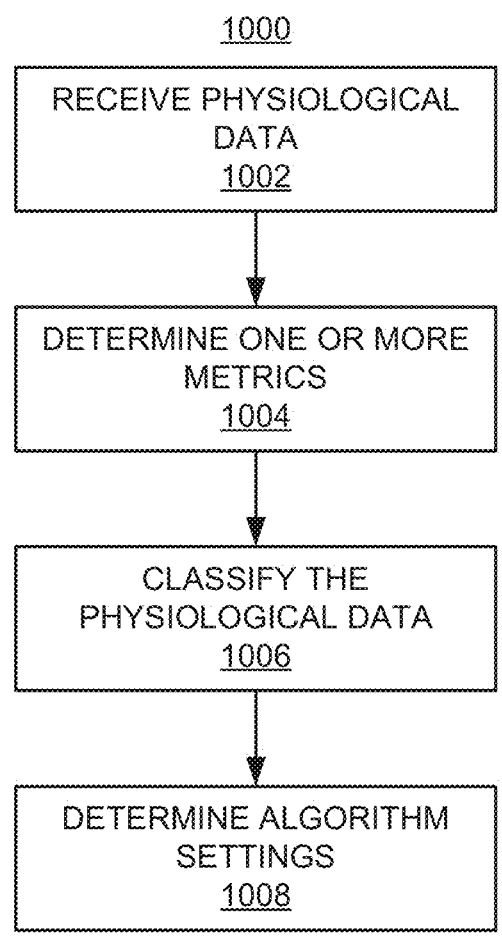
FIG. 10 is a flow diagram of illustrative steps for managing algorithm settings using a classification, in accordance with some embodiments of the present disclosure.

FIG. 10 is a flow diagram 1000 of illustrative steps for managing algorithm settings using a classification, in accordance with some embodiments of the present disclosure. Classification of physiological data may aid in determining algorithm settings and/or calculating a rate, by further directing the analysis of the physiological data. For example, filter settings and amount of filtering, expected pulse rate range, subject classification (e.g., neonate or adult), the presence of a dicrotic notch, pulse shape (e.g., skew), and/or any other suitable classification may be used to determine the type of analysis to perform on physiological data from a physiological signal.

Step 1002 may include the processing equipment receiving physiological data, derived from a physiological signal. Step 1002 may include pre-processing (e.g., using pre-processor 320) the output of a physiological sensor, and then storing a window of the physiological data in any suitable memory or buffer (e.g., QSM 72 of system 10), for further processing by the processing equipment. In some embodiments, the window of data may be recalled from data stored in memory (e.g., RAM 54 of FIG. 2 or other suitable memory) for subsequent processing. For example, referring to system 300 of FIG. 3, the processing equipment may receive a physiological signal from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., memory of system 10 of FIGS. 1-2) after being pre-processed by pre-processor 320. In such cases, step 1002 may include recalling the signals from the memory for further processing.

The physiological signal of step 1002 may include a PPG signal, which may include a sequence of pulse waves and may exhibit motion artifacts, noise from ambient light, electronic noise, system noise, any other suitable signal component, or any combination thereof. Step 1002 may include receiving a particular time interval or corresponding number of samples of the physiological signal. In some embodiments, step 1002 may include receiving a digitized, sampled, and pre-processed physiological signal.

Step 1004 may include the processing equipment determining one or more metrics based on the physiological data of step 1002. The one or more metrics may include de-trend metrics, noise metrics, any other suitable metrics, or any combination thereof. For example, any of the metrics described in the context of FIGS. 11-41 may be determined at step 1004.

Step 1006 may include the processing equipment classifying the physiological data of step 1002 based on the one or more metrics of step 1004. The processing equipment may perform the classification using any suitable set of classes, which may be based on signal quality, signal properties, subject properties, any other suitable types of classes having any suitable number of classes, or combination thereof. Illustrative classifications may include, for example, subject age (e.g., neonate/child/adult), high/low motion artifact (e.g., motion of a subjects limbs), dicrotic notch/no dicrotic notch, high/low pulse skewness, likely pulse rate range, signal noisiness, any other suitable classification having any suitable number of classes, or any combination thereof. In some embodiments, step 1006 may include the processing equipment receiving user input (e.g., to user inputs 56 of system 10). For example, a user may indicate that the received physiological data is from a neonate, does not have a dicrotic notch, and/or likely includes a pulse rate in a particular range. In a further example, the skewness S of n samples (e.g., corresponding to one or more pulse waves) may be determined using Eq. 16:

$$S = \frac{\frac{1}{n}\left(\sum_{i=1}^{n}(x_i - \bar{\mu})^3\right)}{\left(\frac{1}{n}\left(\sum_{i=1}^{n}(x_i - \bar{\mu})^2\right)\right)^{3/2}} \tag{16}$$

where $\bar{\mu}$ is the sample mean, and $x_i$ is sample i. In some embodiments, in which the processing equipment is unable to classify a physiological signal and/or no user indication is received, the processing equipment need not classify the physiological signal and may proceed using any of the techniques disclosed herein.

Step 1008 may include the processing equipment determining one or more algorithm settings based on the classification of step 1006. In some embodiments, the processing equipment may use the classification to determine which Operating Mode to operate in. For example, if a PPG signal is classified as a neonate PPG signal, the signal may be high passed or band-passed to reduce or eliminate frequencies less than about 85 BPM because neonates typically have rate higher than 100 BPM. In a further example, qualification tests to be performed may be changed, or the thresholds may be changed, based on the classification. For example, if a PPG signal is classified as having a dicrotic notch, additional or relatively more stringent tests may be applied to make sure the dicrotic notch is not causing the rate to be calculated as double the true rate. If double the true rate is detected, then the calculated rate may be halved and provided as an output. In some embodiments, algorithm settings such as, for example, indexes for inputting into a look-up table, filter settings, and/or templates may be determined. In some embodiments, one or more settings of a band pass filter such as, for example, a high and low frequency cutoff value (e.g., a frequency range), a representative frequency value, a set of one or more coefficients, any other suitable parameters, or any combination thereof may be determined. Physiological monitoring system 10 may use determined algorithm settings to improve data processing (e.g., reduce computational requirements, improve accuracy, reduce the effects of noise) to extract physiological information in the presence of noise. This may be accomplished by effectively limiting the bandwidth of data to be analyzed, performing a rough calculation to estimate a physiological rate or pulse, or otherwise mathematically manipulating physiological data. In some embodiments, following a change in classification, the processing equipment may determine that algorithm settings are to be reset. In some embodiments, in which more than two classes exist, the processing equipment may determine whether algorithm settings are to be reset based on the relative change in classification. For example, a physiological signal may be classified by noise level, and the processing equipment may determine whether algorithm settings are to be adjusted depending on the change in noise level. In some embodiments, step 1008 may be independent of the classification of step 1006.

In an illustrative example, a window of physiological data may be classified as having a dicrotic notch. The processing equipment may, accordingly, determine that a calculated value (e.g., a correlation lag value, or value derived thereof) corresponds to a harmonic of the physiological rate. In some such circumstances, the processing equipment may modify the calculated value to obtain the physiological rate when the classification of the physiological data is a dicrotic notch classification. For example, if physiological data is classified as having a dicrotic notch, the processing equipment may determine that one half of the calculated value corresponds to the physiological rate.

Classification of the physiological data may be implemented by the processing equipment with the use of one or more metrics. The metrics and techniques discussed in the context of FIGS. 11-41 may be used to classify physiological data based on a metric value, and set one or more algorithm settings based on the classification. For example, if the rate algorithm determines that the physiological data likely has a dicrotic notch, then the rate algorithm may determine not to apply an FIR filter based on a weighted sum of the data and a difference signal derived thereof (more details of such a filter are provided in the description of FIG. 60). In a further example, if the rate algorithm cannot determine satisfactorily whether the physiological data likely has a dicrotic notch, then the rate algorithm may also determine not to apply an FIR filter based on a weighted sum of the data and a difference signal derived thereof. In a further example, an algorithm setting may affect the amount of filtering that is applied to the physiological data. In some embodiments, particular metrics may be used to perform a particular classification by the rate algorithm. For example, the rate algorithm may use the metrics discussed in the context of FIGS. 13-28 to classify physiological data as having a dicrotic notch or not. In a further example, the rate algorithm may use the metrics discussed in the context of FIGS. 30-41 to classify physiological data based on a determined level of noise. In a further example, the rate algorithm may use the metrics discussed in the context of FIGS. 11-41 to set one or more algorithm settings such qualification tests performed, qualification requirements, filter settings, any other suitable settings, or any combination thereof.

Figure 11:
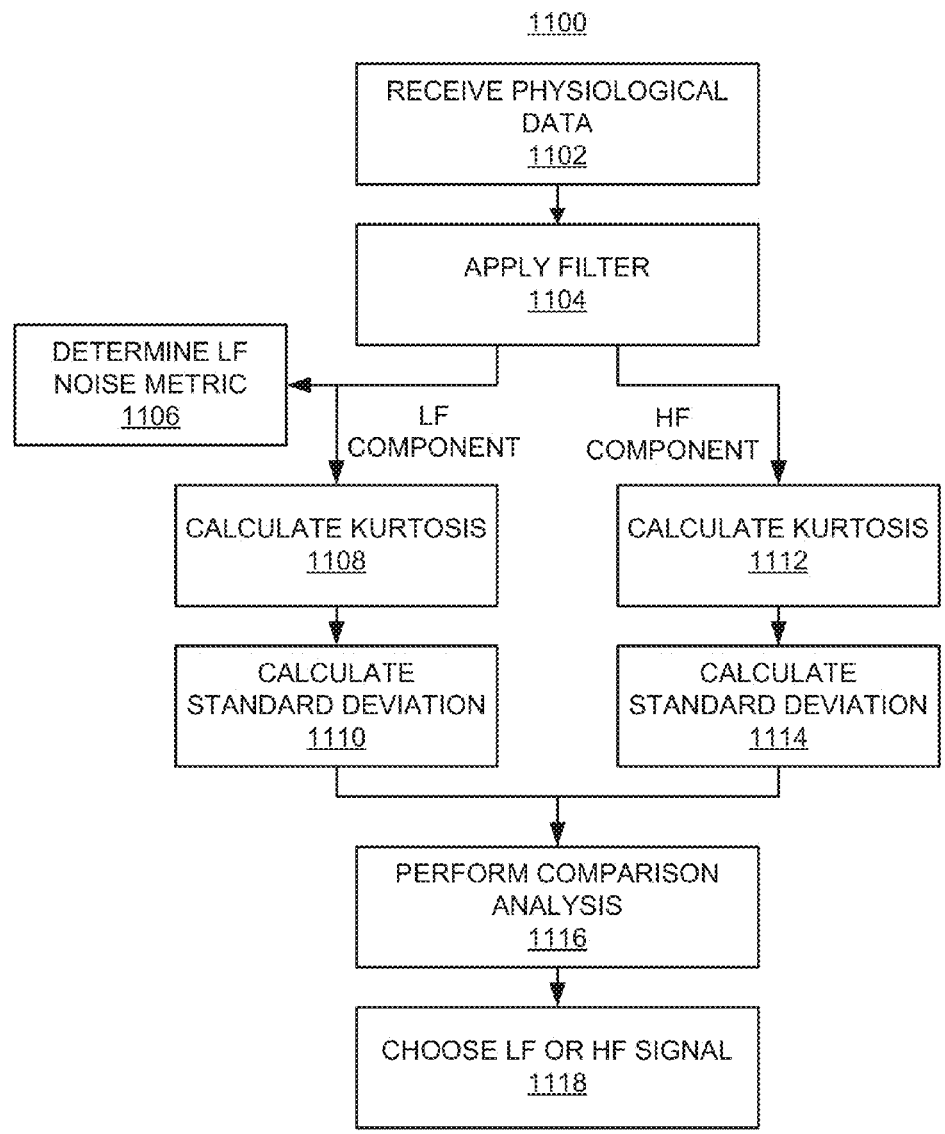
FIG. 11 is a flow diagram of illustrative steps for classifying physiological data, in accordance with some embodiments of the present disclosure.

FIG. 11 is a flow diagram of illustrative steps for classifying physiological data, in accordance with some embodiments of the present disclosure. The steps of illustrative flow diagram 1100 may provide an exemplary embodiment of steps 1004 and 1006 of flow diagram 1000 of FIG. 10. The steps of illustrative flow diagram 1100 may be used by the rate algorithm, for example, to classify the physiological data based on the rate (e.g., low rate, high rate), which may be used to determine one or more algorithm settings (e.g., filter settings, de-trend settings).

Step 1102 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2 or other suitable memory) after being pre-processed by pre-processor 320. In such cases, step 1102 may include recalling data from the memory for further processing.

Step 1104 may include the processing equipment applying a filter such as a low-pass filter (LPF) or high-pass filter (HPF) to the received physiological data of step 1102. In some embodiments, applying the filter may include separating the physiological data into a low frequency component and a high frequency component (i.e., relatively higher frequency activity), as shown in FIG. 11. The processing equipment may apply a filter having any suitable spectral character (e.g., the LPF may be a Bessel filter, Chebyshev filter, elliptic filter, Butterworth filter, or other suitable low-pass filter, having any suitable spectral cutoff). For example, the processing equipment may apply a LPF having a 75 BPM cut-off at step 1104 (e.g., which attenuates frequencies greater than approximately 75 BPM). In a further example, the processing equipment may apply a HPF having a 75 BPM cut-off at step 1104 (e.g., which attenuates frequencies less than approximately 75 BPM). The 75 BPM cut-off is exemplary and any other suitable BPM cutoff can be used to separate the window of physiological data into high and low frequency components.

Step 1106 may include the processing equipment determining a noise metric based on the low frequency component outputted at step 1104. In some embodiments, the processing equipment may apply a LPF (separate from the filter of step 1104) to the LF component, and then compare the input and output signals to the second LPF. For example, step 1104 may include applying a LPF with a cutoff of 75 BPM, and step 1106 may include the processing equipment applying a second LPF with a cutoff of 6 BPM. The processing equipment may determine the difference between the input and output of the 6 BPM LPF, and then determine a root mean square value of the difference as the noise metric.

Step 1108 may include the processing equipment calculating a kurtosis (e.g., the fourth standardized moment of a signal or corrected value thereof) of the LF component outputted at step 1104. In some embodiments, for example, the processing equipment may calculate the kurtosis K for n data points using Eq. 17:

$$K = \frac{\frac{1}{n}\left(\sum_{i=1}^{n}(x_i - \overline{\mu})^4\right)}{\left(\frac{1}{n}\left(\sum_{i=1}^{n}(x_i - \overline{\mu})^2\right)\right)^2} - 3 \qquad (17)$$

where $\overline{\mu}$ is the sample mean, and $x_i$ is sample i. The kurtosis may provide an indication of a relative measure of sharpness of a distribution (e.g., high kurtosis indicates a relatively sharp peak and relatively large tails).

Step 1110 may include the processing equipment calculating a standard deviation of the LF component outputted at step 1104. In some embodiments, the processing equipment may calculate the standard deviation σ for n data points using Eq. 18:

$$\sigma = \sqrt{\frac{1}{n}\left(\sum_{i=1}^{n}(x_i - \overline{\mu})^2\right)} \qquad (18)$$

where $\overline{\mu}$ is the sample mean, and $x_i$ is sample i. The standard deviation may provide an indication of sample variability about a mean value.

Step 1112 may include the processing equipment calculating a kurtosis of the HF component outputted at step 1104. In some embodiments, the processing equipment may calculate the kurtosis K for n data points using Eq. 17, in which the samples and mean are based on the HF component. Step 1114 may include the processing equipment calculating a standard deviation of the HF component outputted at step 1104. In some embodiments, the processing equipment may calculate the standard deviation σ for n data points using Eq. 18, in which the samples and mean are based on the HF component.

It will be understood that steps 1106, 1108, 1110, 1112, and 1114 may be performed in any suitable order between steps 1104 and 1116.

Step 1116 may include the processing equipment performing comparison analysis between the LF component and the HF component outputted at step 1104. In some embodiments, step 1116 may include the processing equipment comparing one or more signal metrics from the LF component and HF component outputted at step 1104. In some embodiments, at step 1116, the processing equipment may compare the kurtosis (e.g., from steps 1108 and 1112), standard deviation (e.g., from steps 1110 and 1114), any other suitable metric, or any combination thereof. For example, the processing equipment may determine which of the LF component and the HF component has a larger kurtosis, standard deviation, and/or other metric value. In some embodiments, step 1116 may include the processing equipment performing independent component analysis (ICA) using the LF component, the HF component, the physiological data of step 1102, or any combination thereof. For example, ICA analysis may be used to separate the component of physiological data associated with a physiological rate from noise components or other undesired component of the data.

Step 1118 may include the processing equipment selecting either the LF component or the HF component outputted at step 1104. In some embodiments, the processing equipment may select one component and disregard the other, non-selected component. For example, the processing equipment may determine at step 1116 that the LF component has a higher kurtosis and/or standard deviation than the HF component, and accordingly may select the LF component for further processing by the rate algorithm.

Figure 12:
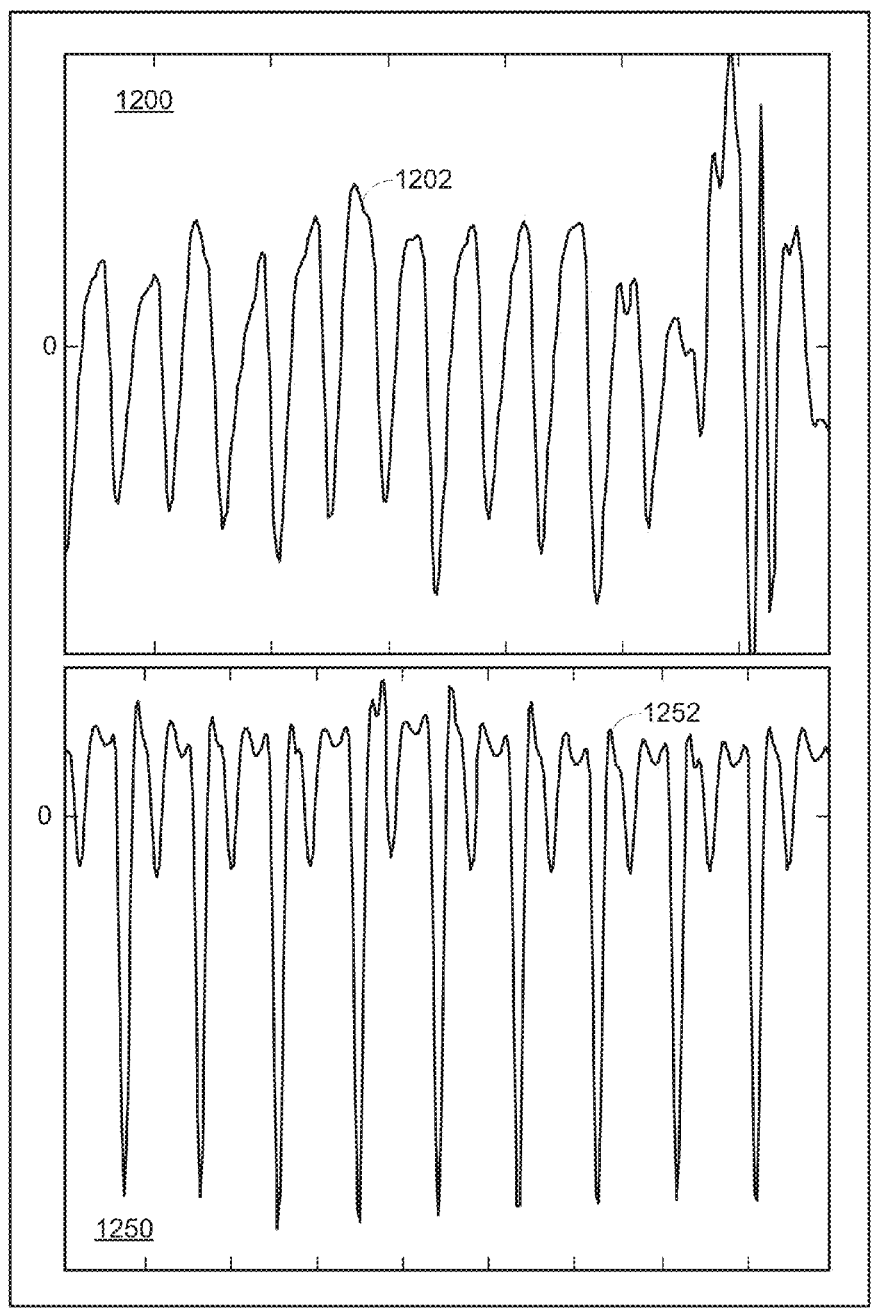
FIG. 12 is a panel showing two plots of illustrative physiological signals, one of which exhibits a dicrotic notch, in accordance with some embodiments of the present disclosure.

FIG. 12 is a panel showing two plots of illustrative physiological signals, one of which exhibits a dicrotic notch, in accordance with some embodiments of the present disclosure. Plots 1200 and 1250 show respective difference signals 1202 and 1252 (e.g., differences or derivatives of adjacent samples suitably scaled) derived from respective PPG signals (not shown, but detected as transmitted light so absorption peak upstroke is negative). Note that the difference signal 1202 is derived from a PPG signal of a neonate and exhibits no dicrotic notch, while difference signal 1252 is derived from a PPG signal of an adult and exhibits a dicrotic notch. Difference signal 1202 exhibits a series of peak/troughs of relatively similar size and shape, while difference signal 1252 exhibits a series of peak/troughs of alternating size and shape. The presence of the dicrotic notch in the PPG signal associated with difference signal 1252 causes a large negative trough associated with the absorption upstroke, and a smaller negative trough associated with the upstroke immediately following the dicrotic notch. The metrics discussed in the context of FIGS. 13-28 may be used to quantify the differences between difference signals such as 1202 and 1252, and accordingly classify physiological data. Accordingly, the processing equipment may use one or more metrics to distinguish physiological data having a dicrotic notch from physiological data that is either from a neonate or otherwise exhibits no dicrotic notch. In some embodiments, the classification of whether physiological data has a dicrotic notch may be used to determine the type of de-trending applied to the physiological data and the metrics may be referred to as de-trending metrics.

In some embodiments, one or more metrics may be used to determine one or more algorithm settings. In some embodiments, de-trending metrics may be used to classify physiological data. For example, a de-trending metric may be sensitive to the presence of a dicrotic notch in physiological data, and the value of the de-trending metric may be used to classify the physiological data. In some embodiments, a difference signal such as, for example, a first derivative signal may be generated from physiological data. In some embodiments, the difference signal may be sorted, and characteristics of the sorted difference signal may be analyzed.

Figure 13:
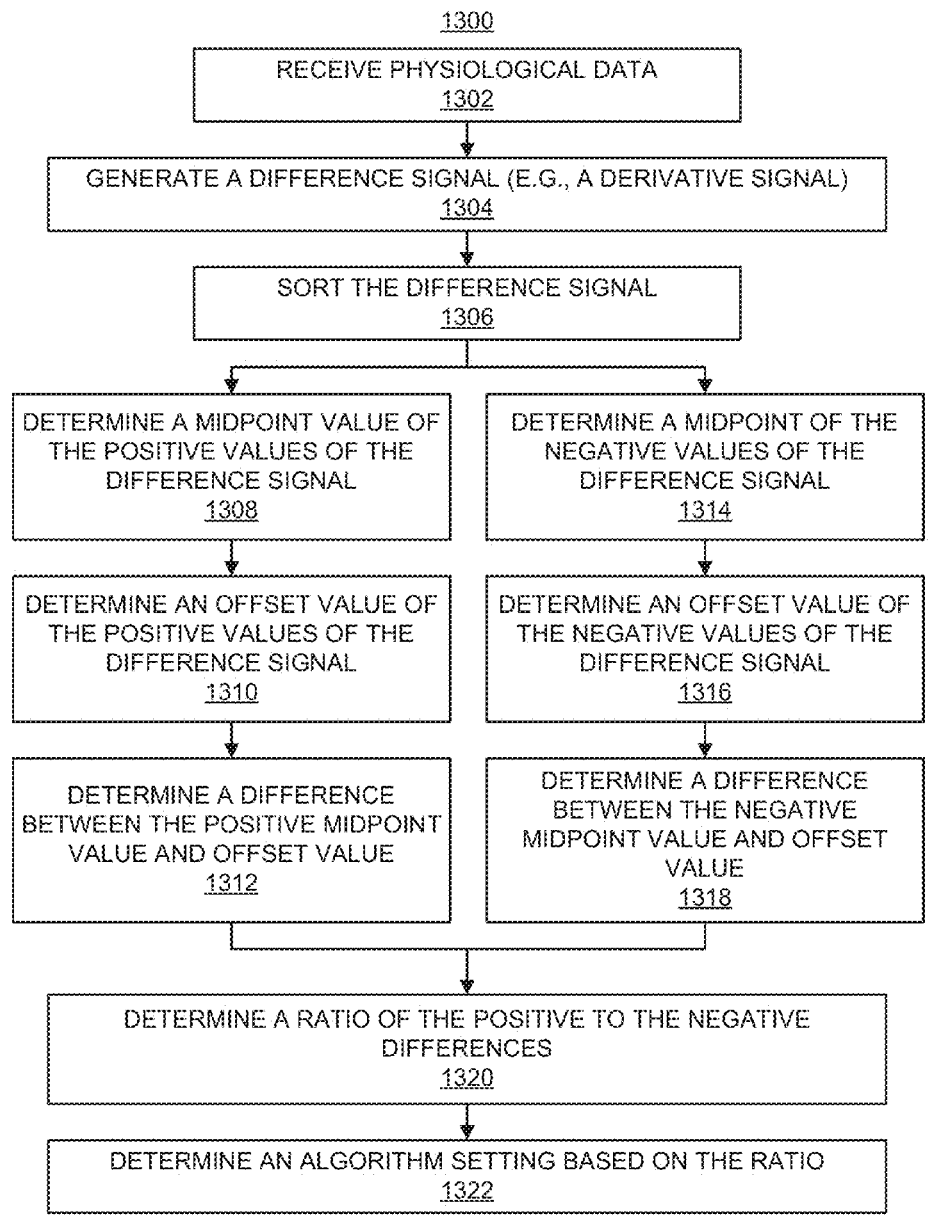
FIG. 13 is a flow diagram of illustrative steps for determining an algorithm setting based on an offset of positive and negative values of a difference signal, in accordance with some embodiments of the present disclosure.
Figure 14:
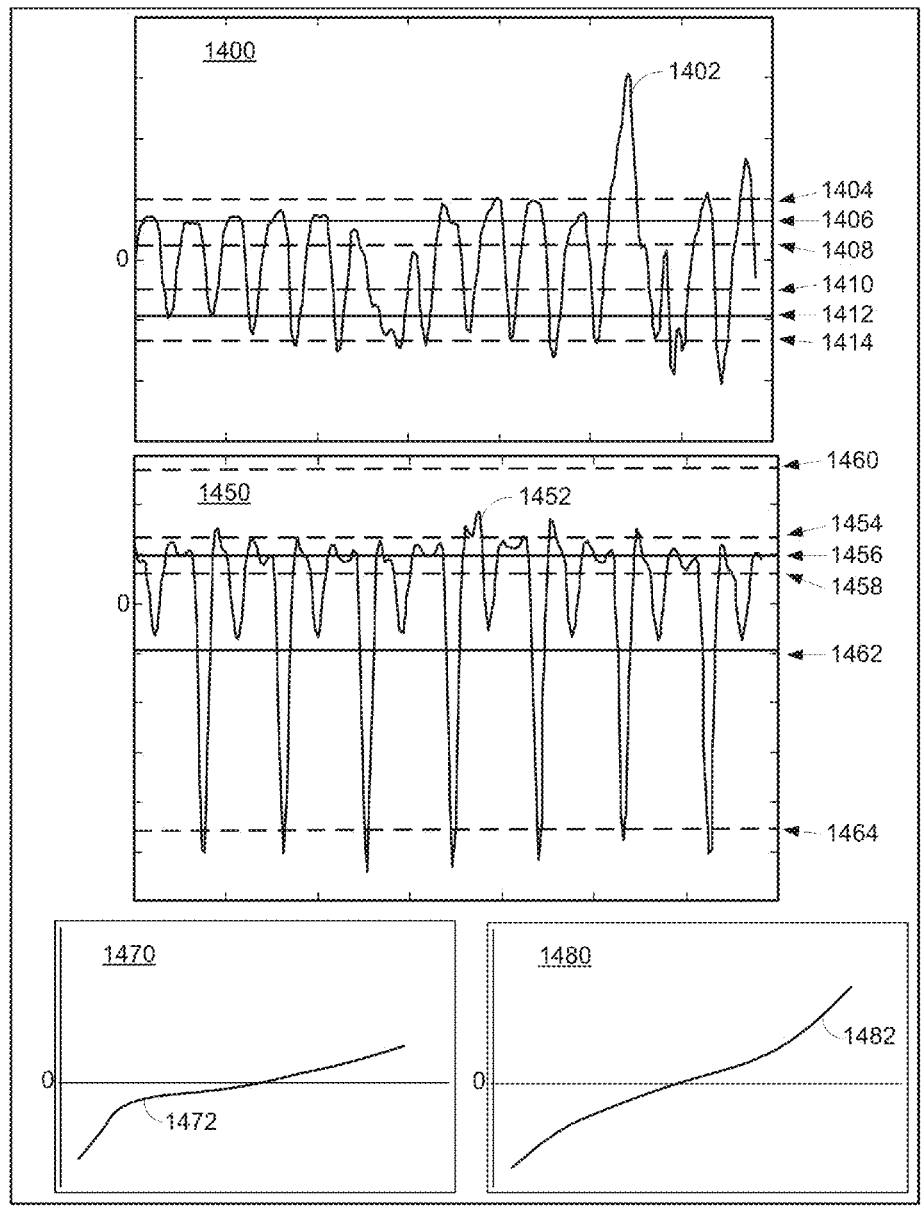
FIG. 14 is a panel showing two illustrative difference signals derived from physiological signals, one of which exhibits a dicrotic notch, along with sorted positive and negative values, in accordance with some embodiments of the present disclosure.

FIG. 13 is a flow diagram 1300 of illustrative steps for determining an algorithm setting based on an offset of positive and negative difference values, in accordance with some embodiments of the present disclosure. FIG. 14 is a panel showing two illustrative difference signals 1402 and 1452 derived from respective physiological signals, one of which exhibits a dicrotic notch, along with sorted positive and negative values 1472 and 1474, in accordance with some embodiments of the present disclosure. FIG. 14 will be referred to below during the discussion of the illustrative steps of flow diagram 1300.

Step 1302 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 1302 may include recalling data from the memory for further processing.

Step 1304 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal.

Step 1306 may include processing equipment sorting the difference values of step 1304. The processing equipment may sort the values in ascending or descending order, either of which causes the negative and positive values to be separated. Referencing sorted values in ascending order, the most negative values come first followed by less negative values, positive values, and finally larger positive values. Accordingly the sorted values can be separated into positive values and negative values, and the two sets of values may be processed separately.

Step 1308 may include processing equipment determining a midpoint value of the positive values of the sorted difference signal. In some embodiments, the processing equipment may determine a median value of the sorted positive values. For example, referencing a vector of 101 sorted positive values, the processing equipment may select the $51^{st}$ data point as the midpoint. For vectors having an even number data points, either of the two middle points may be selected, or a combination (e.g., an average of the two points) may be used.

Step 1310 may include processing equipment determining an offset value of the positive values of the sorted difference signal. In some embodiments, the processing equipment may locate the offset value at a particular relative location in the sorted positive values. For example, the processing equipment may select a data point at a particular location such as 16% from the end of the vector corresponding to the largest positive values. In an illustrative example, referencing a vector of 100 positive values sorted in ascending order, the offset value may be selected as the $84^{th}$ value (e.g., 16% from the end corresponding to the largest values). Any suitable vector location, absolute or relative, may be used to select the offset value, and the 16% value is used merely for illustration.

Step 1312 may include processing equipment determining a difference between the positive midpoint value of step 1308 and the positive offset value of step 1310. In some embodiments, the absolute value of the difference may be determined. Alternatively, instead of or in addition to performing steps 1308-1312, the processing equipment may determine a standard deviation value of the positive values, and use the standard deviation value as the difference value. Any suitable metric may be used to represent the difference in the positive values.

Step 1314 may include processing equipment determining a midpoint value of the negative values of the sorted difference signal. In some embodiments, the processing equipment may determine a median value of the sorted negative values. Step 1316 may include processing equipment determining an offset value of the negative values of the sorted difference signal. In an illustrative example, referencing a vector of 100 negative values sorted in ascending order, the offset value may be selected as the $16^{th}$ value (e.g., 16% from the end corresponding to the most negative values). Any suitable vector location, absolute or relative, may be used to select the offset value, and the 16% value is used merely for illustration. Step 1318 may include processing equipment determining a difference between the negative midpoint value of step 1314 and the negative offset value of step 1316. In some embodiments, the absolute value of the difference may be determined. Alternatively, instead of or in addition to performing steps 1314-1318, the processing equipment may determine a standard deviation value of the negative values, and use the standard deviation value as the difference value. Any suitable metric may be used to represent the difference in the negative values.

Step 1320 may include processing equipment determining a ratio of the positive and negative differences of respective steps 1312 and 1318. In some embodiments, the processing equipment may determine the ratio in a fixed manner such as positive over negative, or negative over positive. In some embodiments, the processing equipment may determine the ratio as the smaller value over the larger value, which normalizes the ratio to between zero and one. In some embodiments, the ratio may be determined as a positive number, and accordingly the processing equipment may determine suitable absolute values.

Step 1322 may include processing equipment determining an algorithm setting based on the determined ratio of step 1320. In some embodiments, the ratio may be compared with a threshold value. For example, referencing a ratio normalized to between zero and one, if the ratio is above 0.75, then the processing equipment may determine that no dicrotic notch is present, and if the ratio is below 0.5, the processing equipment may determine that a dicrotic notch is likely present. Further, if the ratio is between 0.5 and 0.75, the processing equipment can refrain from classifying the data. Alternatively, the processing equipment may use a single threshold rather than two thresholds, and all data may be classified as having a dicrotic notch or not. Accordingly, depending on the comparison of the ratio to the threshold, the processing equipment may classify the physiological data of step 1302, and set one or more algorithm settings. In some embodiments, the processing equipment may bias the classification towards one or the other (e.g., dicrotic notch or no dicrotic notch) depending on what algorithm setting is being set based on the metric. In an illustrative example, if the physiological data is classified as having a dicrotic notch, then the processing equipment may turn off or modify a FIR filter that weights the data and a difference signal derived thereof to prevent a double rate calculation. The presence of a dicrotic notch can cause the difference signal to appear as a double rate condition, with peaks before and after each notch appearing similar to separate pulses.

Referencing FIG. 14, plot 1400 shows difference signal 1402, derived from a PPG signal having no dicrotic notch. Solid line 1406 corresponds to the median for the positive values of difference signal 1402, while dashed lines 1404 and 1408 correspond to a ±1 standard deviation band (based on the positive values). Solid line 1412 corresponds to the median for the negative values of difference signal 1402, while dashed lines 1410 and 1414 correspond to a ±1 standard deviation band (based on the negative values). Note that the ±1 standard deviation bands for the positive and negative values are roughly equal. Plot 1450 shows difference signal 1452, derived from a PPG signal having a dicrotic notch. Solid line 1456 corresponds to the median for the positive values of difference signal 1452, while dashed lines 1454 and 1458 correspond to a ±1 standard deviation band (based on the positive values). Solid line 1462 corresponds the median for the negative values of difference signal 1452, while dashed lines 1460 and 1464 correspond to a ±1 standard deviation band (based on the negative values). Note that the ±1 standard deviation bands for the positive and negative values are significantly different. The difference in positive and negative standard deviation bands for difference signals 1402 and 1452 illustrates some aspects of flow diagram 1300, and the quantification of the difference. For example, the differences between the midpoint value and the offset value in steps 1312 and 1328 may be considered to be a rough approximation of the standard deviation of the positive and negative values. Plot 1400 illustrates that for a PPG signal having no dicrotic notch, the ratio determined in step 1320 may be expected to be close to one (e.g., because the positive and negative standard deviations bands are of similar size). Plot 1450 illustrates that for a PPG signal having a dicrotic notch, the ratio determined in step 1320 may be expected to be significantly less than one (e.g., because the positive and negative standard deviation bands are significantly different).

Plot 1470 shows illustrative sorted difference signal 1472, derived from a difference signal corresponding to physiological data exhibiting a dicrotic notch. Plot 1480 shows illustrative sorted difference signal 1482, derived from a difference signal corresponding to physiological data of a neonate. Differences between the sorted positive and negative values are apparent between difference signals 1472 and 1482. For example, the sorted negative values take different shapes for sorted difference signals 1472 and 1482, due to the presence of the two-tier negative peaks resulting from the dicrotic notch. Sorted difference signal 1472 exhibits a "knee" (e.g., a bend in a curve between regions having two different characteristic slopes) in the negative value portion, indicative of a dicrotic notch. The knee arises from the presence of two sets of troughs, shallow and deep, in a difference signal (e.g., as shown in plot 1450) which give rise to substantially two sets of negative slope values on either side of the knee. Sorted difference signal 1482 does not exhibit a knee in the negative value portion, as there is not expected to be two distinct sets of troughs when no dicrotic notch is present.

Figure 15:
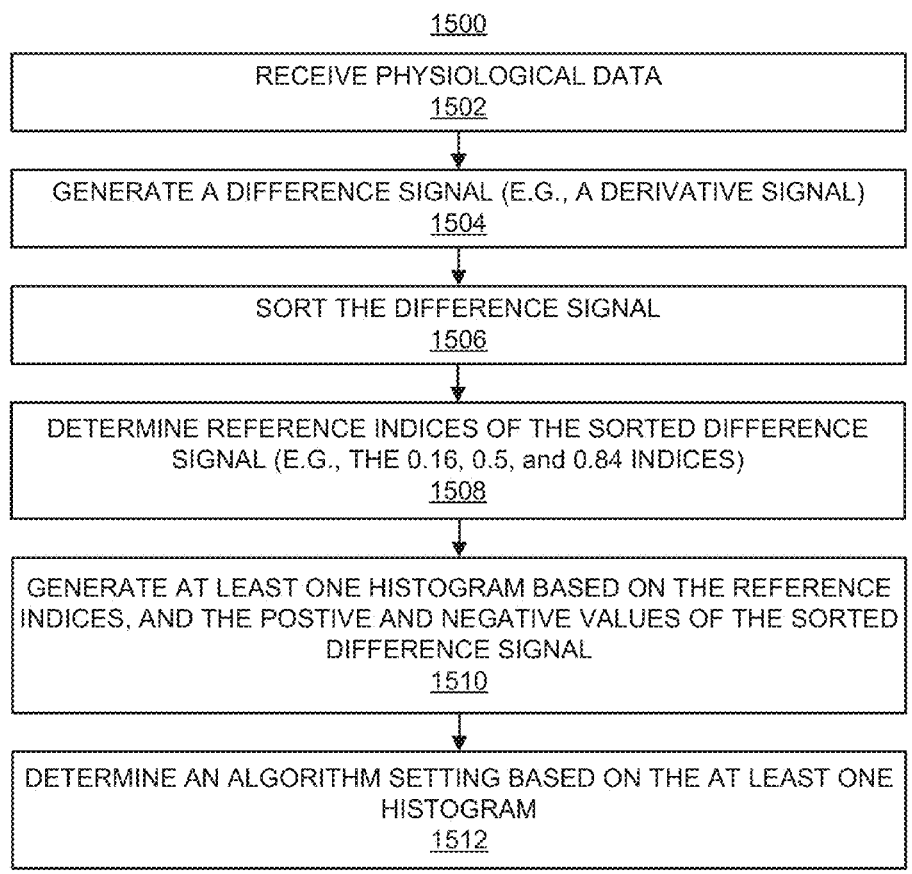
FIG. 15 is a flow diagram of illustrative steps for determining an algorithm setting based on a sorted difference signal, in accordance with some embodiments of the present disclosure.
Figure 16:
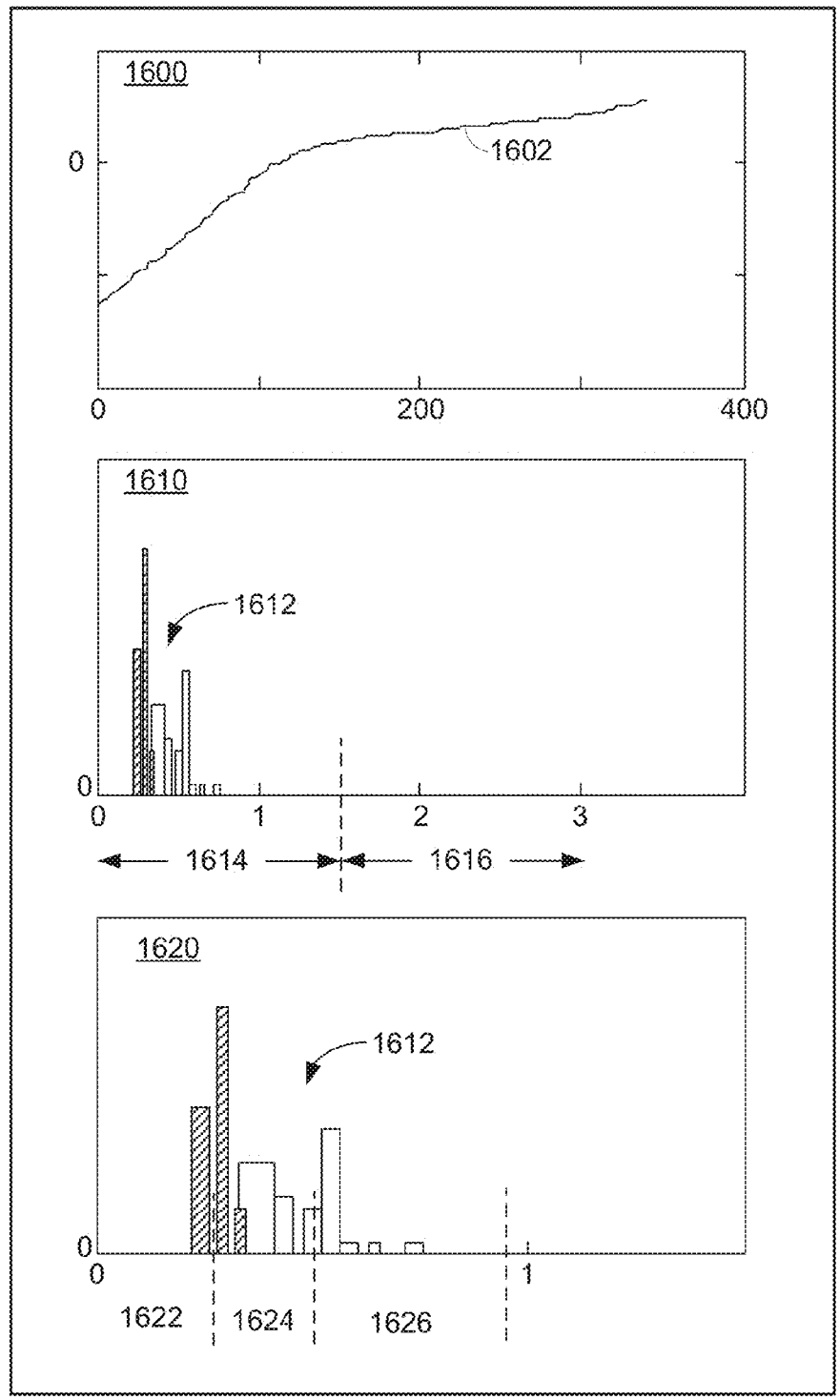
FIG. 16 is a panel showing a sorted difference signal and two histograms, in accordance with some embodiments of the present disclosure.

FIG. 15 is a flow diagram 1500 of illustrative steps for determining an algorithm setting based on a sorted difference signal, in accordance with some embodiments of the present disclosure. FIG. 16 is a panel showing a sorted difference signal and two histograms, in accordance with some embodiments of the present disclosure. FIG. 16 will be referred to below during the discussion of the illustrative steps of flow diagram 1500.

Step 1502 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 1502 may include recalling data from the memory for further processing.

Step 1504 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal.

Step 1506 may include processing equipment sorting the difference values of step 1504. The processing equipment may sort the values in ascending or descending order, either of which causes the negative and positive values to be separated. Referencing sorted values in ascending order, the most negative values come first followed by less negative values, positive values, and finally larger positive values. Accordingly the sorted values can be separated into positive values and negative values, and the two sets of values may be processed separately. Steps 1508-1514 will refer to the "positive values" and the "negative values" of the sorted difference signal separately, although separation of the positive and negative values into separate arrays is not necessarily required. Additionally, the positive values and the negative values will be referred to as vectors (e.g., 1-D collections of values), although any suitable data structure and representation thereof may be used in accordance with the present disclosure. In some embodiments, the negative values may be multiplied by −1, and the resulting values may be re-sorted in ascending order, for example.

Step 1508 may include processing equipment determining a set of reference indices of the sorted difference signal. In some embodiments, the processing equipment may determine a median value of the sorted positive values. For example, referencing a vector of 101 sorted positive values, the processing equipment may select the $51^{st}$ data point at the midpoint. For vectors having an even number data points, either of the two middle points may be selected, or a combination (e.g., an average of the two points) may be used. In some embodiments, the processing equipment may determine an offset value at a particular relative location of a vector of sorted positive values or negative values. For example, for a vector of the positive values, the processing equipment may select a data point at a particular location such as 16% from the end (i.e., index 1) of the vector corresponding to the largest positive values. In an illustrative example, referencing a vector of 100 positive values sorted in ascending order, the offset value may be selected as the $84^{th}$ value (e.g., 16% from the end corresponding to the largest values at index 100). Any suitable vector location, absolute or relative, may be used to select the offset value, and the 16% value is used merely for illustration. The set of reference indices may include median values, offset values, or any combination thereof.

Step 1510 may include processing equipment generating at least one histogram based on the reference indices and the positive and negative values of the sorted difference signal. In some embodiments, the processing equipment may use the reference indices to identify segments of the positive value vector and the negative value vector from which to generate a histogram. For example, the processing equipment select the segment of the positive value vector between first and second reference indices, and the segment of the negative value vector between the first and second reference indices. The processing equipment may generate a histogram by determining the ratio of each value of positive value vector with the corresponding value (e.g., having the same index) of the negative value vector, to generate a vector of ratio values. The processing equipment may generate a histogram based on the ratio values. In some embodiments, a second histogram may be generated similar to the first histogram, albeit using at least one different index of the reference indices than that used to generate the first histogram. For example, considering the example of the previous paragraph, the processing equipment may select the segment of the positive value vector between second and third reference indices, and the segment of the negative value vector between the second and third reference indices, to generate the second histogram. Any suitable number of segments, and corresponding histograms, may be used in accordance with the present disclosure.

Step 1512 may include processing equipment determining an algorithm setting based on the at least one histogram of step 1510. In some embodiments, for example, the processing equipment may generate two histograms at step 1510, determine the respective maximum values of the two histograms, and determine the algorithm setting based on the maximum values. In an illustrative example, the processing equipment may receive physiological data and generate a sorted difference signal. The processing equipment may partition the sorted difference signal into the set of positive values (e.g., the positive value vector) and the set of negative values (e.g., the negative value vector). The processing equipment may then multiply the negative values by −1, and re-sort, although the set of values will still be referred to here as the "negative values." The processing equipment may then determine reference indices of 16%, 50%, and 84% of the length of the shorter of the two vectors. The processing equipment may then generate a set of ratio values (e.g., a ratio value vector) of the ratio of each positive value to the corresponding (e.g., the $i^{th}$ value of the positive value vector by the $i^{th}$ value of the negative value vector) negative value between the 16% and 50% indices. The processing equipment may then generate a histogram of the ratio values and select the maximum value and the corresponding index (e.g., indexed relative to the segment between the 16% and 50% indices). The processing equipment may then generate a second set of ratio values (e.g., a ratio value vector) of the ratio of each positive value to the corresponding (e.g., the $i^{th}$ value of the positive value vector by the $i^{th}$ value of the negative value vector) negative value between the 50% and 84% indices. The processing equipment may then generate a second histogram of the ratio values and select the maximum value and the corresponding index (e.g., indexed relative to the segment between the 50% and 84% indices). Based on the maximum values, the processing equipment may classify the physiological data of step 1502, set one or more algorithm settings, determine a value indicative of noise, or any combination thereof.

FIG. 16 is a panel showing a sorted difference signal and two histograms, in accordance with some embodiments of the present disclosure. Plot 1600 shows sorted difference signal 1602. Plot 1610 shows a histogram 1612 of values based on sorted difference signal 1602, while plot 1620 shows a magnified view of plot 1610. Based on likely behavior, region 1614 of plot 1610 corresponds to values indicative of a physiological signal, while region 1616 corresponds to values indicative of noise. Accordingly, the rate algorithm may classify the physiological data with respect to noise based on a histogram. For example, if a particular fraction of a histogram lies in region 1616, then the rate algorithm may classify the data as being noisy. Further based on likely behavior, region 1622 of plot 1620 may correspond to values indicative of a physiological signal exhibiting a dicrotic notch and a relatively sharp pulse, while region 1624 may correspond to values indicative of a neonate, and region 1626 may corresponds to values indicative of a distorted signal. Accordingly, the rate algorithm may classify the physiological data with respect to the presence of a dicrotic notch based on a histogram. For example, if a particular fraction of a histogram lies in region 1622 or 1624, then the rate algorithm may classify the data as having a dicrotic notch or arising from a neonate, respectively.

Figure 17:
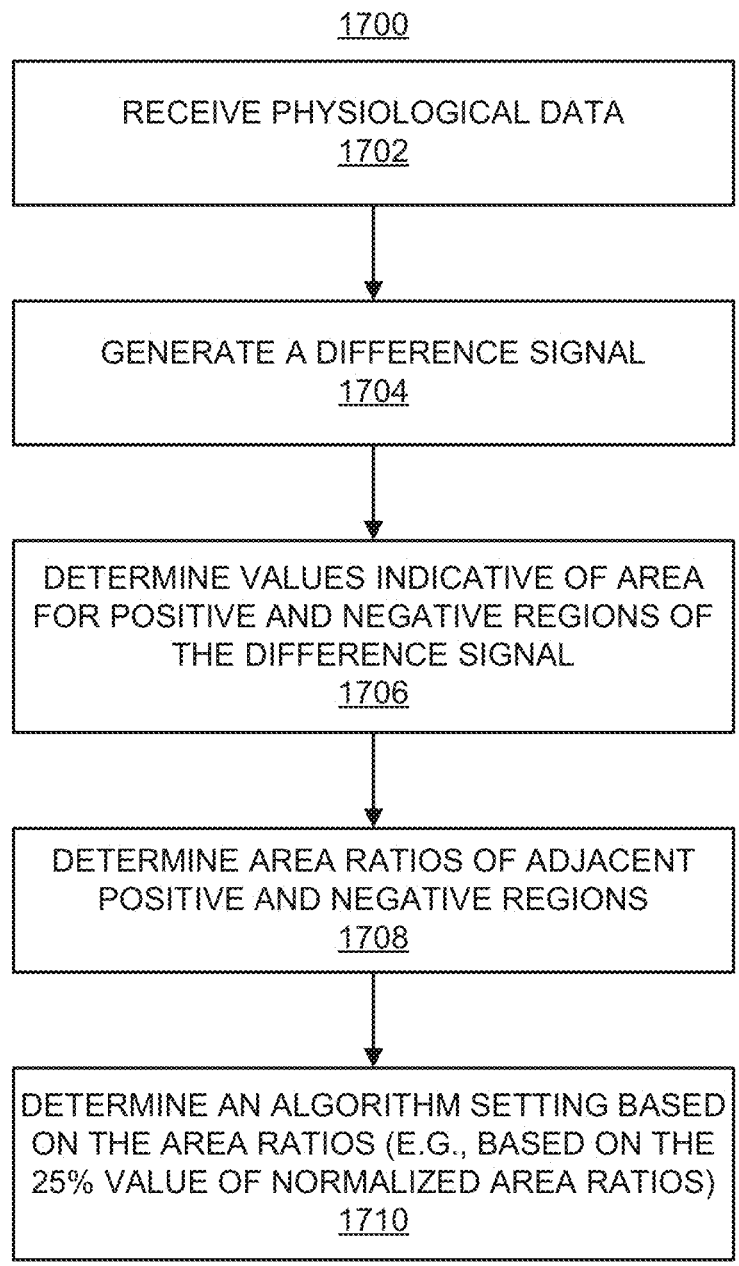
FIG. 17 is a flow diagram of illustrative steps for determining an algorithm setting based on area ratios of positive and negative regions of a difference signal, in accordance with some embodiments of the present disclosure.
Figure 18:
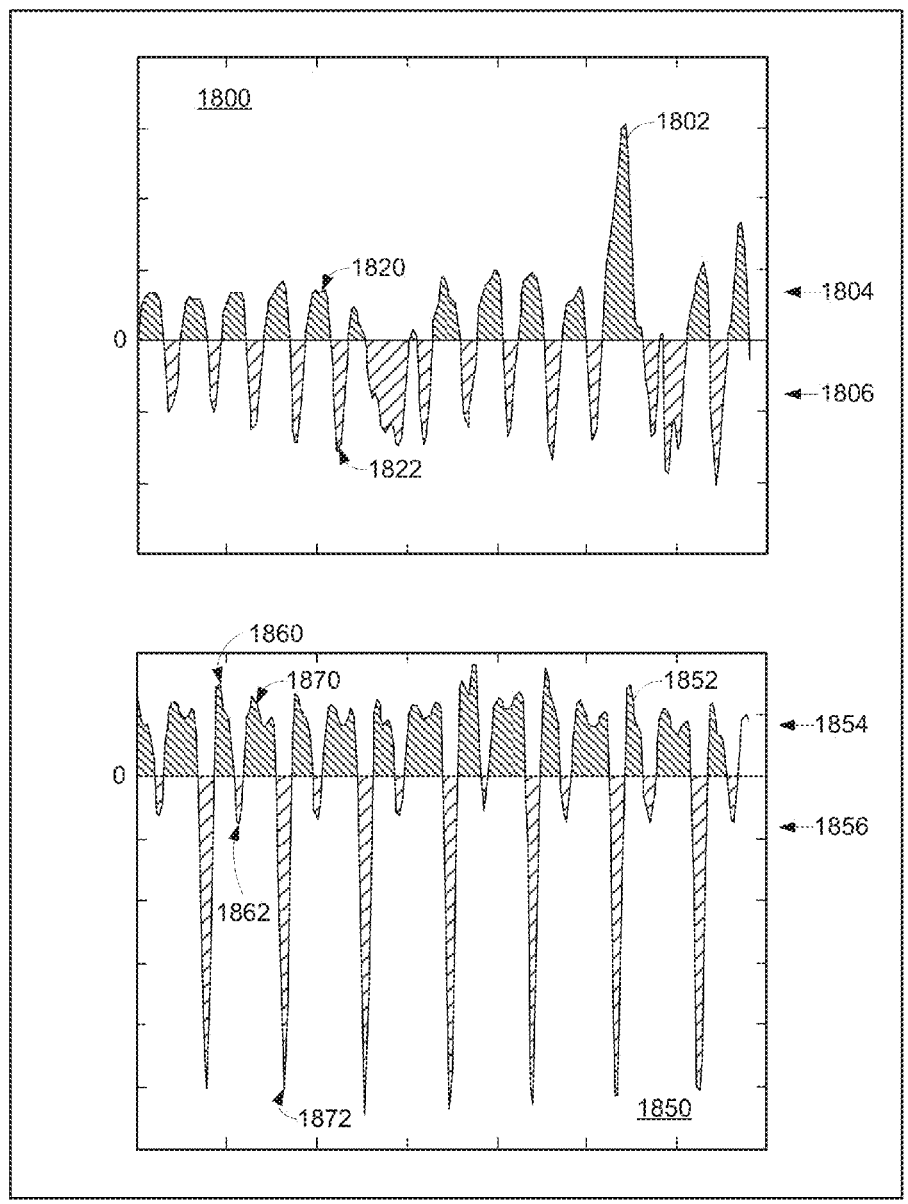
FIG. 18 is a panel showing two illustrative plots of respective difference signals having positive and negative regions, in accordance with some embodiments of the present disclosure.

FIG. 17 is a flow diagram 1700 of illustrative steps for determining an algorithm setting based on area ratios of positive and negative regions of a difference signal, in accordance with some embodiments of the present disclosure. FIG. 18 is a panel showing two illustrative plots 1800 and 1850 of respective difference signals 1802 and 1852 having positive and negative regions, in accordance with some embodiments of the present disclosure. FIG. 18 will be referred to below during the discussion of the illustrative steps of flow diagram 1700.

Step 1702 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 1702 may include recalling data from the memory for further processing.

Step 1704 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal.

Step 1706 may include processing equipment determining values indicative of area for positive and negative regions of the difference signal. The difference signal of 1704 may include a sequence of peaks and troughs corresponding to physiological pulse, along with other components such as noise, and may have exhibit oscillatory character. The peaks may include positive values of the difference signal, while the troughs may include negative values of the difference signal. Accordingly, the peaks (along with the zero line) define a positive region having an area above the ordinate axis, while the troughs (along with the zero line) define a negative region having an area below the ordinate axis. Referencing plot 1800 of FIG. 18, difference signal 1802, derived from a PPG signal exhibiting no dicrotic notch, exhibits a sequence of positive regions 1804 and negative regions 1806. Difference signal 1852 of plot 1850, derived from a PPG signal exhibiting a dicrotic notch, exhibits a sequence of positive regions 1854 and negative regions 1856. Values indicative of area may be determined for each positive and negative region, as indicated by the hatching in FIG. 18. The values indicative of an area of a region may include a numerical integral (e.g., any suitable quadrature such as the Trapezoid rule or Simpson's Rule), analytic integral (e.g., integral of a function fit of a region and the zero line), a summation of values of the region, a rectangular area corresponding to the width and height of each region, any other area metric, or any combination thereof.

Step 1708 may include processing equipment determining area ratios of adjacent positive and negative regions. In some embodiments, the processing equipment may determine an area ratio of each positive region to the immediately following negative region, generating a sequence of ratio values. In some embodiments, the processing equipment may determine an area ratio of each negative region to the immediately following positive region, generating a sequence of ratio values. Any suitable technique may be used to determine area ratios between adjacent positive and negative regions. For example, referencing plot 1800, the ratio of the area of positive region 1820 and the area of negative region 1822 may be determined. It can be seen from plot 1800 that the ratio of areas of positive regions to adjacent negative regions is roughly similar, although some deviation is present. Referencing plot 1850, the ratio of the area of positive region 1860 and the area of negative region 1862 may be determined, and the ratio of the area of positive region 1870 and the area of negative region 1872 may be determined. It can be seen from plot 1850 that the ratio of areas of positive regions to adjacent negative regions will result in a two-tiered set of values, caused by the alternating small and large areas of the negative regions. The output of step 1708 may be a vector of area ratio values derived from the difference signal of step 1704. In some embodiments, the processing equipment may normalize the ratios to span a predetermined range, such 0-1, for example. In some embodiments, the processing equipment may determine the ratio of negative regions to positive regions, in which case the analysis may be altered.

Step 1710 may include processing equipment determining an algorithm setting based on the area ratios of step 1708. In some embodiments, the processing equipment may analyze a sequence of ratio values to determine a metric. For example, the 25% largest value (e.g., larger than about 75% of ratio values and smaller than about 25% of ratio values) of a sequence of ratio values of positive areas to adjacent negative areas may be compared to a threshold. In a further example, the ratio corresponding to the largest 25% of a sequence of ratio values of positive areas to adjacent negative areas may be compared to a threshold value. In a further example, the average of the largest 25% of a sequence of ratio values of positive areas to adjacent negative areas may be compared to a threshold value. The ratio is expected to be near 1 for data not exhibiting dicrotic notches. For data exhibiting dicrotic notches, the ratios may exhibit two tiers due to the two-tiered shaped of troughs in the difference signal. A first tier will be somewhat close to 1, while the second tier will be significantly larger than 1. By picking the 25% value, the processing equipment will likely pick a value in the middle of second tier for dicrotic notches and therefore be high when dicrotic notches are present. However, when dicrotic notches are not present, the selected value is likely close to 1 because the areas ratios are all generally close to 1 (provided noise is sufficiently low). In some embodiments, the processing equipment may normalize the determined ratios, sort the normalized ratios into a sorted array, and select the value at one fourth of the length of the array of sorted ratios. In some embodiments, the processing equipment may compare the 25% value to the 75% value. For data exhibiting a dicrotic notch the 25% and 75% values should each lie in the middle of the two tiers, while for data not exhibiting a dicrotic notch, the values may be expected to be relatively similar.

Figure 19:
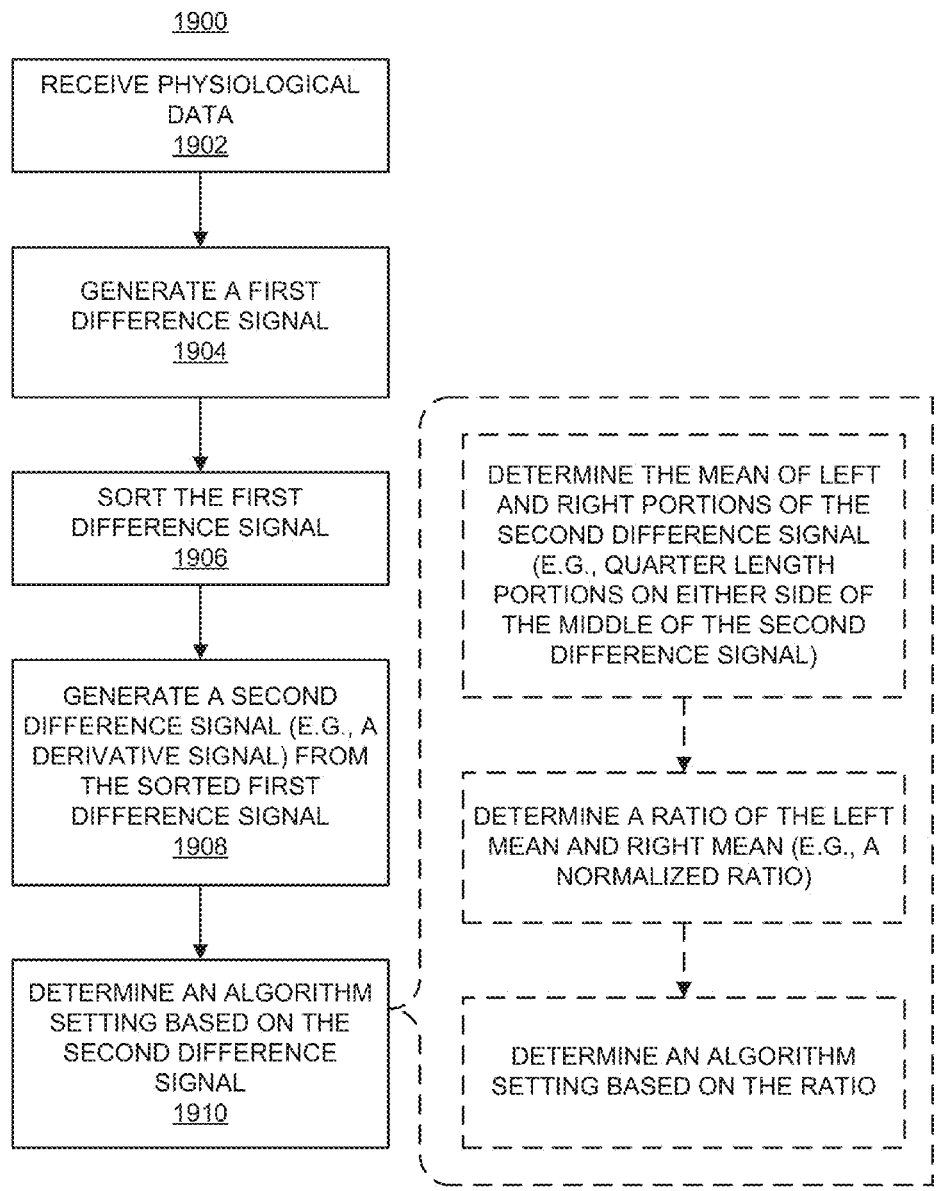
FIG. 19 is a flow diagram of illustrative steps for determining an algorithm setting based on first and second difference signals, in accordance with some embodiments of the present disclosure.
Figure 20:
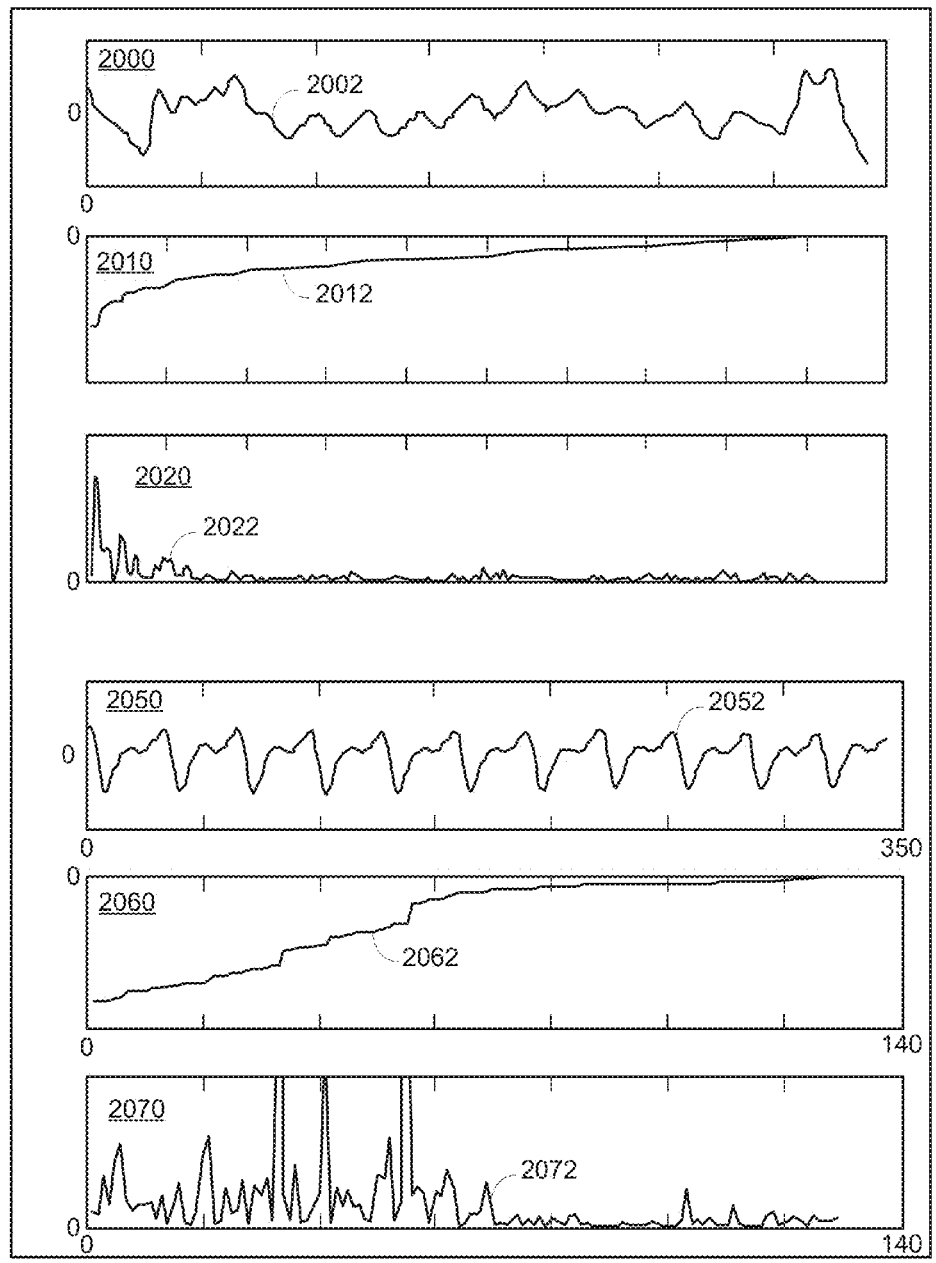
FIG. 20 is a panel showing illustrative PPG signals with and without a dicrotic notch, and corresponding first and second difference signals for each, in accordance with some embodiments of the present disclosure.

FIG. 19 is a flow diagram 1900 of illustrative steps for determining an algorithm setting based on first and second difference signals, in accordance with some embodiments of the present disclosure. FIG. 20 is a panel showing illustrative PPG signals with and without a dicrotic notch, and corresponding first and second difference signals for each, in accordance with some embodiments of the present disclosure. FIG. 20 will be referred to below during the discussion of the illustrative steps of flow diagram 1900.

Step 1902 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 1902 may include recalling data from the memory for further processing.

Step 1904 may include processing equipment generating a first difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a first difference signal. In a further example, the processing equipment may compute a numerical derivative at each point in the data, generating a first difference signal. Any suitable difference technique may be used by the processing equipment to generate the first difference signal.

Step 1906 may include processing equipment sorting the difference values of step 1904. The processing equipment may sort the values in ascending or descending order. Referencing sorted values in ascending order, the most negative values come first followed by less negative values, positive values, and finally larger positive values.

Step 1908 may include processing equipment generating a second difference signal by calculating a sequence of difference values between adjacent samples of the negative values of the sorted first difference signal of step 1906. In some embodiments, the processing equipment may perform a subtraction between values of adjacent data points of the negative values of the sorted first difference signal. In some embodiments, the processing equipment may calculate the differences by calculating a first derivative of the sorted first difference signal. For example, the processing equipment may compute forward differences, backward differences, or central differences between each pair of adjacent points of the sorted first difference signal to generate a second difference signal. In a further example, the processing equipment may compute a numerical derivative at each point of the negative values of the sorted first difference signal, generating a second difference signal. Any suitable difference technique may be used by the processing equipment to generate the second difference signal based on the negative values of the sorted first difference signal of step 1906.

Referencing FIG. 20, plot 2000 shows PPG signal 2002 (taken using an IR LED), which does not exhibit a dicrotic notch. Plot 2010 shows a sorted first difference signal 2012 derived from PPG signal 2002, including only the negative values. Plot 2020 shows a second difference signal 2022 derived from sorted difference signal 2012. Plot 2050 shows PPG signal 2052 (taken using an IR LED), exhibiting a dicrotic notch. Plot 2060 shows a sorted first difference signal 2062 derived from PPG signal 2052, including only the negative values. Plot 2070 shows a second difference signal 2072 derived from sorted difference signal 2062. Sorted first difference signal 2012 exhibits an initially steep slope which levels out relatively quickly. In contrast, sorted first difference signal 2062 exhibits a relatively steadier slope, which levels out relatively later than that of sorted first difference signal 2012. Accordingly, second difference signal 2022 exhibits activity early, which declines relatively quickly, while second difference signal 2072 exhibits activity further along, declining relatively later than second difference signal 2022. The processing equipment may be configured to quantify the behavior of the second difference signal, which may allow the processing equipment to distinguish differences in character between, for example, illustrative second difference signals 2022 and 2072. Quantification of behavior may be used to classify physiological data as having a dicrotic notch or not having a dicrotic notch.

Step 1910 may include processing equipment determining an algorithm setting based on the second difference signal of step 1908. In some embodiments, portions of the second difference may be compared to determine a metric. For example, referencing plot 2020 of FIG. 20, the ratio (or the difference) of the averages of the second and third quartiles of second difference signal 2022 may be determined and compared to a threshold. The ratio of the averages of the second and third quartiles of second difference signal 2022 is likely near one and the difference of the averages of the second and third quartiles of second difference signal 2022 is likely near zero. The processing equipment may compare the ratio to a threshold, compare the difference to a threshold, or both, to classify the data. In some embodiments, the ratio and difference may be combined into a single metric, which may be compared to a threshold. In a further example, referencing plot 2070 of FIG. 20, the ratio (or the difference) of the averages of the second and third quartiles of second difference signal 2072 may be determined and compared to a threshold. The ratio of the averages of the second and third quartiles of second difference signal 2072 is likely not near one (and relatively further from one than the ratio for second difference signal 2022) and the difference of the averages of the second and third quartiles of second difference signal 2072 is likely nonzero (and relatively further from zero than the difference for second difference signal 2022). Accordingly, the processing equipment may detect the presence of a dicrotic notch (and optionally classify the physiological data) using a metric based on the second difference signal.

Figure 21:
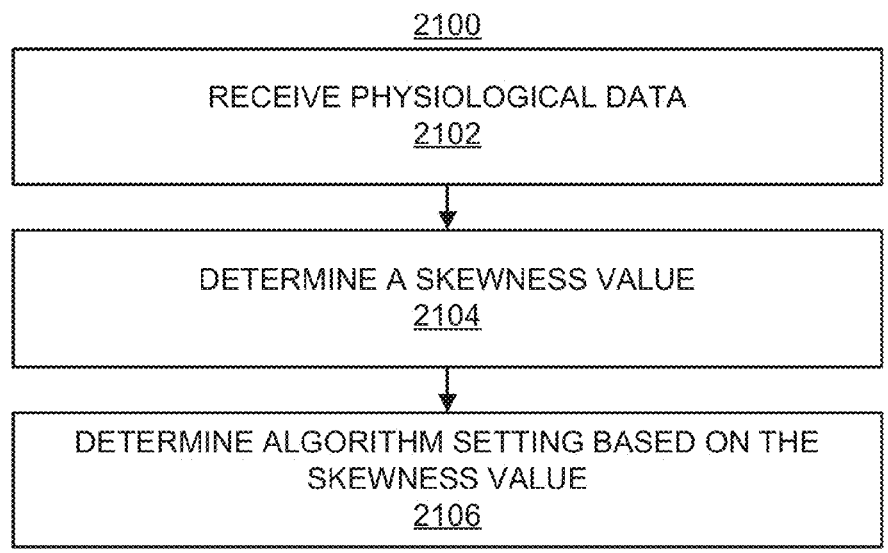
FIG. 21 is a flow diagram of illustrative steps for determining an algorithm setting based on a skewness value of a physiological signal, in accordance with some embodiments of the present disclosure.
Figure 22:
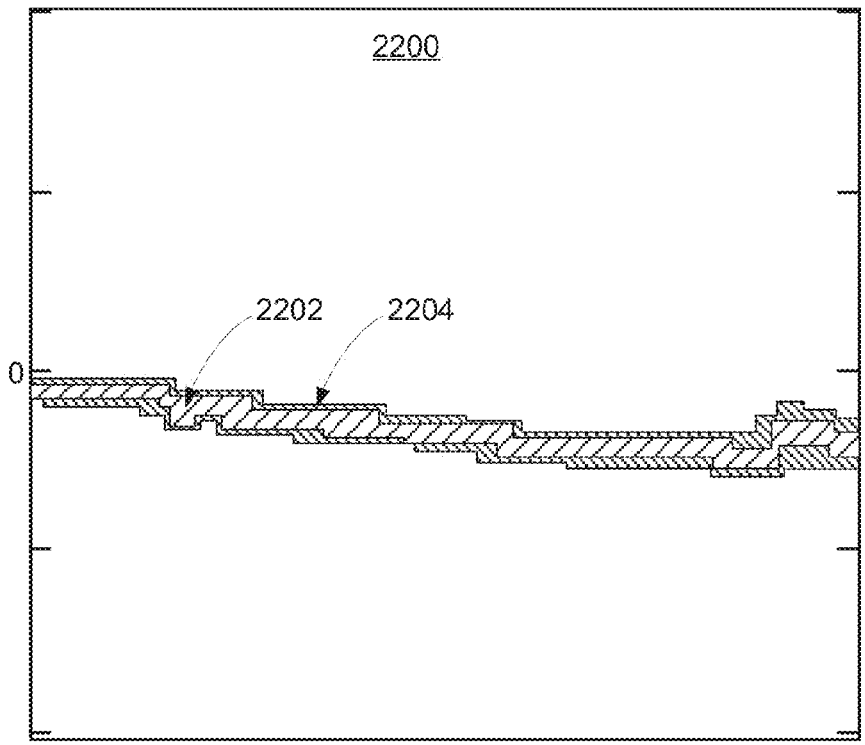
FIG. 22 is a panel showing an illustrative contour plot of instances of skewness value and correlation lag value, in accordance with some embodiments of the present disclosure.

FIG. 21 is a flow diagram 2100 of illustrative steps for determining an algorithm setting based on a skewness value of a physiological signal, in accordance with some embodiments of the present disclosure. FIG. 22 is a panel showing an illustrative contour plot 2200 of instances of skewness value and correlation lag value, in accordance with some embodiments of the present disclosure. FIG. 22 will be referred to below during the discussion of the illustrative steps of flow diagram 2100.

Step 2102 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 2102 may include recalling data from the memory for further processing.

Step 2104 may include processing equipment determining a skewness value based on the received physiological data of step 2102. In some embodiments, the processing equipment may use an expression such as Eq. 16 to determine the skewness value. In some embodiments, the processing equipment may perform one or more signal conditioning operations prior to determining the skewness value. For example, in some embodiments, the processing equipment may subtract the mean value of the physiological data to center the data about zero.

Step 2106 may include processing equipment determining an algorithm setting based on a reference relationship between the determined skewness metric and a value indicative of a physiological rate. In some embodiments, the reference relationship may be represented by a function, a look-up table, a mapping, any other suitable representation, or any combination thereof. For example, the processing equipment may determine whether to apply a FIR filter to the physiological data based on the skew metric. In a further example, the processing equipment may determine an amount of filtering to apply to the physiological data based on the skew metric.

FIG. 22 is a panel showing an illustrative contour plot 2200 of instances of skewness value and correlation lag value, in accordance with some embodiments of the present disclosure. The abscissa of plot 2200 represents the correlation lag values, and the ordinate represents the values indicative of skewness in arbitrary units. Region 2202 corresponds to relatively higher number instances, while region 2204 corresponds to an intermediate number of instances, while the remaining two-dimensional space of plot 2200 corresponds to relatively lower number of instances. Regions 2202 and 2204 show that as lag value increases, the skew values generally become more negative. Therefore, the skew of physiological data may be indicative of the lag value or rate corresponding to the physiological signal. In some embodiments, a look-up table, data structure, or other reference including data relating a skewness value and a value indicative of correlation lag (e.g., such as that represented by plot 2200) may be stored in memory. For example, in some implementations, the processing equipment may determine a skewness value based on a physiological signal, and refer to a look-up table to determine a lag value estimate based on the skewness value. In a further example, a function (e.g., piecewise or continuous) or other relationship may be derived to approximately describe the relationship shown in plot 2200. The skew value or lag value estimate may be used to classify the physiological data. For example, a skew value below a threshold may be indicative of physiological data of an adult or a person who may have a dicrotic notch. As another example, a skew value above a threshold may be indicative of physiological data of a neonate or a person who may not have a dicrotic notch. The skew value, lag value estimate, and/or classification may be used to determine an algorithm setting as described in connection with step 2106 of FIG. 21.

Figure 23:
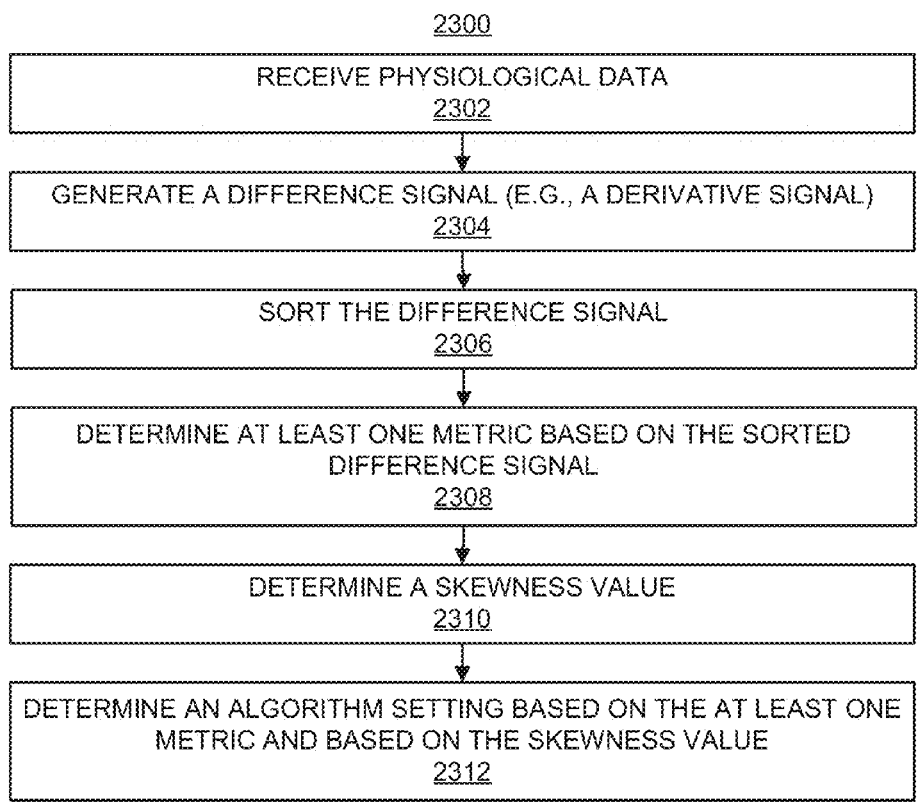
FIG. 23 is a flow diagram of illustrative steps for determining an algorithm setting based on a skewness value and a difference signal of the physiological signal, in accordance with some embodiments of the present disclosure.
Figure 24:
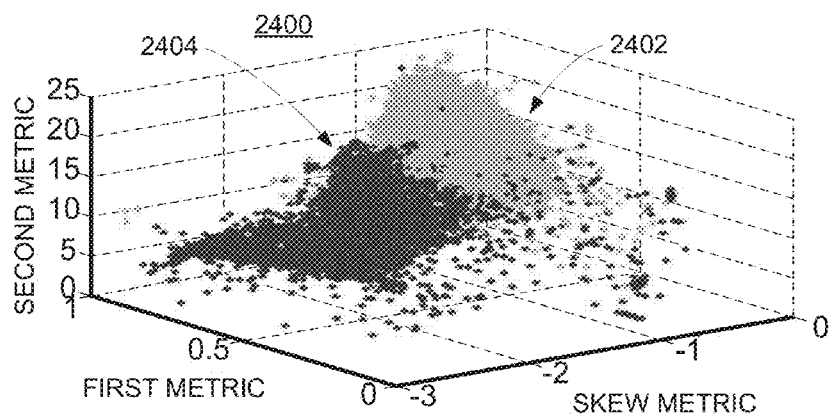
FIG. 24 is a panel showing an illustrative plot of classifier data based on a skewness value and a sorted difference signal, in accordance with some embodiments of the present disclosure.

FIG. 23 is a flow diagram 2300 of illustrative steps for determining an algorithm setting based on a skewness value and a difference signal of the physiological signal, in accordance with some embodiments of the present disclosure. FIG. 24 is a panel showing an illustrative plot 2400 of classifier reference data based on a skewness value and a sorted difference signal, in accordance with some embodiments of the present disclosure. FIG. 24 will be referred to below during the discussion of the illustrative steps of flow diagram 2300.

Step 2302 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 2302 may include recalling data from the memory for further processing.

Step 2304 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal.

Step 2306 may include processing equipment sorting the difference values of step 2304. The processing equipment may sort the values in ascending or descending order, either of which causes the negative and positive values to be separated. Referencing sorted values in ascending order, the most negative values come first followed by less negative values, positive values, and finally larger positive values. Accordingly the sorted values can be separated into positive values and negative values, and the two sets of values may be processed separately.

Step 2308 may include processing equipment determining at least one metric based on the sorted difference signal of step 2306. In some embodiments, the processing equipment may determine the at least one metric using the illustrative techniques described in the context of FIGS. 11-22, or below in the context of FIGS. 25-41, or a combination thereof.

Step 2310 may include processing equipment determining a skewness value based on the received physiological data of step 2302. In some embodiments, the processing equipment may use an expression such as Eq. 16 to determine the skewness value. In some embodiments, the processing equipment may perform one or more signal conditioning operations prior to determining the skewness value. For example, in some embodiments, the processing equipment may subtract the mean value of the physiological data to center the data about zero.

Step 2312 may include processing equipment determining an algorithm setting based on the determined skewness value and the at least one metric. In some embodiments, the algorithm setting may be based on a reference relationship between the skewness value and the at least one metric that be represented by a function, a look-up table, a mapping, a neural network, any other suitable representation, or any combination thereof.

Figure 25:
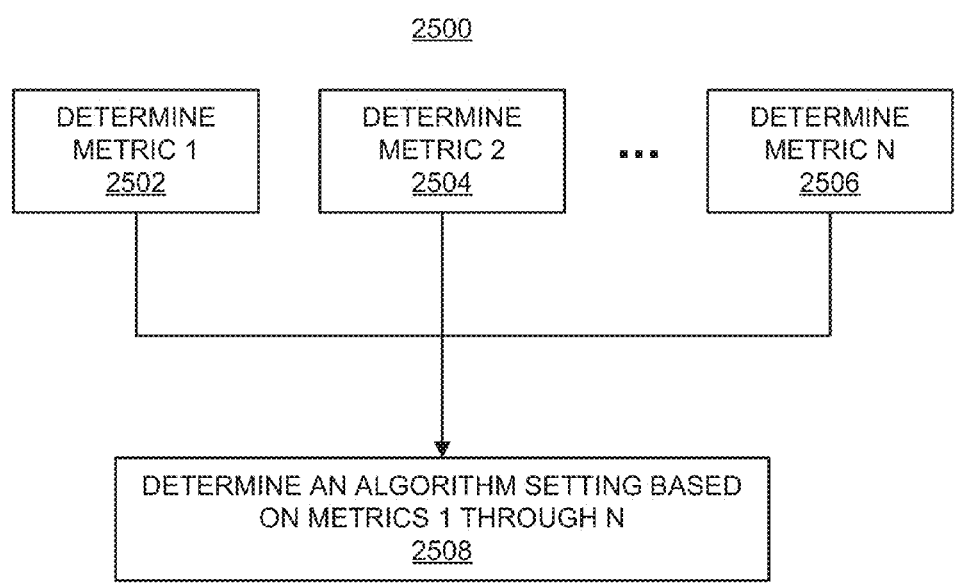
FIG. 25 is a flow diagram of illustrative steps for determining an algorithm setting based on a combination of metrics, in accordance with some embodiments of the present disclosure.

FIG. 24 is a panel showing an illustrative plot 2400 of classifier reference data based on a skewness value and two metrics derived from a sorted difference signal, in accordance with some embodiments of the present disclosure. Plot 2400 shows the classification of physiological data based on a skewness value, a first metric value calculated using the illustrative techniques of flow diagram 1300, and a second metric value calculated using the illustrative techniques of flow diagram 1500. Region 2402 corresponds to data for neonates, while region 2404 corresponds to data exhibiting a dicrotic notch. The relatively clean grouping shown in plot 2400 may be used to classify physiological data. In some embodiments, the data in plot 2400 may be filtered data to improve the distinct grouping of the data. Data, such as that represented by plot 2400 may be used as a reference to classify physiological data, and accordingly may be stored in suitable memory in any suitable format (e.g., a data table, a set of data tables, a function, or any other suitable format). In some embodiments, data of instances such as that shown in plot 2400 may be inputted into a nearest-neighbor probability calculation to determine, for each value triple (i.e., each set of three values that can be represented by a point in the 3-D space of plot 2400), a probability that the data belongs to a classification. The regions of high probability may align substantially with respective regions 2402 and 2404, albeit with some smoothing from the nearest-neighbor calculation. In some embodiments, The foregoing techniques for determining an algorithm setting may be used alone or in combination to determine an algorithm setting. FIG. 25 is a flow diagram 2500 of illustrative steps for determining an algorithm setting based on a combination of metrics, in accordance with some embodiments of the present disclosure.

Step 2502 may include processing equipment determining a first metric, using any suitable technique in accordance with the present disclosure. For example, the processing equipment may determine the first metric using any of the techniques described in the context of FIGS. 11-24, or below in the context of FIGS. 26-41. Step 2504 may include processing equipment determining a second metric, using any suitable technique in accordance with the present disclosure. For example, the processing equipment may determine the second metric using any of the techniques described in the context of FIGS. 11-24, or below in the context of FIGS. 26-41. Step 2506 may include processing equipment determining an Nth metric, using any suitable technique in accordance with the present disclosure. For example, the processing equipment may determine the Nth metric using any of the techniques described in the context of FIGS. 11-24, or below in the context of FIGS. 26-41. In some embodiments, each metric of steps 2502-2506 may be of a different type (e.g., determined using a different technique). In some embodiments, each metric of steps 2502-2506 may be of the same type, although different settings may be used (e.g., determined using the same technique but using different thresholds, offsets, or other settings).

Step 2508 may include processing equipment determining an algorithm setting based on the metrics of steps 2502-2506. In some embodiments, two or more of metrics may be combined by, for example, averaging, summing, multiplying, performing any other suitable combination technique, or any combination of techniques thereof. In some embodiments, the processing equipment may select a metric from among the metrics. For example, the processing equipment may select the largest metric, or the smallest metric. In some embodiments, the processing equipment may exclude a metric from a combination of the metrics. For example, the processing equipment may exclude the largest metric, the smallest metric, or both, when determining a combined metric value such as, for example, an average, a sum, a product, any other suitable combined metric value, or any combination thereof.

Figure 26:
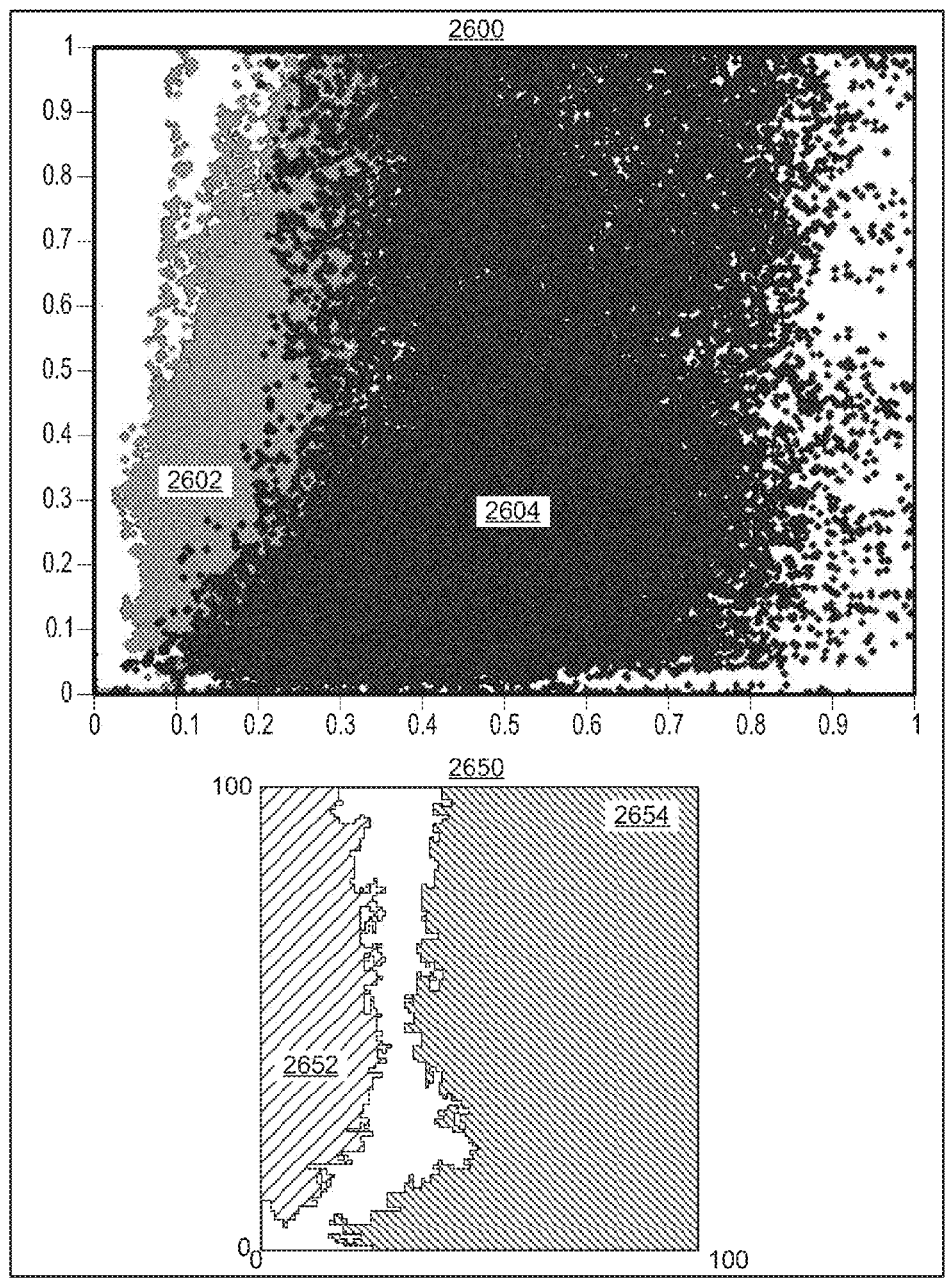
FIG. 26 is a panel showing an illustrative set of de-trending metric values and illustrative contours for an illustrative combination of de-trending metrics, in accordance with some embodiments of the present disclosure.

FIG. 26 is a panel showing an illustrative set of de-trending metric values and illustrative contours for an illustrative combination of de-trending metrics, in accordance with some embodiments of the present disclosure. Plot 2600 shows sets of points 2602 and 2604, corresponding to dicrotic notch and neonate data, respectively, derived by generating coordinate pairs of two de-trending metric values for multiple data sets. The abscissa and ordinate of plot 2600 ranges from zero to one, indicating normalized de-trending metric values. Plot 2650 shows an illustrative contour plot generated by using a nearest-neighbor probability classifier (e.g., 10-point technique as shown in FIG. 26) based on sets of points 2602 and 2604 of plot 2600. The abscissa and ordinate of plot 2650 ranges from zero to one hundred, indicating one hundred times the de-trending metric values of plot 2600 (i.e., a simple multiplicative scaling). The contour plot includes two regions 2652 and 2654, corresponding to a high probability of a dicrotic notch and a high probability of a neonate, respectively. Note that the region between regions 2652 and 2654 corresponds to relatively lower probabilities of either a dicrotic notch or neonate signal type.

Figure 27:
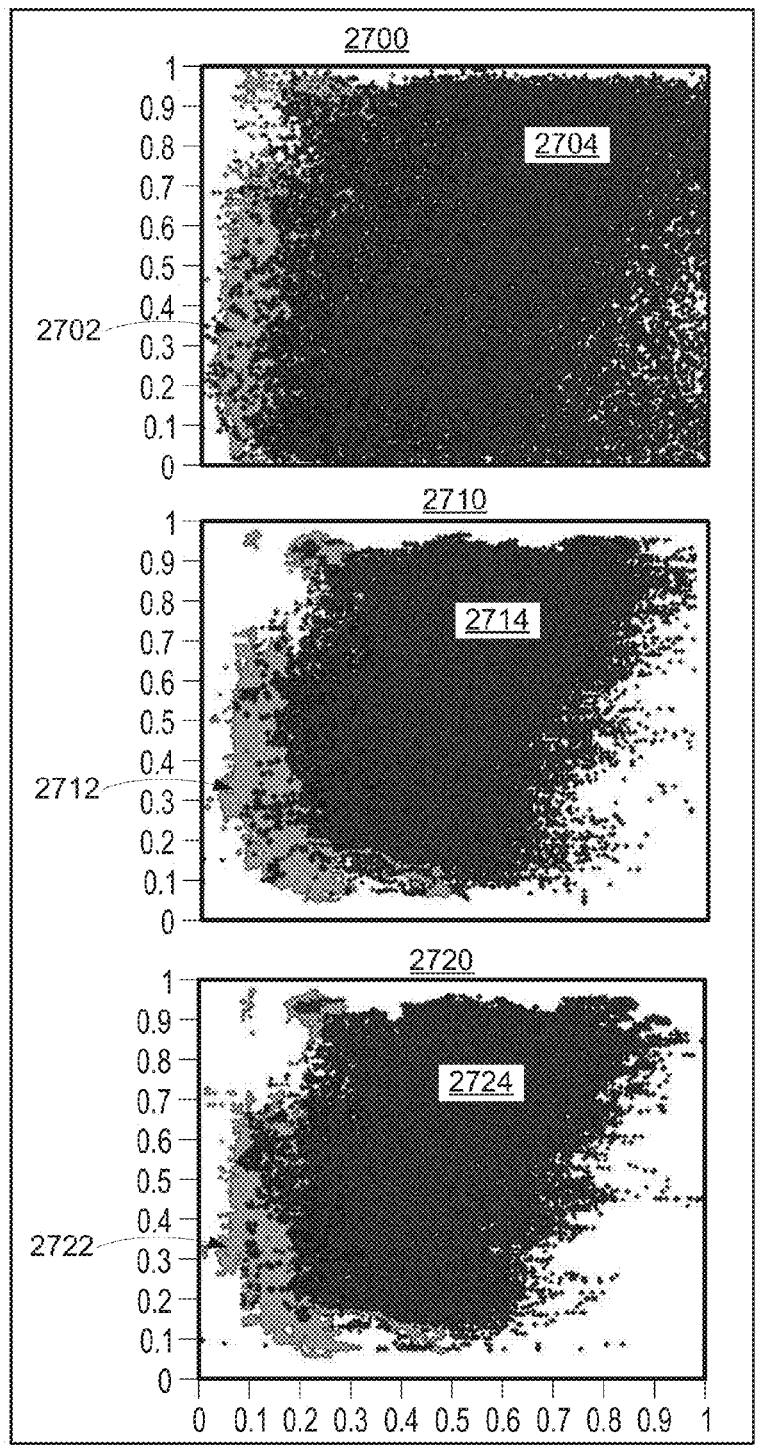
FIG. 27 is a panel showing three illustrative sets of de-trending metric values, taken for different window sizes, in accordance with some embodiments of the present disclosure.

FIG. 27 is a panel showing three illustrative sets of de-trending metric values, taken for different window sizes, in accordance with some embodiments of the present disclosure. The abscissa and ordinate of plots 2700, 2710, and 2720 both range from zero to one, indicating normalized de-trending metric values. Plot 2700 shows sets of points 2702 and 2704, corresponding to dicrotic notch and neonate data, respectively, derived by generating coordinate pairs of two de-trending metric values for multiple data sets using six-second windows. Plot 2710 shows sets of points 2712 and 2714, corresponding to dicrotic notch and neonate data, respectively, derived by generating coordinate pairs of two de-trending metric values for multiple data sets using eighteen-second windows. Plot 2720 shows sets of points 2722 and 2724, corresponding to dicrotic notch and neonate data, respectively, derived by generating coordinate pairs of two de-trending metric values for multiple data sets using thirty-second windows. As the window size increases from the six-second window, it can be seen that the sets partition more cleanly, indicating that a classification may be performed more accurately.

Figure 28:
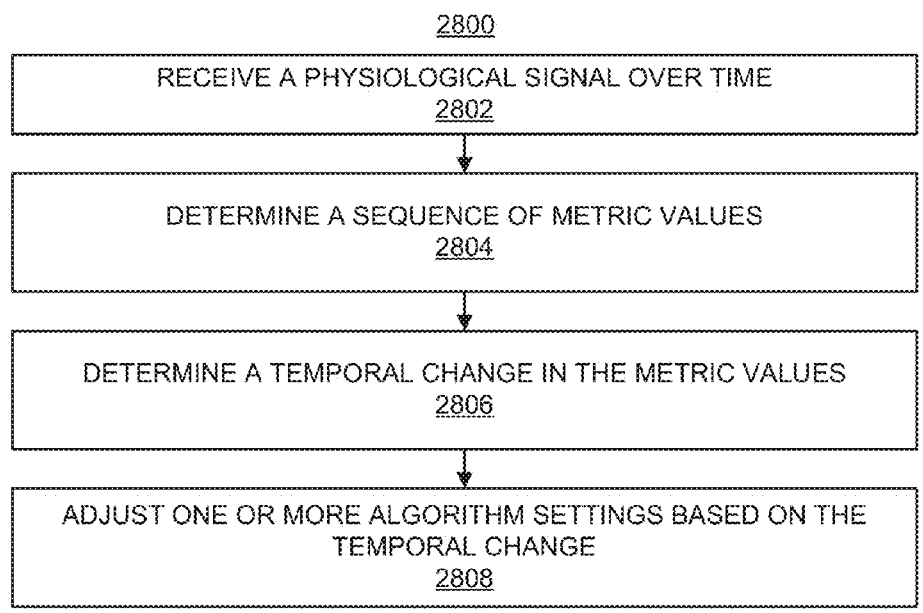
FIG. 28 is a flow diagram of illustrative steps for temporally monitoring metrics, in accordance with some embodiments of the present disclosure.

In some embodiments, empirical data may be used to set an algorithm setting. For example, processing equipment may map two metrics to a particular classification. The mapping may include a look-up table, a function describing the classification boundary, a nearest neighbor classifier, a neural network, or any other linear or non-linear mapping, or any combination thereof. Referencing FIG. 26, the processing equipment may, for example, fit a function to the boundary between regions 2602 and 2604. Note that any suitable combination of any suitable number of metrics may be mapped to a classification. In some embodiments FIG. 28 is a flow diagram 2800 of illustrative steps for temporally monitoring metrics, in accordance with some embodiments of the present disclosure.

Step 2802 may include processing equipment receiving physiological data over time from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 2802 may include recalling data from the memory for further processing.

Step 2804 may include processing equipment determining a sequence of metric values over time. In some embodiments, for example, the processing equipment may determine a metric value or a noise metric value every second based on the most recent window of physiological data.

Step 2806 may include processing equipment determining a temporal change in the sequence of metric values of step 2804. In some embodiments, the processing equipment may determine a difference between consecutive metric values, and if the difference exceeds a threshold, the processing equipment may determine that a temporal change has occurred. In some embodiments, the processing equipment may determine a difference between each metric value and a reference value (e.g., an initial metric value), and if the difference exceeds a threshold, the processing equipment may determine that a temporal change has occurred. In some embodiments, the processing equipment may determine that a temporal change has occurred when the difference exceeds a threshold for a certain amount of time.

Step 2808 may include processing equipment adjusting one or more algorithm settings based on the metric values. For example, if a temporal change exceeds a threshold, the processing equipment may perform any of the techniques described in the context of FIGS. 11-28, or below in the context of FIGS. 30-41 to classify the physiological signal again.

In some embodiments, the processing equipment may determine one or more algorithm settings, and adjust the one or more algorithm settings in response to one or more metric values. For example, the processing equipment may receive physiological data, and determine a metric value indicative of a physiological classification. The physiological classification may be based on the presence of a dicrotic notch (e.g., dicrotic notch, no dicrotic notch, neonate), physiological rate (e.g., large or small heart rate), pulse shape, any physiological classification, or any combination thereof. The processing equipment may determine an algorithm setting based on the physiological classification such as, for example, a mode, a qualification test, a qualification criterion, a threshold value, a signal conditioning setting, any other suitable algorithm setting, or any combination thereof. In some instances, subsequent to determining the algorithm setting, the processing equipment may determine a second metric value indicative of a different physiological classification than determined previously based on subsequent physiological data. The second metric value may be the same metric above having an updated value, or a different metric, which indicates the different physiological classification. The processing equipment may then determine an algorithm setting based on the different physiological classification such as, for example, a mode, a qualification test, a qualification criterion, a threshold value, a signal conditioning setting, any other suitable algorithm setting different from the previous algorithm setting, or any combination thereof. Accordingly, the processing equipment may update algorithm settings as changes occur in the physiological data, in the state of the rate algorithm, or both.

Figure 29:
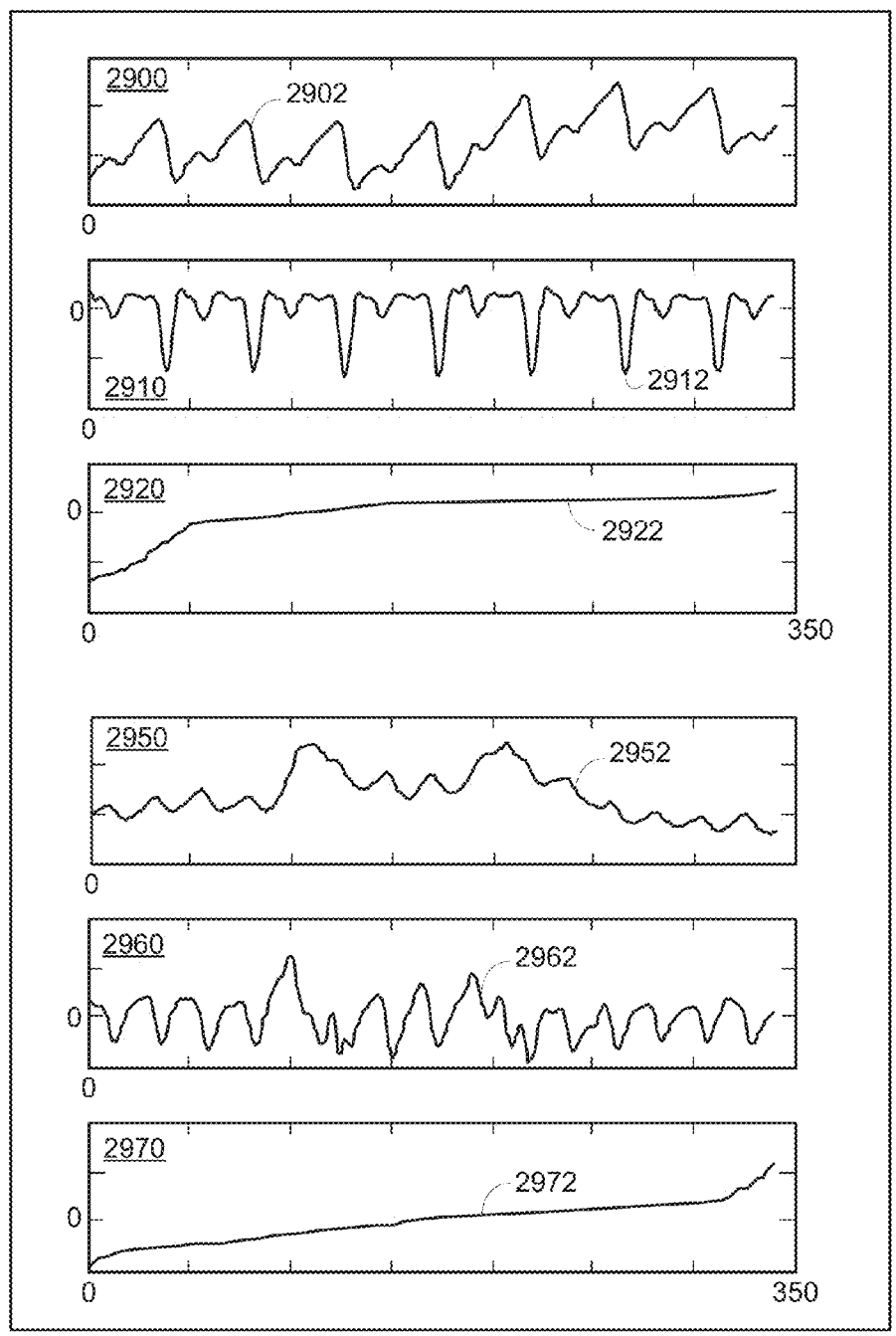
FIG. 29 is a panel showing illustrative PPG signals with and without a dicrotic notch, corresponding difference signals for each, and corresponding sorted difference signals for each in accordance with some embodiments of the present disclosure.

In some embodiments, one or more metrics indicative of noise (e.g., a noise metric) in the physiological data may be used to determine one or more algorithm settings. A noise metric may provide an indication of the relative noise level, absolute noise level, type of noise, any other noise property, or any combination thereof. For example, physiological data corresponding to a physiological rate may be expected to exhibit substantially oscillatory behavior. Differences, such as a first derivative, in the physiological data may also be expected to exhibit oscillatory behavior and occur in an expected range. FIG. 29 is a panel showing illustrative PPG signals with and without a dicrotic notch, corresponding difference signals for each, and corresponding sorted difference signals for each in accordance with some embodiments of the present disclosure. The abscissas of the plots of FIG. 29 are in units of sample number, while the ordinates are shown in arbitrary units. Plot 2900 shows PPG signal 2902 (indicative of transmitted intensity) having a dicrotic notch. Plot 2910 shows difference signal 2912 derived by calculating differences (e.g., forward difference, backward differences, central difference, derivatives, or any other suitable difference) at each point of PPG signal 2902. Plot 2920 shows sorted difference signal 2922, generated by sorting the values of difference signal 2912 in ascending order by value. Plot 2950 shows PPG signal 2952 (indicative of transmitted intensity), which does not exhibit a dicrotic notch. Plot 2960 shows difference signal 2962 derived by calculating differences at each point of PPG signal 2952. Plot 2970 shows sorted difference signal 2972, generated by sorting the values of difference signal 2262 in ascending order by value. Sorted difference signals 2922 and 2972 exhibit different shapes, which may be taken into account by the processing equipment when determining a noise metric. The illustrative techniques discussed in the context of FIGS. 30, 32, 36, 37, 39 and 41 may applied to any suitable physiological data such as, for example, those shown in FIG. 29 to classify the data, set an algorithm setting, or both.

Figure 30:
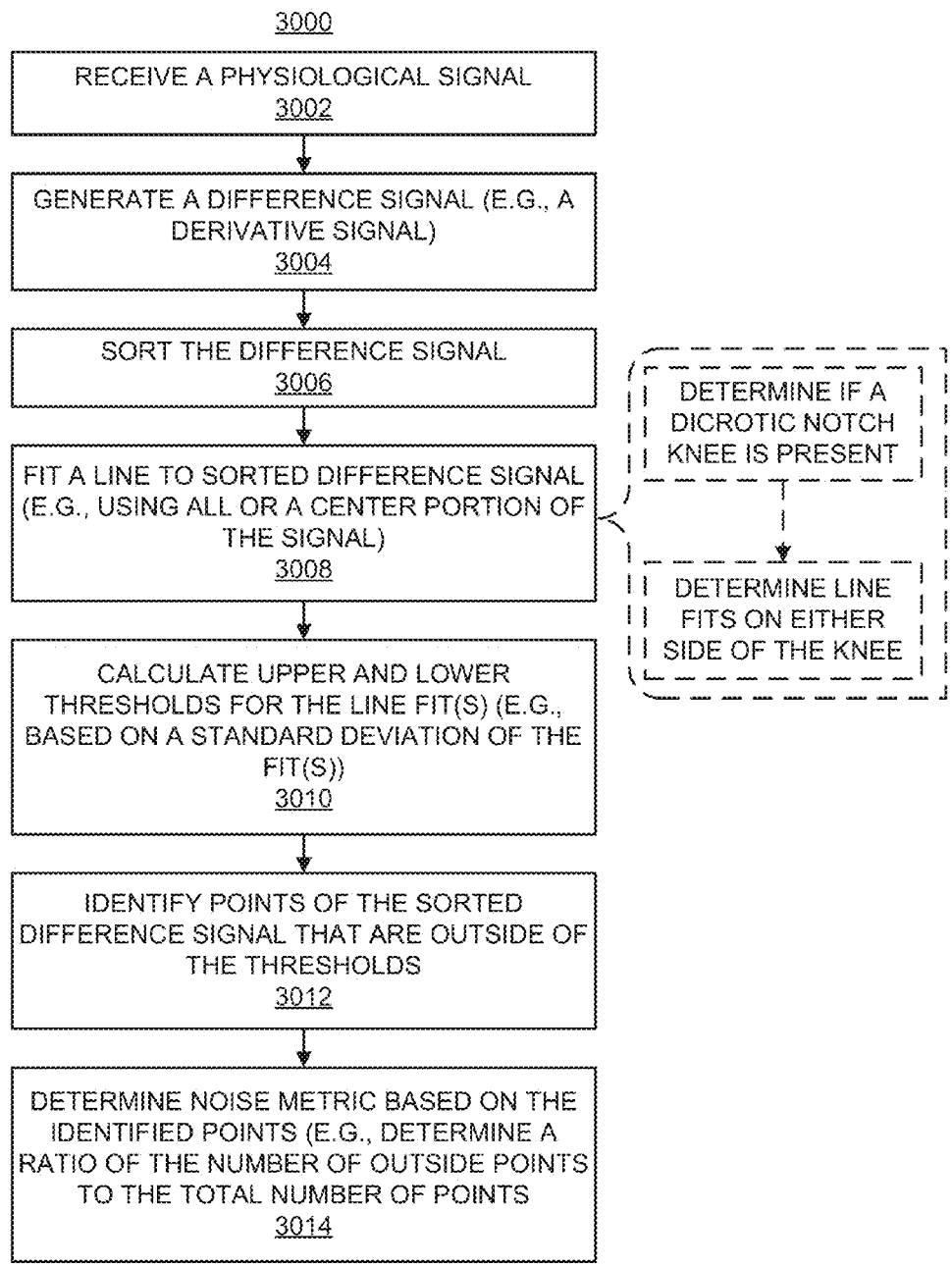
FIG. 30 is a flow diagram of illustrative steps for determining a noise metric from a line fit of a sorted difference signal, in accordance with some embodiments of the present disclosure.
Figure 31:
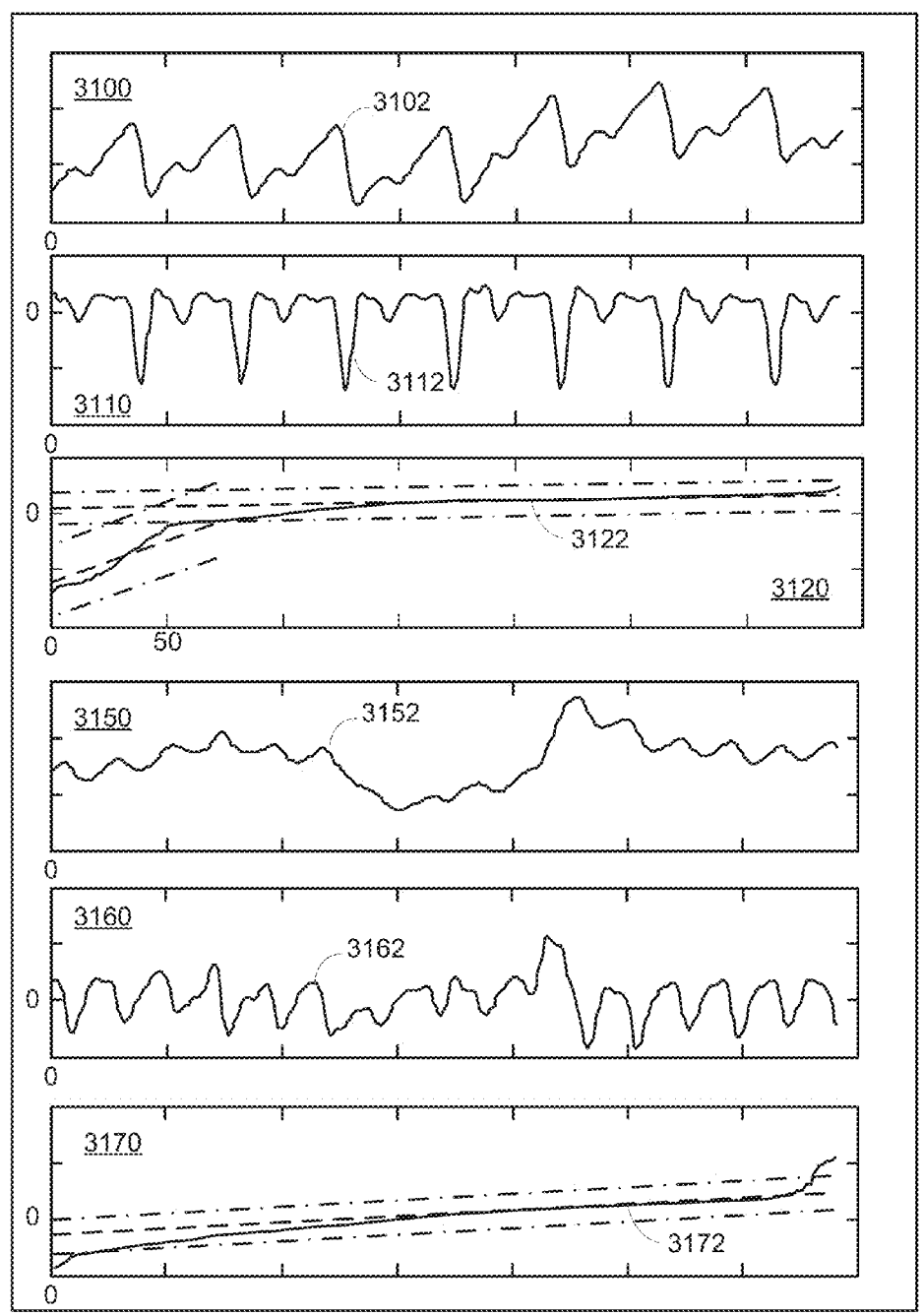
FIG. 31 is a panel showing illustrative PPG signals with and without a dicrotic notch, corresponding difference signals for each, corresponding sorted difference signals for each, and corresponding line fits for each, in accordance with some embodiments of the present disclosure.

FIG. 30 is a flow diagram 3000 of illustrative steps for determining a noise metric from a line fit of a sorted difference signal, in accordance with some embodiments of the present disclosure. FIG. 31 is a panel showing illustrative PPG signals with and without a dicrotic notch, corresponding difference signals for each, corresponding sorted difference signals for each, and corresponding line fits for each, in accordance with some embodiments of the present disclosure. FIG. 31 will be referred to below during the discussion of the illustrative steps of flow diagram 3000.

Step 3002 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 3002 may include recalling data from the memory for further processing.

Step 3004 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal.

Step 3006 may include processing equipment sorting the difference values of step 3004. The processing equipment may sort the values in ascending or descending order, either of which causes the negative and positive values to be separated. Referencing sorted values in ascending order, the most negative values come first followed by less negative values, positive values, and finally larger positive values.

Step 3008 may include processing equipment fitting a line to at least a portion of the sorted difference signal of step 3006. In some embodiments, the processing equipment may perform a linear regression (e.g., a least-squares regression or a weighted least-squares regression) using at least a portion of the sorted difference signal. In some embodiments, the processing equipment may fit a line using every point of the sorted difference signal. In some embodiments, the processing equipment may fit a line using a portion of the sorted difference signal. For example, the processing equipment may omit one or more points at one or both ends of the sorted difference signal when determine the line fit. In some embodiments, the line fit may include a slope value and an ordinate intercept value (e.g., using a y=mx+b linear form where m is the slope and b is the intercept). In some embodiments, the processing equipment may determine if a dicrotic notch is present (e.g., based on a de-trending metric), and determine line fits on either side of the knee in the sorted difference signal. For example, plot 2920 of FIG. 29 shows sorted difference signal 3122 (e.g., derived from a PPG signal having a dicrotic notch), exhibiting a knee at an abscissa value of about 50.

Step 3010 may include processing equipment calculating upper and lower thresholds for the line fit of step 3008. In some embodiments, the upper and lower thresholds may be lines parallel to the line fit (i.e., having the same slope) with the vertical-intercept (or other reference point) at a fixed difference from the line fit (e.g., the thresholds may be given by y=mx+b±C where C is the fixed difference). In some embodiments, the upper and lower thresholds may be lines with slopes other than the slope of the line fit (e.g., the thresholds may be given by y=nx+$b_1$ and y=px+$b_2$ where n and p are the upper and lower threshold slopes). The upper and lower thresholds may be generated by the processing equipment using any suitable function.

Step 3012 may include processing equipment identifying points of the sorted difference signal that are outside of the thresholds calculated at step 3010. Plot 3100 of FIG. 31 shows PPG signal 3102 (indicative of transmitted intensity) having a dicrotic notch. Plot 3110 shows difference signal 3112 derived by calculating differences (e.g., forward difference, backward differences, central difference, derivatives, or any other suitable difference) at each point of PPG signal 3102. Plot 3120 shows sorted difference signal 3122, generated by sorting the values of difference signal 3112 in ascending order by value. Plot 3150 shows PPG signal 3152 (from a neonate), which does not exhibit a dicrotic notch. Plot 3160 shows difference signal 3162 derived by calculating differences at each point of PPG signal 3152. Plot 3170 shows sorted difference signal 3172, generated by sorting the values of difference signal 3162 in ascending order by value. The dashed lines in plots 3120 and 3170 represent line fits (a piecewise line fit in plot 3120), while the dashed-dotted lines represent upper and lower thresholds for each line fit.

Step 3014 may include processing equipment determining a noise metric based on the identified points of step 3012. In some embodiments, the processing equipment may calculate the ratio of points identified at step 3012 to the total number of points of the sorted difference signal. For example, the noise metric may be set equal to the ratio of points identified at step 3012 to the total number of points (e.g., relatively low numbers of noise points result in a noise metric relatively nearer to zero).

Referencing FIG. 31, PPG signal 3102 and corresponding difference signal 3112 exhibit relatively low noise in the signal, with the pulses being relatively consistently spaced and having a relatively consistent shape. Accordingly, as expected, no noise points are identified. PPG signal 3152 and corresponding difference signal 3162 exhibit distortion based on the baseline shifts and the varying shape of the pulses. Accordingly, as expected, noise points are identified at the ends of sorted difference signal 3172. Typically a low noise PPG signal will have a relatively smooth corresponding sorted difference signal because the differences are expected to fall within a certain distribution. With increasing levels of noise, the number of extreme (e.g., outside of the certain distribution) positive difference values and extreme negative difference values increases. As a result, the negative end of the sorted difference signal will typically begin to significantly bend downwards and the positive end of the sorted difference signal will start to bend upwards. This effect of noise can be seen in plot 3170, particularly at the positive end.

Figure 32:
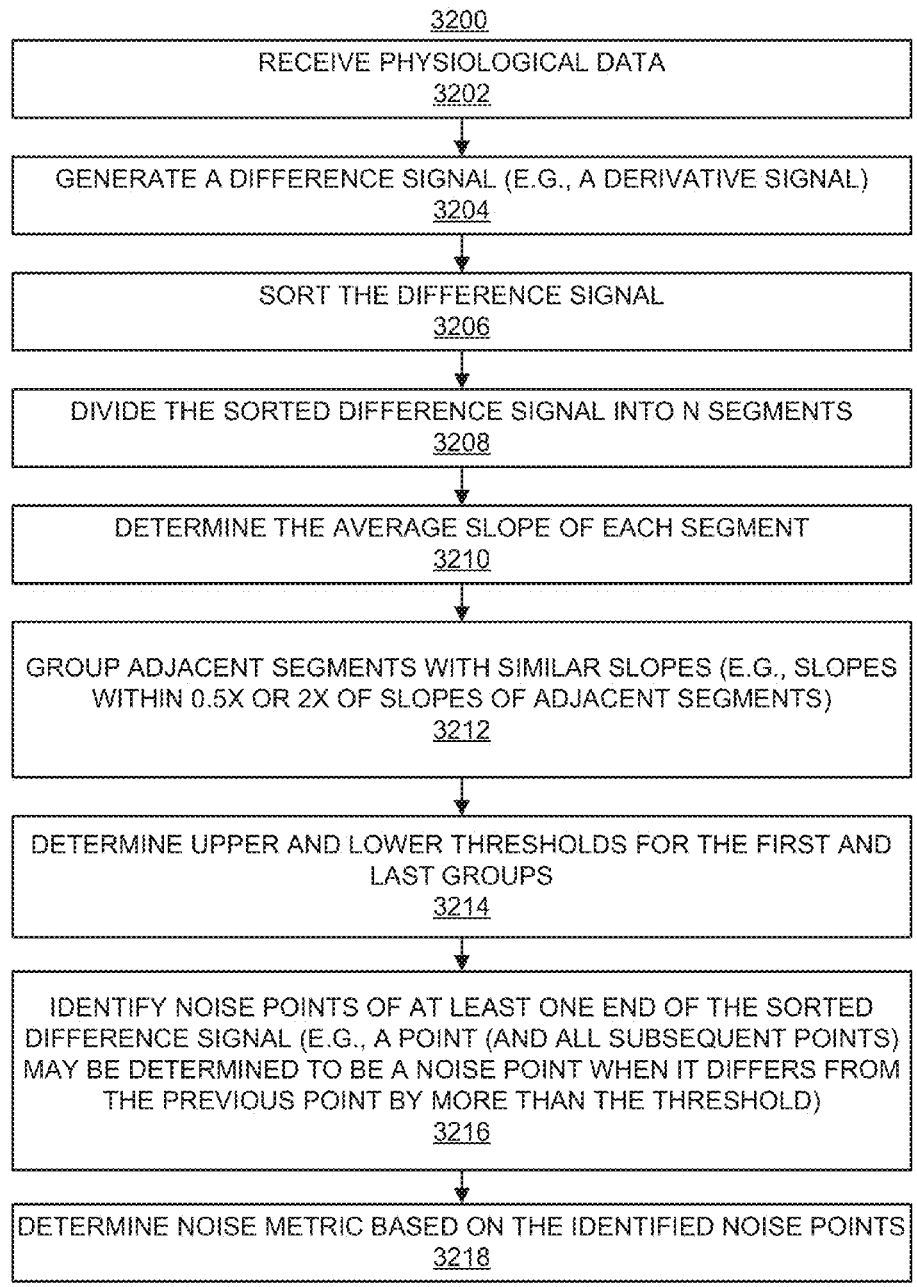
FIG. 32 is a flow diagram of illustrative steps for determining a noise metric from a segmented line fit of a sorted difference signal, in accordance with some embodiments of the present disclosure.
Figure 33:
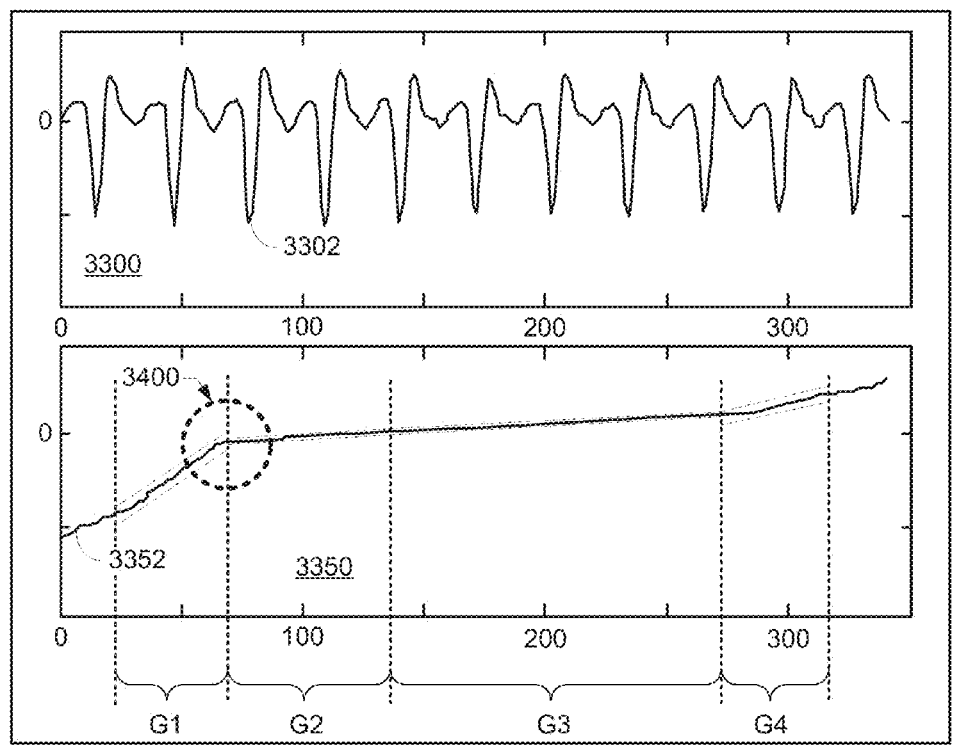
FIG. 33 is a panel showing an illustrative difference signal derived from a PPG signal, a sorted difference signal, and corresponding segmented line fits, in accordance with some embodiments of the present disclosure.
Figures 34, 35:
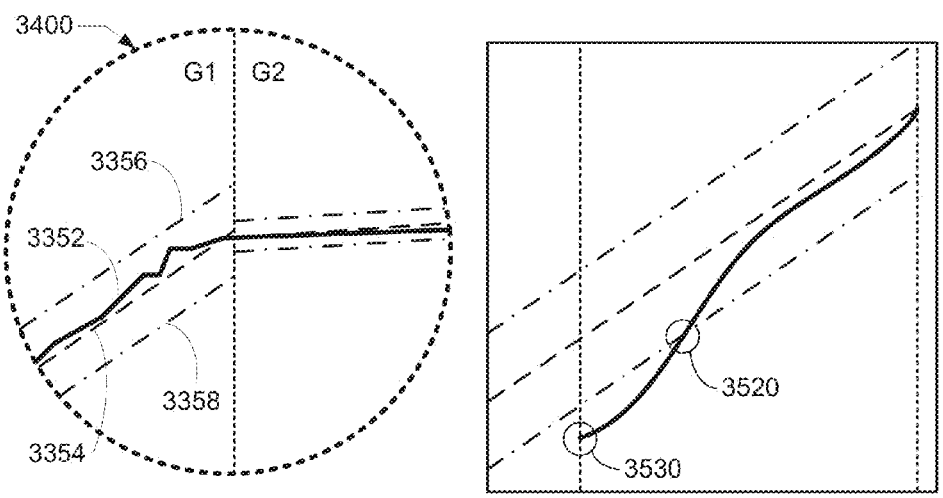
FIG. 34 is a partial view of the sorted difference signal of FIG. 33, taken from circle 3400, showing portions of two groups, in accordance with some embodiments of the present disclosure.
FIG. 35 is a plot of an illustrative first segment of a sorted difference signal, and corresponding thresholds, in accordance with some embodiments of the present disclosure.

FIG. 32 is a flow diagram 3200 of illustrative steps for determining a noise metric from a segmented line fit of a sorted difference signal, in accordance with some embodiments of the present disclosure. FIG. 33 is a panel showing an illustrative difference signal derived from a PPG signal, a sorted difference signal, and corresponding segmented line fits, in accordance with some embodiments of the present disclosure. Additionally, FIG. 34 is a partial view of the sorted difference signal of FIG. 33, taken from circle 3400, showing portions of two groups, in accordance with some embodiments of the present disclosure. FIGS. 33-35 will be referred to below during the discussion of the illustrative steps of flow diagram 3200.

Step 3202 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 3202 may include recalling data from the memory for further processing.

Step 3204 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal. As an illustrative example, plot 3300 of FIG. 33 shows difference signal 3302, which is a calculated first derivative signal of a PPG signal.

Step 3206 may include processing equipment sorting the values of the difference signal of step 3204. The processing equipment may sort the values in ascending or descending order. Referencing sorted values in ascending order, the most negative values come first followed by less negative values, positive values, and finally larger positive values.

Step 3208 may include processing equipment dividing the sorted difference signal of step 3206 into N segments. In some embodiments, the N segments may be of equal length (e.g., each may include the same number of samples). In some embodiments, the N segments may have different lengths. The value N may be any suitable positive integer, greater than or equal to one. In some embodiments, step 3208 may include the processing equipment determining a beginning and ending data point number corresponding to each segment, a length of each segment (e.g., number of data points), any other suitable metric for dividing a signal into one or more segments, or any combination thereof. In some embodiments, the processing equipment may generate N new signals, each corresponding to one of the N segments.

Step 3210 may include processing equipment determining the average slope of each segment of the N segments of step 3208. In some embodiments, the processing equipment may perform a linear regression (e.g., a least-squares regression or a weighted least-squares regression) for each segment to determine the slope. In some embodiments, the processing equipment may determine the average slope of a segment as the slope of the line coincident with the endpoints of that segment. The processing equipment may use any suitable technique to determine an average slope of each segment.

Step 3212 may include processing equipment grouping adjacent segments with similar slopes. Based on the average slopes of each segment, as determined at step 3210, the processing equipment may group segments into collective, larger segments if the slopes are sufficiently similar. In some embodiments, the slopes of each adjacent pair of segments may be compared, and if the slopes are sufficiently similar, the segments may be grouped. For example, the ratio of the slopes of each adjacent pair of segments may be determined, and if the ratio is between 0.5 and 2 then the segments may be grouped. Any suitable range of ratios may be used to group segments, in accordance with the present disclosure. The resulting number of groups may be less than or equal to the initial number of segments N. As an illustrative example, plot 3350 of FIG. 33 shows sorted difference signal 3352, which includes sorted data points of difference signal 3302. Sorted difference signal 3352 is illustratively grouped into four groups, G1, G2, G3 and G4, as shown by the vertical dotted lines in FIG. 33. The ends of the sorted difference signal are referred to herein as terminal ends.

Step 3214 may include processing equipment determining upper and lower thresholds of the first and last groups of steps

3212. The resulting one or more groups of step 3212 may include a first group (e.g., the leftmost group, using the abscissa of plot 3310 of FIG. 33 as a reference) and a last group (e.g., the rightmost group, using the abscissa of plot 3310 of FIG. 33 as a reference). The first group may be associated with relatively more negative, or smaller, values of the sorted difference signal. The last group may be associated with relatively more positive, or larger, values of the sorted difference signal. As an illustrative example, plot 3350 of FIG. 33 shows upper and lower thresholds for the four groups, G1, G2, G3 and G4 by each pair of dashed-dotted lines corresponding to each group. The partial view of FIG. 34, taken from circle 3400 in FIG. 33, shows a magnified view of portions of groups G1 and G2. The line including the average slope is shown by dashed line 3354. The upper and lower thresholds are shown by dashed-dotted lines 3356 and 3358, respectively. In some embodiments, the upper and lower thresholds of the first and last groups may extend to respective terminal ends of the sorted difference signal. Relative to the line fit, the threshold may be offset a fixed amount, offset a function of the slope of the line fit, offset a function of the goodness of the line fit, or a combination thereof.

Step 3216 may include processing equipment identifying noise points of at least one end of the sorted difference signal of step 3206. In some embodiments, the processing equipment may identify noise points in the sorted difference signal as lying outside of the upper and lower thresholds of step 3214. For example, steep changes in slope may cause a portion of the sorted difference signal to lie outside a set of thresholds for a group. Points identified as lying outside of the thresholds may be identified as noise points. In some embodiments, points lying outside of the upper and lower thresholds, and all points from the first excursion to the terminal end of the group may be identified as noise, regardless of whether some or all lie within the thresholds. In some embodiments, the processing equipment may start at the interior end of the first and last groups, away from the terminal ends, and progress outward towards to the terminal ends. For example referencing group G1 of FIG. 33, the processing equipment may begin at the point at or near the junction of groups G1 and G2, and progress leftward to the end of the sorted difference signal.

As an illustrative example, sorted difference signal 3352 of plot 3350 of FIG. 33 lies within the upper and lower thresholds for all of the four groups, G1, G2, G3 and G4. Accordingly, the processing equipment would not necessarily identify any noise points in this circumstance. As a further illustrative example, FIG. 35 is a plot of a portion of a first group of an illustrative sorted difference signal 3502, and corresponding thresholds, in accordance with some embodiments of the present disclosure. Sorted difference signal 3502 is shown to cross lower threshold 3508 at point 3520. Accordingly, in this circumstance, the processing equipment may identify noise points as all points between (and possibly including) point 3520 and the group endpoint 3530 at the terminal end of the first group.

In some embodiments, the segments do not extend to the end of the sorted difference signal, as fitting the lines to noise points may be undesirable. The thresholds associated with the first and last groups may, however, extend to the end of the sorted difference signal to locate noise points at each respective end. In some embodiments, the processing equipment need not determine both maximum and minimum thresholds for each line. For example, the processing equipment may only calculate a minimum threshold for the negative end of the sorted difference signal and a maximum threshold for the positive end, because noise points would be expected to diverge accordingly at the ends rather than flatten out.

Figure 36:
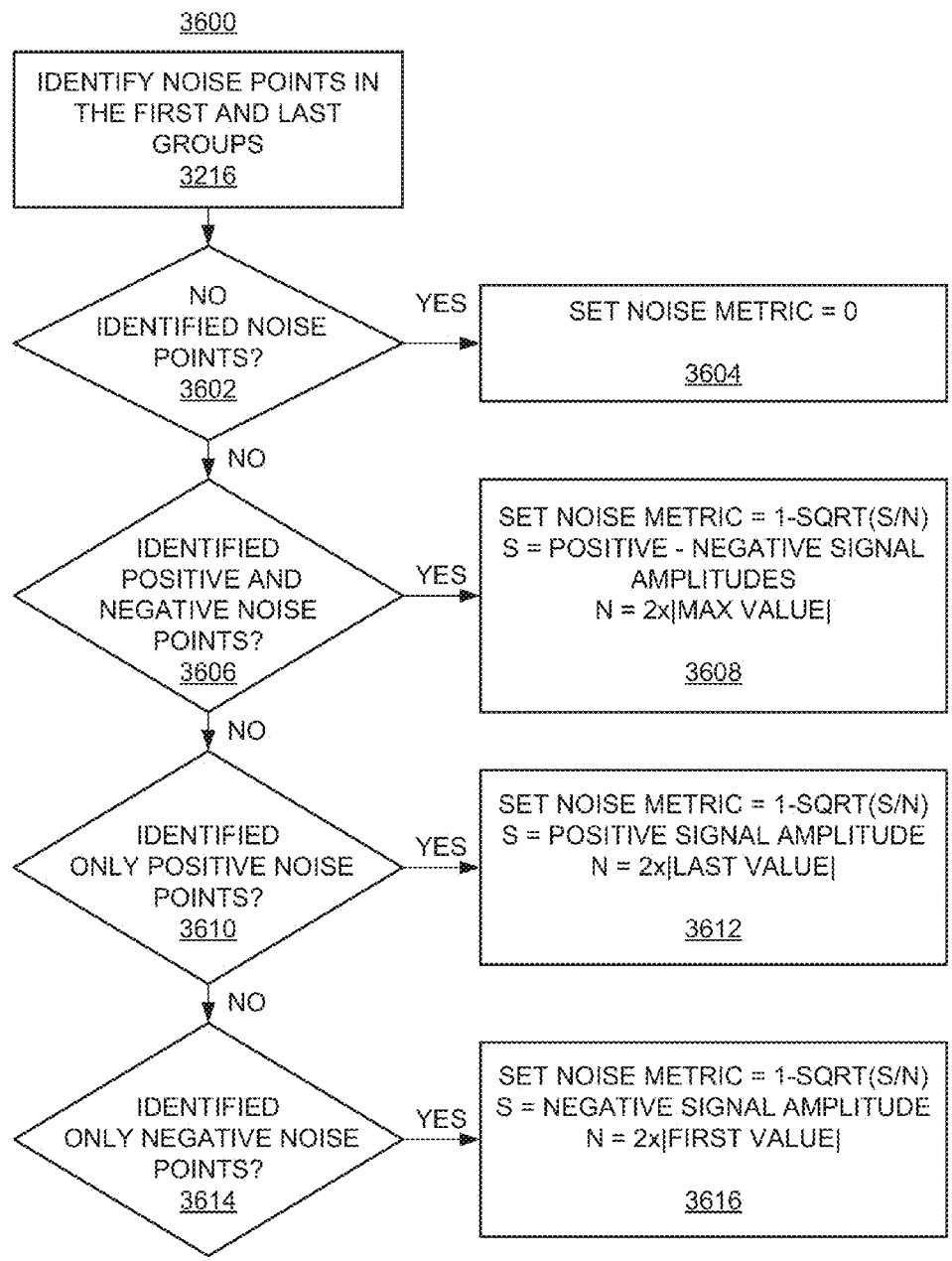
FIG. 36 is a flow diagram of illustrative steps for determining a noise metric based on identified noise points, in accordance with some embodiments of the present disclosure.

Step 3218 may include processing equipment determining a noise metric based on the identified noise points of step 3216. In some embodiments, the ratio of the number of noise points to total points may be determined (e.g., using the illustrative techniques of flow diagram 3000). For example, the noise metric may be set equal to the ratio of noise points to total points (e.g., relatively low numbers of noise points result in a noise metric relatively nearer to zero). In some embodiments, a noise metric may be determined at step 3218 based on a signal-to-noise type comparison. For example, FIG. 36 is a flow diagram 3600 of illustrative steps for determining a noise metric based on identified noise points, using a signal-to-noise type comparison, in accordance with some embodiments of the present disclosure. The processing equipment may determine the noise metric based on the noise points identified at step 3216, if any. Step 3602 may include determining whether no noise points were identified, in which case the processing equipment may set the noise metric equal to zero at step 3604. Step 3606 may include determining whether both positive and negative noise points were identified, in which case at step 3608 the processing equipment may determine the noise metric M based on Eq. 19:

$$M = 1 - \sqrt{\frac{S}{N}} \tag{19}$$

in which S is the difference between the positive and negative signal amplitudes, and N is equal to two times the maximum of the last signal value and the first signal value of the sorted difference signal. Step 3610 may include determining whether only a positive noise point was identified, in which case at step 3612 the processing equipment may determine the noise metric M based on Eq. 19 in which S is the positive signal amplitude, and N is equal to two times the maximum of the last value of the sorted difference signal. Step 3614 may include determining whether only a negative noise point was identified, in which case at step 3616 the processing equipment may determine the noise metric M based on Eq. 19 in which S is the negative signal amplitude, and N is equal to two times the maximum of the first value of the sorted difference signal. Flow diagram 3600 is merely illustrative, and the processing equipment may determine any suitable metric indicative of noise. For example, the processing equipment may determine the difference between the maximum and minimum values of the sorted difference signal as a metric. In further example, the processing equipment may determine the difference between the positive and negative signal amplitudes as a metric.

Figure 37:
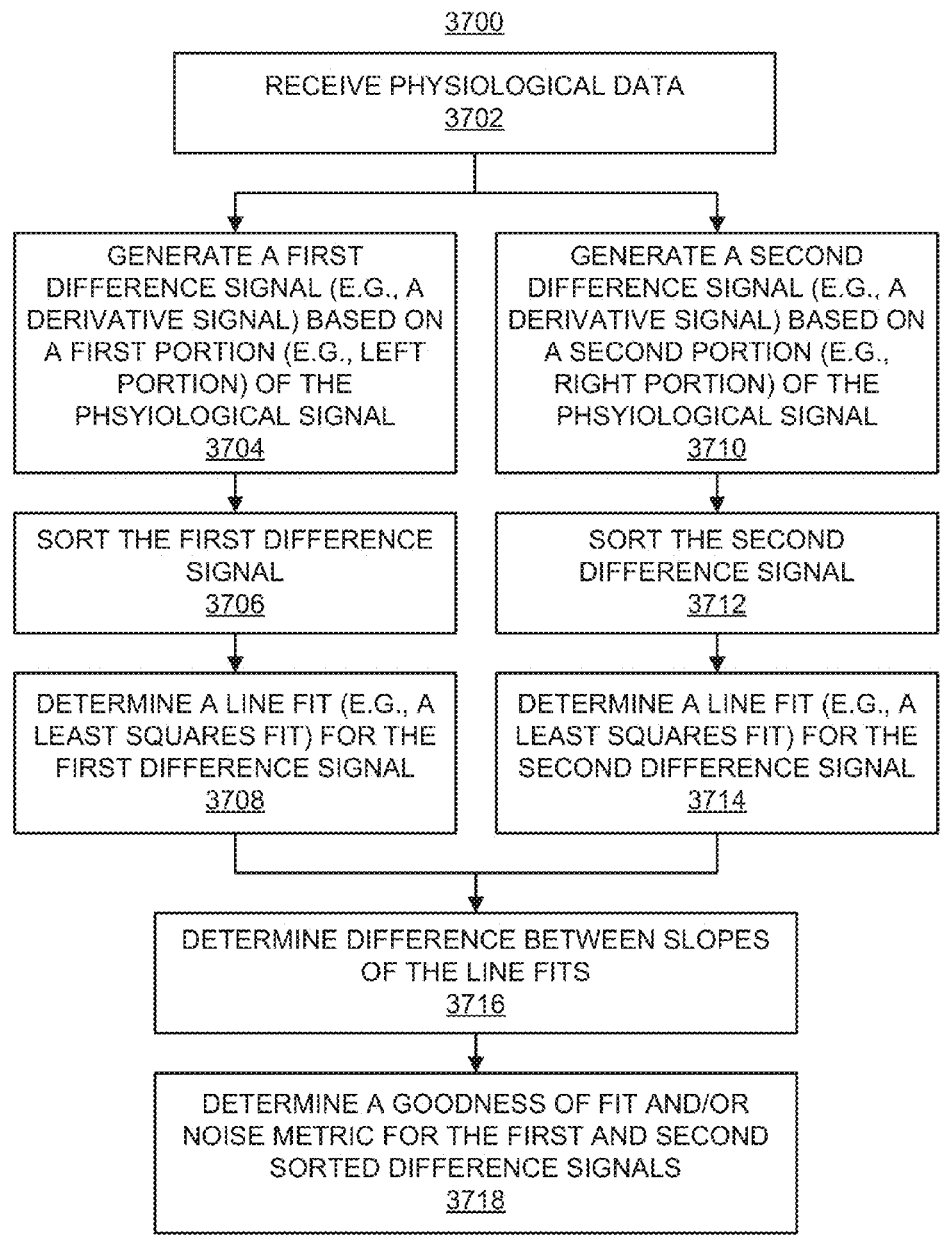
FIG. 37 is a flow diagram of illustrative steps for determining a noise metric based on two portions of physiological data, in accordance with some embodiments of the present disclosure.
Figure 38:
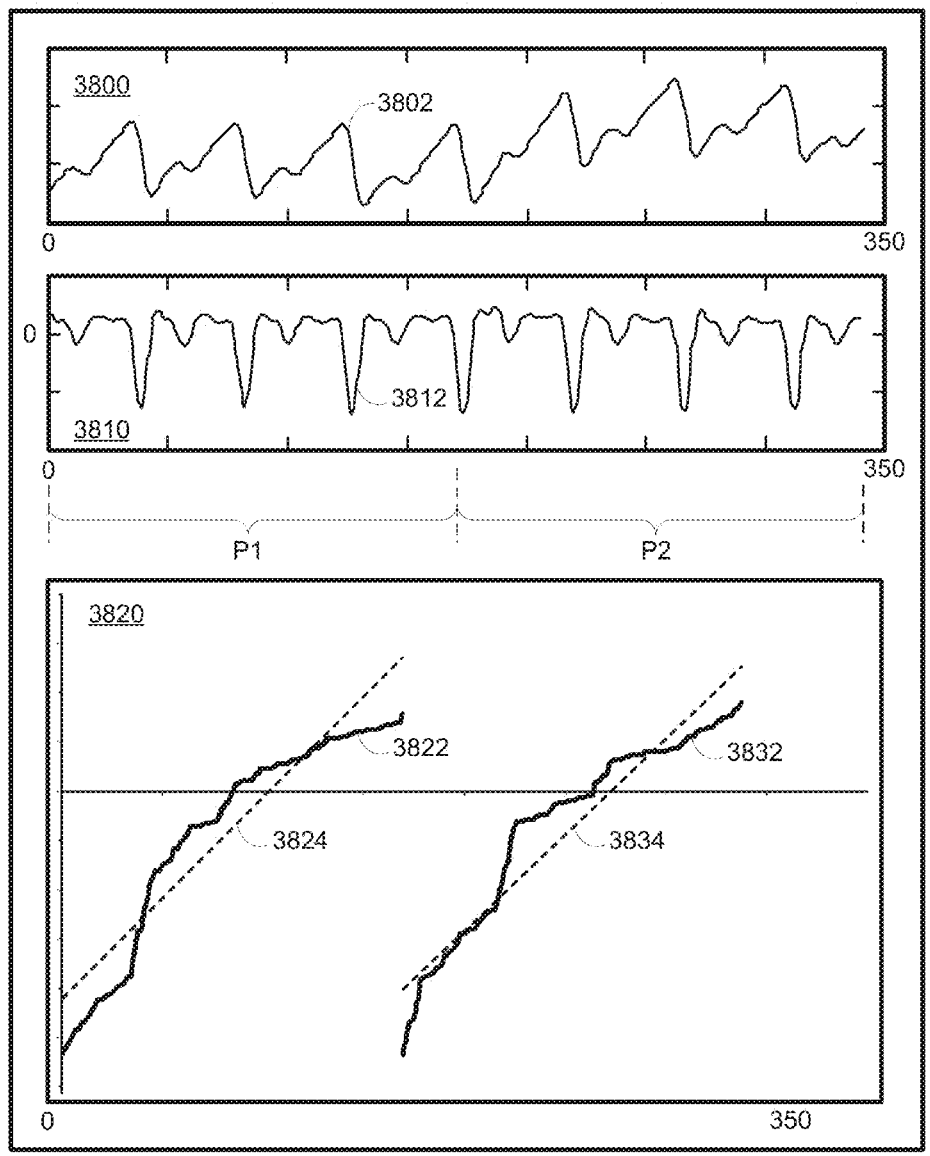
FIG. 38 is a panel showing an illustrative PPG signal, difference signals derived from the PPG signal, and corresponding sorted difference signals, in accordance with some embodiments of the present disclosure.

FIG. 37 is a flow diagram 3700 of illustrative steps for determining a noise metric based on two portions of physiological data, in accordance with some embodiments of the present disclosure. FIG. 38 is a panel showing an illustrative PPG signal, a difference signal derived from the PPG signal, and corresponding sorted difference signals, in accordance with some embodiments of the present disclosure. FIG. 38 will be referred to below during the discussion of the illustrative steps of flow diagram 3700. The analysis of two portions of the physiological signal may aid in identifying noise, quantifying noise, determining an onset of or reduction in noise, or a combination thereof. For example, when noise is low, adjacent portions of physiological data having sufficient size (e.g., a multiple of the period, or otherwise large size compared to the period of a physiological rate) should have similar sorted difference signals. As noise appears the buffer, the shape and distribution of points in the sorted difference signal containing the noise are expected to be different than the portion that does not contain the noise. Further, if both portions include noise, consistency between the two sorted difference signals is not necessarily expected. Accordingly, the illustrative techniques of flow diagram 3700 may provide a convenient noise metric especially with intermittent noise and identifying when noise begins.

Step 3702 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 3702 may include recalling data from the memory for further processing.

Step 3704 may include processing equipment generating a first difference signal based on a first portion of the physiological data of step 3702 (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points of a portion of the physiological data to generate a first difference signal. In a further example, the processing equipment may compute a numerical derivative at each point of a portion of the physiological data, generating a first difference signal. Any suitable difference technique may be used by the processing equipment to generate the first difference signal.

Step 3706 may include processing equipment sorting the values of the first difference signal of step 3704. The processing equipment may sort the values of the first difference signal in ascending or descending order. Referencing sorted values in ascending order, the most negative values come first followed by less negative values, positive values, and finally larger positive values.

Step 3708 may include processing equipment determining a line fit of the sorted first difference signal of step 3706. In some embodiments, the processing equipment may perform a linear regression (e.g., a least-squares regression or a weighted least-squares regression) using at least a portion of the sorted first difference signal. In some embodiments, the processing equipment may fit a line using every point of the sorted difference signal. In some embodiments, the processing equipment may fit a line using a portion of the sorted difference signal. For example, the processing equipment may omit one or more points at one or both ends of the sorted difference signal when determining the line fit. In some embodiments, the line fit may include a slope value and an ordinate intercept value (e.g., using the y=mx+b linear form where m is the slope and b is the intercept).

Similar to performing steps 3704-3708, the processing equipment may perform steps 3710-3714 using a second portion of physiological data. Step 3710 may include processing equipment generating a second difference signal based on a second portion of the physiological data of step 3702. Step 3712 may include processing equipment sorting the values of the second difference signal. Step 3714 may include processing equipment determining a line fit of the sorted second difference signal. The first and second portions of the physiological data may be, but need not be, exclusive of each other. The physiological data may be partitioned into two portions using any suitable technique. In some embodiments, the first and second portions may be of equal length (e.g., each may include the same number of samples or time interval). In some embodiments, the first and second portions may have different lengths (e.g., each may include the same number of samples or time interval).

In an illustrative example, six seconds of data, captured at a sampling rate of 57 Hz, may be received (i.e., about 342 samples). The first 171 samples (i.e., samples 1-171) may be included in the first portion, and the second 171 samples (i.e., samples 172-342) may be included in the second portion. Plot 3800 of FIG. 38 shows PPG signal 3802 having about 342 samples, while plot 3810 of FIG. 38 shows difference signal 3812, which is a calculated first derivative signal of PPG signal 3802. First and second portions are denoted by "P1" and "P2" in FIG. 38, corresponding to first and second difference signals, respectively, each having about 171 samples. In some embodiments, the processing equipment may determine the first and second difference signals as portions of a single difference signal, as shown in plot 3810 where the first portion "P1" of difference signal 3812 may be considered the first difference signal, and the second portion "P2" of difference signal 3812 may be considered the second difference signal. Alternatively, PPG signal 3802 could be partitioned into portions and two separate corresponding difference signals could be calculated and sorted. Plot 3820 of FIG. 38 shows sorted first difference signal 3822 and sorted second difference signal 3832. Although shown as having offset sample numbers for illustration (e.g., allowing slopes of the line fits to be directly compared but not necessarily the intercepts), the sorted difference signals 3822 and 3832 could each be numbered about 1-171 samples (e.g., allowing both the slopes and intercepts of the line fits to be compared). Sorted first difference signal 3822 includes the sorted data points of first portion "P1" of difference signal 3812, while sorted second difference signal 3832 includes the sorted data points of second portion "P2" of difference signal 3812. Note that difference signal 3812 may have a different length than PPG signal 3802 due to the difference calculation technique. For example, using a forward difference, a difference signal may include one less point than the corresponding physiological data from which it was derived.

Step 3716 may include processing equipment determining a difference between slopes of the line fits determined at steps 3708 and 3714. The line fits may be expected to provide similar slopes if the physiological data does not include relatively large amounts of noise. Differences in the slopes of the line fits may indicate that either or both of the first and second portions of the physiological data include appreciable noise. In some embodiments, the difference in slopes may include calculating a difference between the slopes, a normalized difference between the slopes, a bounded difference of the slopes, a ratio of the slopes, any other suitable comparison metric, or any combination thereof. In some embodiments, the use of portions of equal length may allow a direct comparison of slopes of corresponding line fits, because each sorted difference signal will have equivalent domain lengths along an abscissa, as well as an equivalent range of expected difference values. Plot 3820 of FIG. 38 shows line fit 3824 corresponding to sorted first difference signal 3822, and line fit 3834 corresponding to sorted first difference signal 3832, with each line fit generated using a least squares regression. In the illustrated example, the calculated slopes, in arbitrary units, for line fit 3824 and 3834 are 0.2048 and 0.1952, respectively. Using these illustrative numbers, the processing equipment may, for example, determine a normalized ratio of 0.95 (i.e., minimum divided by maximum), a percent difference of 5% (i.e., normalizing by the average value), a difference of 0.0096 (i.e., subtracting minimum from maximum), along with any other suitable comparison metric.

Step 3718 may include processing equipment determining a goodness of fit, a noise metric, or both, for the first and second sorted difference signals. In some embodiments, the processing equipment may compare a comparison metric from step 3816 with one or more thresholds to determine the goodness of fit, a noise metric, or both. For example, the processing equipment may compare the normalized ratio of the slopes with a threshold such as 0.8, and if the ratio is between 0.8 and 1.0, then the fit is considered good. In some embodiments, the comparison metric itself, or calculation derived thereof, may be used as a goodness of fit value. For example, any or all of Eqs. 20-22 may be used to determine the goodness of fit and/or a noise metric:

$$\text{Noise Metric} = 1 - \frac{\text{Slope}_{min}}{\text{Slope}_{max}} \quad (20)$$

$$\text{Noise Metric} = \text{Slope}_{max} - \text{Slope}_{min} \quad (21)$$

$$\text{Noise Metric} = \frac{\text{Slope}_{max} - \text{Slope}_{min}}{\text{Slope}_{avg}} \quad (22)$$

where $\text{Slope}_{min}$ is the less of the slope values, $\text{Slope}_{max}$ is the greater of the slope values, and $\text{Slope}_{Avg}$ is the average of the slope values.

In some embodiments, the processing equipment may perform step 3718 without performing steps 3708, 3714, and 3716. For example, the processing equipment need not fit a line to the either of the difference signals to determine a noise metric based on the first and second portions. In a further example, referencing portions of equal length, the sorted values of the first and second portions may be plotted against each other (e.g., if plotted, the values of the first portion may correspond to the abscissa and the values of the second portion may correspond to the ordinate), and a correlation coefficient may be determined. The set of points need not be plotted, and may be generated using Eq. 23, as shown below:

$$P_i = (X_{1,i}, X_{2,i}) \quad (23)$$

in which $P_i$ is the point for index i, and $X_{1,i}$ and $X_{2,i}$ are the values of the first and second portions, respectively. In a further example, a set of points may be generated using Eq. 23, and the normalized difference between the generated set of points and a set of points having the same abscissa value and ordinate value (e.g., if plotted, the points would lie on a line through the origin having a slope of one).

In some embodiments, the processing equipment may apply any suitable statistical technique to the two sorted difference signals. For example, the processing equipment may apply a KS Test to the first and second portions by comparing the sorted difference signals to a predetermined distribution. In a further example, the processing equipment may use a function other than a line as a fitting reference. For example, the processing equipment may fit a polynomial of any order to the first and second difference signals, or any other suitable function, and compare the fitted functions to each other or to a reference function.

In some embodiments, the illustrative techniques of flow diagram 3700 may be applied to more than two portions of physiological data. For example, a window of physiological data may be partitioned into three portions, and three difference signals may be determined and sorted to yield three line fits which may be compared. Any suitable number of portions may be used to determine a goodness of fit, noise metric, or both, in accordance with the illustrative techniques of flow diagram 3700.

Figure 39:
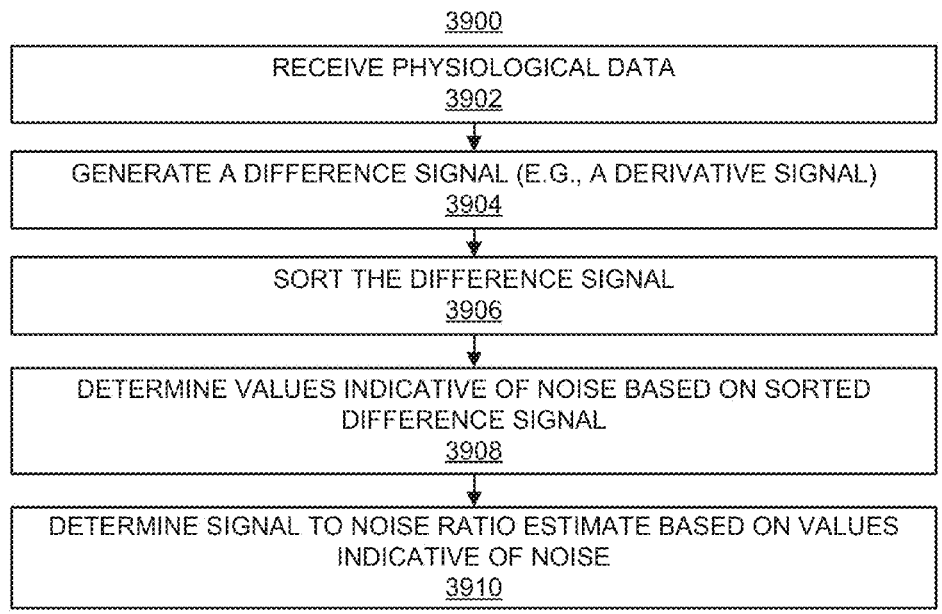
FIG. 39 is a flow diagram of illustrative steps for estimating signal-to-noise ratio based on a sorted difference signal, in accordance with some embodiments of the present disclosure.

FIG. 39 is a flow diagram 3900 of illustrative steps for estimating signal-to-noise ratio based on a sorted difference signal, in accordance with some embodiments of the present disclosure.

Step 3902 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 3902 may include recalling data from the memory for further processing.

Step 3904 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal.

Step 3906 may include processing equipment sorting the difference values of step 3904. The processing equipment may sort the values in ascending or descending order. Referencing sorted values in ascending order, the most negative values come first followed by less negative values, positive values, and finally larger positive values.

Step 3908 may include processing equipment determining at least two values indicative of noise (e.g., a noise metric) using any of the techniques described in the context of FIGS. 30-41, along with any metrics determined using the techniques described in the context of FIGS. 11-28, or any combination thereof. For example, the processing equipment may determine noise metric values using the techniques described in the context of FIGS. 30-41, along with any metrics determined using the techniques described in the context of FIGS. 11-28, and then select the maximum noise metric value (e.g., with higher noise metric values corresponding to noisier physiological data) using Eq. 24:

$$\text{Noise Metric} = \text{MAX}(V_1, V_2, V_3) \quad (24)$$

in which $V_1$, $V_2$, and $V_3$ are the noise values from the three techniques. In some embodiments, the processing equipment may select a single value, generate a combined value using a suitable technique (e.g., an average, a weighted average, a product, or some other combination), determine a noise metric based on a lookup table using one or more noise metrics as an input, perform any other suitable calculation of a noise metric, or any combination thereof.

Step 3910 may include processing equipment determining a signal-to-noise ratio estimate based on the values indicative of noise, or a metric derived thereof, from step 3908. In some embodiments, the reference relationship between the signal-to-noise ratio and the values indicative of noise may be represented by a function, a look-up table, a mapping, any other suitable representation, or any combination thereof. In some embodiments, the reference relationship may be stored in memory, and accessed by the processing equipment.

Figure 40:
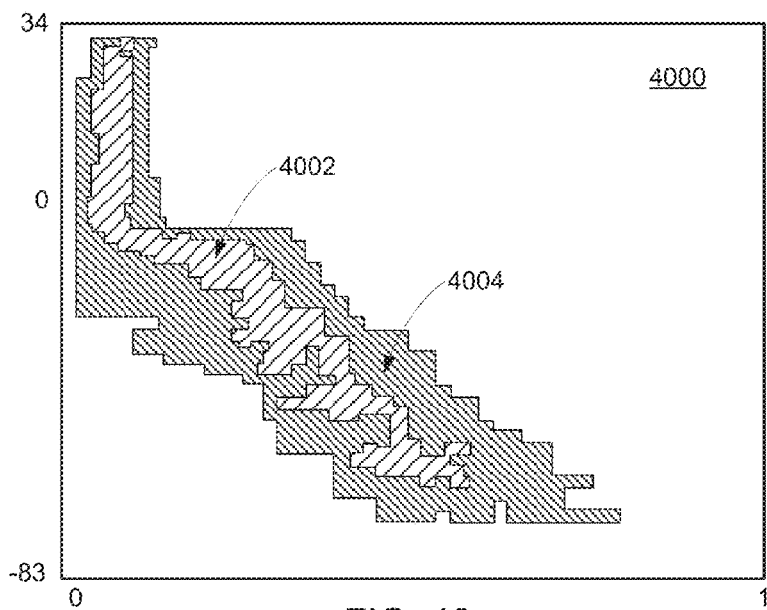
FIG. 40 is a panel showing an illustrative contour plot of instances of signal-to-noise ratio values and ordered statistic noise metric values, in accordance with some embodiments of the present disclosure.

FIG. 40 is a panel showing an illustrative contour plot 4000 of instances of signal-to-noise ratio values and ordered statistic noise metric values, in accordance with some embodiments of the present disclosure. The abscissa of plot 4000 represents the noise metric values, and the ordinate represents the values indicative of signal-to-noise ratio in units of decibels (dB). Region 4002 corresponds to relatively higher number instances, while region 4004 corresponds to an intermediate number of instances, while the remaining two-dimensional space of plot 4000 corresponds to relatively lower number of instances. In some embodiments, a look-up table, data structure, or other reference including data relating a noise metric and a value indicative of signal-to-noise ratio (e.g., such as that represented by plot 4000) may be stored in memory. For example, in some implementations, the processing equipment may determine a noise metric value based on physiological signal, and refer to a look-up table to determine a signal-to-noise estimate based on the noise metric value. In a further example, a function (e.g., piecewise or continuous) or other relationship may be derived to approximately describe the relationship shown in plot 4000.

Figure 41:
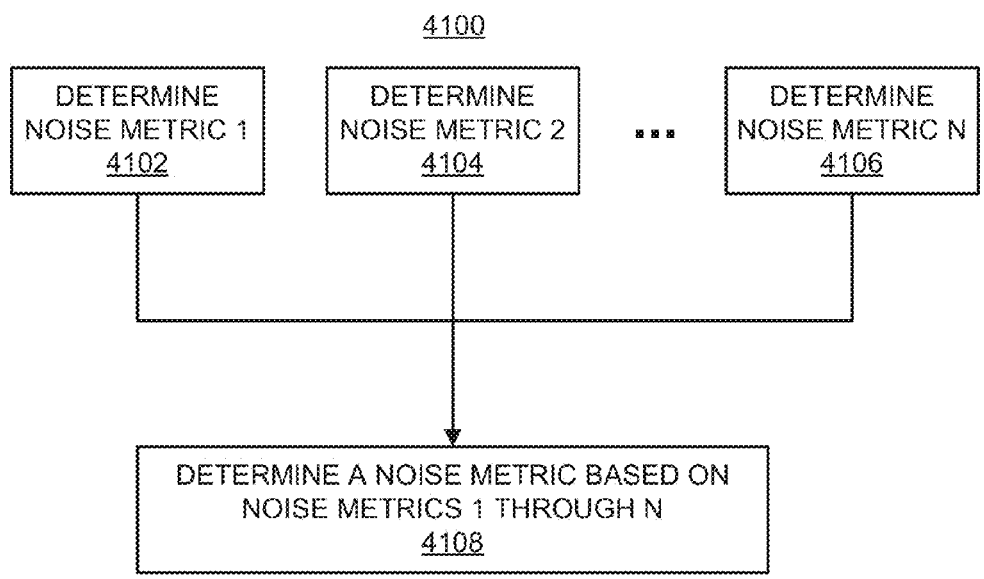
FIG. 41 is a flow diagram of illustrative steps for determining a resultant noise metric based on a combination of noise metrics, in accordance with some embodiments of the present disclosure.

FIG. 41 is a flow diagram 4100 of illustrative steps for determining a resultant noise metric based on a combination of noise metrics, in accordance with some embodiments of the present disclosure.

Step 4102 may include processing equipment determining a first noise metric, using any suitable technique in accordance with the present disclosure. For example, the processing equipment determine the first noise metric using any of the techniques described in the context of FIGS. 30-41, along with any metrics determined using the techniques described in the context of FIGS. 11-28. Step 4104 may include processing equipment determining a second noise metric, using any suitable technique in accordance with the present disclosure. For example, the processing equipment may determine the second noise metric using any of the techniques described in the context of FIGS. 30-41, along with any metrics determined using the techniques described in the context of FIGS. 11-28. Step 4106 may include processing equipment determining an Nth noise metric, using any suitable technique in accordance with the present disclosure. For example, the processing equipment may determine the $N^{th}$ noise metric, where N can be 2 or greater, using any of the techniques described in the context of FIGS. 30-41, along with any metrics determined using the techniques described in the context of FIGS. 11-28. In some embodiments, each metric of steps 4102-4106 may be of a different type (e.g., determined using a different technique). In some embodiments, each noise metric of steps 4102-4106 may be of the same type, although different settings may be used (e.g., determined using the same technique but using different thresholds, offsets, or other settings).

Step 4108 may include processing equipment determining an algorithm setting based on the noise metrics of steps 4102-4106. In some embodiments, the processing equipment may combine the noise metrics into a single noise metric. For example, the processing equipment may sum, average, multiply, divide, subtract, or otherwise condense the noise metrics to determine a resulting metric value indicative of noise. In some embodiments, the processing equipment may use the noise metrics a an input to a look-up table, reference function, or other reference to determine a resultant noise metric. For example, the processing equipment may access a N-dimensional look-up table, with each of the N dimensions corresponding to values of a particular noise metric (e.g., a 3-D look-up table indexed by values of three metrics). Such a table may be generated, for example, from historical data or an analytical model. In some embodiments, the processing equipment may consider multiple metrics of steps 4102-4106 accordingly to conditional logic. For example, the processing equipment may increase the amount of signal processing if the value of a particular noise metric exceeds a threshold, even if another metric suggests that the signal contains a dicrotic notch the value of a particular noise metric.

In some embodiments, signal conditioning may be applied to a physiological signal to aid in processing the signal for rate information. Signal conditioning may include filtering, detrending, smoothing, normalizing, derivative limiting, any other suitable conditioning, or any combination thereof. Physiological pulse rates may generally fall into a particular range (e.g., 20-300 BPM for humans), and accordingly signal conditioning may be used to reduce the presence or effects of signal components outside of this particular range. Further, a narrower pulse range may be expected for a subject, based on previous data for example, and a signal may be conditioned accordingly. The presence of noise may also be addressed using signal conditioning. For example, ambient radiation (e.g., from artificial lighting, monitors, or sunlight) may impart a noise component in a physiological signal. In a further example, electronic noise (e.g., system noise) may also impart a noise component in a physiological signal. In a further example, motion or other subject activity may alter a physiological signal, possibly obscuring signal components of interest for extracting rate information. In some embodiments, the Signal Conditioning techniques discussed herein may apply to operation in any Mode, or while performing any other suitable task that may be performed by the processing equipment that may involve a physiological signal. Any of the signal conditioned technique disclosed herein, alone or in any combination, may be applied, for example, in the context of step 412 of flow diagram 400 of FIG. 4.

Figure 42:
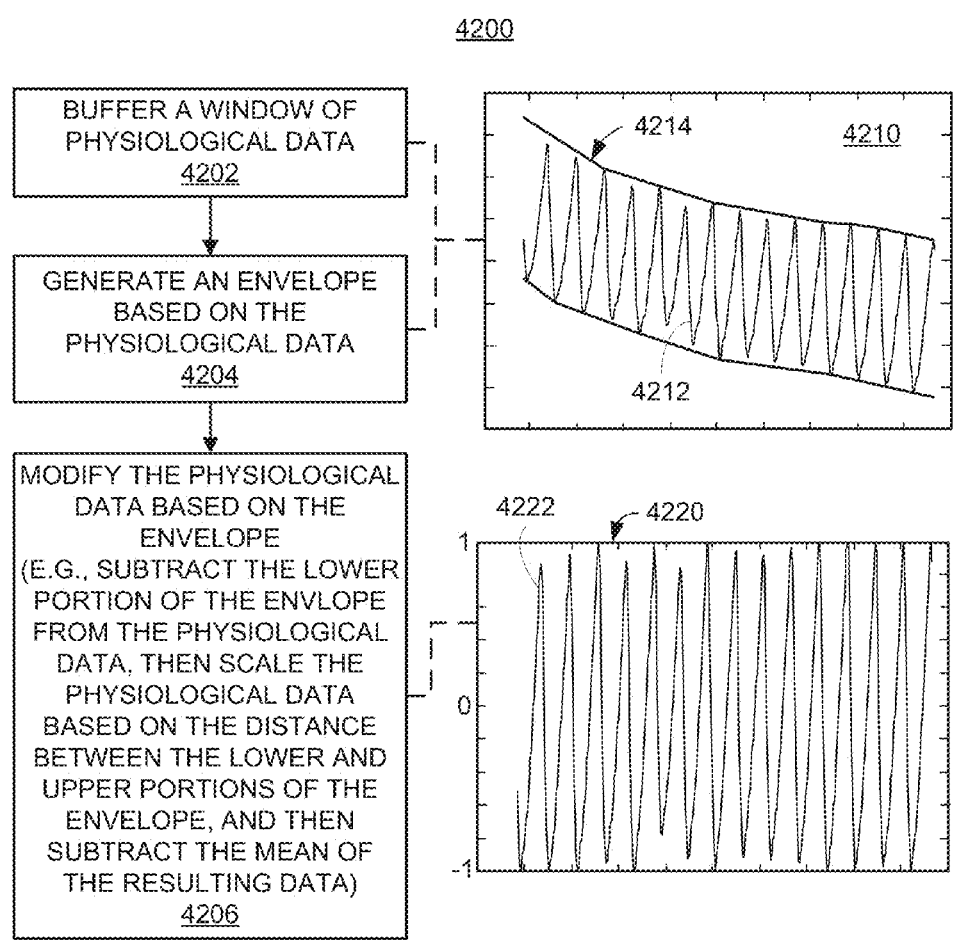
FIG. 42 is a flow diagram of illustrative steps for modifying physiological data using an envelope, in accordance with some embodiments of the present disclosure.

FIG. 42 is a flow diagram 4200 of illustrative steps for modifying physiological data (e.g., a segment of an intensity signal) using an envelope, in accordance with some embodiments of the present disclosure. In some embodiments, the illustrative steps of flow diagram 4200 may aid in conditioning a physiological signal by adjusting a baseline, scaling at least some peaks, or both. In some embodiments, the illustrative steps of flow diagram 4200 may aid in reducing the effects of low frequency components (e.g., a constant or drifting baseline, peak amplitude changes) during subsequent processing of the window of data.

Step 4202 may include processing equipment receiving a window of data, derived from a physiological signal. In some embodiments, the window may include a particular time interval (e.g., the most recent six seconds of a processed physiological signal). Step 4202 may include pre-processing (e.g., using pre-processor 320) the output of a physiological sensor, and then storing a window of the processed data in any suitable memory or buffer (e.g., QSM 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity. Panel 4210 shows an illustrative window of data42 derived from a physiological signal.

Step 4204 may include the processing equipment generating an envelope (e.g., varying upper and lower limits) based on the window of data of step 4202. The envelope may include an upper trace, which may be an outline of the peak data values, and a lower trace, which may be an outline of the valley data values. In some embodiments, the upper and lower traces may be generated using a mathematical formalism such as, for example, a linear or spline fit through the data points. The upper and lower traces may coincide with all, some, or no data points, depending on the enveloping technique used. Any suitable technique may be used to generate an envelope of the window of data. Panel 4210 shows an illustrative envelope 4214 generated for window of data 4212.

Step 4206 may include the processing equipment modifying the physiological data of step 4202 based on the envelope of step 4204. In some embodiments, step 4206 may include generating a new window of data. For example, the midpoint of the difference between the lower and upper trace at each location may be set as a new origin (e.g., a baseline). The upper and lower traces may then be scaled to respective desired values at each point (e.g., 1 and 0, respectively, or 1 and −1, respectively) and the window of data may be similarly amplitude scaled at each point. In a further example, the lower trace may be subtracted from the window of data. The window of data may then be scaled to respective desired values at each point (e.g., to between 2 and 0) based on the difference between the lower and upper traces. The mean may then be subtracted, centering the window of data about zero. Referencing Eq. 25 below, either of the two previous examples gives a modified window of data $M_{-1,1}(x_i)$ for each data point i at data point location $x_i$, ranging from −1 to 1, in which $f(x_i)$ is the initial window of data, $g(x_i)$ is the lower trace, and $h(x_i)$ is the upper trace. Referencing Eq. 26 below, either of the two previous examples gives a modified window of data $M_{0,1}(x_i)$ for each data point i at data point location $x_i$, ranging from 0 to 1, in which $f(x_i)$ is the initial window of data, $g(x_i)$ is the lower trace, and $h(x_i)$ is the upper trace. Any suitable mathematical formula, such as Eqs. 25 or 26, or any other suitable equation, may be used to modify a window of data based on an envelope.

$$M_{-1,1}(x_i) = \frac{2(f(x_i) - g(x_i))}{h(x_i) - g(x_i)} - 1 \quad (25)$$

$$M_{0,1}(x_i) = \frac{f(x_i) - g(x_i)}{h(x_i) - g(x_i)} \quad (26)$$

In some embodiments, the processing equipment may down-weight outlier points in the buffered window of data. In some embodiments, the processing equipment may down-weight one or more points at each end of the buffered window of data.

Panel 4220 shows an illustrative modified window of data 4222, scaled to range from −1 to 1, centered about zero. Note that the lower and upper traces have been scaled to lie horizontal at −1 and 1, respectively, and window of data 4222 has been scaled accordingly. As compared to window of data 4212, modified window of data 4222 is shown to have a baseline of zero (rather than the trending baseline of window of data 4212), and a more consistent range of peak and valley values. Modified window of data 4222 may be used in any of the disclosed operation Modes, or any other suitable processes accepting a window of data derived from a physiological signal as an input.

Figure 43:
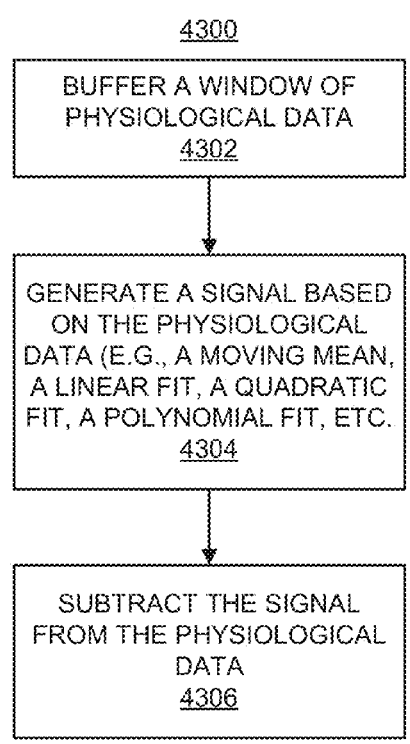
FIG. 43 is a flow diagram of illustrative steps for modifying physiological data by subtracting a trend, in accordance with some embodiments of the present disclosure.

FIG. 43 is a flow diagram 4300 of illustrative steps for modifying physiological data by subtracting a trend, in accordance with some embodiments of the present disclosure. In some embodiments, the illustrative steps of flow diagram 4300 may aid in conditioning a physiological signal by modifying a baseline. In some embodiments, the illustrative steps of flow diagram 4300 may aid in reducing the effects of low frequency components (e.g., a constant or drifting baseline) during subsequent processing of the window of data.

Step 4302 may include processing equipment buffering a window of data, derived from a physiological signal. In some embodiments, the window may include a particular time interval (e.g., the most recent six seconds of a processed physiological signal). Step 4302 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity.

Step 4304 may include the processing equipment generating a signal based on the window of data of step 4302. The generated signal may represent a baseline or otherwise a trend in the window of data of step 4302. In some embodiments, the signal generated at step 4304 may include a moving mean, a linear fit (e.g., from a linear regression), a quadratic fit, any other suitable polynomial fit (e.g., using a "least-squares" regression), any other suitable functional fit (e.g., exponential, logarithmic, sinusoidal), any piecewise combination thereof, or any other combination thereof. Any suitable technique for generating a signal indicative of a trend may be used at step 4304. In some embodiments, each data point within the window of data may be given equal weighting. In some embodiments the processing equipment may down-weight outlier points or one or more points at each end of the buffered window of data.

Step 4306 may include the processing equipment subtracting the generated signal of step 4304 from the window of data of step 4302. In some embodiments, step 4306 may include generating a new window of data (e.g., the window data of step 4302 with the signal of step 4304 removed), which may be further processed, stored in any suitable memory, or both. Subtraction of the signal of step 4304 from the window of data of step 4302 may aid in processing the data for rate information by removing low frequency components. Further illustration of the signal subtraction of flow diagram 4300 is provided by FIGS. 44-46.

Figure 44:
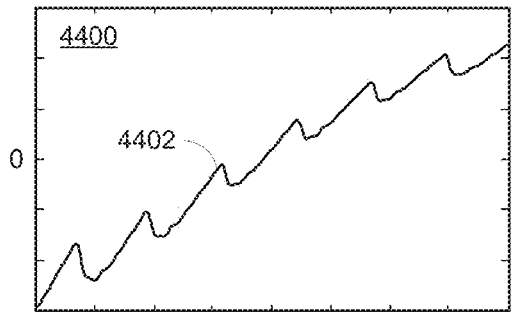
FIG. 44 is a plot of an illustrative window of data with the mean removed, in accordance with some embodiments of the present disclosure.

FIG. 44 is a plot 4400 of an illustrative window of data 4402 with the mean removed, in accordance with some embodiments of the present disclosure. The abscissa of plot 4400 is presented in units proportional to sample number, while the ordinate is presented in arbitrary units, with zero notated. Window of data 4402 is shown to include an increasing baseline, even with the mean value of the data removed. Accordingly, subtraction of the mean may provide unsatisfactory results when used with data having a changing baseline. In some such circumstances, a linear baseline, or other suitable trending baseline, may be subtracted from the window of data rather than a mean value. In some cases, in which the baseline of a window of data may be relatively constant, a mean subtraction may be preferred to a more complex baseline fit.

Figure 45:
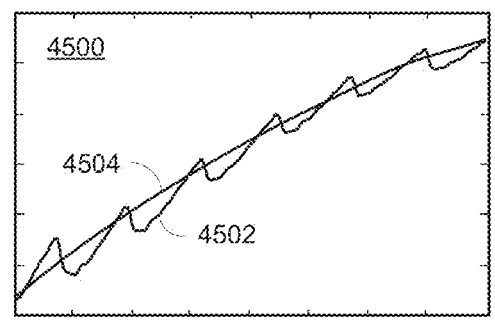
FIG. 45 is a plot of an illustrative window of data and a quadratic fit, in accordance with some embodiments of the present disclosure.
Figure 46:
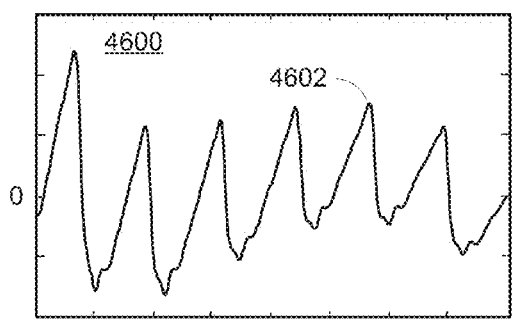
FIG. 46 is a plot of the illustrative window of data of FIG. 45 with the quadratic fit subtracted, in accordance with some embodiments of the present disclosure.

FIG. 45 is a plot 4500 of an illustrative window of data 4502 and a quadratic fit 4504, in accordance with some embodiments of the present disclosure. The abscissa of plot 4500 is presented in units proportional to sample number, while the ordinate is presented in arbitrary units. As compared to FIG. 44, quadratic fit 4504 follows the trending baseline of window of data 4502 more closely than a mean subtraction would be capable of. FIG. 46 shows a plot 4600 of modified window of data 4602 derived from illustrative window of data 4502 of FIG. 45 with quadratic fit 4504 subtracted, in accordance with some embodiments of the present disclosure. The abscissa of plot 4600 is presented in units proportional to sample number, while the ordinate is presented in arbitrary units, with zero notated. Modified window of data 4602 is substantially centered about zero, with a relatively constant baseline of zero.

Figure 47:
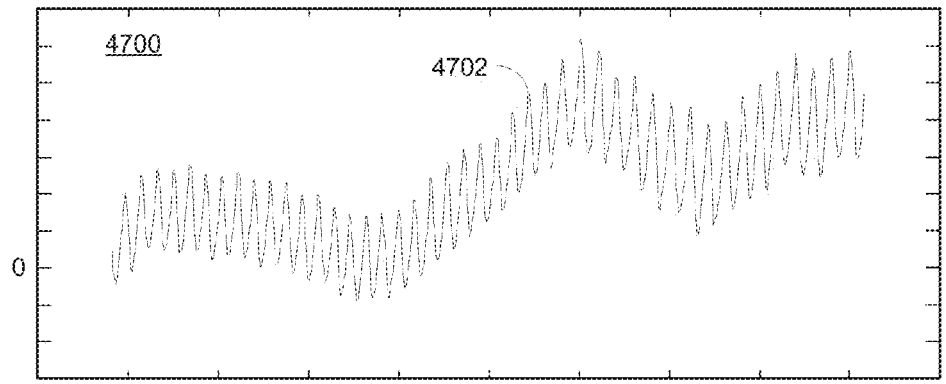
FIG. 47 is a plot of an illustrative modified window of data derived from an original window of data with the mean subtracted, in accordance with some embodiments of the present disclosure.
Figure 48:
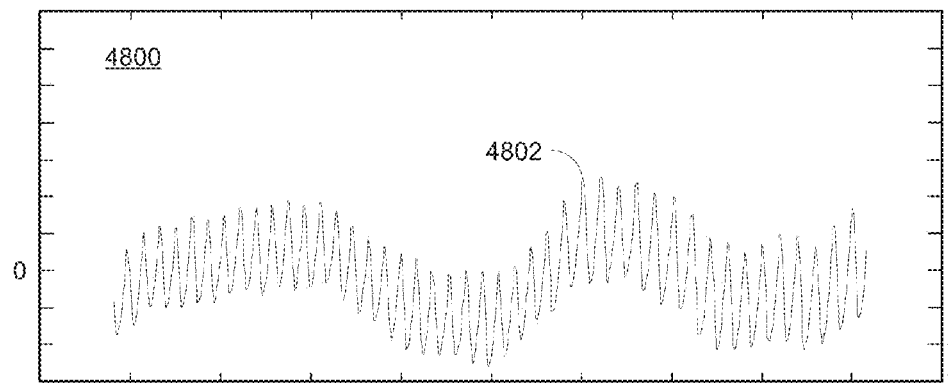
FIG. 48 is a plot of an illustrative modified window of data derived from the same original window of data as FIG. 47 with a linear baseline subtracted, in accordance with some embodiments of the present disclosure.
Figure 49:
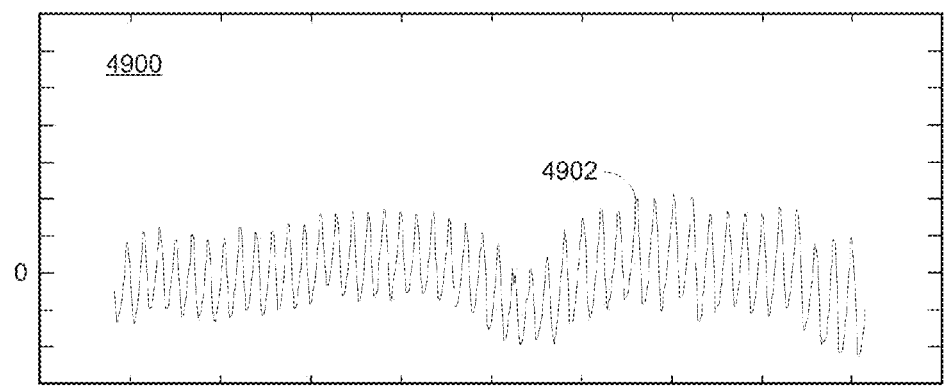
FIG. 49 is a plot of an illustrative modified window of data derived from the same original windows of data as FIGS. 47 and 48 with a quadratic baseline subtracted, in accordance with some embodiments of the present disclosure.

FIG. 47 is a plot 4700 of an illustrative modified window of data 4702 derived from an original window of data with the mean subtracted, in accordance with some embodiments of the present disclosure. The abscissa of plots 4700, 4800, and 4900 of FIGS. 47-49 are presented in units proportion to time (or sample number), while the ordinate is presented in arbitrary units, with zero notated. Modified window of data 4702 exhibits significant low frequency activity that is not substantially reduced nor eliminated by mean subtraction. Accordingly, modified window of data 4702 may present challenges for some techniques for extracting rate information. Note that modified window of data 4702 spans seven tick marks along the ordinate, in arbitrary units.

FIG. 48 is a plot 4800 of an illustrative modified window of data 4802 derived from the same original window of data as FIG. 47 with a linear baseline subtracted, in accordance with some embodiments of the present disclosure. Note that modified window of data 4802 spans almost six tick marks along the ordinate, in similar units of plot 4700, and accordingly exhibits relatively less (e.g., smaller amplitude) low frequency activity than modified window of data 3802.

FIG. 49 is a plot 4900 of an illustrative modified window of data 4902 derived from the same original windows of data as FIGS. 47 and 48 with a quadratic baseline subtracted, in accordance with some embodiments of the present disclosure. Note that modified window of data 4902 spans almost four tick marks along the ordinate, in similar units of plots 4700 and 4800, and accordingly exhibits relatively less (e.g., smaller amplitude) low frequency activity than either of modified windows of data 4702 and 4802. In some circumstances, the subtraction of a quadratic fit may provide better results than a mean subtraction or linear subtraction. In some circumstances, the subtraction of a higher order polynomial fit, or any other suitable fit, may provide better results than a mean subtraction, linear subtraction, or quadratic subtraction. In some circumstances, a relatively simpler baseline fit may be preferred to a more complex baseline fit.

In some embodiments, processing equipment may apply a derivative limiter to a window of data, or signal derived thereof. A physiological pulse may be expected to exhibit oscillatory behavior, while baseline shifts or other non-oscillatory behavior may likely be attributable to noise (e.g., subject movement, electromagnetic interference). Further, the first derivative of a primarily oscillatory signal may also exhibit oscillatory behavior. Relatively large baseline shifts may be accompanied by a corresponding increase in the value of the derivative of the data. The baseline shift may be observable as a relatively larger peak (positive or negative) in the first derivative as compared to other peaks in the first derivative corresponding to purely oscillatory activity of the signal. In some embodiments, a comparison of the differences or derivatives of physiological data against a suitable threshold may be used as a noise metric. For example, values of the physiological data falling below a suitable threshold value may be considered to exhibit low noise. Similarly, values of the physiological data above a suitable threshold value may be considered to exhibit high noise. In some embodiments, a stability function such as, for example, a Lyapunov function that relates to oscillator stability, may be used to identify noise in physiological data. In some embodiments, the identification of high positive or negative slopes or noise can be used to limit derivative values in the window of data. The following discussion in the context of FIGS. 50-55 provides some illustrative techniques for applying a derivative limiter to physiological data.

Figure 50:
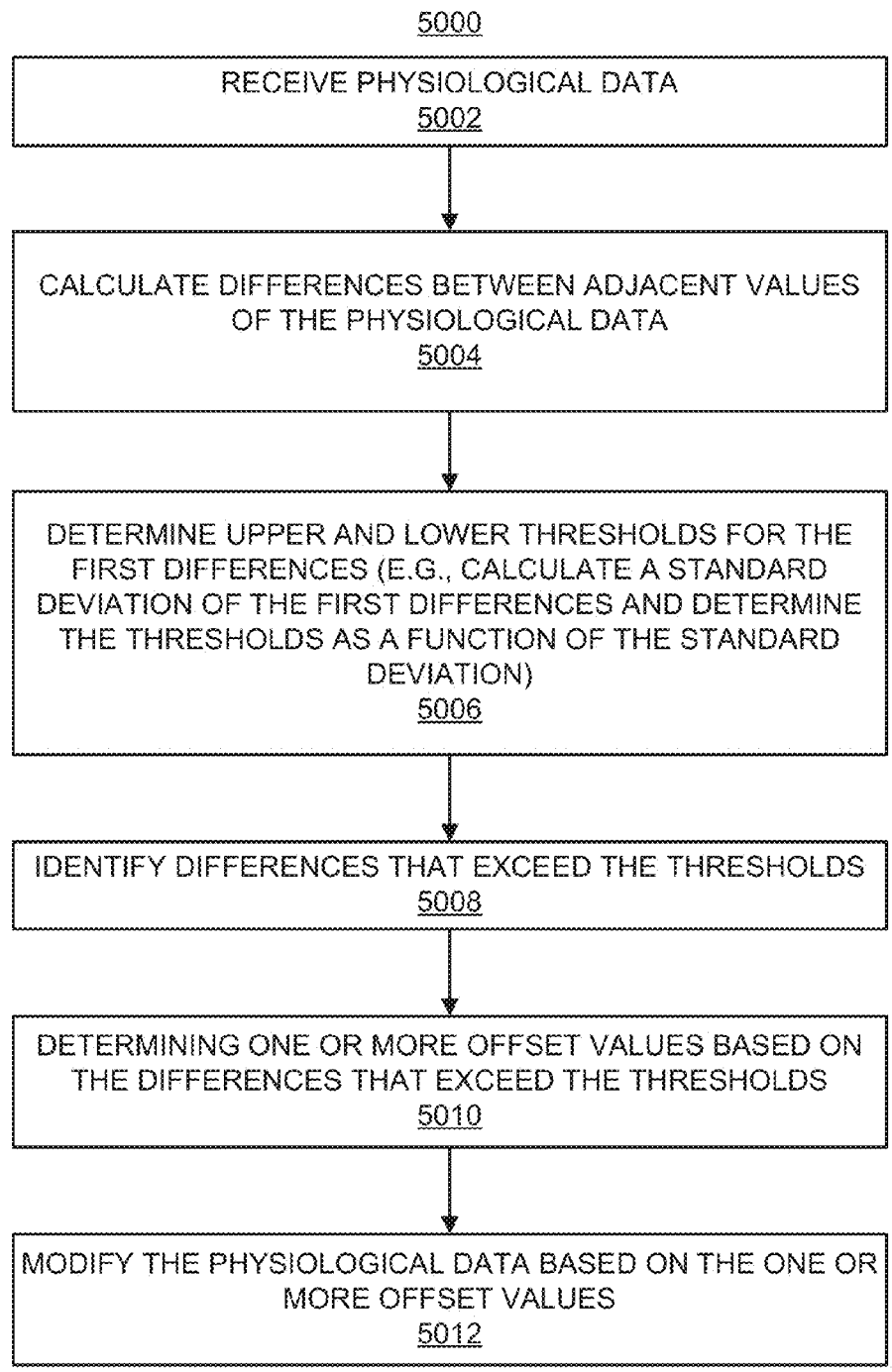
FIG. 50 is a flow diagram of illustrative steps for modifying physiological data using a derivative limiter, in accordance with some embodiments of the present disclosure.
Figure 51:
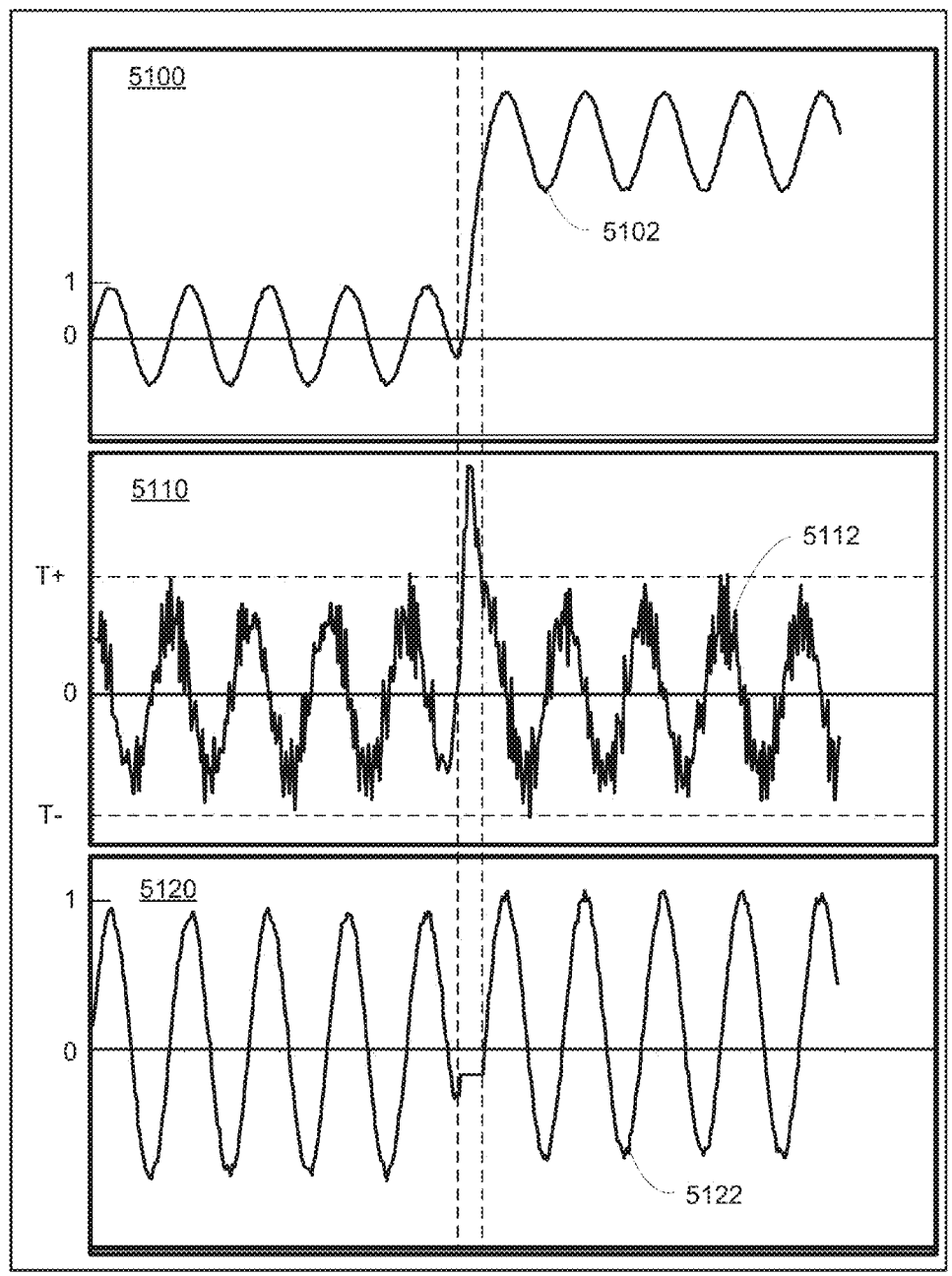
FIG. 51 is a panel of three plots showing an illustrative window of data having a baseline shift, a first derivative of the window of data, and a modified window of data, in accordance with some embodiments of the present disclosure.

FIG. 50 is a flow diagram 5000 of illustrative steps for modifying physiological data using a derivative limiter, in accordance with some embodiments of the present disclosure. The illustrative techniques of flow diagram 5000 may be used to modify localized sections of a buffer of data. When there is a high slope or baseline shift in the buffer of data, bandpass filters and polynomial de-trending, for example, may not adequately remove the artifact without distorting the surrounding data. In some circumstances, a relatively noise-free PPG signal likely has a certain range of slopes or differences. If there are slopes or differences outside of the expected range, then under some circumstances it may be assumed that they are due to noise, and the physiological data may be modified accordingly. FIG. 51 is a panel of three plots showing an illustrative window of data having a baseline shift, a first derivative of the window of data, and a modified window of data, in accordance with some embodiments of the present disclosure. FIG. 51 will be referred to below during the discussion of the illustrative steps of flow diagram 5000.

Step 5002 may include processing equipment receiving physiological data, for example, by buffering a window of data derived from a physiological signal. In some embodiments, the physiological data may include a particular time interval of samples (e.g., the most recent six seconds of a processed physiological signal). Step 5002 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity. In some embodiments, the received physiological data may have previously undergone de-trending (e.g., polynomial de-trending using any suitable order polynomial) or other signal conditioning. Plot 5100 of FIG. 51 shows an illustrative window of data 5102 exhibiting a baseline shift.

Step 5004 may include processing equipment calculating differences between adjacent samples of the physiological data. In some embodiments, the processing equipment may perform a subtraction between values of adjacent samples. In some embodiments, the processing equipment may calculate the differences by calculating a first derivative of the physiological data. The processing equipment may calculate a series of differences between each adjacent pair of samples, and may accordingly generate a difference signal using the calculated differences. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment.

Step 5006 may include processing equipment determining upper and lower thresholds for the differences calculated at step 5004. The upper and lower thresholds may be determined based on the difference values themselves. For example, a threshold may be determined using the standard deviation of the physiological data, difference signal, or both. As shown in Eq. 27:

$$\text{thresholds} = \pm K\sigma \quad (27)$$

upper and lower thresholds may be proportional by proportionality constant K to the standard deviation σ of the differences. The upper and lower thresholds need not be symmetrical nor constant, and may each have unique K values. For example, pulses in a PPG signal are typically asymmetrical and the upper and lower K values may be different to reflect the different expected positive and negative differences. Plot 5110 of FIG. 51 shows difference signal 5112 (i.e., a calculated derivative of the illustrative window of data 5102), computed using a forward difference (although any suitable numerical difference or differentiation may be used). In some embodiments, thresholds may be determined based on one or more peaks in the difference signal. For example, in some embodiments, an upper threshold may be determined based on the height of all peaks excluding the highest peak (e.g., the threshold may be 1.5 times the average of the peaks heights excluding the highest peak). Any suitable upper and lower threshold may be used in accordance with the present disclosure. In some embodiments, a threshold may be based on algorithm settings. For example, if stronger de-trending is selected, the threshold values may be tightened (e.g., thresholds become relatively closer which makes exceeding them more likely).

Step 5008 may include processing equipment identifying differences of step 5004 that exceed the thresholds of step 5006. The difference signal may be compared to the upper and lower thresholds, and values exceeding the threshold range may be identified. Plot 5110 of FIG. 51 shows the difference signal 5112 of the data of plot 5100 along with upper and lower threshold values, T+ and T−, respectively). The highest peak in the difference signal corresponds to the baseline offset shown in plot 5100. The points of intersection of the highest peak with the upper threshold are shown by the vertical dashed lines. The difference signal crosses the upper threshold T+ due to the positive baseline shift. A similar negative baseline shift would result in a negative peak (a trough) which would cross the lower threshold. The processing equipment may identify a sample number, time value, coordinate pair, any other suitable description of a point, or any combination thereof for samples that exceed a threshold. In some embodiments, the processing equipment may identify the start and end of when the difference signal first exceeds a threshold.

Step 5010 may include processing equipment determining one or more offset values based on the identified differences of step 5008. Step 5012 may include processing equipment modifying the physiological data based on the one or more offset values determined at step 5010. In some embodiments, once the offset is subtracted, the processing equipment may bandpass filter the resulting signal, de-trend the resulting signal (e.g., polynomial de-trending using any suitable order polynomial), or both. Plot 5120 of FIG. 51 shows modified data 5122, derived from the physiological data of panel 5100, and modified using the threshold crossings of plot 5110. In the illustrated example of plot 5120 of FIG. 51, values are held constant for points corresponding to difference values exceeding the threshold, and an offset is applied at the rightmost threshold crossing to make the modified data continuous. It can be seen from a comparison of plots 5100 and 5120 of FIG. 51 that the illustrative techniques of flow diagram 5000 aid in reducing the baseline shift of the physiological data, and accordingly aid in subsequent processing.

The processing equipment may use any suitable offset and modification in the context of flow diagram 5000 of FIG. 50. In an illustrative example, the processing equipment may make adjacent values whose corresponding difference exceeds a threshold equal to each other (i.e., made to have a difference of 0). In a further illustrative example, the processing equipment may remove one or more of the values and shift remaining left or right portion of the data up or down. In a further illustrative example, the processing equipment may shift the left or right portion up or down to decrease the difference between the adjacent values (the difference can be a difference corresponding to the threshold or determined based on adjacent differences). In a further illustrative example, the processing equipment may add hysteresis to the modifications (e.g., confirm x number of subsequent differences are below threshold and if not, continue holding the previous value or continue current modification being used). In a further illustrative example, the processing equipment may smooth out the difference that exceeds a threshold by modifying not only the difference that exceeded the threshold, but also adjacent differences to smooth out the modification (e.g., the values and the first derivatives may be matched at each threshold crossing to smooth the resulting transitions).

Figure 52:
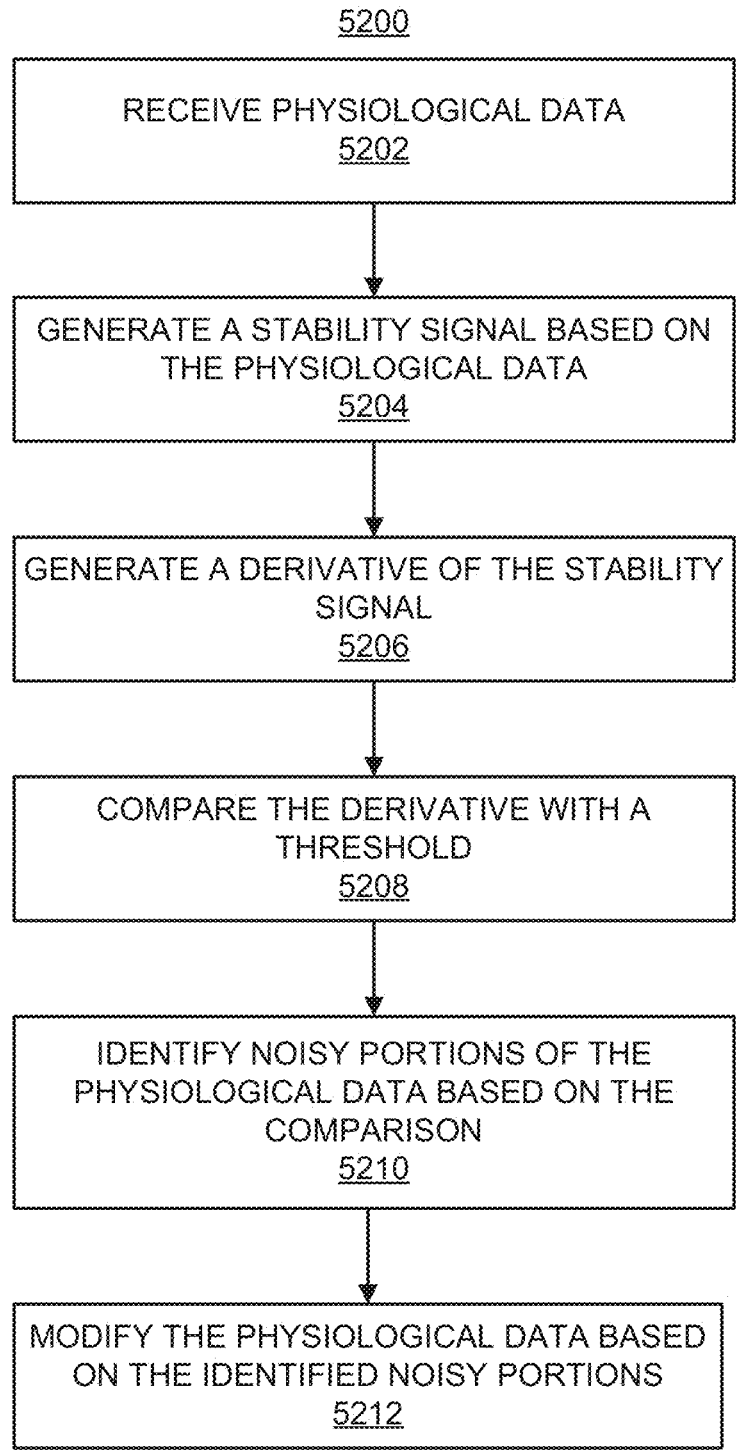
FIG. 52 is a flow diagram of illustrative steps for modifying physiological data using a stability function, in accordance with some embodiments of the present disclosure.
Figure 53:
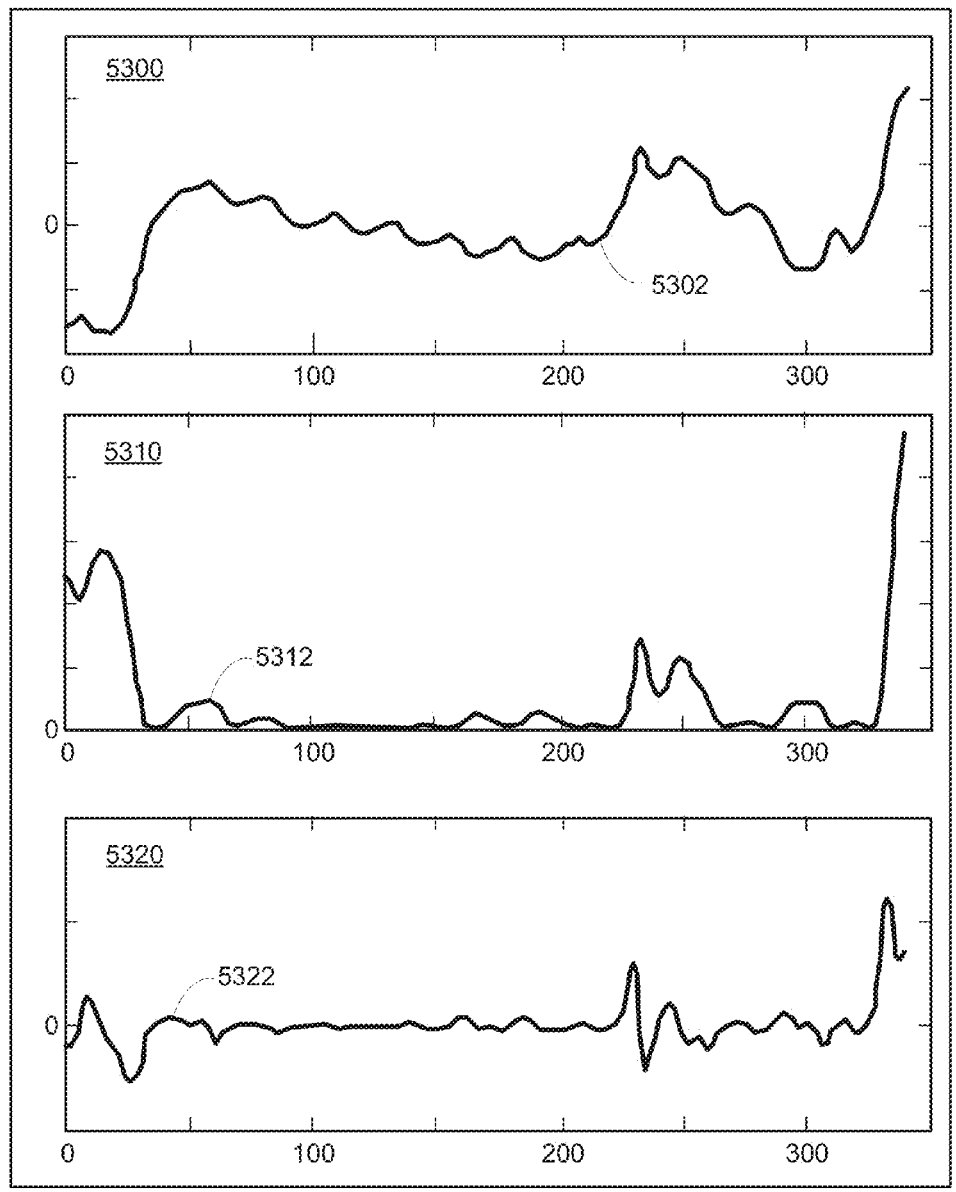
FIG. 53 is a panel of three plots showing an illustrative window of data, a stability function, and a derivative of the stability function, in accordance with some embodiments of the present disclosure.

FIG. 52 is a flow diagram 5200 of illustrative steps for modifying physiological data using a stability function, in accordance with some embodiments of the present disclosure. In some embodiments, the stability function may be used to scale physiological data for which the baseline varies over time (e.g., at a characteristic time scale larger than the period of the physiological pulse). In some embodiments, the first derivative of the stability function may be analyzed rather than a difference signal (e.g., as discussed in the context of flow diagram 5000 of FIG. 50) to identify and/or modify noisy portions of physiological data. FIG. 53 is a panel of three plots 5300, 5310, and 5320 showing an illustrative window of data 5302, a stability function 5312, and a derivative of the stability function 5322, respectively, in accordance with some embodiments of the present disclosure. FIG. 53 will be referred to below during the discussion of the illustrative steps of flow diagram 5200.

Step 5202 may include processing equipment receiving physiological data, for example, by buffering a window of data derived from a physiological signal. In some embodiments, the physiological data may include a particular time interval of samples (e.g., the most recent six seconds of a processed physiological signal). Step 5202 may include pre-processing (e.g., using pre-processor 320) the output of a physiological sensor, and then storing a window of the processed data in any suitable memory or buffer (e.g., queue serial module 72 of FIG. 2), for further processing by the processing equipment. In some embodiments, the window of data may be recalled from data stored in memory (e.g., RAM 54 of FIG. 2 or other suitable memory) for subsequent processing. In some embodiments, the window size (e.g., the number of samples or time interval of data to be buffered) of data is selected to capture multiple periods of oscillatory physiological activity. In some embodiments, the received physiological data may have previously undergone de-trending (e.g., polynomial de-trending using any suitable order polynomial) or other signal conditioning. Panel 5300 shows an illustrative window of physiological data exhibiting a varying baseline.

Step 5204 may include processing equipment generating a stability signal based on the physiological data. In some embodiments, the stability signal may be a Lyapunov function, for example, generated using the following Eq. 28:

$$L = \left(\frac{dx}{dt}\right)^2 + x^2 \qquad (28)$$

where x are the sample values, dx/dt are the derivative values (calculated using any suitable numerical or analytical method), and L is the Lyapunov function. Panel 5310 shows a Lyapunov function generated from the physiological data using Eq. 28. Step 5206 may include processing equipment generating a derivative of the stability signal. Panel 5320 shows a first derivative of the Lyapunov function of panel 5310. Typically, Lyapunov functions are used to analyze the stability of a linear or non-linear dynamic system. The system under test is considered stable when the time derivative of the Lyapunov function is zero. In the context of a physiological signal, the time derivative of a Lyapunov function may provide an indication of the noise level in the physiological data.

Step 5208 may include processing equipment comparing the derivative of the stability function of step 5206 with a threshold. The derivative of the stability function may provide an indication of the noise level in the physiological data. In some embodiments, the processing equipment may generate the threshold at step 5208. For example, the threshold may include one or more predetermined values, which may be constant or variable. In a further example, the processing equipment may determine the threshold based on the standard deviation of the derivative of the stability function (e.g., the threshold may be equal to a multiple of the standard deviation). In some embodiments, the processing equipment may identify threshold crossings of the derivative of the stability function, if any.

Step 5210 may include processing equipment identifying relatively noisy portions of the physiological data based on the comparison of step 5208. Portions of the derivative of the stability signal may be identified based on one or more threshold crossings. For example, the portion of the derivative of the stability function between a pair of threshold crossings may be identified as relatively noisy. In a further example, every point of the derivative of the stability function exceeding the threshold may be identified as relatively noisy.

Step 5212 may include processing equipment modifying the physiological data based on the noisy portions identified at step 5210. In some embodiments, the processing equipment may determine portions of the derivative of the stability signal outside of threshold values (e.g., between a pair of threshold crossings) and limit the derivative values of the physiological data to one or more threshold value(s) in those portions.

Figure 54:
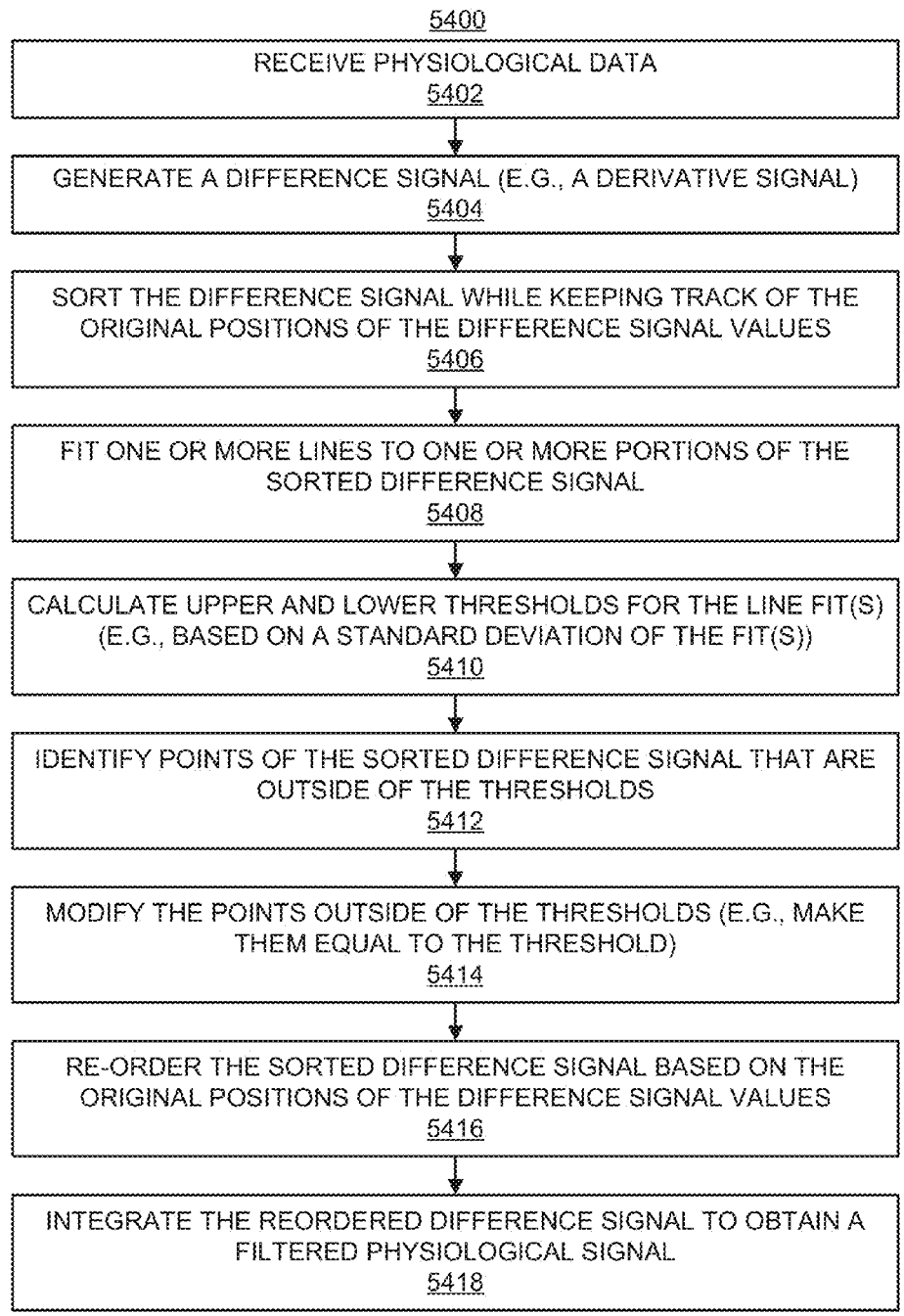
FIG. 54 is a flow diagram of illustrative steps for modifying physiological data using a corrected difference signal, in accordance with some embodiments of the present disclosure.
Figure 55:
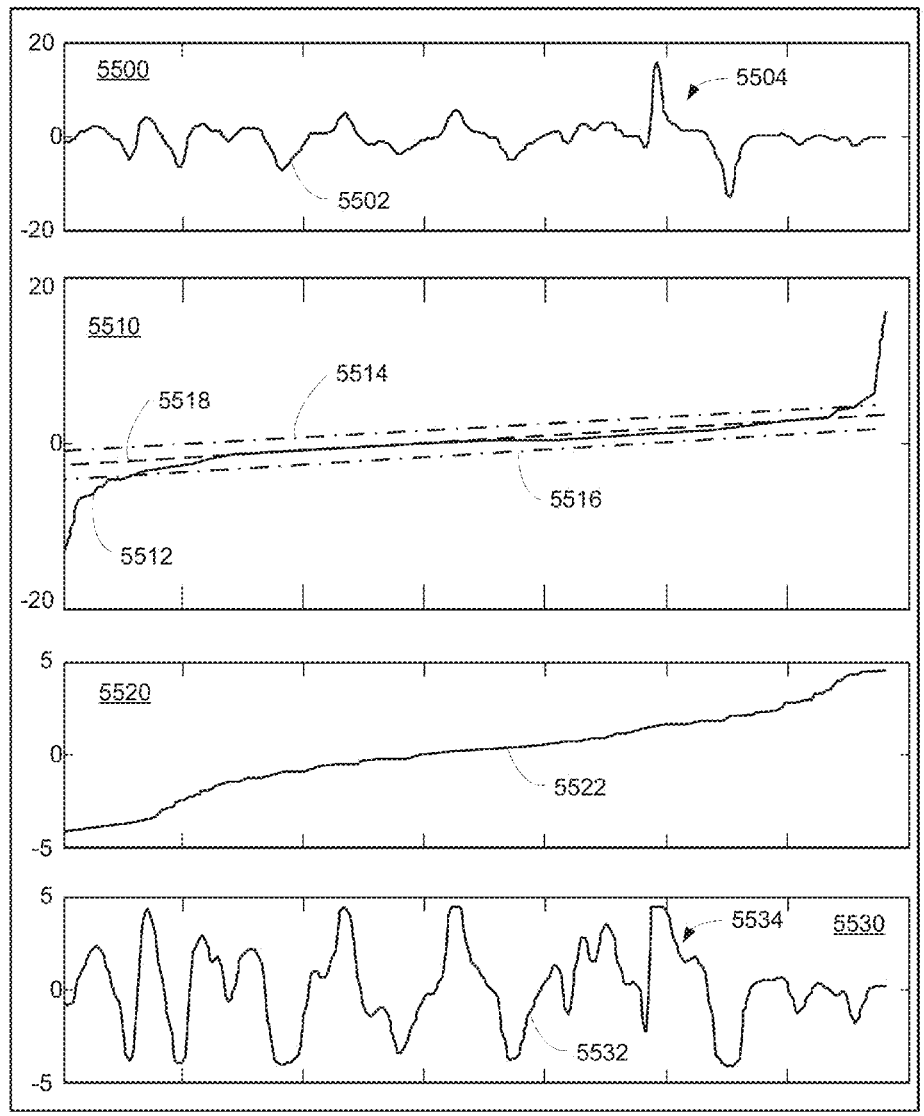
FIG. 55 is a panel of plots showing an illustrative difference signal, a sorted difference signal, a corrected difference signal, and a corrected difference signal, in accordance with some embodiments of the present disclosure.

FIG. 54 is a flow diagram 5400 of illustrative steps for modifying physiological data using a corrected difference signal, in accordance with some embodiments of the present disclosure. FIG. 55 is a panel of plots showing an illustrative difference signal, a sorted difference signal, a corrected sorted difference signal, and a corrected difference signal, in accordance with some embodiments of the present disclosure. FIG. 55 will be referred to below during the discussion of the illustrative steps of flow diagram 5400.

Step 5402 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 5402 may include recalling data from the memory for further processing.

Step 5404 may include processing equipment generating a difference signal (e.g., by calculating a sequence of difference values between adjacent samples of the physiological data). In some embodiments, the processing equipment may perform a subtraction between values of adjacent samples. In some embodiments, the processing equipment may calculate the differences by calculating a first derivative of the physiological data. For example, the processing equipment may compute forward differences, backward differences, or central differences between each pair of adjacent points to generate a difference signal. In a further example, the processing equipment may compute a numerical derivative at each point in the data, generating a difference signal. Any suitable difference technique may be used by the processing equipment to generate the difference signal. Panel 5500 shows an illustrative difference signal 5502 generated from a window of physiological data. Note that region 5504 exhibits a relatively large peak and trough, typically indicative of noise.

Step 5406 may include processing equipment sorting the difference values of step 5404, while keeping track of the original position of each sorted point. In some embodiments, an index or other identifier may be used to retain the original position information of the sorted difference values. The processing equipment may sort the values in ascending or descending order. Referencing sorted values in ascending order, the most negative values come first followed by less negative values, positive values, and finally larger positive values.

Step 5408 may include processing equipment fitting one or more lines to one or more portions of the sorted difference signal of step 5406. In some embodiments, the processing equipment may perform a linear regression (e.g., a least-squares regression or a weighted least-squares regression) using at least a portion of the sorted difference signal. In some embodiments, the processing equipment may fit a line using every point of the sorted difference signal. In some embodiments, the processing equipment may fit a line using a portion of the sorted difference signal. For example, the processing equipment may omit one or more points at one or both ends of the sorted difference signal when determine the line fit. In some embodiments, the line fit may include a slope value and an ordinate intercept value (e.g., using the y=mx+b linear form where m is the slope and b is the intercept).

Step 5410 may include processing equipment determining upper and lower thresholds for the sorted difference signal of step 5406. The upper and lower thresholds may be determined based on the difference values themselves. For example, a threshold may be determined using the standard deviation of the physiological data, difference signal, or both. In an illustrative example, Eq. 27 may be applied, in which the upper and lower thresholds may be proportional by proportionality constant K to the standard deviation σ of the difference signal. The upper and lower thresholds need not be symmetrical nor constant, and may each have unique K values.

Step 5412 may include processing equipment identifying points of the sorted difference signal of step 5406 that exceed the thresholds of step 5410. The difference signal may be compared to the upper and lower thresholds, and values exceeding the threshold range may be identified. Panel 5510 of FIG. 55 shows a sorted difference signal 5512 derived from difference signal 5502 of panel 5500, along with line fit 5518, and respective upper and lower thresholds 5514 and 5516. The points associated with the peak and trough in region 5504 of difference signal 5502 are evident as the relatively large positive values and large negative values at the ends of sorted difference signal 5512. Sorted difference signal 5512 is shown to exceed thresholds 5514 and 5516, and accordingly points outside of the thresholds may be identified. The processing equipment may identify a sample number, time value, coordinate pair, any other suitable description of a point, or any combination thereof that correspond to points exceeding the upper or lower thresholds.

It will be understood that the steps 5408, 5410, and 5412 are merely illustrative, and any suitable technique for identifying points may be used. For example, any of the illustrative techniques described in the context of FIGS. 30 and 32 may be used.

Step 5414 may include processing equipment modifying the points of the sorted difference signal identified at step 5412. In some embodiments, the processing equipment may set each sorted difference value outside of the thresholds equal to the threshold, thus limiting large difference value excursions. In some embodiments, the processing equipment may apply a transition function to force the sorted difference signal to the nearest threshold asymptotically. Any suitable technique may be used by the processing equipment to modify one or more points to reduce excursions of the sorted difference signal outside of the thresholds. For example, in some embodiments, the processing equipment may modify the one or more values by setting them equal to the same value as the last point that was within the threshold. In a further example, the processing equipment may modify the one or more values by setting them equal to a predetermined value such as zero or any other suitable value less than the threshold. Panel 5520 of FIG. 55 shows a modified sorted difference signal 5522 derived from sorted difference signal 5512 of panel 5510. In order to generate modified sorted difference signal 5522, the values of sorted difference signal 5512 exceeding the thresholds, as shown in panel 5510, have been set equal to the appropriate threshold values. The ends of modified sorted difference signal 5522 are shown to be substantially linear (e.g., similar to thresholds 5514 and 5516), and exhibit relatively smaller difference values.

Step 5416 may include processing equipment reordering the modified sorted difference signal of step 5414 based on the original positions of each data point. The output from performing step 5416 may be a modified difference signal, with the largest difference values (positive and/or negative) modified to relatively smaller values. Panel 5530 of FIG. 55 shows a modified difference signal 5532 derived from modified sorted difference signal 5522 of panel 5520. As compared to difference signal 5502 of panel 5500, modified difference signal 5532 exhibits, for example, a relatively smaller peak and trough in region 5534, which corresponds to region 5504 of panel 5500.

Step 5418 may include processing equipment integrating the modified difference signal of step 5416 to generate a filtered physiological signal. In some embodiments, the processing equipment may use any suitable analytic integral (e.g., using a functional fit to a modified difference signal), numerical integral (e.g., Euler's method, Runge-Kutta method, a predictor-corrector method, or any other suitable technique of any suitable order), any other suitable technique, or any combination thereof. For example, the processing equipment may use a first value of zero, and generate each subsequent value by adding the corresponding difference value to the preceding value, and then apply a baseline offset equivalent to the mean of the original physiological data. In a further example, the processing equipment may use an Euler-trapezoid predictor-corrector technique to perform the integral of step 5418.

In some embodiments, processing equipment may apply a normalization to a window of data, or signal derived thereof. A physiological pulse may be expected to exhibit oscillatory behavior, while baseline shifts or other non-oscillatory behavior may likely be attributable to noise (e.g., subject movement, electromagnetic interference). Further, changes in the amplitude of oscillatory activity may be undesirable. In some embodiments, a window of physiological data may be partitioned into a positive signal and a negative signal, which may each be further processed and combined to modify the physiological data. In some embodiments, a filtered signal may be used to modify the physiological data. The following discussion in the context of FIGS. 56-59 provides some illustrative techniques for normalizing to physiological data.

Figure 56:
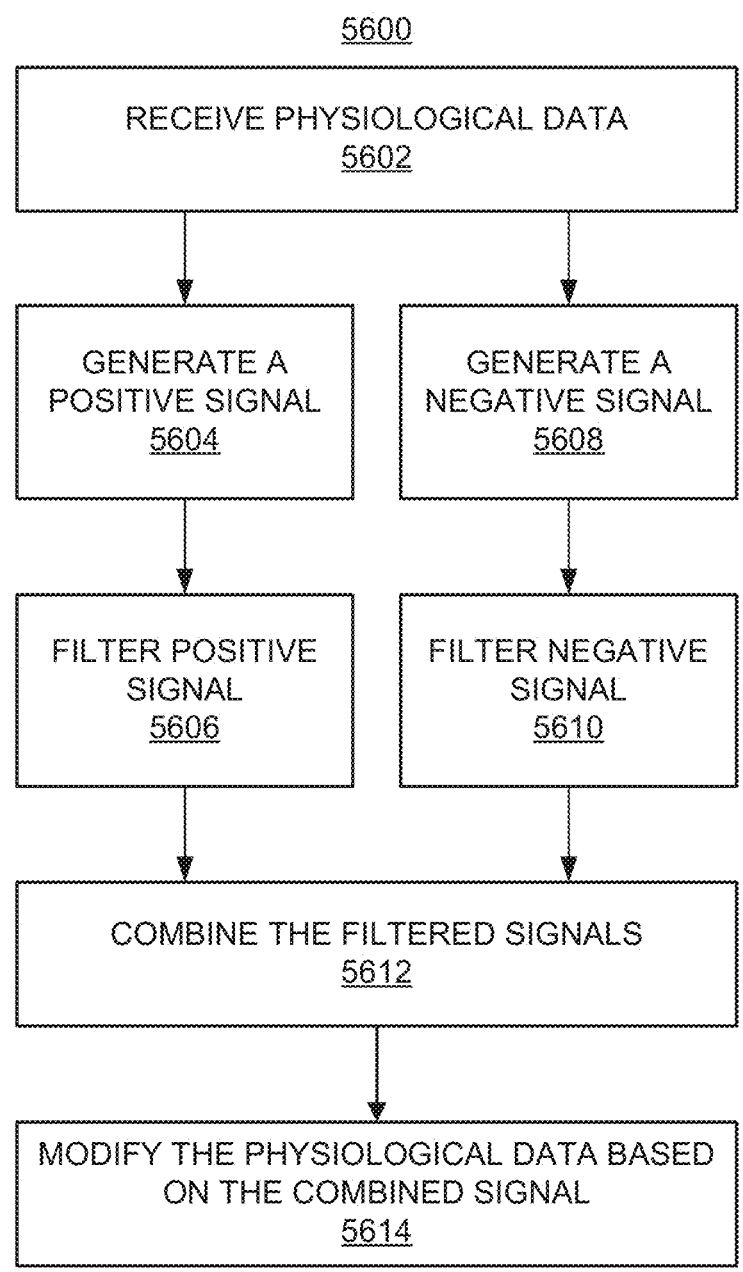
FIG. 56 is a flow diagram of illustrative steps for modifying physiological data using a positive signal and a negative signal, in accordance with some embodiments of the present disclosure.
Figure 57:
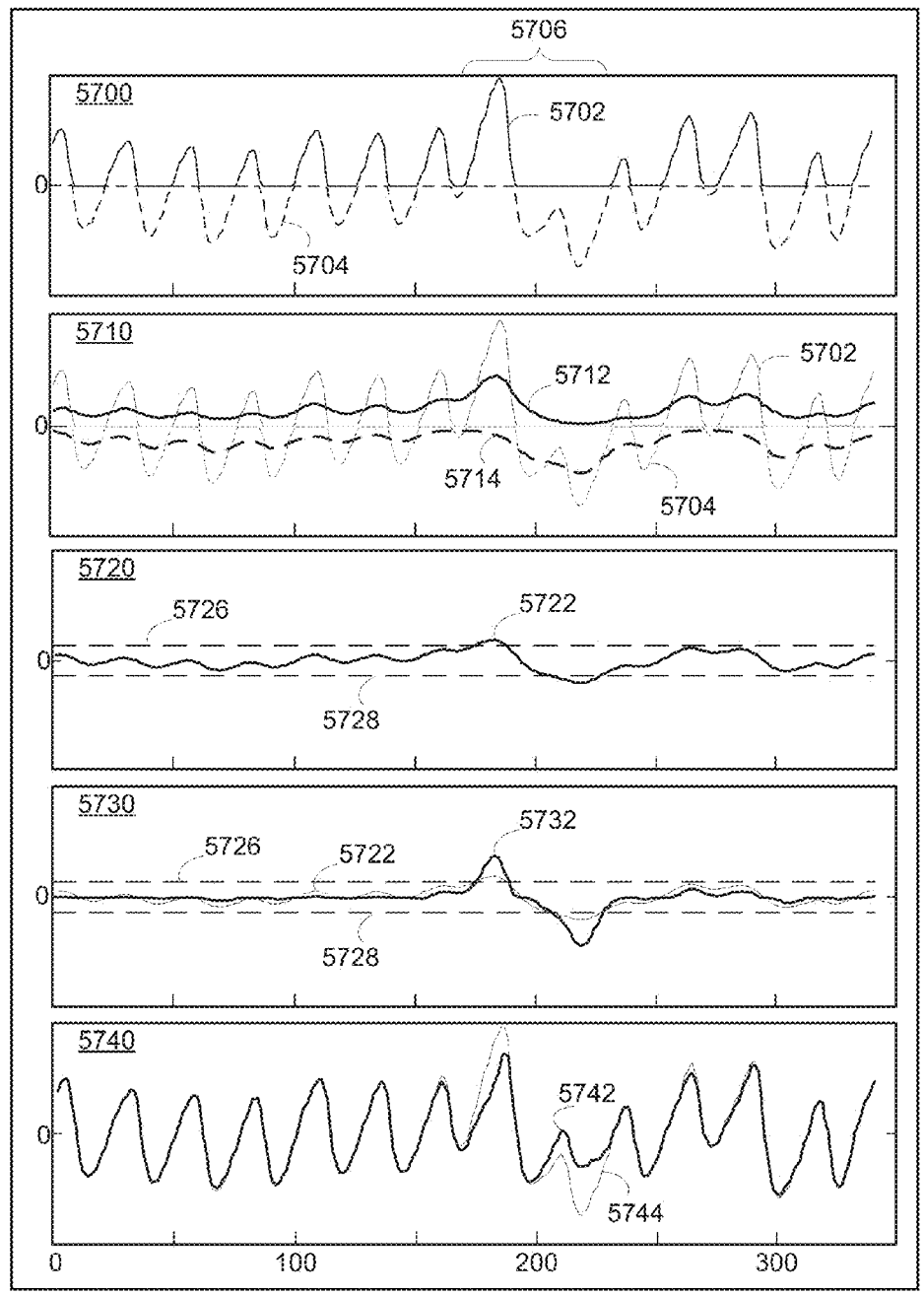
FIG. 57 is a panel of five plots showing an illustrative window of physiological data having varying amplitude, filtered signals, combined signals, and a modified window of data, in accordance with some embodiments of the present disclosure.

FIG. 56 is a flow diagram 5600 of illustrative steps for modifying physiological data using a positive signal and a negative signal, in accordance with some embodiments of the present disclosure. FIG. 57 is a panel of five plots showing an illustrative window of physiological data having varying amplitude, filtered signals, combined signals, and a modified window of data, in accordance with some embodiments of the present disclosure. FIG. 57 will be referred to below during the discussion of the illustrative steps of flow diagram 5600.

Step 5602 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 5602 may include recalling data from the memory for further processing.

Step 5604 may include processing equipment generating a positive signal based on the physiological data of step 5602. In some embodiments, the processing equipment may generate the positive signal from the positive values of the physiological data of step 5602. In some embodiments, the processing equipment may insert zeros in the positive signal where the physiological data is negative. Step 5608 may include processing equipment generating a negative signal based on the physiological data of step 5602. In some embodiments, the processing equipment may generate the negative signal from the negative values of the physiological data of step 5602. In some embodiments, the processing equipment may insert zeros in the negative signal where the physiological data is positive. For example, plot 5700 of FIG. 57 shows positive signal 5702 and negative signal 5704 generated from the same physiological data. The physiological data exhibits a relatively large peak and trough in region 5706. Further processing of such physiological data may benefit from normalization techniques, which may aid in reducing relatively large excursions in the physiological data.

Step 5606 may include processing equipment filtering the positive signal of step 5604. In some embodiments, the processing equipment may apply a low pass filter to the positive signal. Any suitable LPF, having any suitable cutoff and spectral character (e.g., Butterworth filters, Chebyshev filters, Bessel filters, RC filters, or other suitable filter), may be used at step 5606. Step 5610 may include processing equipment filtering the negative signal of step 5608. In some embodiments, the processing equipment may apply a low pass filter to the negative signal. Any suitable LPF, having any suitable cutoff and spectral character (e.g., Butterworth filters, Chebyshev filters, Bessel filters, RC filters, or other suitable filter), may be used at step 5610. For example, plot 5710 of FIG. 57 shows illustrative filtered positive signal 5712 and filtered negative signal 5714.

Step 5612 may include processing equipment combining the filtered positive signal and the filtered negative signal of respective steps 5606 and 5610. In some embodiments, the processing equipment may sum the filtered positive signal and the filtered negative signal of respective steps 5606 and 5610. In some embodiments, the processing equipment may sum the filtered positive signal and the filtered negative signal of respective steps 5606 and 5610 using weights. The processing equipment may apply any suitable combination technique at step 5612 to combine the filtered positive signal and the filtered negative signal of respective steps 5606 and 5610. For example, plot 5720 of FIG. 57 shows illustrative combined signal 5722, generated by adding filtered positive signal 5712 and filtered negative signal 5714 of plot 5710.

Step 5614 may include processing equipment modifying the physiological data of step 5602 based on the combined signal of step 5612. In some embodiments, the combined signal may be subtracted from the physiological data, which may aid in reducing relatively large excursions in the physiological data. In some embodiments, the combined signal may be further modified and then subtracted from the physiological data. For example, plot 5720 of FIG. 57 shows illustrative combined signal 5722, along with thresholds 5726 and 5728 generated by the processing equipment. The thresholds may be constant values, variable values, based on the properties of the physiological data (e.g., the positive and negative thresholds may be equal to the standard deviation of the physiological data), a signal derived thereof (e.g., the positive and negative thresholds may be equal to the averages of the respective positive and negative signals), any other suitable information, or any combination thereof. Plot 5730 of FIG. 57 shows illustrative combined signal 5722, and scaled combined signal 5732, generated from scaling combined signal 5722 based on thresholds 5726 and 5728. The scaling may be linear, polynomial of order two or greater, exponential, logarithmic, any other function scaling, any other suitable scaling, or any combination thereof. For example, the processing equipment may apply any of illustrative Eqs. 29-30 shown below:

$$M_i = KC_i \left(\frac{C_i}{T_j}\right)^n \qquad (29)$$

$$M_i = KC_i e^{A(C_i - T_j)} \qquad (30)$$

to the combined signal (having values $C_i$ for index i) to generate a modified combined signal (having values $M_i$ for index i) at step 5614. Note that in Eqs. 29-30, $T_j$ represents an appropriate threshold value (e.g., positive threshold for positive values, negative threshold for negative values), while K, A, and n each represent an adjustable constant. For example, referencing Eqs. 29-30, the constant K may be set to a value of one, so that the combined signal and modified combined signal are equal at the threshold crossings (e.g., as shown in plot 5730). Plot 5740 shows the original physiological data 5744 and modified physiological data 5742, generated by subtracting modified combined signal 5732 from original physiological data 5744. Modified physiological data 5742 exhibits relatively reduced excursions in region 5706 as compared to original physiological data 5744.

Figure 58:
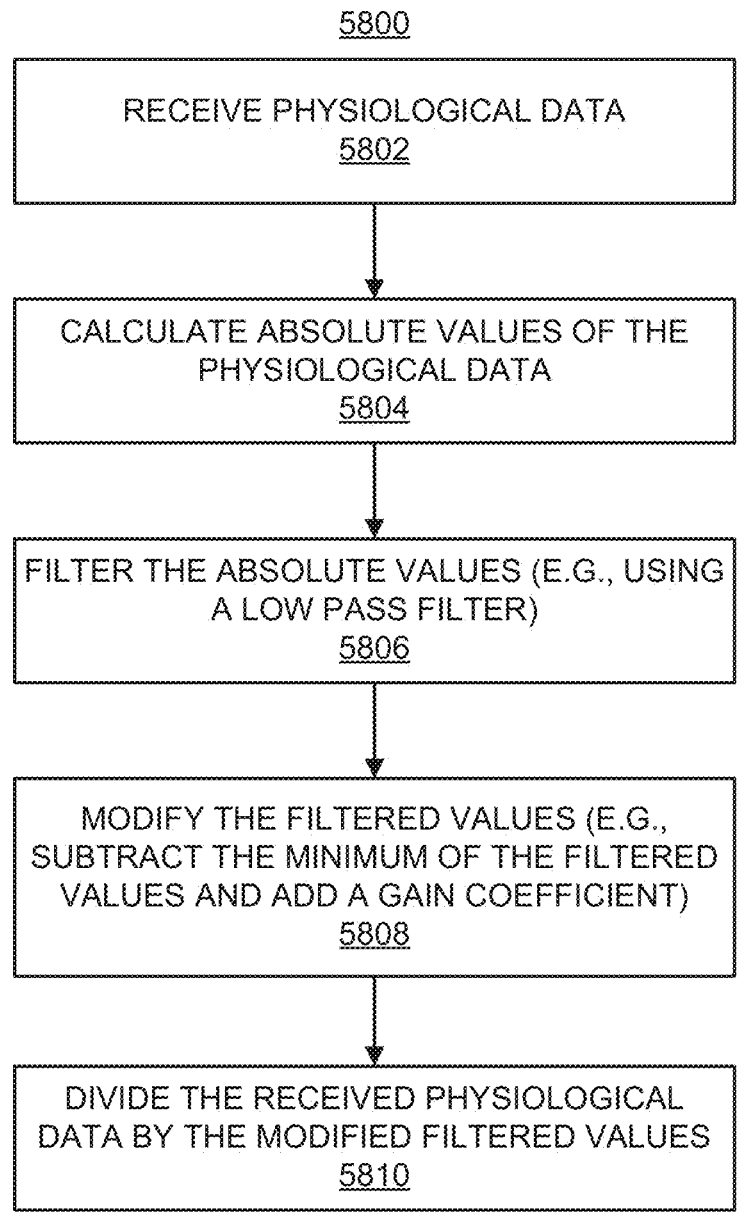
FIG. 58 is a flow diagram of illustrative steps for modifying physiological data using a filtered signal, in accordance with some embodiments of the present disclosure.
Figure 59:
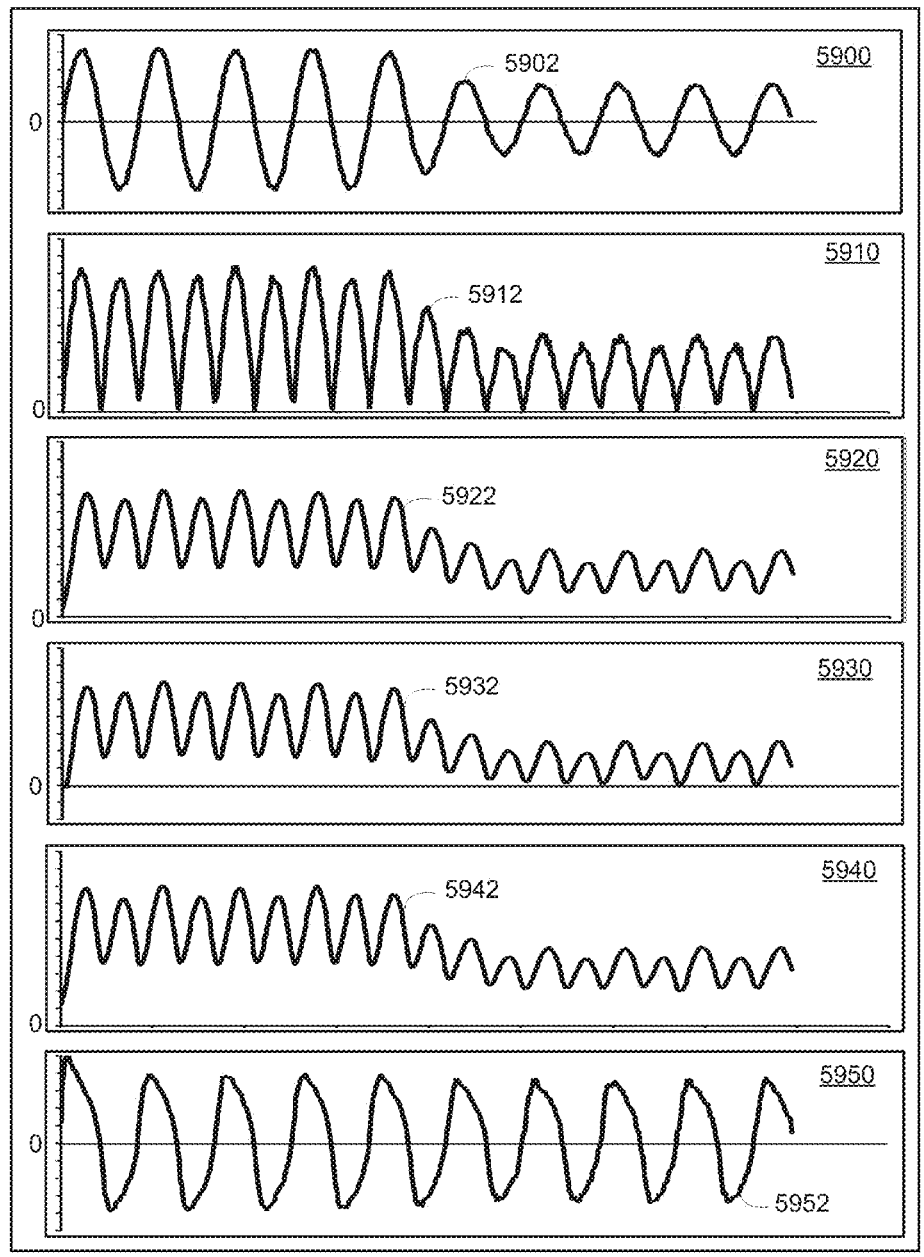
FIG. 59 is a panel of six plots showing an illustrative window of physiological data, an absolute value signal, a filtered signal, a shifted signal, and a modified window of data, in accordance with some embodiments of the present disclosure.

FIG. 58 is a flow diagram 5800 of illustrative steps for modifying physiological data using a filtered signal, in accordance with some embodiments of the present disclosure. FIG. 59 is a panel of six plots showing an illustrative window of physiological data, an absolute value signal, a filtered signal, a shifted signal, and a modified window of data, in accordance with some embodiments of the present disclosure. FIG. 59 will be referred to below during the discussion of the illustrative steps of flow diagram 5800.

Step 5802 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 5802 may include recalling data from the memory for further processing. For example, plot 5900 of FIG. 59 shows illustrative data 5902 exhibiting a significant change in amplitude.

Step 5804 may include processing equipment calculating absolute values of the physiological data of step 5802. The result of step 5804 may be a sequence of absolute values, having only positive values (and possibly zeros). For example, plot 5910 of FIG. 59 shows absolute values 5912 derived from illustrative data 5902.

Step 5806 may include processing equipment filtering the absolute values of step 5804. In some embodiments, the processing equipment may apply a low pass filter to the absolute values of step 5804. Any suitable LPF, having any suitable cutoff and spectral character (e.g., Butterworth filters, Chebyshev filters, Bessel filters, RC filters, or other suitable filter), may be used at step 5806. For example, plot 5920 of FIG.

59 shows filtered values 5922 derived from absolute values 5912. The illustrative LPF used to generate filtered values has the form of Eqs.

$$F_1 = Z_1 \quad (31)$$

$$F_i = aZ_i + bZ_{i-1} \quad (32)$$

in which $Z_i$ is the unfiltered signal (i.e., the absolute values), $F_i$ is the filtered signal, using index i, and filter coefficients a and b (which may sum to one). It will be understood that any suitable LPF technique (e.g., a direct form II transpose structure) may be applied by the processing equipment to generate filtered values at step 5806.

Step 5808 may include processing equipment modifying the filtered values of step 5806. In some embodiments, the processing equipment may modify the filtered values by scaling, shifting, or both. For example, plot 5930 of FIG. 59 shows subtracted values 5932 derived from filtered values 5922. Subtracted values 5932 are derived from filtered values 5922 by subtracting the minimum value of filtered values 5922, excluding end portions, from all values of filtered values 5922. Accordingly, subtracted values 5932 are down-shifted values of filtered values 5922. Further, plot 5940 of FIG. 59 shows modified values 5942 derived from subtracted values 5932 by adding a constant gain value to each of subtracted values 5932. In some embodiments, a subtraction and a gain value addition may be performed, although these operations may be condensed into a single value shift. Modified values, such as modified values 5942, may be used to modify physiological data exhibiting significant amplitude changes.

Step 5810 may include processing equipment dividing the received physiological data of step 5802 by the modified filtered values of step 5808. For example, the processing equipment may modify filter values as shown in Eq. 33, and modify the physiological data of step 5802 using Eq. 34:

$$M_i = F_i - K_1 + K_2 \quad (33)$$

$$Y_i = \frac{X_i}{M_i} \quad (34)$$

in which $F_i$ are the filtered values, $K_1$ and $K_2$ are the shifts, $M_i$ are the modified filtered values, $X_i$ are the physiological data values (as received at step 5802), and $Y_i$ are the modified physiological data values, all for index i that may range from 1 to N for N data points. Plot 5950 of FIG. 59 shows modified data 5952 derived from data 5902 and modified filter values 5942 using Eq. 34. The amplitude variation in modified data 5952 is relatively less than the amplitude variation in data 5002, and exhibits normalization indicative of the illustrative techniques of flow diagram 5800.

Figure 60:
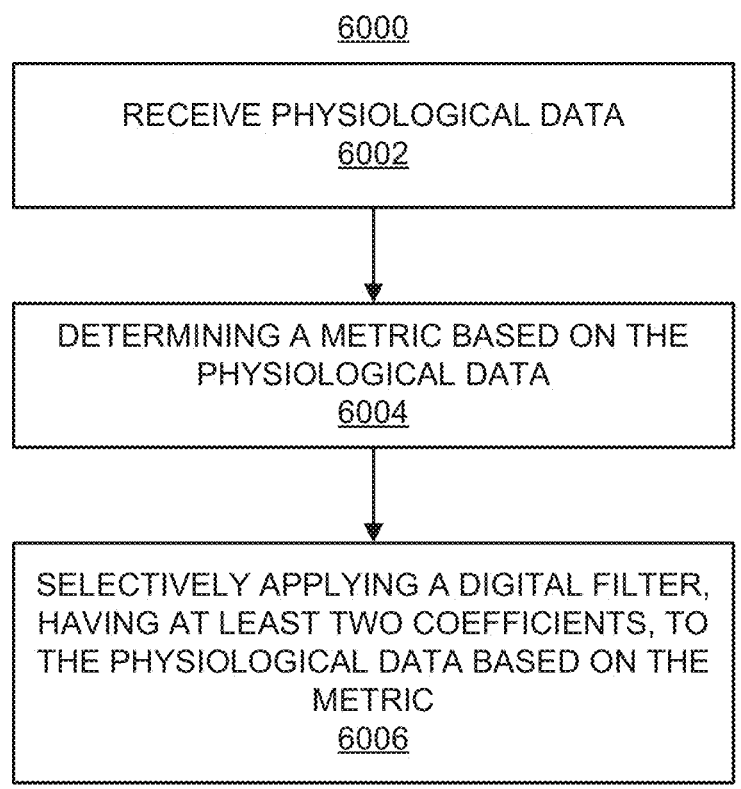
FIG. 60 is a flow diagram of illustrative steps for selectively applying a filter to physiological data, in accordance with some embodiments of the present disclosure.

FIG. 60 is a flow diagram 6000 of illustrative steps for selectively applying a filter to physiological data, in accordance with some embodiments of the present disclosure.

Step 6002 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 6002 may include recalling data from the memory for further processing.

Step 6004 may include processing equipment determining a metric based on the received physiological signal of step 6002. For example, the processing equipment may determine the metric in accordance with any of the techniques discussed in the context of FIGS. 11-41, any other suitable techniques, or any combination thereof. The determined metric may be indicative of de-trending, noise, a physiological classification (e.g., presence of a dicrotic notch) any other value indicative of the physiological data, any other signal conditioning property derived based on the physiological data, or any combination thereof.

Step 6006 may include processing equipment selectively applying a digital filter, having at least two filter coefficients, to the physiological data of step 6002 based on the metric of step 6004. The filter coefficients may correspond to a weighted sum of the physiological signal and a difference signal that corresponds to the physiological signal. For example, the digital filter may output filter data $F_i$ calculated using Eq. 35:

$$F_i = C_1 X_i + C_2 (X_i - X_{i-1}) = aX_i + bX_{i-1} \quad (35)$$

where $X_i$ is a sample point of the physiological data, $X_{i-1}$ is the previous sample point of the physiological data, $C_1$ and $C_2$ are coefficients, and a and b are the filter coefficients, which may assume any suitable value. Any suitable difference calculation, or other numerical derivative calculation, may be used such as, for example, a backward difference, a forward difference, or a central difference. The digital filter may be implemented as, for example, a finite impulse response (FIR) filter having at least two coefficients. Selectively applying the digital filter based on the metric may provide a technique to reduce the effects of noise in the physiological data. For example, physiological data from a neonate may exhibit a relatively high frequency component corresponding to a physiological rate, and a relatively low frequency component corresponding to noise. Application of the digital filter of step 6006 may reduce the low frequency noise component in the filtered data, as the derivative of the low frequency noise would be expected to be relatively less than the derivative associated with the higher frequency component. In some embodiments, the processing equipment may adjust the filter coefficients based on a noise metric, calculated rate, or both. For example, at relatively greater levels of noise and at relatively higher rates (e.g., where there is a lower probability of a dicrotic notch), the processing equipment may more heavily weight the derivative (e.g., increase $C_2$). In some embodiments, for example, the digital filter of step 6006 may not be applied when the physiological data is classified as having a dicrotic notch. The derivative of physiological data having a dicrotic notch may make the dicrotic notch appear as an additional pulse. In a further example, at lower physiological rates, the processing equipment may more heavily weight the physiological signal relative to the derivative.

Figure 61:
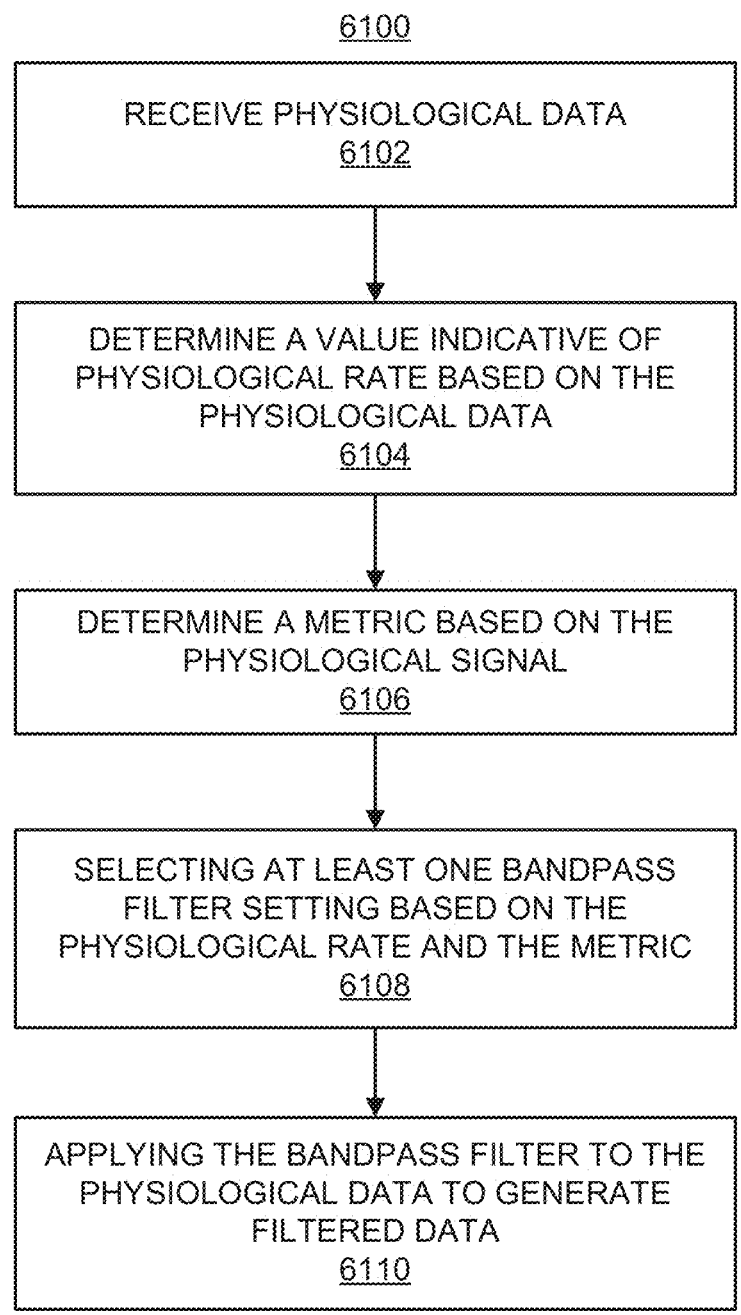
FIG. 61 is a flow diagram of illustrative steps for applying a bandpass filter having adjustable settings to physiological data, in accordance with some embodiments of the present disclosure.

FIG. 61 is a flow diagram 6100 of illustrative steps for applying a bandpass filter having adjustable settings to physiological data, in accordance with some embodiments of the present disclosure. In some circumstances, the processing equipment may apply a bandpass filter to physiological data received over time. In order to reduce the likelihood that the bandpass filter is tuned to noise (as opposed to the correct rate), the processing equipment may determine one or more metrics indicative of the level of noise in the physiological data. Accordingly, under some circumstances, one or more settings of the bandpass filter may be adjusted based on the one or more metrics, a calculated rate, or both.

Step 6102 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 6102 may include recalling data from the memory for further processing.

Step 6104 may include processing equipment determining a value indicative of physiological rate based on the physiological data of step 6102. In some embodiments, the processing equipment may use any of the techniques disclosed herein to calculate a physiological rate (e.g., a heart rate) derived from the physiological data, a correlation lag value derived from the physiological data, any other suitable value indicative of a physiological rate or period thereof, or any combination thereof. In some embodiments, different processing modules may determine the value indicative of physiological rate and apply the bandpass filter, in which case the processing modules may communicate information to one another.

Step 6106 may include processing equipment determining a metric based on the received physiological signal of step 6102. For example, the processing equipment may determine the metric in accordance with any of the techniques discussed in the context of FIGS. 11-41, any other suitable techniques, or any combination thereof. The determined metric may be indicative of de-trending, noise, any other value indicative of the physiological data, any other signal conditioning property derived based on the physiological data, or any combination thereof.

Step 6108 may include processing equipment selecting at least one bandpass filter setting based on the determined value indicative of physiological rate of step 6104 and based on the metric of step 6106. The at least one bandpass filter setting may include a center frequency, a bandwidth, a lower cutoff and an upper cutoff frequency, a shape parameter, a type of bandpass filter, any other suitable parameter affecting the spectral character of the filter (e.g., in units of frequency, angular frequency, wavenumber, period, or other suitable units), any other suitable setting, or any combination thereof. The selection of the bandpass filter may be based on a comparison of the metric of step 6106 to a threshold that may depend on the value indicative of physiological rate.

Step 6110 may include processing equipment applying the bandpass filter, having the selected at least one setting of step 6108, to the physiological data. The processing equipment may apply the bandpass filter to the physiological data to generate a filtered signal. The processing equipment may apply any suitable type of analog or digital bandpass filter having, for example, any suitable passband characteristics and any suitable roll-off characteristics. In some embodiments, the bandpass filter may be implemented as a combination of a lowpass filter and a highpass filter, having suitable cutoff characteristics. In some embodiments, the bandpass filter may be centered about a frequency value corresponding to the physiological rate, and have a bandwidth determined based on the metric of step 6106.

In an illustrative example, the processing equipment may determine a noise metric based on the physiological data. The processing equipment may compare the noise metric to a threshold value. If the noise metric is determined to be below the threshold value (e.g., the signal is relatively less noisy), which may be based on physiological rate, the processing equipment may increase the bandwidth of the bandpass filter, or cease bandpass filtering altogether to prevent the data components corresponding to desired physiological rate from being filtered out of the physiological data. For example, if the rate calculation is incorrectly calculating rate based on noise (e.g., because the bandpass filter is being tuned to the frequency of the noise), this technique will enable the rate calculation to correct itself and lock onto the desired rate. Conversely, if the noise metric is determined to exceed a threshold value (e.g., the signal is relatively more noisy), which may be based on physiological rate, the processing equipment may decrease the bandwidth of the bandpass filter, or begin bandpass filtering to reduce the noise components in the processed physiological data.

In some embodiments, processing equipment may perform a correlation calculation using conditioned physiological data. The correlation calculation may include selecting a template from the physiological data, and correlating the template with the physiological data at a sequence of lag values. The correlation may include an autocorrelation (e.g., the same set of data is correlated against itself), a cross-correlation with other data points or a reference (e.g., a set of data is correlated against another set of data or reference not sharing any data points), or a combination thereof. The correlation calculation may provide several desirable benefits such as, for example, providing a normalized output, providing an indication of periodicity, providing relatively sharper peaks than otherwise present in the physiological data, and/or providing a metric of how much periodic character the physiological data exhibits. Any of the techniques discussed in the context of FIGS. 62-85 may be applied, for example, at step 414 of flow diagram 400 of FIG. 4.

Figure 62:
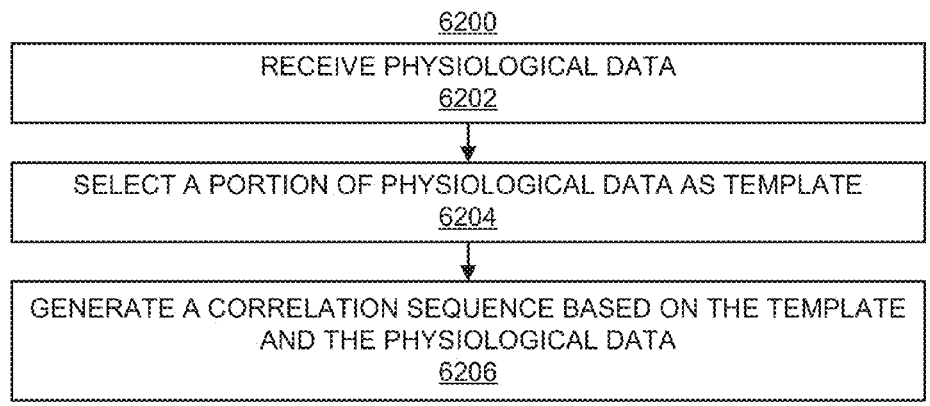
FIG. 62 is a flow diagram of illustrative steps for performing a correlation using a window of physiological data, in accordance with some embodiments of the present disclosure.
Figure 64:
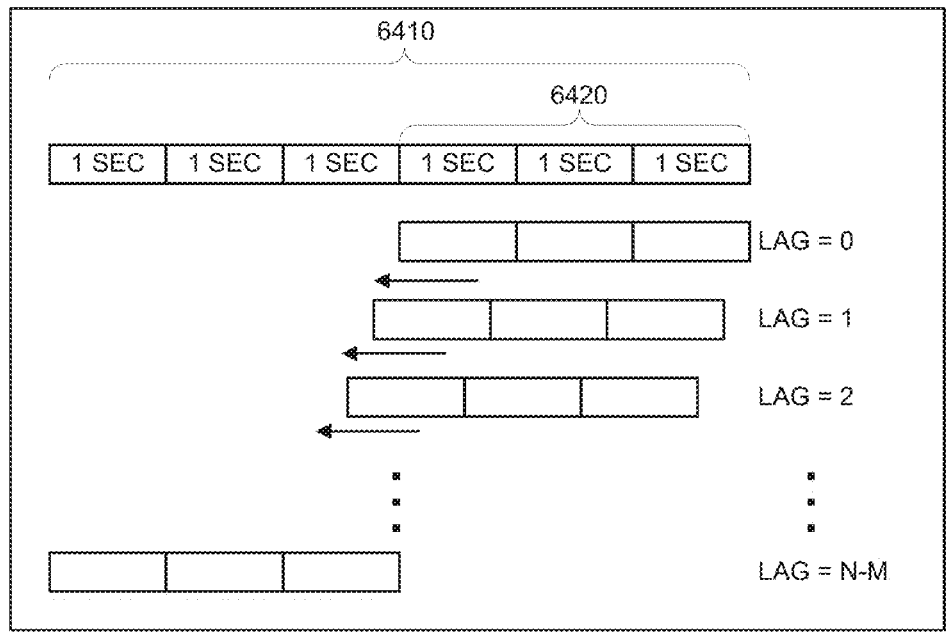
FIG. 64 is a diagram showing an illustrative window of physiological data and a template at several lags, in accordance with some embodiments of the present disclosure.
Figure 65:
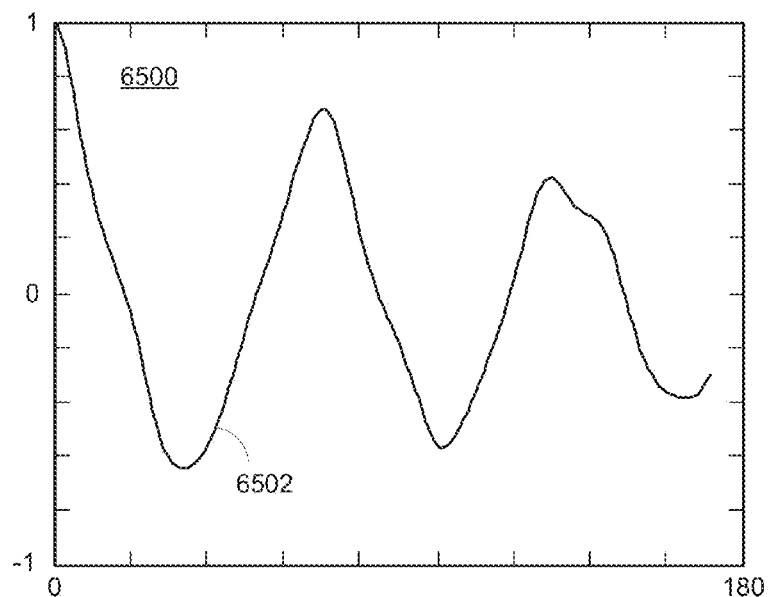
FIG. 65 is a plot showing an illustrative correlation sequence for a window of physiological data, in accordance with some embodiments of the present disclosure.

FIG. 62 is a flow diagram of illustrative steps for performing a correlation using a window of physiological data, in accordance with some embodiments of the present disclosure. FIG. 64 is a diagram showing an illustrative window of physiological data and a template at several lags, in accordance with some embodiments of the present disclosure. FIG. 65 is a plot showing an illustrative correlation sequence for a window of physiological data, in accordance with some embodiments of the present disclosure. FIGS. 64-65 will be referred to below during the discussion of the illustrative steps of flow diagram 6200.

Step 6202 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 6202 may include recalling data from the memory for further processing.

Step 6204 may include processing equipment selecting a portion of the physiological data as a template. In some embodiments, the template may include a predetermined number of samples of the physiological data. For example, referencing a six second window of data, the processing equipment may select the most recent three seconds of the data as the template. In some embodiments, the template size may be constant (e.g., a three second template). In some embodiments, the template size may depend on a previously calculated rate (e.g., larger templates may be used for lower rates). In some embodiments, the template size may depend on one or more algorithm settings (e.g., the window of data and template may be larger while operating in an initialization mode or fast start mode).

Step 6206 may include processing equipment generating a correlation sequence based on the physiological data of step 6202 and template of step 6204. In some embodiments, the processing equipment may generate the correlation sequence by multiplying the template values by corresponding values of an equal size of the physiological data at a particular lag. Step 6206 may include the processing equipment normalizing the physiological data of step 6202 and the selected portion of step 6204. In some embodiments, the processing equipment may use any suitable signal conditioning technique on the physiological data (e.g., de-trending and/or normalization techniques, scaling, shifting, or any other suitable operation). For example, the processing equipment may normalize the physiological data, the template, or both, to vary between zero and one, negative one and positive one, or any other predetermined range. In a further example, the processing equipment may first apply the techniques of any of signal conditioning techniques discussed in the context of FIGS. 42-61 at step 6206. In a further example, the processing equipment may normalize the physiological data, template, or both, by dividing by the norm of the array of values to be normalized. In some embodiments, normalized data may have a mean value of zero (i.e., be centered about zero).

For example, referencing window of data of N points and a template of the most recent M data points, the processing equipment may use Eq. 36 as shown below:

$$C_j = \sum_{i=1}^{M} S_i * X_{j,i} \quad (36)$$

to generate each value of the correlation sequence $C_j$ for lag j, in which template S includes template values $S_i$ for index i (which ranges from 1 to M), and $X_{j,i}$ is the physiological data value at index i, at a lag of j. For a template of the most recent M values of the physiological data, the set of values of the physiological data used at any lag j may be determined from the set of N values of physiological data as shown in Eq. 37:

$$\bar{X}_j = [X_{(N-M)-j+1}, X_{(N-M)-j+2}, X_{(N-M)-j+3}, \ldots, X_{(N-M)-j+(M-1)}, X_{(N-M)-j+M}] \quad (37)$$

which results in a set of M values of the physiological data. FIG. 64 shows an illustrative window of data 6410, which is roughly six seconds long. A template 6420 is shown, corresponding to the most recent three seconds of the physiological data. A correlation sequence may be generated after the physiological data and template are normalized. The physiological data and the template may be, for example, normalized by subtracting their respective mean values and dividing by their respective standard deviation values. Further, the correlation value may be normalized based on the number of sample points in the template, resulting in a correlation value that varies between −1 and 1. As the lag increases from zero to (N−M), the template is correlated with values of the physiological data increasingly to the left, as indicated by the direction of the arrows in FIG. 64. Note that the complete correlation sequence will include ((N−M)+1) values. FIG. 65 shows a plot 6500 of illustrative correlation sequence 6502 derived from six seconds of physiological data using a three second template (at a sampling rate of about 57 Hz). The abscissa of plot 6500 is in units of point lag (e.g., a lag of 10 corresponds to a shift of 10 points to the left, referencing FIG. 64). The physiological data and template used to generate correlation sequence 6502 were normalized, and accordingly correlation sequence 6502 was normalized to be bounded by negative one and positive one.

Figure 63:
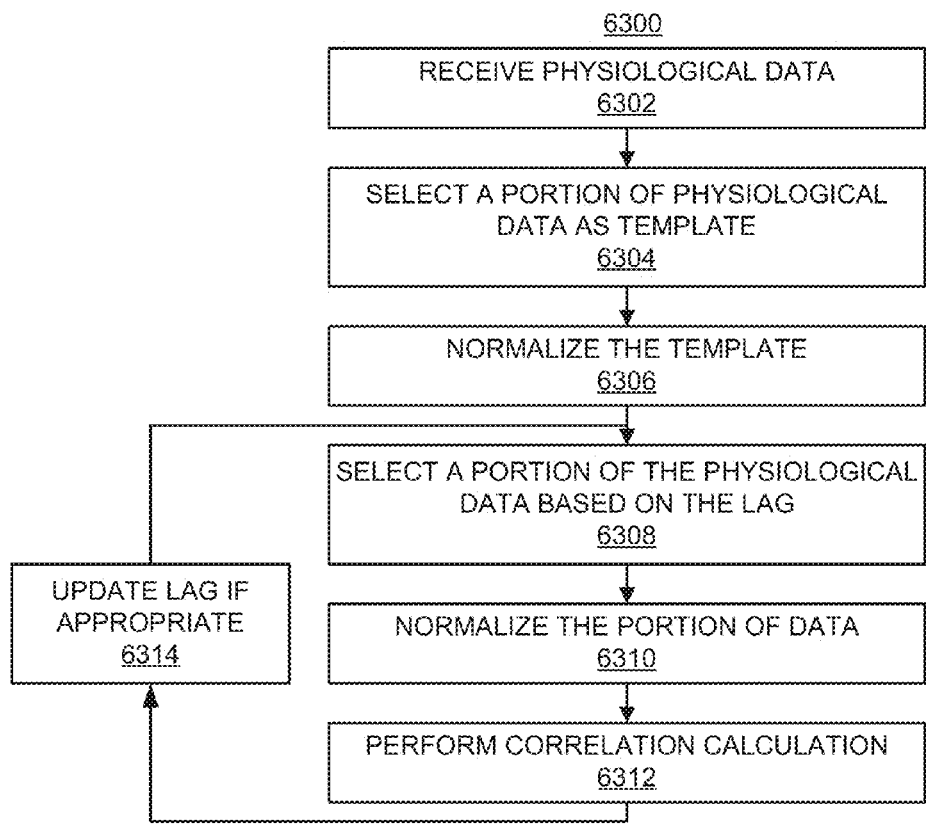
FIG. 63 is a flow diagram of illustrative steps for generating a correlation sequence using a window of physiological data, in accordance with some embodiments of the present disclosure.

FIG. 63 is a flow diagram 6300 of illustrative steps for generating a correlation sequence using a window of physiological data, in accordance with some embodiments of the present disclosure.

Step 6302 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 6302 may include recalling data from the memory for further processing.

Step 6304 may include processing equipment selecting a portion of the physiological data as a template. In some embodiments, the template may include a predetermined number of samples of the physiological data. For example, referencing a six second window of data, the processing equipment may select the most recent three seconds of the data as the template. In some embodiments, the template size may be constant (e.g., a three second template). In some embodiments, the template size may depend on a previously calculated rate (e.g., larger templates may be used for lower rates). In some embodiments, the template size may depend on one or more algorithm settings (e.g., the window of data and template may be larger while operating in an initialization mode or fast start mode).

Step 6306 may include the processing equipment normalizing the physiological data of step 6302 and the selected portion of step 6304. In some embodiments, the processing equipment may use any suitable signal conditioning technique (e.g., de-trending and/or normalization techniques, scaling, shifting, or any other suitable operation). For example, the processing equipment may normalize the physiological data, the template, or both, to vary between zero and one, negative one and positive one, or any other predetermined range. In a further example, the processing equipment may apply the techniques of any of the signal conditioning techniques discussed in the context of FIGS. 42-61. In a further example, the processing equipment may normalize the physiological data, template, or both, by dividing by the norm of the array of values to be normalized. In some embodiments, normalized data may have a mean value of zero (i.e., be centered about zero).

Step 6308 may include processing equipment selecting a portion of the physiological data based on a lag and the size of the template of step 6304. Step 6310 may include normalizing the selected portion of data of step 6308 (e.g., using the same of step 6306 or a different technique). Step 6312 may include performing a correlation calculation using the template and the selected portion of data of step 6308. Step 6314 may include updating the lag value if appropriate. In some embodiments, steps 6308-6314 may be performed using a loop for a range of lag values. A first lag value may be used to perform step 6308 during the first iteration, and the lag value may be updated (e.g., incremented) at step 6314 for each subsequent iteration to some final value. For example, the first lag value may be zero, and the processing equipment may select the same data points of the physiological data as the template to perform the correlation (e.g., giving a correlation value of one for suitably normalized data and template). After performing the correlation calculation, the processing equipment may increment the lag value by one at step 6314 and repeat steps 6308-6312 to generate another point of the correlation sequence. In reference to FIG. 64, the final lag value may be equal to (N−M), and the loop of flow diagram 6300 may be ceased when the processing equipment determines that the final lag value has been reached (e.g., at step 6314). It will be understood that the illustrative correlation calculations discussed in the context of FIGS. 62-65 are examples, and any suitable correlation calculation may be used, with a template of any suitable size and including any suitable data points (e.g., the most recent data, or any other suitable data), to generate a correlation sequence. It will also be understood that the processing equipment may calculate correlation sequence values for any suitable set of one or more lag values. For example, in some embodiments, the processing equipment may only calculate correlation sequence values for lag values corresponding to relevant physiological rates (e.g., 20 to 300 BPM corresponding to lag values ranging from 3 to 0.2 seconds, respectively)

Figure 66:
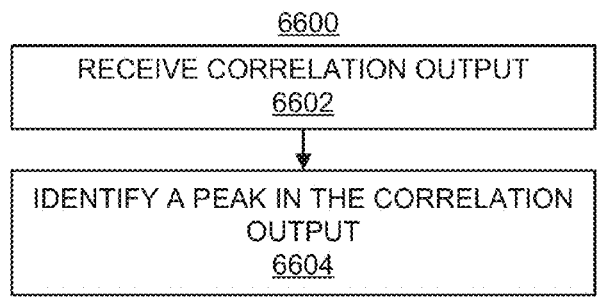
FIG. 66 is a flow diagram of illustrative steps for identifying a peak of a correlation output greater than a threshold, in accordance with some embodiments of the present disclosure.

FIG. 66 is a flow diagram 6600 of illustrative steps for identifying a peak of a correlation output greater than a threshold, in accordance with some embodiments of the present disclosure. FIG. 69 is a plot 6900 showing an illustrative correlation sequence 6902 for a window of physiological data, and several thresholds, in accordance with some embodiments of the present disclosure. FIG. 69 will be referred to below during the discussion of the illustrative steps of flow diagrams 6600 and the illustrative steps of flow diagrams 6700 and 6800 of FIGS. 67 and 68, respectively, which are discussed further below. A correlation output may include one or more peaks corresponding to relatively high correlation between two sets of data points. The illustrative steps of 6600, 6700, and 6800 may be used to identify a particular peak, corresponding to a period (e.g., in lag value, time or sample number) of a physiological rate.

Step 6602 may include processing equipment receiving correlation output (e.g., a correlation sequence). In some embodiments, the correlation output may have been generated using the illustrative techniques of flow diagram 6200 of FIG. 62. In some embodiments, step 6602 may include recalling the correlation output from memory. In some embodiments, the same processing equipment (e.g., the same module or integrated circuit) may generate the correlation output and perform the steps of flow diagram 6600, and accordingly, step 6602 need not be performed.

Step 6604 may include processing equipment identifying a peak in the correlation output of step 6602. In some embodiments, step 6604 may include generating a threshold. The threshold may be generated using a predetermined value, a predetermined function, a value based on a previously calculated rate, a value based on the current operating Mode, a value based one or more metrics derived from the physiological data (e.g., de-trending metrics, noise metrics), using any other suitable technique, or any combination thereof. The processing equipment may identify threshold crossings by comparing all or some of the correlation output to the threshold. The processing equipment may use any suitable peak finding techniques to identify the peak such as, for example, identifying a maximum, identifying an upstroke (i.e., positive slope) and downstroke (i.e., negative slope), applying a threshold, comparing one or more peaks to identify a particular peak (e.g., a largest peak, a peak occurring first in terms of lag), any other suitable peak finding technique, or any combination thereof.

Figure 67:
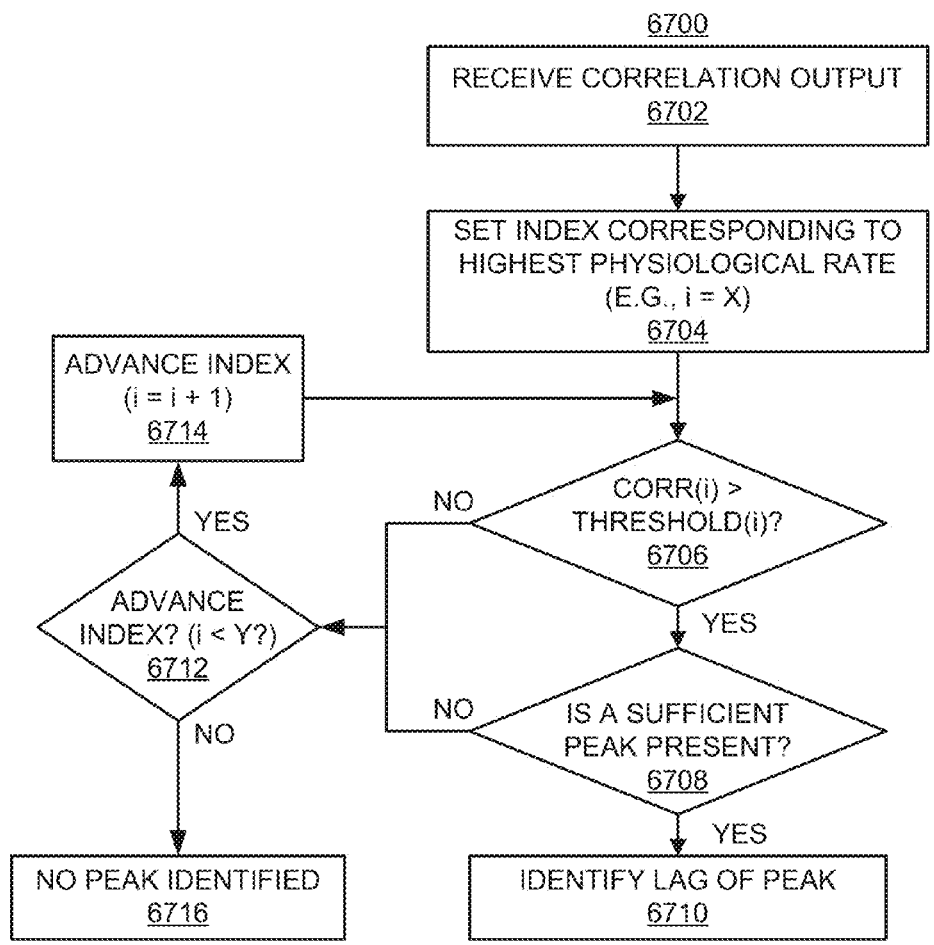
FIG. 67 is a flow diagram of further illustrative steps for identifying a peak of a correlation output greater than a threshold, in accordance with some embodiments of the present disclosure.

FIG. 67 is a flow diagram 6700 of further illustrative steps for identifying a peak of a correlation output greater than a threshold, in accordance with some embodiments of the present disclosure.

Step 6702 may include processing equipment receiving correlation output (e.g., a correlation sequence). In some embodiments, the correlation output may have been generated using the illustrative techniques of flow diagram 6200 of FIG. 62. In some embodiments, step 6702 may include recalling the correlation output from memory. In some embodiments, the same processing equipment (e.g., the same module or integrated circuit) may generate the correlation output and perform the steps of flow diagram 6700, and accordingly, step 6702 need not be performed.

Step 6704 may include processing equipment setting an index corresponding to a highest expected physiological rate. The processing equipment may use the index to indicate the data point of the correlation sequence under test. In some embodiments, the expected range of heart rates may range from 20 to 300 BPM, with the highest expected rate being 300 BPM. At a correlation lag of zero, the correlation sequence value for normalized data and template may have a value of one. The next peak in the correlation may be expected roughly at a lag equal to the period associated with the physiological rate associated with the physiological data. Accordingly, lags relatively smaller than the period associated with the highest expected rate need not be analyzed in some such circumstances. Step 6704 may include setting an index, in units of lag, to the minimum lag still expected to correspond to a physiological rate (e.g., the highest expected physiological rate), as shown by "X" in step 6704. For example, for a maximum expected rate of 300 BPM (i.e., 5 Hz or a period of 0.2 seconds), and a sampling rate of 50 Hz (e.g., the interval between lag points is 0.02 seconds), the minimum expected lag may be about 0.2 seconds, or about 11 lag points (i.e., an index of 11 if the zero lag point has index 1).

Step 6706 may include processing equipment determining whether the correlation sequence point corresponding to the current index is larger than (or equal to) a threshold. In some embodiments, the processing equipment may directly compare the threshold value and the correlation sequence point. In some embodiments, the processing equipment may determine a difference, a ratio, any other suitable comparison metric, or any combination thereof, to determine the relative magnitudes of the correlation sequence point and the threshold.

In some embodiments, step 6706 may include generating the threshold against which the correlation sequence point is compared. The threshold may be a constant value, a line, a polynomial of higher order than one, any other suitable value or function, or any combination thereof. For example, a sequence of threshold values $T_i$ may be generated using Eq. 38:

$$T_i = K\sqrt{i} \tag{38}$$

in which index i corresponds to the lag value of the correlation sequence and K is a coefficient that may be constant, but need not be. In a further example, the sequence of threshold values may be generated using a shifted (along any suitable direction) square root function. In a further example, the sequence of threshold values may be generated using a function that asymptotes or substantially trends toward a square root function. Plot 6900 of FIG. 69 shows three sets of threshold values 6910, 6912, and 6914 generated using Eq. 38, having K values of about 1.5/20, 1.3/20, and 1.1/20, respectively. In some embodiments, the threshold type, or adjustable constants thereof, may be determined depending on the operating Mode. For example, more stringent thresholds (e.g., larger threshold values) may be used in Mode 1, to ensure higher confidence in the physiological rate before progressing to other Modes. In some embodiments, the processing equipment may search for two crossings of the correlation sequence and threshold, corresponding to an upstroke and downstroke. In some embodiments, the processing equipment may only identify the first point (i.e., the point having the lowest lag value) that crosses the threshold. In some embodiments, the threshold may depend on whether the subject is a neonate, and accordingly may depend on the properties of the physiological data.

If, at step 6706, the processing equipment determines that the correlation sequence point corresponding to the current index is larger than the threshold, then the processing equipment may proceed to step 6708. Step 6708 may include processing equipment determining whether a sufficient peak is present. In some embodiments, the processing equipment may identify a peak based on the peak width. For example, the processing equipment may determine a full-width at half maximum (FWHM) value, or other suitable width metric to identify a peak as sufficient. In some embodiments, the processing equipment may require that a peak have a particular number of points with positive slope before the maximum value, and a particular number of negative points with negative slope after the maximum to be a peak. For example, the processing equipment may require that a peak have 4 points with positive slope and 4 points with negative slope for a peak to be sufficient. In a further example, referencing FIG. 69, the point determined to cross the threshold may depend on the threshold value. For the three thresholds 6910, 6912, and 6914, correlation sequence 6902 exhibits different threshold crossing points. The first peak, not including the peak at a lag value of zero, is shown to cross thresholds 6912 and 6914, but not threshold 6910. The second peak, not including the peak at a lag value of zero, is shown to the cross all three thresholds 6910, 6912, and 6914.

If, at step 6708, the processing equipment determines that a sufficient peak is present, then the processing equipment may proceed to step 6710. Step 6710 may include processing equipment identifying the first peak qualified at step 6708 as a peak of the correlation output. In some embodiments, the processing equipment may identify one or more lag values associated with the peak. For example, the processing equipment may identify the maximum value of the first peak. If the processing equipment starts at the lowest relevant lag value (e.g., corresponding to the highest expected rate), once the first peak is identified the processing equipment need not search further, which may save computing resources. In some embodiments, the processing equipment may analyze subsequent points to determine that the peak is sufficient, and need not analyze any further points.

If, at either of steps 6706 or 6708, the processing equipment determines that a criteria has not been met at the current index (e.g., the correlation sequence value does not exceed the threshold, or the peak is not sufficient), the processing equipment may then proceed to step 6712. Step 6712 may include the processing equipment determining whether to advance the index to the next value. In some embodiments, there may be an upper limit on the index, and the processing equipment may determine that the index is not to be advanced when the upper limit is reached. For example, an expected range of heart rates may range from 20 to 300 BPM, with the lowest expected rate being 20 BPM. Accordingly, lags relatively larger than the period associated with the lowest expected rate (e.g., 3 seconds for a rate of 20 BPM) need not be analyzed in some such circumstances, as shown by "Y" in step 6712. If the processing equipment determines that the index is not to be advanced at step 6712, then the processing equipment may proceed to step 6716, and determine that no peak has been identified. If the processing equipment determines that the index is to be advanced at step 6712, then the processing equipment may proceed to step 6714 (e.g., increment the index), and then perform at least one of steps 6706-6710 again.

Figure 68:
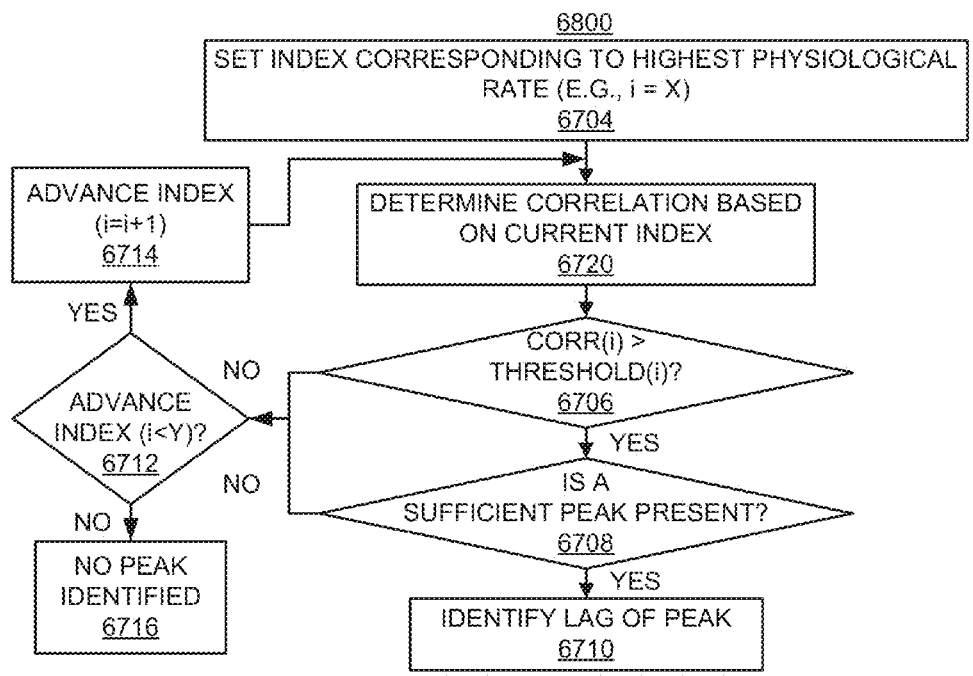
FIG. 68 is a flow diagram of illustrative steps for identifying a peak of a correlation output as the correlation output is generated, in accordance with some embodiments of the present disclosure.
Figure 69:
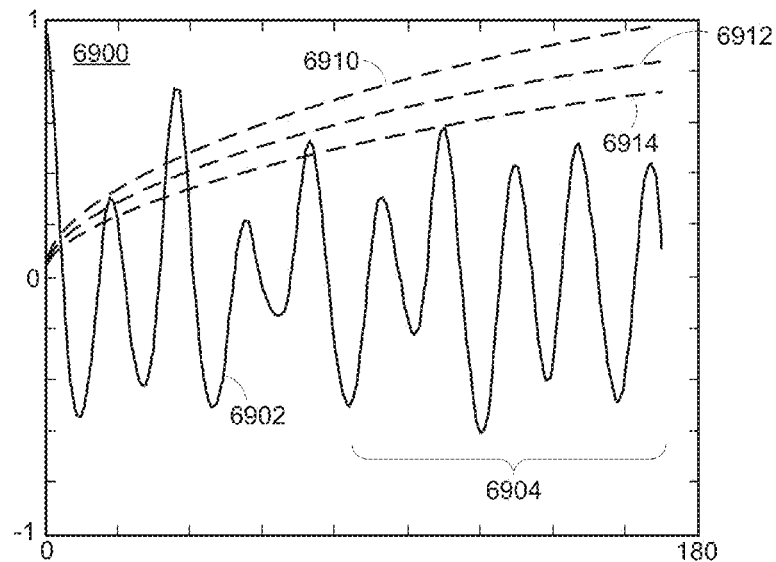
FIG. 69 is a plot showing an illustrative correlation sequence for a window of physiological data, and several thresholds, in accordance with some embodiments of the present disclosure.

FIG. 68 is a flow diagram 6800 of illustrative steps for identifying a peak of a correlation output as the correlation output is generated, in accordance with some embodiments of the present disclosure. Flow diagram 6800 is a modified version of flow diagram 6700 of FIG. 67, in which correlation sequence values are analyzed as they are generated rather than after generation the entire set of correlation sequence values. Similarly numbered steps in flow diagram 6800 may operate similarly as described in the discussion of flow diagram 6700. As shown in FIG. 69, the first threshold crossings, and corresponding identified peaks may occur at relatively small lag values, and the correlation sequence for higher lag values, shown illustratively by region 6904, need not be generated. The processing equipment may therefore save significant computing resources by generating only a portion of the correlation sequence.

Step 6720 of flow diagram 6800 may include processing equipment determining a correlation based on the current index. Accordingly, points in the correlation sequence are generated one at a time, compared against a threshold, and if a sufficient peak is present, a peak may be identified without generating the entire correlation sequence. The illustrative steps of flow diagram 6800 may use relatively less computing resources than the illustrative steps of flow diagram 6700 under some circumstances. In some embodiments, step 6720 may include performing any of the illustrative steps of, for example, flow diagrams 6200 and 6300 of FIGS. 62 and 63, respectively.

Figure 70:
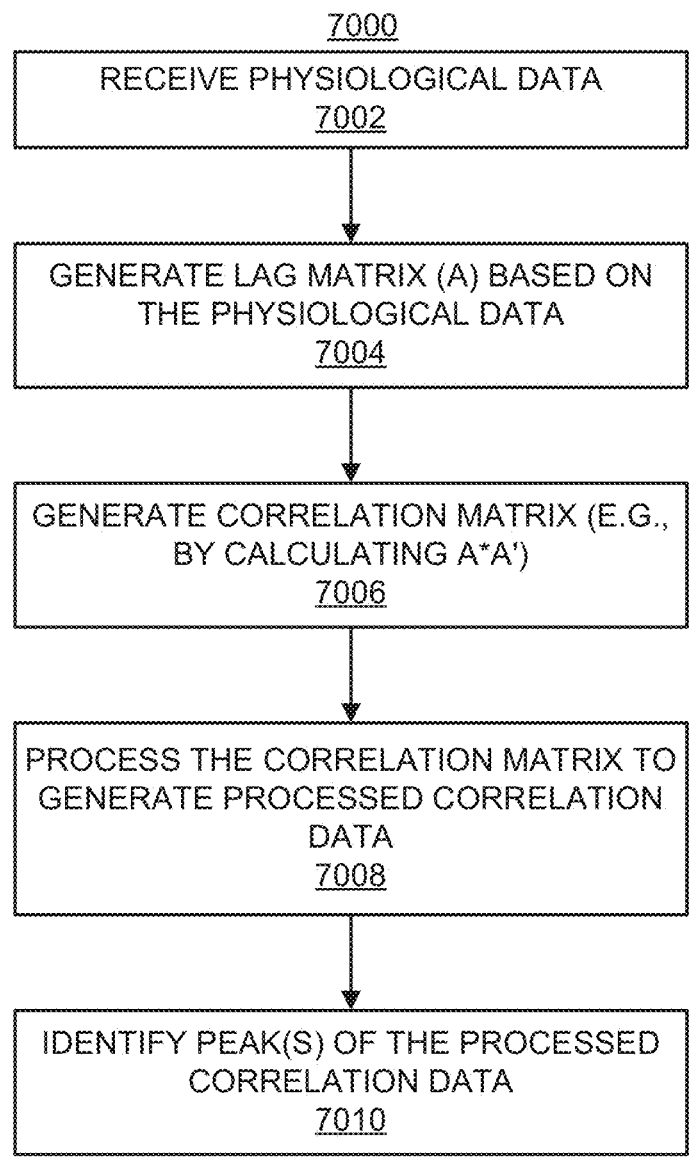
FIG. 70 is a flow diagram of illustrative steps for performing a correlation calculation using a correlation matrix, in accordance with some embodiments of the present disclosure.
Figure 71:
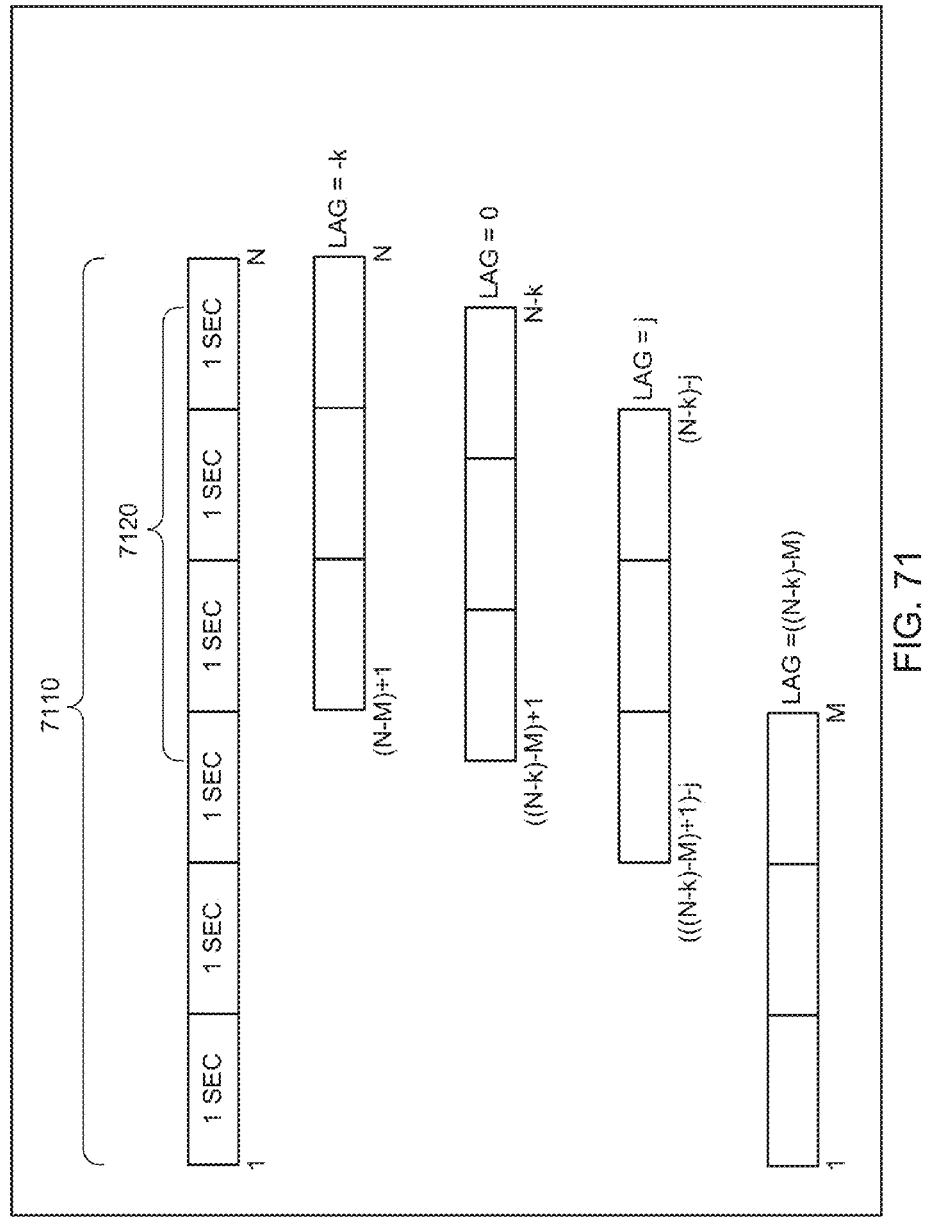
FIG. 71 is a block diagram showing an illustrative window of physiological data with generalized templates and lags, in accordance with some embodiments of the present disclosure.

FIG. 70 is a flow diagram 7000 of illustrative steps for performing a correlation calculation using a correlation matrix, in accordance with some embodiments of the present disclosure. The correlation matrix technique may use multiple templates selected from the physiological data, and may be used to generate multiple correlation sequences. The correlation matrix technique may be especially desirable when the physiological data includes noisy portions, because at least some of the templates and resulting correlations may avoid the noisy portion. FIG. 71 is a block diagram showing an illustrative window of physiological data with generalized templates and lags, in accordance with some embodiments of the present disclosure. FIG. 72 is a diagram showing an illustrative lag matrix and correlation matrix, in accordance with some embodiments of the present disclosure. FIGS. 71-72 will be referred to below during the discussion of the illustrative steps of flow diagram 7000.

Step 7002 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 7002 may include recalling data from the memory for further processing.

Step 7004 may include processing equipment generating a lag matrix based on the received physiological data of step 7002. The lag matrix may include multiple sets of data points, each having the same length as a desired correlation template. In some embodiments, each row of the lag matrix may correspond to a set of data points, offset by one sample from adjacent rows. For example, FIG. 71 shows a window of physiological data 7110, which has an illustrative length of about six seconds and N data points. FIG. 71 also shows illustrative template 7120, having a length of M data points, corresponding to data points ((N−k)−M)+1 through (N−k) of physiological data 7110, where k is an index of the number of data points that template 7120 is offset from the right end of physiological data 7110. Accordingly, for lag j, Eq. 39 shown below:

$$\overline{X}_j = [X_{((N-k)-M)-j+1}, X_{((N-k)-M)-j+2}, X_{((N-k)-M)-j+3}, \ldots, X_{((N-k)-M)-j+(M-1)}, X_{((N-k)-M)-j+M}] \quad (39)$$

may be used to determine the corresponding data points of physiological data 7110 to be used in the correlation calculation. Note that Eq. 39 may be used as a generalized version of Eq. 37, for a template selected from any suitable portion of the physiological data (e.g., using index k). The indices shown in FIG. 71 correspond to Eq. 39, although some indices have been simplified algebraically for convenience. The lag matrix may include multiple collections of data points that correspond to the selected template at different lag values. For example, referencing FIG. 72, the processing equipment may apply, for example, Eq. 40:

$$A_{rc} = X_{(N-M)+c-(r-1)} \quad (40)$$

to generate lag matrix A, in which $A_{rc}$ is the matrix value a row r and column C, N is the total number of data points, M is the template size, and $X_{(N-M)+c-(r-1)}$ is the sample value at the given index. Accordingly, lag matrix A has a size of (N−M)+1 rows by M columns. Each row of the lag matrix A may be a collection of M data points corresponding to a particular lag value. Each successive row has a lag of one more data point than the previous row, as shown by lag matrix 7210 of FIG. 72. Note that the entries of lag matrix 7210 as shown in FIG. 72 are index values, while an actual lag matrix includes the sample values at the respective indices. The indices are presented for clarity, rather than the sample values themselves.

Step 7006 may include processing equipment generating a correlation matrix based on the lag matrix of step 7004. In some embodiments, the processing equipment may generate a correlation matrix C using Eq. 41:

$$C = A*A' \quad (41)$$

in which A is the lag matrix and A' is the transpose of the lag matrix. Accordingly, correlation matrix C may be square, and may have a size of (N−M)+1 rows by (N−M)+1 columns. In an illustrative example, the rows of lag matrix A may be considered collections of data corresponding to lag values j, and the columns of the transposed lag matrix A' may be considered templates, each having a particular offset index k (e.g., as described in FIG. 71). Accordingly, the values of the correlation matrix $C_{k,j}$ for a particular offset k and lag j may be arranged as shown by correlation matrix 7230 of FIG. 72. The correlation matrix may include correlation values for each M point template (e.g., indexed by k) at each lag value j. For example, each column of the correlation matrix may represent a correlation sequence generated using a template of a particular index k, for all lag values j. As shown by correlation matric 7230, each successive column corresponds to a different template, at a value of index k greater by one point than the template of the previous column. Note that positive lag values correspond to the template shifted left from the zero lag value, and negative values correspond to the template shifted right from the zero lag value. Alternatively, the rows of lag matrix A may be considered templates, and the columns of the transposed lag matrix A' may be considered as collections of data corresponding to lag values j, in which case the values of the correlation matrix may be arranged as $C_{j,k}$. In some embodiments, the processing equipment may normalize the template, the corresponding data to be correlated with the template, and/or the correlation value itself, for each correlation calculation (i.e., each value in the correlation matrix C).

Step 7008 may include processing equipment processing the correlation matrix of step 7006 to generate processed correlation data. In some embodiments, using normalized templates and corresponding data, the values on the diagonal (e.g., row index=column index) of the square correlation matrix C may be one, corresponding to a lag of zero (e.g., see correlation matrix 7230 of FIG. 72 with j values of zero on the diagonal) for each template. In some such embodiments, step 7008 may include applying a rotation operation to rotate the diagonal values 45° to be vertically or horizontally oriented in the processed correlation matrix. The size of the rotated matrix may be larger than the original correlation matrix. In some embodiments, processing the correlation matrix may include averaging values of the correlation matrix along one or more directions, therefore generating a one dimensional array values rather than a two dimensional matrix. For example, following a rotation, peak values in the processed correlation matrix may substantially align along a row or column, and the values along the row or column may be averaged, depending on the rotation. In a further example, the processing equipment may average values of a correlation matrix along a direction of fixed lag value.

Step 7010 may include processing equipment identifying one or more peaks of the processed correlation data of step 7008. In some embodiments, step 7010 may include generating the threshold. The threshold may be generated using a predetermined value, a predetermined function, using any other suitable technique, or any combination thereof. The processing equipment may identify threshold crossings by comparing all or some of the correlation output to the threshold. The processing equipment may use any suitable peak finding techniques to identify the peak such as, for example, identifying a maximum, identifying an upstroke (i.e., positive slope) and downstroke (i.e., negative slope), applying a threshold, comparing one or more peaks to identify a particular peak (e.g., a largest peak, a peak occurring first in terms of lag value), any other suitable peak finding technique, or any combination thereof.

Figure 73:
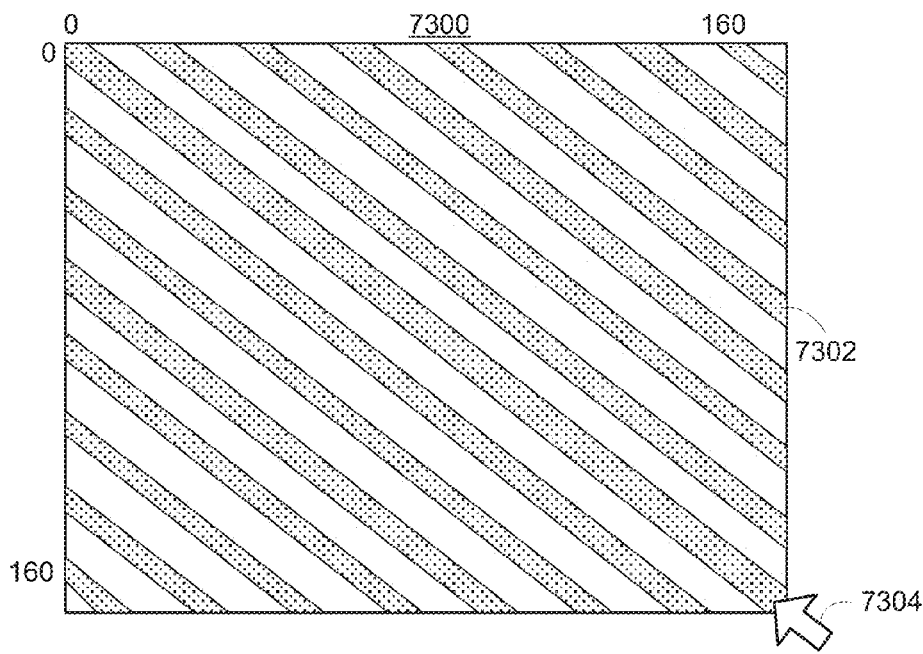
FIG. 73 is a plot showing a graphical representation of an illustrative correlation matrix, in accordance with some embodiments of the present disclosure.
Figure 74:
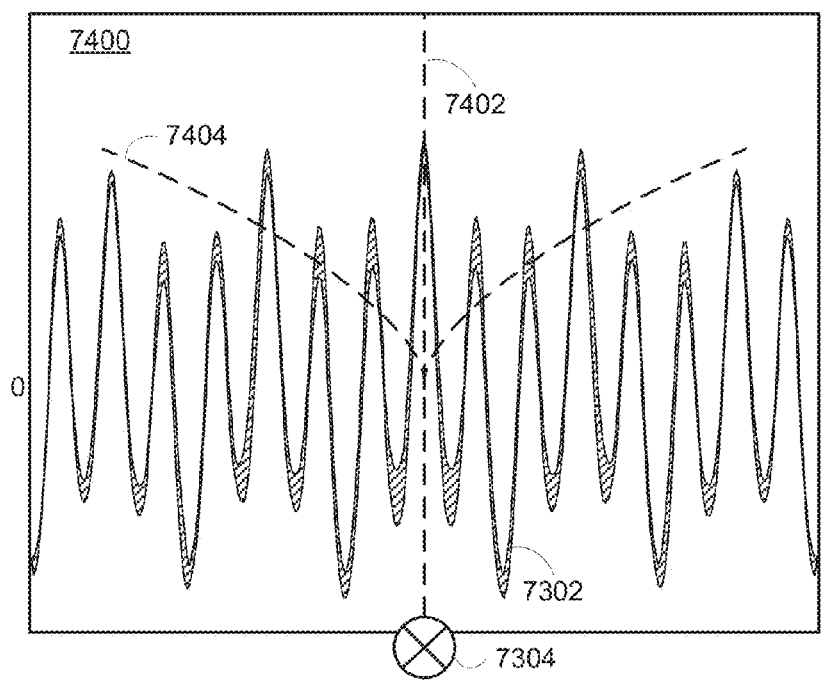
FIG. 74 is a plot showing a graphical representation of the illustrative correlation matrix of FIG. 73 facing a primary direction, in accordance with some embodiments of the present disclosure.

FIG. 73 is a plot 7300 showing a graphical representation 7302 of an illustrative correlation matrix, in accordance with some embodiments of the present disclosure. Graphical representation 7302 of the correlation matrix includes a series of peaks normal to the coordinate axes (i.e., into and out of the page), indicated by the shaded diagonal regions. Graphical representation 7302 of the correlation matrix has a primary direction shown by arrow 7304 along which the lag is zero, or a multiple of the period associated with the physiological rate. FIG. 74 is a plot 7400 showing graphical representation 7302 of the illustrative correlation matrix of FIG. 73 facing a primary direction (i.e., the direction of arrow 7304, directed into the page in FIG. 74) to show the range of correlation matrix values, in accordance with some embodiments of the present disclosure. The relatively largest peak shown in FIG. 74 corresponds to a lag value of zero, with additional peaks on either side corresponding to multiples of the period associated with the physiological rate. In some embodiments, the processing equipment may apply a matrix operation such as, for example, a 45° CW rotation to a correlation matrix, so that a primary direction substantially aligns along a row or a column. The units of plot 7400 are not the same as the units of plot 7300 due to the direction and orientation of view. In some embodiments, the processing equipment may use one or more properties of the correlation matrix to aid in identifying a peak, determining a lag value, or both. For example, using a processed correlation matrix generated by a 45° CW rotation and averaging of the columns (e.g., to give a one-dimensional array), the processing equipment may use a lag value of zero as a reference, as shown by dashed line 7402 in FIG. 74. From the reference, which is associated with a maximum peak, the processing equipment may analyze lag values incrementally outward in each direction to identify a first peak. The processing equipment may use threshold 7404, which may be similar to the thresholds of plot 6900, referenced to the zero lag position and extending symmetrically in each direction, to identify the first peak. The processing equipment may accordingly determine the lag value associated with the peak, in which the lag value may be indicative of a period associated with a physiological rate. In some embodiments, the processing equipment may identify a peak in each direction and average the associated lag values. In some embodiments, the processing equipment may identify a peak in each direction and identify the peak as the peak having the lesser associated lag value.

As discussed above, a correlation calculation provides a single correlation value for each lag value between two segments of physiological data (e.g., a template and corresponding portion of data at a lag value). The segments of physiological data may include a relatively large amount of information, which is not necessarily fully represented by the single correlation value. In some embodiments, statistical regression analysis (SRA) may be used to, for example, aid in performing a correlation calculation, modify a correlation calculation, identify a peak in a correlation sequence, or a combination thereof, by analyzing information additional to the correlation value of the two segments of physiological data. For example, SRA may be used to determine a metric based on the two segments, and the metric may be used to weight the correlation values of a correlation calculation using the two segments. In a further example, SRA may be used to determine a metric, which may be used to identify a peak in a correlation output. The SRA techniques disclosed herein may be especially useful when, for example, applied to lag values correspond to peaks that just exceed or just do not exceed a threshold (e.g., are very near a threshold), where peak identification may be sensitive to variations in data and more information on the correlation may be desired. FIGS. 75-85 are included as illustrative examples, although it will be understood that the illustrative SRA techniques disclosed herein do not necessarily require generating any plots.

Figure 75:
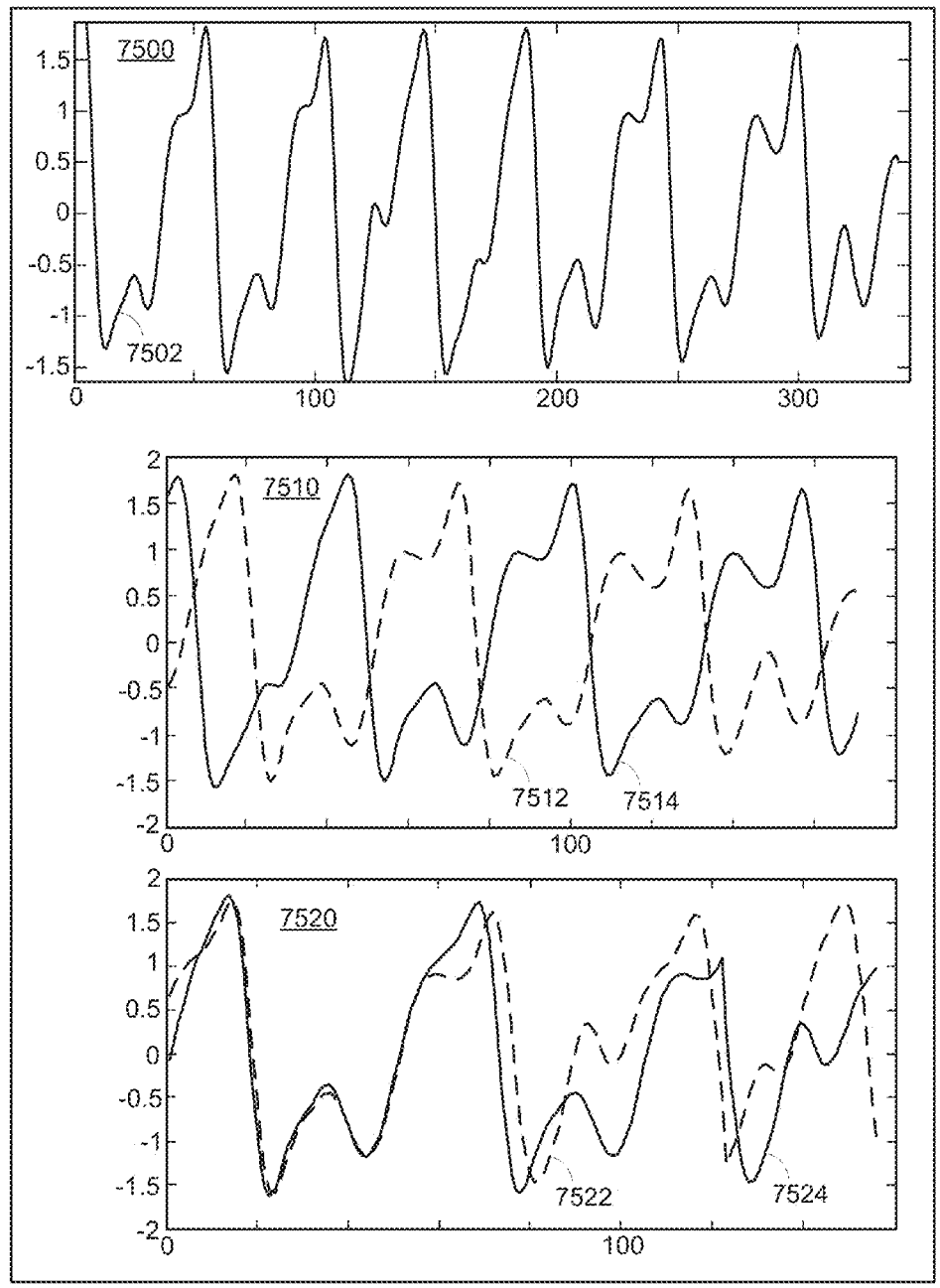
FIG. 75 is a panel of three plots showing an illustrative window of data, and two sets of two segments of physiological data having a relative lag, in accordance with some embodiments of the present disclosure.

FIG. 75 is a panel of three plots 7500, 7510, and 7520, respectively showing an illustrative window of data 7502, and two sets of two segments of physiological data having a relative lag, in accordance with some embodiments of the present disclosure. The abscissa of plots 7500, 7510, and 7520 is shown in units of sample number (at a sampling grate of about 57 Hz), while the ordinates are shown in arbitrary units. Illustrative window of data 7502, including about 342 data points, exhibits six full peaks of de-trended physiological data. The physiological rate associated with window of data 7502 (and segments 7512, 7514, 7522 and 7524 thereof) is near 1 Hz (e.g., having a period of about 1 second), with some variation. Physiological data 7502 is roughly periodic, having a series of peaks and troughs spaces by a period corresponding to a physiological rate (e.g., the period is the reciprocal of the rate in suitable units). A correlation calculation of a segment of data 7502 with another segment of data 7502 at a lag of zero or an integer multiple of the period will give a relatively large value (e.g., a correlation coefficient of near one, or "correlated") because the peaks and troughs of one segment will substantially line up with the respective peaks and troughs of the other segment. Alternatively, a correlation calculation of a segment of data 7502 with another segment of data 7502 at a lag of a half period or a half period plus an integer multiple of the period will give a relatively large negative value (e.g., a correlation coefficient of near negative one, or "anti-correlated") because the peaks and troughs of one segment will substantially line up with the respective troughs and peaks of the other segment. Lags values between half and full periods are expected to result in intermediate correlation values. Plot 7510 shows segment 7512 and segment 7514, each including about 171 points, having a relative lag of 28 samples (e.g., about a half period). Plot 7520 shows segment 7522 and segment 7524, each including about 171 points, having a relative lag of 55 samples (e.g., about a full period). Segments 7512 and 7514 result in a relatively large negative correlation value (e.g., a negative correlation value for de-trended segments), while segments 7522 and 7524 result in relatively high correlation (e.g., a positive correlation value for de-trended segments). In some embodiments, SRA may be used to extract further information than just a correlation value between two segments. For example, correlation calculations performed at two different lag values may result in similar correlation values, but the data may of the data segments may line up more closely in at one of the lag values, indicating the likely true period. It will be understood that any suitably sized window of data, and segment thereof, may be used in accordance with the present disclosure, and that a window size of 342 samples is used for illustration. It will also be understood that any suitable sampling rate may be used in accordance with the present disclosure, and that roughly 57 Hz is used for illustration.

Figure 76:
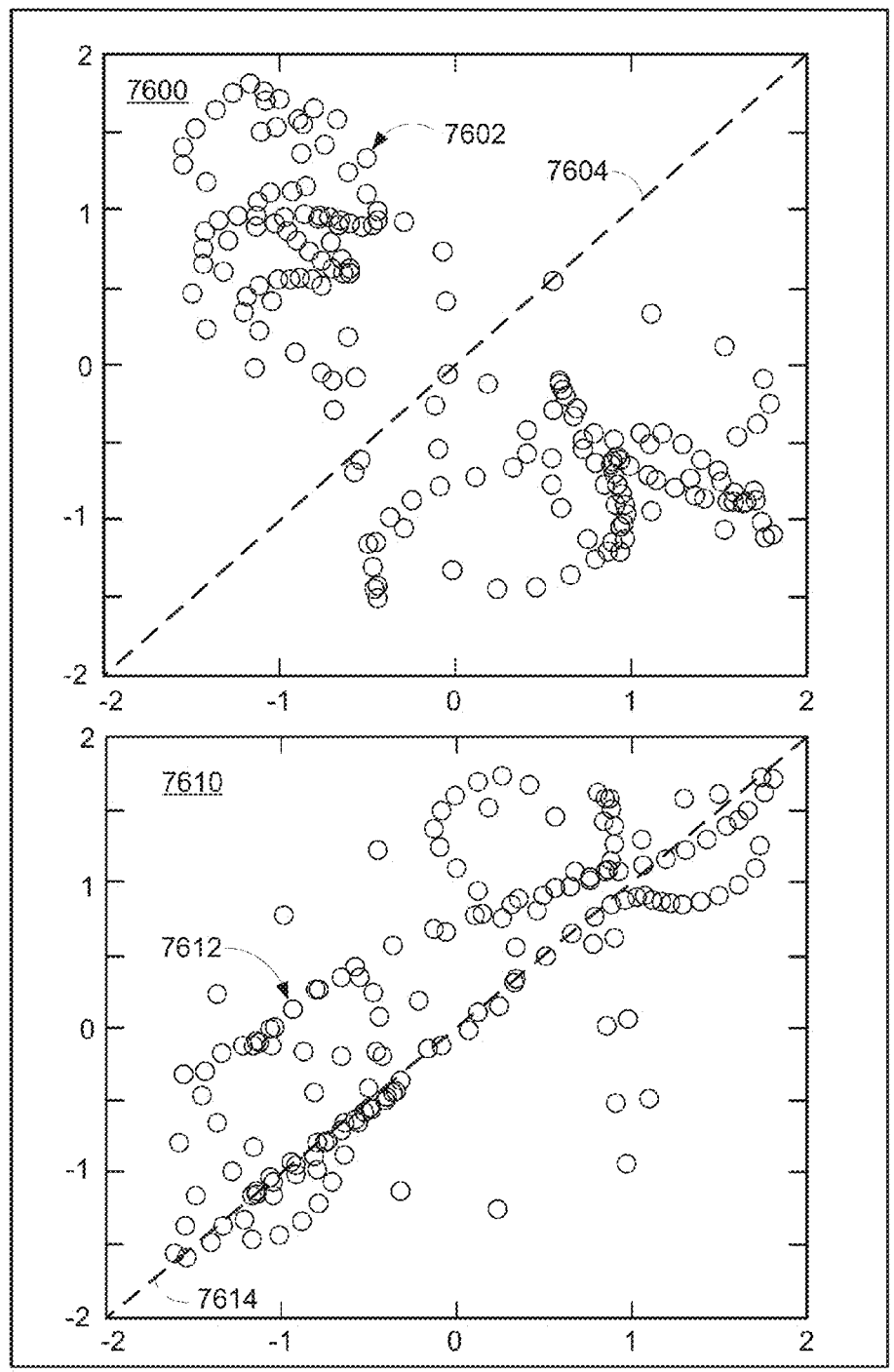
FIG. 76 is a panel of two illustrative plots each showing a set of a template and corresponding data of FIG. 75 plotted against each other, in accordance with some embodiments of the present disclosure.

In some embodiments, a first and second segment of physiological data may be paired to generate a set of value pairs, thus reducing the two segments to a single set of value pairs that may be analyzed. Each value pair may include a value of the first segment, and a corresponding value of the second segment (e.g., graphically, this can be represented by points in two-dimensional space, where each axis represents values from a respective segment). Using such a construct in a graphical example, value pairs corresponding to highly correlated segments will tend towards a line of slope one, through the origin (e.g., the line y=x). Using the same construct in this graphical example, value pairs corresponding to highly anti-correlated segments will tend towards a line of slope negative one, through the origin (e.g., the line y=−x). Further, using the same construct in a graphical example, value pairs corresponding to non-correlated segments would be expected to be randomly distributed in the two-dimensional plane about the origin (e.g., in a Gaussian distribution). FIG. 76 is a panel of two illustrative plots 7600 and 7610 each showing a set of a template and corresponding data of FIG. 75 plotted against each other, in accordance with some embodiments of the present disclosure. Plot 7600 shows value pairs 7602 corresponding to segments 7512 and 7514, in which for each sample value shown in plot 7510, the values of segments 7512 and 7514 are combined as a coordinate pair in plot 7600. The value pairs 7602 may be generated using Eq. 42, as shown below:

$$P_i = (S_{1,i}, S_{2,i}) \qquad (42)$$

in which $P_i$ is a value of value pairs 7602 for index i, and $S_{j,i}$ are the values of segments 7512 and 7514 of FIG. 75 (either order may be used) for index j (e.g., ranging from 1 to 2 corresponding to a first and second segment in either order). Plot 7610 shows a value pairs 7612 corresponding to segments 7522 and 7524 of FIG. 75, in which for each sample value shown in plot 7520, the values of segments 7522 and 7524 are combined as a coordinate pair in plot 7610 (e.g., using Eq. 42). Value pairs 7602 are indicative of the relatively high anti-correlation of segments 7512 and 7514 of FIG. 75, exhibited by the relatively large deviation of value pairs 7602 from line 7604 having unit slope and passing through the origin of plot 7600 (e.g., the slope of the trend line of value pairs 7602 is much closer to −1). Value pairs 7612 are indicative of the relatively high correlation of segments 7522 and 7524 of FIG. 75, exhibited by the relative agreement of value pairs 7612 with line 7614 having unit slope and passing through the origin of plot 7610. While a correlation value may provide a single representative value of each of sets of points 7602 and 7612, additional information is available if desired, as discussed below in the context of FIG. 77, for example. For example, correlation values calculated at two different lag values may have similar correlation values which may indicate a peak, but their distribution of value pairs (e.g., generated using Eq. 42) may differ. A lag value truly corresponding to the period of a physiological rate is expected to result in value pairs that line up well with a line such as line 7614. A lag value that does not correspond to the period of a physiological rate is expected to result in value pairs that do not line up well with a line such as line 7614. Accordingly, SRA may aid in discerning a true peak from an artifact peak in a correlation calculation based on physiological data.

The distribution of value pairs in plots 7600 and 7610 of FIG. 76 also provide insight into how well the original segments are correlated. Segments of physiological data centered about zero exhibiting peaks and troughs will typically have larger slopes near value so of zero and small slopes near the maximum and minimum values (e.g., the slope at the zenith of a peak or the bottom of a trough is substantially zero). Accordingly, upstrokes and downstrokes typically include fewer data points, while there are relatively more data points near the maximums and minimums (e.g., at the peaks and troughs). Value pairs 7602 show relatively large groupings of points in the upper left and lower right corners, substantially corresponding to pairings of peak values with trough values from the two segments. Alternatively, value pairs 7612 show relatively large groupings of points in the lower left and upper right corners, substantially corresponding to pairings of peak values with peak values, and trough values with trough values from the two segments. The groupings of value pairs 7602 and 7612 are oriented in different directions, essentially normal to one another. While a horizontal or vertical distribution of value pairs 7602 and 7612 may respectively appear similar, for example, a 45° rotation of the value pairs aligns the point groupings in sometimes more convenient directions (e.g., horizontal or vertical). Flow diagrams 7700, 7900, 8100, and 8200 of FIGS. 77, 79, 81, and 82 discussed below provide some description of techniques for analyzing distributions of value pairs.

Figure 77:
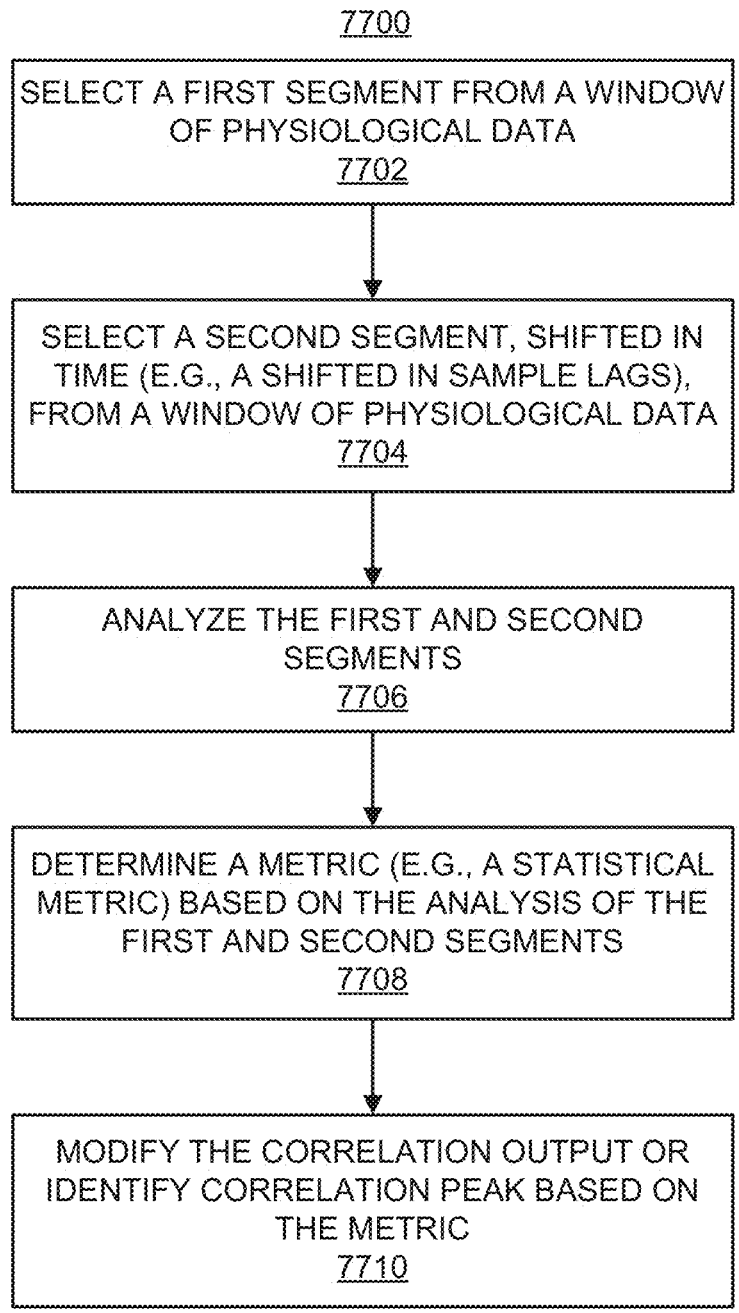
FIG. 77 is a flow diagram of illustrative steps for determining a metric from two segments of physiological data, and using the metric to modify correlation output or identify a correlation peak, in accordance with some embodiments of the present disclosure.

FIG. 77 is a flow diagram 7700 of illustrative steps for determining a metric from two segments of physiological data, and using the metric to modify correlation output or identify a correlation peak, in accordance with some embodiments of the present disclosure. In some embodiments, the processing equipment may generate a correlation sequence based on the first and second segments using a sequence of lag values. The illustrative techniques of flow diagram 6600 may be used to determine further information regarding the two segments.

Step 7702 may include processing equipment selecting a first segment from a window of physiological data. In some embodiments, the first segment may have a predetermined length in time or number of samples. For example, referencing FIG. 75, segment 7514 includes about 171 samples of roughly 342 samples of a full window of data. In some embodiments, the length of the first segment may depend on a previously calculated rate (e.g., relatively longer segments may be used for relatively lower rates).

Step 7704 may include processing equipment selecting a second segment from the window of physiological data, shifted in time (e.g., lag in sample number) relative to the first segment of step 7702. In some embodiments, the second segment may have the same length as the first segment (e.g., the same total number of samples). In some embodiments, the lag may be determined based on a previously calculated rate. For example, the processing equipment may select a lag equal to the period associated with a previously calculated rate. In some embodiments, multiple lags may be selected, and accordingly, multiple second segments may be selected, creating multiple pair of the first segment and second segments.

Step 7706 may include processing equipment analyzing the first and second segments of steps 7702 and 7704. In some embodiments, step 7706 may include determining a correlation value between the first and second segments. In some embodiments, step 7706 may include generating new value pairs from the first and second segments using, for example, Eq. 42.

Step 7708 may include processing equipment determining a metric based on the analysis of step 7706. In some embodiments, the metric may indicate how well the first and second segments are correlated. In some embodiments, the metric may indicate a comparison between new value pairs generated from the first and second segments and reference value pairs (e.g., a reference distribution or other function). The metric may be normalized to range from zero to one, or scaled to any other suitable range. In some embodiments, the metric may be based on a statistical calculation.

Step 7710 may include processing equipment modifying a correlation output, identifying a peak in a correlation output, or both, based on the metric of step 7708. In some embodiments, the processing equipment may use the metric of step 7708 to weight one or more points of a correlation sequence between the first and second segments. For example, if the determined metric indicates poor correlation between the first and second segments, then the processing equipment may down-weight the corresponding point of a correlation sequence between the first and second segments. In some embodiments, the processing equipment may implement the illustrative techniques of flow diagram 7700 to identify a peak in a correlation sequence. For example, the illustrative techniques of flow diagram 7700 may be used with step 6604 of flow diagram 6600 of FIG. 66 or step 6706 of flow diagrams 6700-6800 of FIGS. 67-68.

Figure 78:
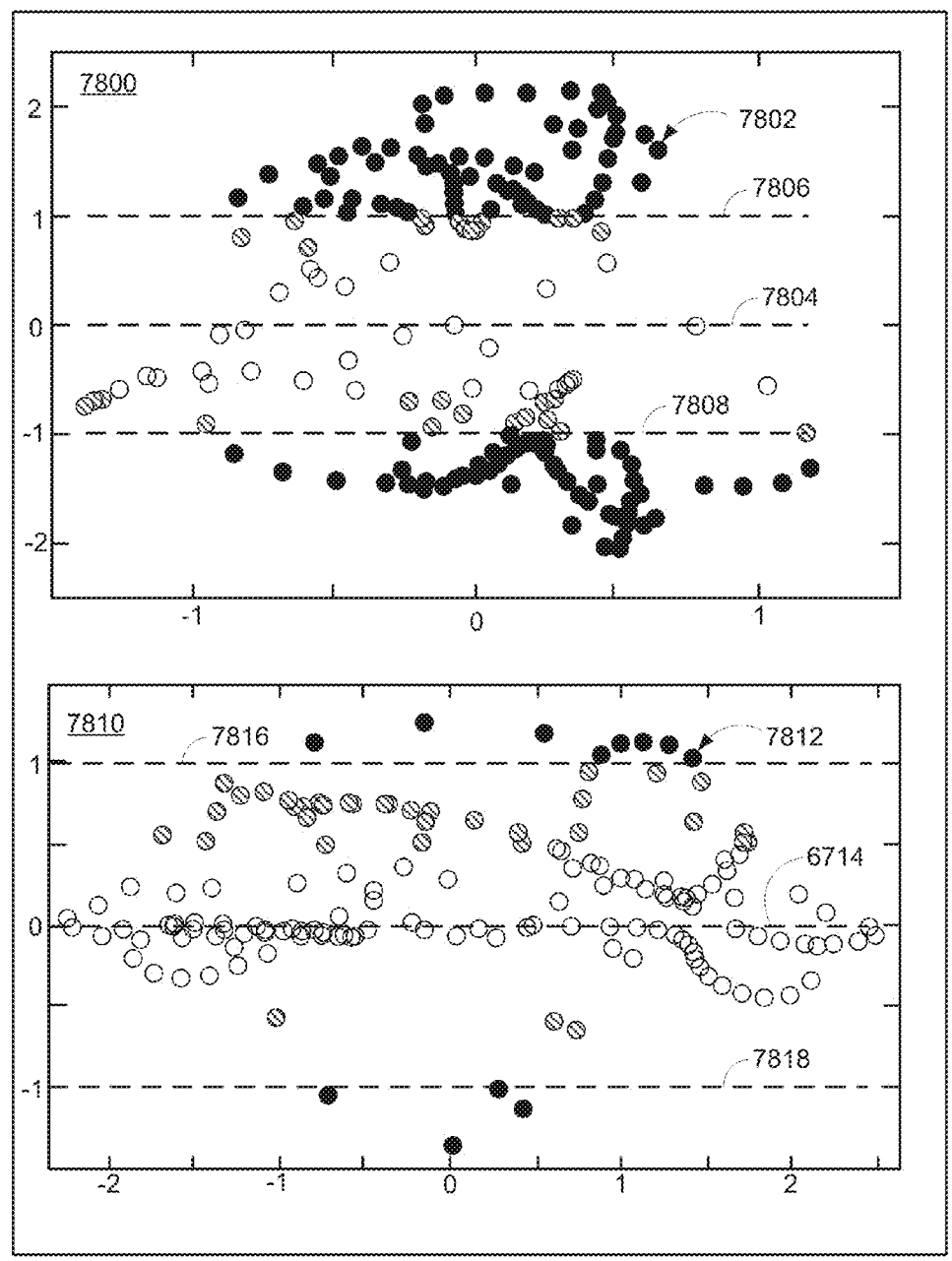
FIG. 78 is a panel of two plots corresponding to the plots of FIG. 76 after an illustrative transformation of the data, in accordance with some embodiments of the present disclosure.

FIG. 78 is a panel of two plots corresponding to the plots of FIG. 76 after an illustrative transformation of the data, in accordance with some embodiments of the present disclosure. The illustrated transformation in FIG. 78 includes a 45° clockwise (CW) rotation of the value pairs, orienting lines 7604 and 7614 of FIG. 76 horizontal in plots 7800 and 7810, respectively. It will be understood that this transformation is illustrated for clarity, and that any suitable transformation, or no transformation, may be performed on value pairs generated from a first and second segment. The techniques discussed below in the context of FIGS. 79-85 may be applied to untransformed or transformed data. In some circumstances, the 45° CW rotation may simplify further calculations because the correlation axis is rotated to horizontal, allowing convenient partitioning of horizontal and vertical properties of a set of data points. The 45° CW rotation may be generated for a value pair, for example, using Eq. 43:

$$\begin{bmatrix} x_{i,r} \\ y_{i,r} \end{bmatrix} = \begin{bmatrix} \cos\theta & -\sin\theta \\ \sin\theta & \cos\theta \end{bmatrix} \begin{bmatrix} x_i \\ y_i \end{bmatrix} \quad (43)$$

in which original points $(x_i, y_i)$ are rotated by an angle $\theta$ of $-45°$, resulting in corresponding rotated points $(X_{i,r}, y_{i,r})$. Value pairs 7802 of plot 7800 were generated by performing the 45° CW rotation of value pairs 7602 of FIG. 76. Value pairs 7812 of plot 7810 were generated similarly from value pairs 7612 of FIG. 76. In some embodiments, the data used to generate value pairs 7802 and 7812 may have undergone a mean subtraction and normalization based on the standard deviation of the data. In each of plots 7800 and 7810, points between −0.5 and 0.5 are not filled, points between 0.5/−0.5 and 1/−1 are hatched, and points outside of −1 and 1 are filled black. References lines 7806 and 7808 indicate the ordinate value of one, while reference lines 7816 and 7818 indicate the ordinate value of negative one. Value pairs 7802 exhibit relatively more points outside of −1 and 1 (i.e., filled black in FIG. 78) than value pairs 7812, indicating relatively more points of value pairs 7802 deviating from the line 7804 than points of value pairs 7812 deviating from the line 7814. Accordingly, one or more metrics may be determined which may quantify such differences, which may indicate how well the original segments are correlated.

Figure 79:
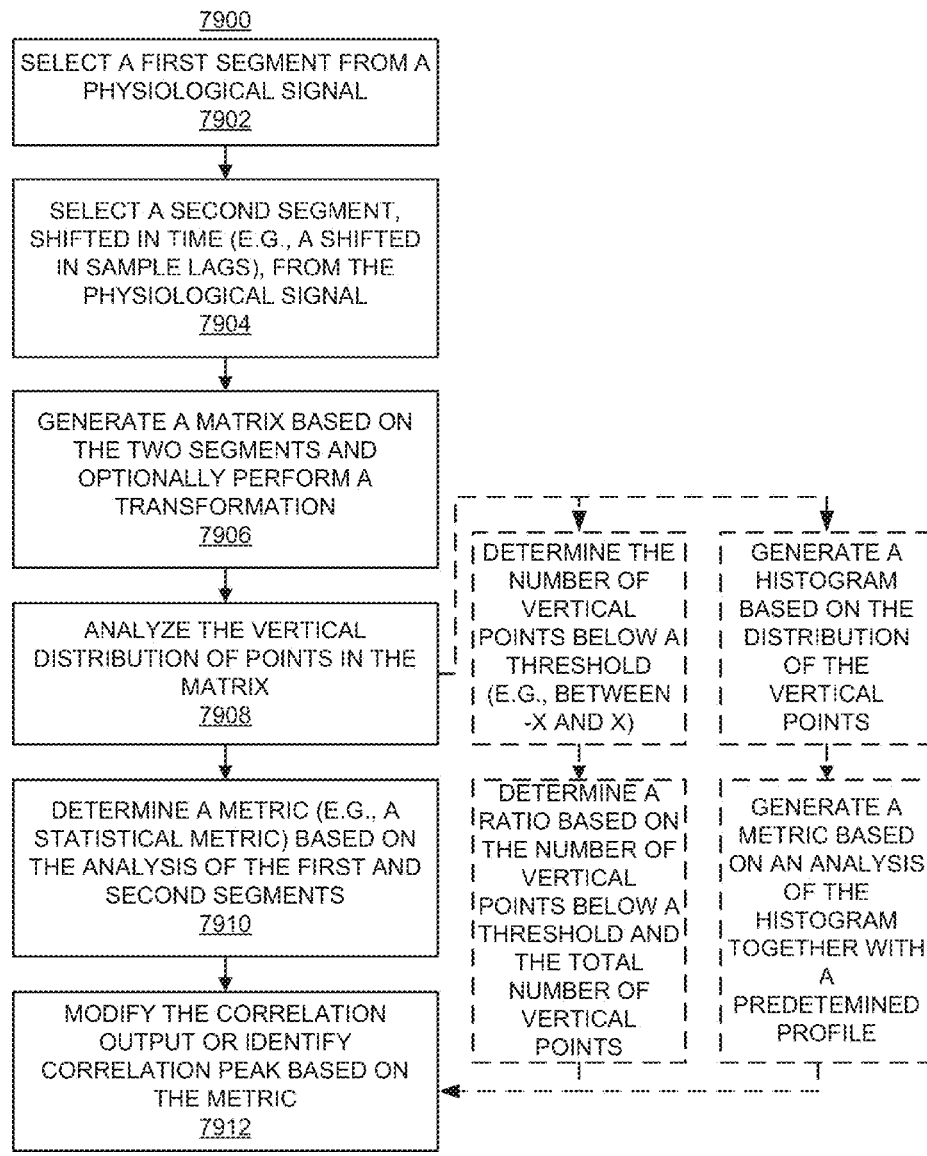
FIG. 79 is a flow diagram of illustrative steps for determining a metric from a vertical distribution, and using the metric to modify correlation output or identify a correlation peak, in accordance with some embodiments of the present disclosure.

FIG. 79 is a flow diagram 7900 of illustrative steps for determining a metric from a vertical distribution, and using the metric to modify correlation output or identify a correlation peak, in accordance with some embodiments of the present disclosure. In some embodiments, referencing plots 7800 and 7810 of FIG. 78, analysis of the vertical distribution of rotated value pairs (e.g., of a matrix following a 45° CW rotation) may provide correlation information. For example, value pairs 7802 of plot 7800 have a relatively broad vertical distribution as compared to value pairs 7812 of plot 7810. Further, value pairs 7802 of plot 7800 have a double-peaked vertical distribution as compared to value pairs 7812 of plot 7810 which exhibit substantially a single peak. For correlated segments, the vertical distribution is expected to exhibit substantially a single peak near zero, while the vertical distribution for anti-correlated segments is expected to exhibit two peaks spaced on both sides of zero. It will be understood the value pairs need not be rotated, and that the illustrative techniques described below may be applied in any suitable direction. Rotation of the value pairs by −45° merely provides a convenient illustrative example.

Step 7902 may include processing equipment selecting a first segment from a window of physiological data. In some embodiments, the first segment may have a predetermined length in time or number of samples. For example, referencing FIG. 75, segment 7514 includes about 171 samples of the roughly 342 samples of a full window of data. In some embodiments, the length of the first segment may depend on a previously calculated rate (e.g., relatively longer segments may be used for relatively lower rates).

Step 7904 may include processing equipment selecting a second segment from the window of physiological data, shifted in time (e.g., lag in sample number) relative to the first segment of step 7902. In some embodiments, the second segment may have the same length as the first segment (e.g., the same total number of samples). In some embodiments, the lag may be determined based on a previously calculated rate. For example, the processing equipment may select a lag equal to the period associated with a previously calculated rate. In some embodiments, multiple lags may be selected, and accordingly, multiple second segments may be selected, creating multiple pair of the first segment and second segments.

Step 7906 may include processing equipment generating a matrix based on the first and second segments of steps 7902 and 7904. In some embodiments, the matrix may be generated using, for example, Eq. 42 to generate a set of value pairs (e.g., a 2×N matrix of N value pairs) based on the segments. In some embodiments, a transform may be optionally performed on the matrix (e.g., mean subtraction, normalization, rotation). For example, the value pairs may be rotated by −45° using Eq. 43. In such examples following the rotation, referencing a geometric interpretation, the value pairs may each include a horizontal value (e.g., the "x" value" in typical Cartesian coordinates), and a vertical value (e.g., the "y" value" in typical Cartesian coordinates). It will be understood that horizontal and vertical are referenced to rotated value pairs, although any suitable directional axes may be used as references. For example, referencing un-rotated value pairs, the directional axes given by "y=x" and "y=−x" may be used as references.

Step 7908 may include processing equipment analyzing the vertical distribution of points in the matrix of step 7906. In some embodiments, step 7908 may include processing equipment analyzing points in a direction substantially perpendicular to a correlation axis (e.g., perpendicular to lines 7604 and 7614 of FIG. 76, and lines 7804 and 7814 of FIG. 78). For example, referencing FIG. 76, step 7908 may include analyzing the distribution of value pairs 7602 relative to line 7604, although the data points need not be plotted to perform step 7908. In a further example, referencing FIG. 78, step 7908 may include analyzing the distribution of value pairs 7802 relative to line 7804, although the data points need not be plotted to perform step 7908. As discussed above, segments having a lag value of an integer multiple of the period associated with the physiological rate are expected to have vertical distributions exhibiting a single peak at zero. For example, highly correlated segments (i.e., a correlation coefficient of near one) would all lie on the horizontal axis after a −45° rotation, and therefore the vertical distribution would resemble a Delta function (e.g., the distribution is nearly single valued, with the instance of all other values being substantially zero). The Delta function is sharper than a Gaussian, with a much smaller spread, and serves as a theoretical limit in this example, although physiological data will have some variation and will likely not achieve a Delta function.

Step 7910 may include processing equipment determining a metric base on the analysis of step 7908. In some embodiments, the metric may be indicative of the shape in the vertical distribution. For example, the metric may be indicative of the distribution peak, spread, or both. In some embodiments, the metric may be a value normalized between zero and one. In some embodiments, the analysis may include determining a number of value pairs having a vertical value within two threshold values (e.g., between −1 and 1, between −0.5 and 0.5, between −1 and 1 excluding points between −0.5 and 0.5, or any other suitable threshold range). In some embodiments, the ratio of value pairs having a vertical value in a particular threshold range to the total number of pairs may be used as a metric. For example, the number of value pairs having a vertical value outside of −1 and 1 may be divided by the total number of value pairs to give a metric. In some embodiments, the analysis may include determining a distribution of vertical values of the value pairs. For example, the processing equipment may generate a histogram of the vertical values of the value pairs. In a further example, the processing equipment may generate a cumulative distribution (e.g., an integral or sum of the histogram), and analyze the cumulative distribution of vertical values.

Figure 81:
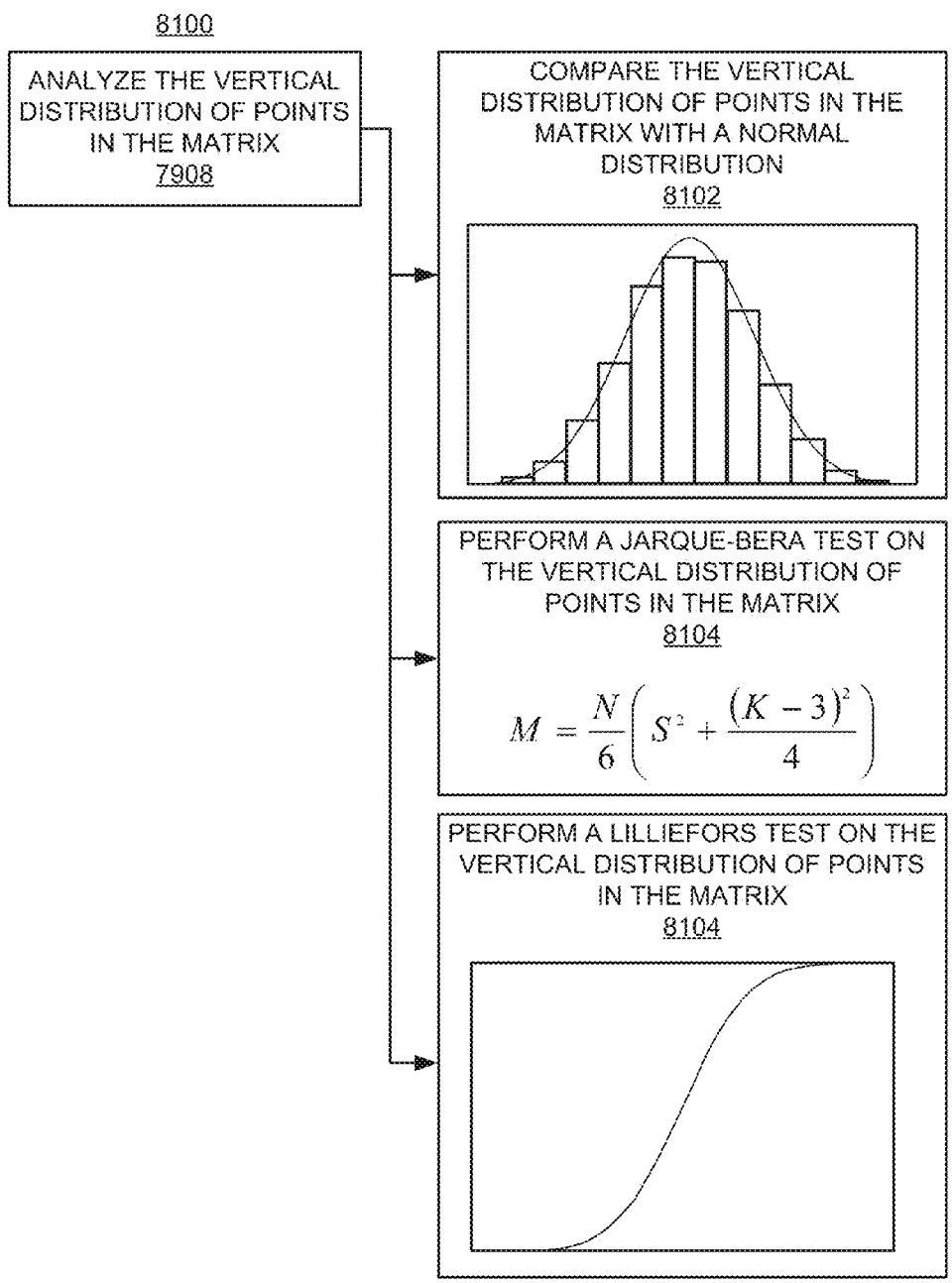
FIG. 81 is a flow diagram of illustrative steps analyzing a vertical distribution, in accordance with some embodiments of the present disclosure.

In some embodiments, the analysis may include a normality test or other statistical test. In some embodiments, the analysis may include generating a reference distribution (a histogram or cumulative distribution derived thereof), and comparing the distribution of vertical values with the reference distribution. For example, the processing equipment may determine a mean and standard deviation of the vertical values, generate a normal distribution with the same standard deviation and mean, and determine a difference (e.g., a sum of squared differences between each value and the corresponding value of the normal distribution) between the distribution of vertical values and the normal distribution. In a further example, the processing equipment may determine a skewness value, kurtosis value, or both, based on the vertical values and compare this value(s) with a threshold or reference values. In a further example, the processing equipment may perform a Jarque-Bera (JB) Test using, for example, Eq. 44:

$$M = \frac{N}{6}\left(S^2 + \frac{(K-3)^2}{4}\right) \qquad (44)$$

in which test metric M is based on number of points N, sample skewness S, and sample kurtosis K. The test metric M is zero for a normal distribution and increase as the vertical values deviate from a normal distribution. In some embodiments, for example, the test metric M may be compared to a threshold to determine whether to modify a correlation value, or scaled and used as a confidence value directly to modify a correlation value. In a further example, the processing equipment may perform a Kolmogorov-Smirnoff test such as, for example, a Lilliefors Test based on the cumulative distribution of vertical values, with the metric being the maximum discrepancy, a sum of differences, or any other suitable value indicative of the difference. In some embodiments, for example, the value indicative of the difference may be compared to a threshold to determine whether to modify a correlation value, or scaled and used as a confidence value directly to modify a correlation value. FIG. 81 is a flow diagram 8100 of illustrative steps for analyzing a vertical distribution, in accordance with some embodiments of the present disclosure. In some embodiments, the analysis of step 7908 of flow diagram 7900 may include comparing the distribution of points in the vertical direction with a reference distribution. For example, in some embodiments, the processing equipment may compare the vertical distribution of points (e.g., generated using a histogram) with a normal distribution, as shown by step 8102. The processing equipment may, for example, determine the square root of the sum of squared differences between the distribution of vertical values and the reference distribution, and use the difference as a confidence metric (e.g., where larger differences correspond to reduced confidence in correlation between the segments). In a further example, in some embodiments, the processing equipment may perform a Jarque-Bera test (e.g., using Eq. 44) on statistical metrics derived from the vertical distribution of points, as shown by step 8104. The processing equipment may, for example, determine the Jarque-Bera metric, and use the difference as a confidence metric (e.g., where larger differences correspond to reduced confidence in correlation between the segments). In a further example, in some embodiments, the processing equipment may perform a Lilliefors test on the vertical distribution of points, or a cumulative distribution derived thereof, as shown by step 8104. The processing equipment may, for example, determine the maximum difference between the cumulative distribution of vertical values and a reference cumulative distribution, and use the difference as a confidence metric (e.g., where a larger difference correspond to reduced confidence in correlation between the segments).

Step 7912 may include processing equipment modifying a correlation output, identifying a peak in a correlation output, or both, based on the metric of step 7910. In some embodiments, the processing equipment may use the metric of step 7910 to weight one or more points of a correlation sequence between the first and second segments. For example, if the determined metrics indicates poor correlation between the first and second segments, then the processing equipment may down-weight the corresponding point of a correlation sequence between the first and second segments. In some embodiments, the processing equipment may implement the illustrative techniques of flow diagram 7900 to identify a peak in a correlation sequence. For example, the illustrative techniques of flow diagram 7900 may be used with step 6604 of flow diagram 6600 of FIG. 66 or step 6706 of flow diagrams 6700-6800 of FIGS. 67-68.

Figure 80:
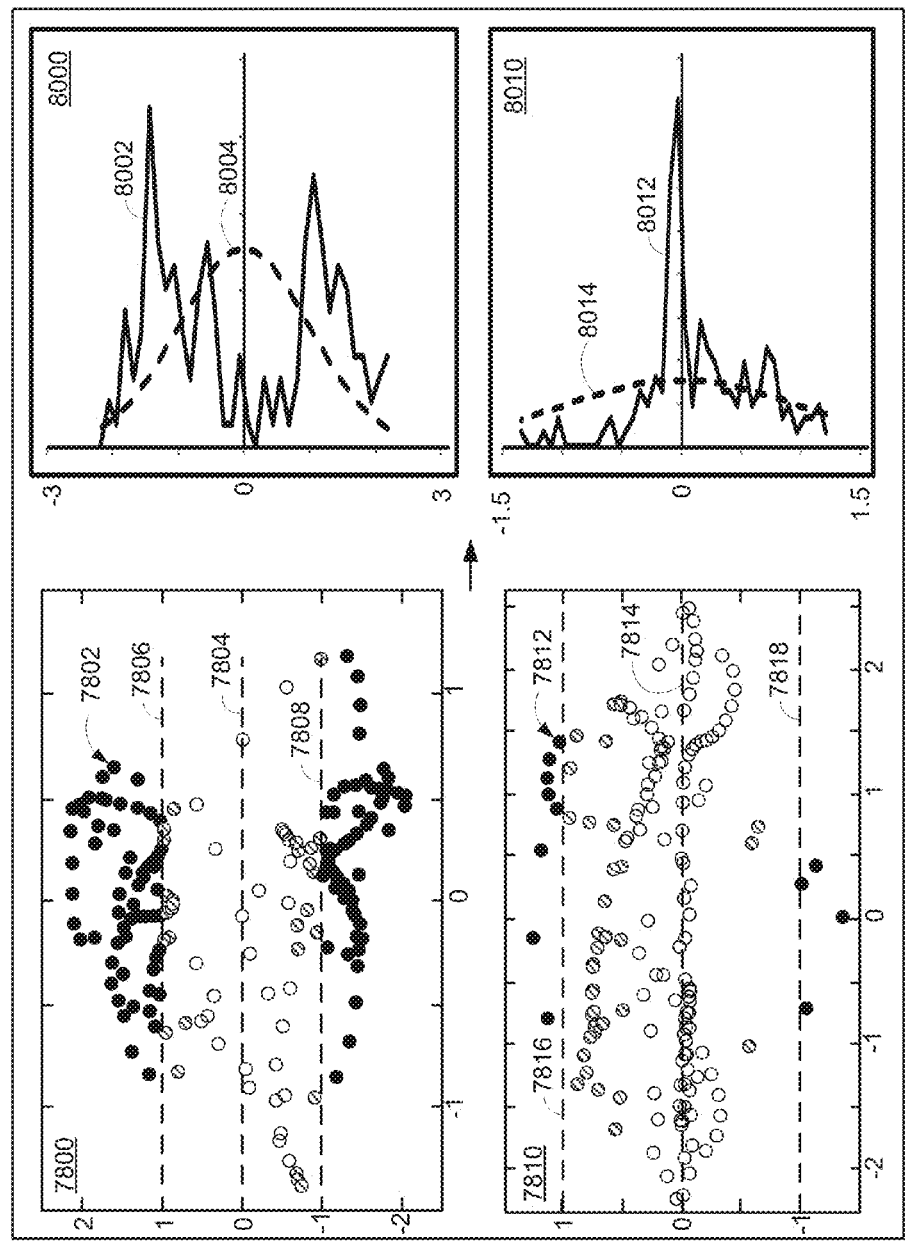
FIG. 80 is a panel of the two plots of FIG. 78 and two respective plots of corresponding vertical distributions, in accordance with some embodiments of the present disclosure.

FIG. 80 is a panel of the two plots 7800 and 7810 of FIG. 78 and two respective plots of corresponding vertical distributions, in accordance with some embodiments of the present disclosure. Plot 8000 shows vertical distribution 8002 corresponding to value pairs 7802, along with Gaussian profile 8004 for reference. Plot 8010 shows vertical distribution 8012 corresponding to value pairs 7812, along with Gaussian profile 8014 for reference. Vertical distributions 8002 and 8012 are generated from histograms of respective value pairs 7802 and 7812, normalized to an area under the curve of one. Gaussian profiles 8004 and 8014 are also scaled to an area under the curve of one, for reference. Vertical distribution 8002 exhibits two primary peaks, indicative of the relatively large number of value pairs 7802 outside of the −1 to 1 threshold (i.e., points filled black in plot 7800 of FIG. 80). Vertical distribution 8012 exhibits a single primary peaks, indicative of the relatively large number of value pairs 7812 near zero. Accordingly, comparison of a vertical distribution with a reference profile may indicate information about the correlation calculation. For example, the relatively high correlation associated with value pairs 7812 may correspond to a single primary peak in vertical distribution 8012. While the distribution of vertical values of value pairs 7812 do not exactly follow Gaussian profile 8014, they do exhibit a central peak. The distribution of vertical values of value pairs 7802 follow Gaussian profile 8004 even less closely, and exhibit two peaks rather than one. Accordingly, the metric discussed in the context of step 7910 of flow diagram 7900 of FIG. 79 may indicate that the distribution of vertical values of value pairs 7812 are relatively closer to a Gaussian profile, and the corresponding segments of physiological data are likely correlated. Also accordingly, the metric discussed in the context of step 7910 of flow diagram 7900 of FIG. 79 may indicate that the distribution of vertical values of value pairs 7802 are relatively different from a Gaussian profile, and the corresponding segments of physiological data are likely anti-correlated. The coarseness of the histogram generated from the vertical values may impact the shape of the histogram. For example, in some circumstances, as the histogram "bins" are made coarser, tall peaks in the distribution may be smoothed laterally. In an illustrative example, the relatively large peak in vertical distribution 8012 may be smoothed laterally with coarser histogram bins, thus lessening the difference between vertical distribution 8012 and Gaussian profile 8014. Any suitable level of coarseness may be used in generating a histogram and corresponding cumulative distribution, and determining a difference between a distribution and a reference distribution.

Figure 82:
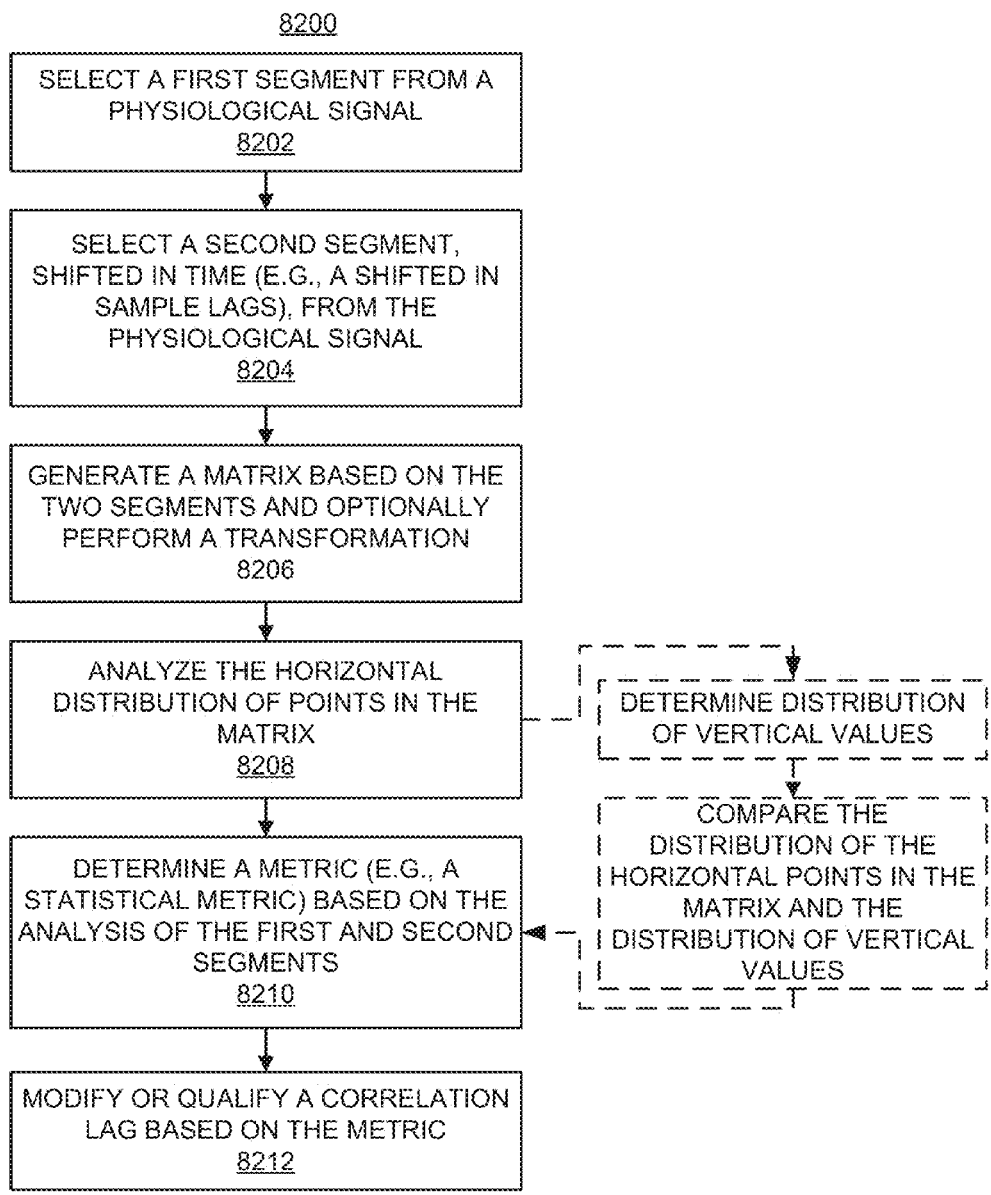
FIG. 82 is a flow diagram of illustrative steps for determining a metric from a horizontal distribution, and using the metric to modify correlation output or identify a correlation peak, in accordance with some embodiments of the present disclosure.

FIG. 82 is a flow diagram 8200 of illustrative steps for determining a metric from a horizontal distribution, and using the metric to modify correlation output or identify a correlation peak, in accordance with some embodiments of the present disclosure. For correlated segments, the horizontal distribution is expected to exhibit two peaks on either side of zero, while the horizontal distribution for anti-correlated segments is expected to exhibit a single peak near zero. This is due to the grouping of value pairs and their orientation along a particular direction, as discussed above in the context of FIG. 76. Value pairs generated from correlated segments will include peak-peak value pairs and trough-trough value pairs, with value pairs including smaller values being less numerous due to the high slopes of the data at those regions. Accordingly, after a −45° rotation the groupings substantially lie near the horizontal axis, on opposite sides of zero resulting in a substantially two peaked distribution in the horizontal values. Value pairs generated from anti-correlated segments will include peak-trough value pairs and trough-peak value pairs, with value pairs including smaller values being less numerous due to the high slopes of the data at those regions. Accordingly, after a −45° rotation the groupings substantially lie near the vertical axis, on opposite sides of zero resulting in a substantially single peaked distribution in the horizontal values. It will be understood the value pairs need not be rotated, and that the illustrative techniques described below may be applied in any suitable direction. Rotation of the value pairs by −45° merely provides a convenient illustrative example.

Step 8202 may include processing equipment selecting a first segment from a window of physiological data. In some embodiments, the first segment may have a predetermined length in time or number of samples. In some embodiments, the length of the first segment may depend on a previously calculated rate (e.g., relatively longer segments may be used for relatively smaller rates).

Step 8204 may include processing equipment selecting a second segment from the window of physiological data, shifted in time relative (e.g., lag in sample number) to the first segment of step 8202. In some embodiments, the second segment may have the same length as the first segment (e.g., the same total number of samples). In some embodiments, the lag may be determined based on a previously calculated rate. For example, the processing equipment may select a lag equal to the period associated with a previously calculated rate. In some embodiments, multiple lags may be selected, and accordingly, multiple second segments may be selected, creating multiple pair of the first segment and second segments.

Step 8206 may include processing equipment generating a matrix based on the first and second segments of steps 8202 and 8204. In some embodiments, the matrix may be generated using, for example, Eq. 42 to generate a set of coordinate pairs (e.g., a 2×N matrix of N coordinate pairs) based on the segments. In some embodiments, a transform may be optionally performed on the matrix (e.g., mean subtraction, normalization, rotation). For example, a 45° CW rotation may be performed on the matrix using Eq. 43, for example, which may simplify subsequent calculations.

Step 8208 may include processing equipment analyzing the horizontal distribution of points in the matrix of step 8206. In some embodiments, step 8208 may include processing equipment analyzing points in a direction substantially parallel to a correlation axis (e.g., parallel to lines 7604 and 7614 of FIG. 76, and lines 7804 and 7814 of FIG. 78). For example, referencing FIG. 76, step 8208 may include analyzing the distribution of value pairs 7602 along line 7604, although the data points need not be plotted to perform step 8208. In a further example, referencing FIG. 78, step 8208 may include analyzing the distribution of value pairs 7802 along line 7804, although the data points need not be plotted to perform step 8208. Step 8210 may include processing equipment determining a metric base on the analysis of step 8208.

Step 8212 may include processing equipment modifying a correlation output, identifying a peak in a correlation output, or both, based on the metric of step 8210. In some embodiments, the processing equipment may use the metric of step 8210 to weight one or more points of a correlation sequence between the first and second segments. For example, if the determined metric indicates poor correlation, or anti-correlation between the first and second segments, then the processing equipment may down-weight the corresponding point of a correlation sequence between the first and second segments. In a further example, if the determined metric indicates good correlation (e.g., the existence of two peaks in the distribution of horizontal values) between the first and second segments, then the processing equipment may down-weight the corresponding point of a correlation sequence between the first and second segments. In some embodiments, the processing equipment may implement the illustrative techniques of flow diagram 8200 to identify a peak in a correlation sequence. For example, the illustrative techniques of flow diagram 8200 may be used with step 6604 of flow diagram 6600 of FIG. 66 or step 6706 of flow diagrams 6700-6800 of FIGS. 67-68.

Figure 83:
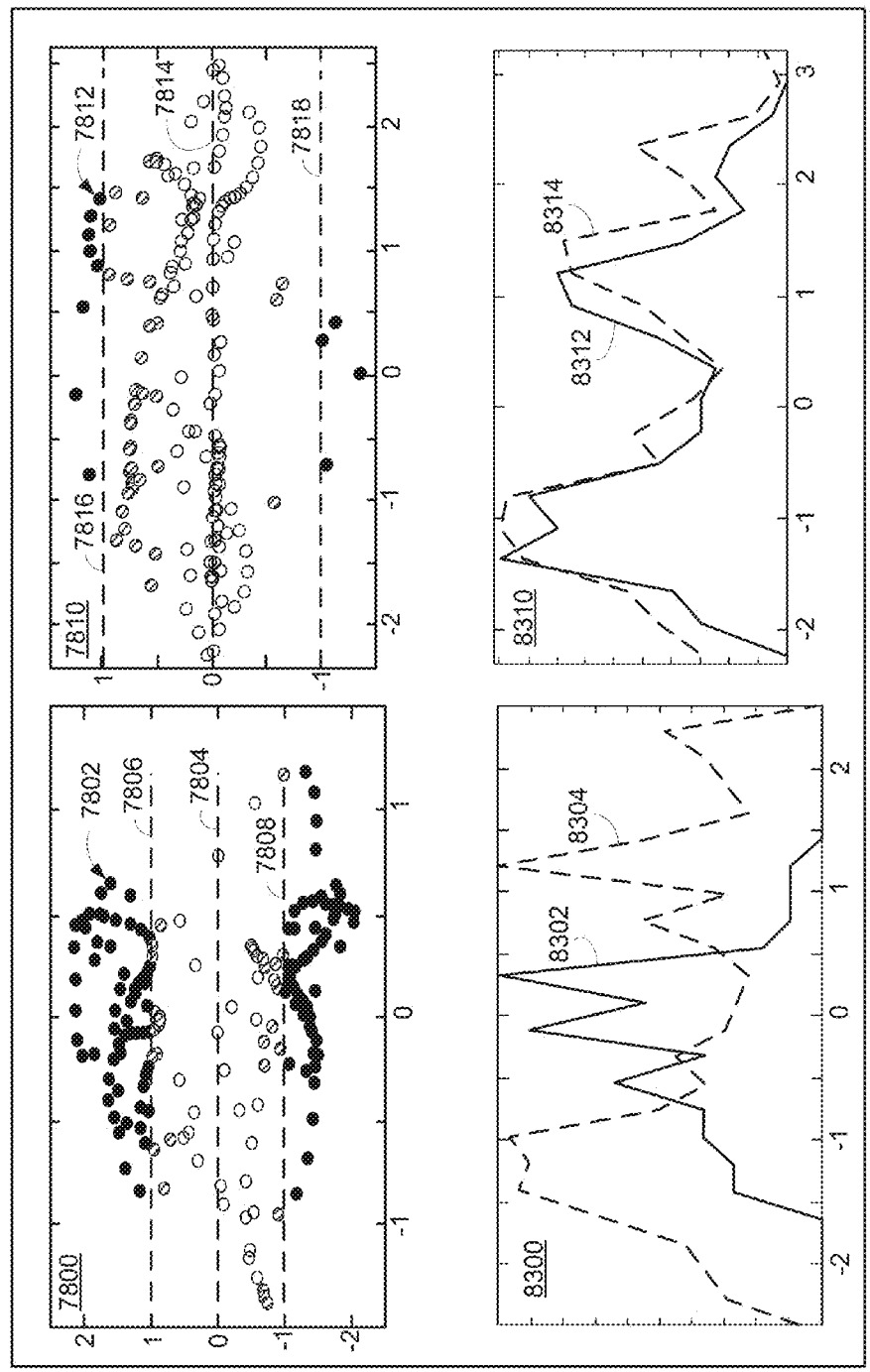
FIG. 83 is a panel of the two plots of FIG. 76 and two respective plots of corresponding horizontal distributions, in accordance with some embodiments of the present disclosure.

For example, FIG. 83 is a panel of the two plots of FIG. 78 and two respective plots 8300 and 8310 of corresponding horizontal distributions, in accordance with some embodiments of the present disclosure. Referencing plots 8300 and 7800, horizontal values 8302 are the horizontal distribution derived from value pairs 7802. Horizontal values 8304 are the horizontal distribution derived by generating a coordinate pair using Eq. 42, using segment 7512 of FIG. 75 as both segments (i.e., a lag of zero), and then rotating the value pairs CW 45°. As shown in plot 8300, rotated value pairs generated from correlated segments (in this example, at a lag of zero) exhibit two peaks, while rotated value pairs from substantially anti-correlated segments exhibit a single peak centered at zero. Referencing plots 8310 and 7810, horizontal distribution 8312 is the horizontal distribution derived from value pairs 7812. Horizontal distribution 8314 is generated based on Eq. 42, using segment 7522 of FIG. 75 as both segments (i.e., a lag of zero), and then rotating the value pairs CW 45°. As shown in plot 8310, rotated value pairs generated from well correlated segments such as segments spaced by a lag value of zero, or a substantially integer multiple of the period associated with the physiological rate, exhibit two peaks in their horizontal distribution.

Figure 84:
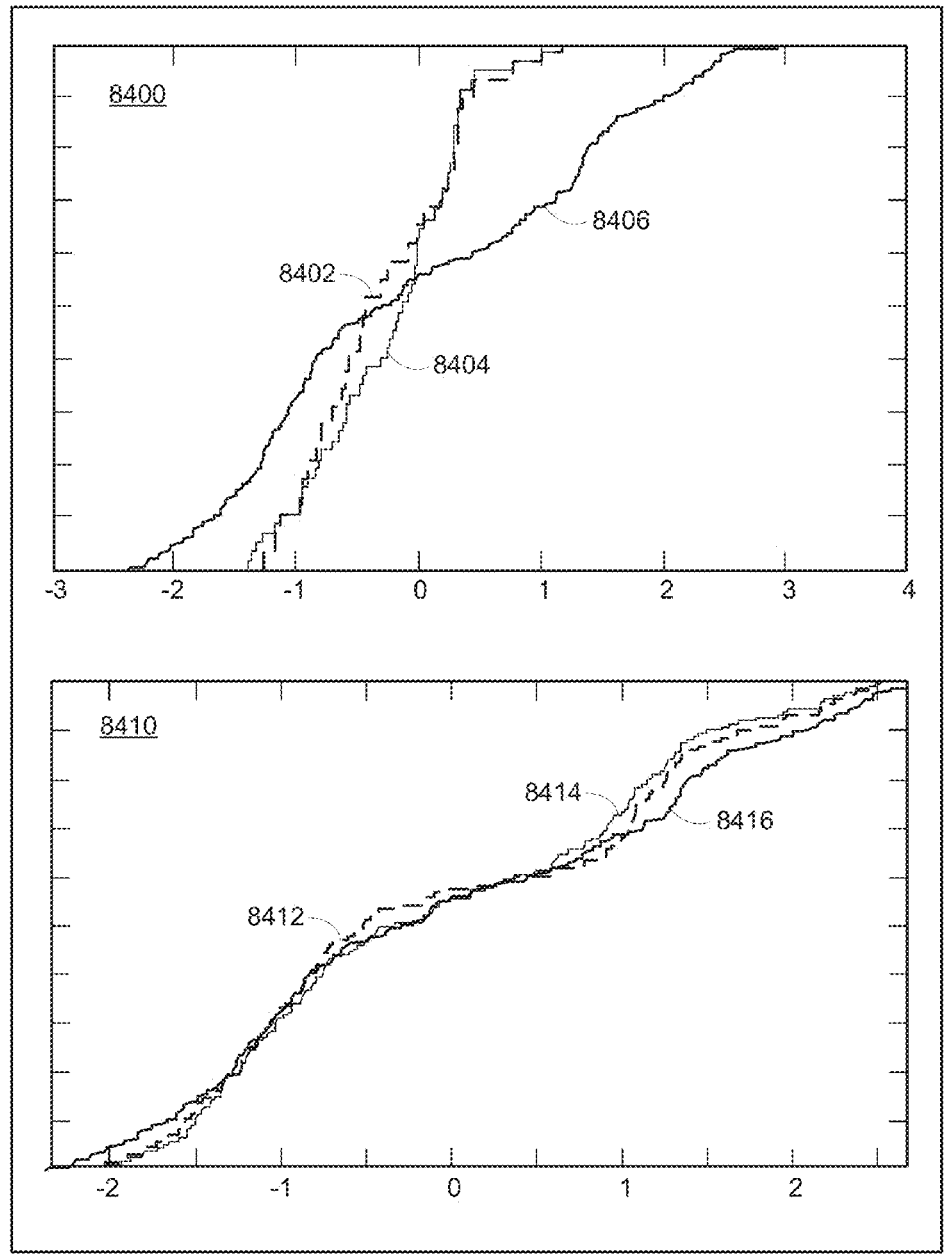
FIG. 84 is a panel of the two plots of illustrative cumulative distributions of horizontal values, in accordance with some embodiments of the present disclosure.

FIG. 84 is a panel of the two plots of illustrative cumulative distributions of horizontal values, in accordance with some embodiments of the present disclosure. Plot 8400 shows cumulative distribution functions (CDF) 8402, 8404, and 8406. Plot 8410 shows cumulative distribution functions (CDF) 8412, 8414, and 8416. CDFs 8406 and 8416 each correspond to original physiological data (e.g., paired with itself as both the first and second segment with a lag of zero), and exhibit a bimodal shape (e.g., as seen by the two regions of relatively higher slope). This shape of the CDF indicates that the histogram of horizontal values exhibits two peaks, indicative of good correlation. CDFs 8402 and 8404 shown in plot 8400 each correspond to transformed data at a particular lag value, which is likely not indicative of a period associated with a physiological rate. In some embodiments, CDFs 8402 and 8404 may correspond to a subset of the transformed data. For example, when the transformed data is centered at zero, CDF 8402 may correspond to the data within plus and minus one half of a standard deviation and CDF 8404 may correspond to the data within plus and minus one standard deviation. In some circumstances, using a subset of the transformed data may provide a better cumulative distribution. CDFs 8402 and 8404 exhibit a shape indicative of histograms of horizontal values exhibiting a single peak, which is not indicative of good correlation between the corresponding segments. CDFs 8412 and 8414 of plot 8410 each correspond to transformed data at a particular lag value, which is likely indicative of a physiological rate. CDFs 8412 and 8414 exhibit a shape indicative of histograms of horizontal values exhibiting two peaks, which is indicative of good correlation between the corresponding segments. In some embodiments, CDFs 8412 and 8414 may correspond to a subset of the transformed data. For example, when the transformed data is centered at zero, CDF 8412 may correspond to the data within plus and minus one half of a standard deviation and CDF 8414 may correspond to the data within plus and minus one standard deviation. Accordingly, if a CDF such as either of CDFs 8406 and 8416 corresponding to original physiological data is used as a reference CDF, the processing equipment may determine a difference metric between the reference CDF and the cumulative distribution of horizontal values at the lag value other than zero. The processing equipment may use the difference value to qualify or disqualify a peak, modify a correlation value (e.g., decrease a value if the difference is large, and increase the correlation value if the difference is small), determine a confidence value, or a combination thereof.

Figure 85:
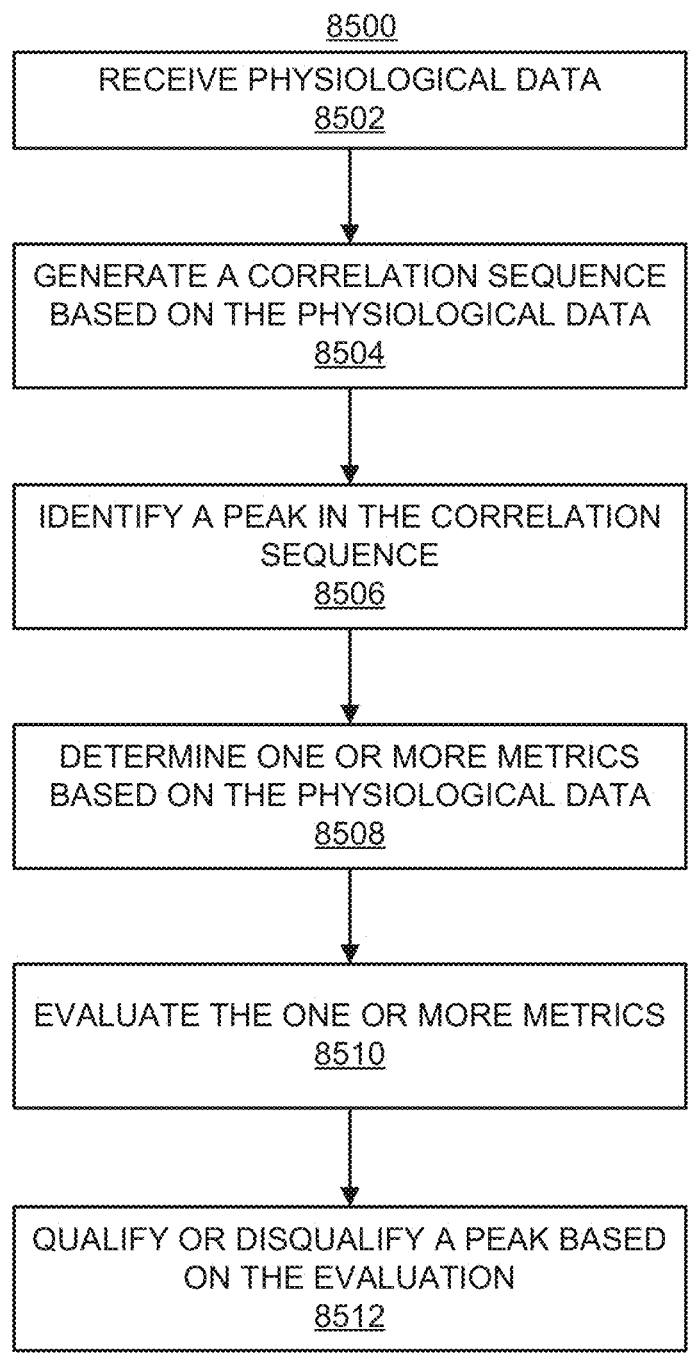
FIG. 85 is a flow diagram of illustrative steps for applying statistical regression analysis, in accordance with some embodiments of the present disclosure.

FIG. 85 is a flow diagram 8500 of illustrative steps for applying statistical regression analysis, in accordance with some embodiments of the present disclosure.

Step 8502 may include processing equipment receiving physiological data, or conditioned data derived thereof, from a physiological sensor, memory, any other suitable source, or any combination thereof. In some embodiments, physiological signals generated by input signal generator 310 of FIG. 3 may be stored in memory (e.g., RAM 54 of FIG. 2, QSM 72 and/or other suitable memory), conditioned, or both, after being pre-processed by pre-processor 320 of FIG. 3. In such cases, step 8502 may include recalling data from the memory for further processing.

Step 8504 may include processing equipment generating a correlation sequence based on segments of the physiological data of step 8502. The correlation sequence may include a sequence of correlation values corresponding to different lag values. In some embodiments, the processing equipment may generate the correlation sequence by multiplying and summing values of a first segment of the physiological segment with corresponding values of a second segment of the physiological data, shifted in time by a particular lag, for multiple lag values. Step 8504 may include the processing equipment normalizing the physiological data, or segments thereof, of step 8502. In some embodiments, the processing equipment may use any suitable signal conditioning technique (e.g., de-trending and/or normalization techniques, scaling, shifting, or any other suitable operation). For example, the processing equipment may normalize segments of physiological data to vary between zero and one, negative one and positive one, or any other predetermined range. In an illustrative example, the processing equipment may receive physiological data at step 8502, select a segment of the data (e.g., the most recent data of a predetermined size), and generate a correlation sequence for all lag values between the segment and second segments of the physiological data (e.g., lag values ranging from zero to N where N is the number of samples of the segment) at step 8504.

Step 8506 may include processing equipment identifying a peak in the correlation sequence. In some embodiments, the processing equipment may use a threshold to determine if a peak is sufficient. If the correlation sequence includes one or more points exceeding the threshold, the processing equipment may proceed to step 8508. The threshold may include any suitable value or values such as, for example, a fixed value, a function, a piece-wise function, or other set of values. If the correlation sequence does not include one or more points exceeding the threshold, the processing equipment may determine that no valid lag was identified, in which case the processing equipment may generate a new correlation sequence with more recent data, repeating steps 8502-8506. In some embodiments, the processing equipment may identify a value of the correlation sequence that exceeds the threshold. In some embodiments, the processing equipment may identify a peak by identifying a maximum value in the correlation sequence, and determining that a predetermined number of correlation sequence values at adjacent smaller lags have positive slope (e.g., an upstroke), and that a predetermined number of correlation sequence values at adjacent larger lags have negative slope (e.g., a downstroke).

Step 8508 may include processing equipment determining one or more metrics based on the physiological data. In some embodiments, step 8508 may include the processing equipment performing one or more SRA techniques, such as those described in the context of FIGS. 77, 79, 81 and 82, to determine the one or more metrics. For example, the processing equipment may perform a Lilliefors Test, a Jarque-Bera (JB) Test, a Kolmogorov Smirnov (KS) Test, any other suitable test, or any combination thereof, to determine the one or more metrics. For example, for each of the lag value corresponding to an identified peak, a predetermined number of previous lag values, and a predetermined number of subsequent lag values, the processing equipment may generate a matrix of value pairs between the segment and respective second segment and perform a 45° CW rotation of the data (e.g., as described in the context of flow diagram 7700 of FIG. 77). The processing equipment may then normalize the data accordingly. The processing equipment may then calculate one or more of a Lilliefors metric, a JB metric, a KS metric, and the fraction of the residual within an amount (e.g., one half) of a standard deviation of the transformed data (e.g., the number of value pairs between references lines 7806 and 7808 in plot 7800 of FIG. 83 divided by the total number of value pairs in plot 7800). The processing equipment may combine the metrics for the lag values (e.g., identified lag, previous lags, and subsequent lags).

Step 8510 may include processing equipment evaluating the one or more metrics determined at step 8508. In some embodiments, the processing equipment may perform one or more tests at step 8508, and evaluate the outcome of the one or more tests at step 8510. For example, the processing equipment may perform a Jarque-Bera Test at step 8508, and then evaluate the JB metric against a look-up table to determine whether the JB Test has passed. In a further example, the processing equipment may perform a Lilliefors Test, a Jarque-Bera Test, a Kolmogorov Smirnov Test, and determine a metric value at step 8508, and then evaluate the results of the four tests at step 8510. For example, if the Lilliefors Test, JB Test, and KS Test are determined to have been passed, the processing equipment may accordingly increase the correlation value corresponding to the identified lag value relative to the remaining values of the correlation sequence. If only some of the Tests are determined to have been passed, the processing equipment may maintain the correlation value corresponding to the identified lag value. If none of the Tests are determined to have been passed, the processing equipment may decrease the correlation value corresponding to the identified lag value. In some embodiments, the processing equipment may compare the correlation value corresponding to the identified lag value to a threshold, and if the correlation value exceeds the threshold, the processing equipment may then evaluate the test results (e.g., metrics) from step 8508.

Step 8512 may include processing equipment qualifying or disqualifying a peak based on the evaluation of step 8510. In some embodiments, if the processing equipment evaluates the results of or more tests at step 8510, and determines that the one or more tests has passed, the processing equipment may qualify an identified peak. In some embodiments, if the processing equipment evaluates the results of or more tests at step 8510, and determines that the one or more tests have not passed, the processing equipment may disqualify an identified peak. In some embodiments, the processing equipment may modify a correlation value based on the one or more evaluated metrics. For example, an evaluated metric may include a Jarque-Bera metric which is used to up-weight or down-weight the corresponding correlation value. In some embodiments, the processing equipment may modify one or more values of the correlation sequence based on the evaluated one or more metrics, and qualify or disqualify a peak based on the modified correlation sequence.

In some embodiments, the processing equipment may perform a qualification of one or more correlation lag values (e.g., as shown by step 418 of flow diagram 400 of FIG. 4). Qualification of the determined one or more correlation lag values may provide a more robust operation, and reduce the misidentification of noise activity as a physiological rate. For example, Qualification Techniques may be used to detect instances in which the system has locked on to one half, double, or other multiple of the actual physiological rate. Qualification may provide an indication of how consistent the lag value is, and how well the lag value characterizes the period of a physiological rate.

Figure 86:
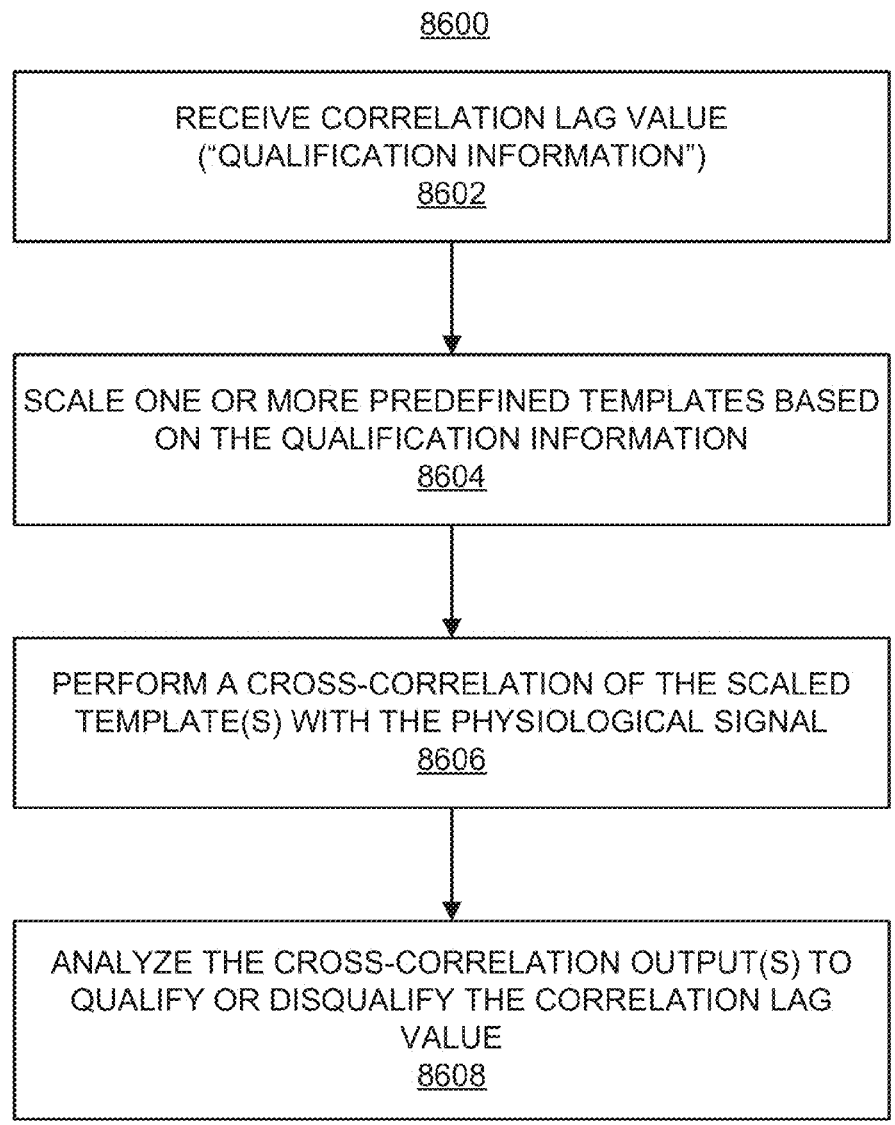
FIG. 86 is a flow diagram of illustrative steps for qualifying or disqualifying a value that may be indicative of a physiological rate using a cross-correlation, in accordance with some embodiments of the present disclosure.

FIG. 86 is a flow diagram 8600 of illustrative steps for qualifying or disqualifying value that may be indicative of a physiological rate using a cross-correlation, in accordance with some embodiments of the present disclosure.

Step 8602 may include processing equipment receiving qualification information. Qualification information may include a correlation lag value, a qualification metric, any other suitable information used in qualifying a correlation lag value, or any combination thereof. In some embodiments the qualification information may be generated at an earlier time, and stored in suitable memory (e.g., RAM 54, ROM 52, or other memory of physiological monitoring system 10 of FIGS. 1-2). Accordingly, in some embodiments, step 8602 may include recalling the qualification information from memory. In some embodiments, a single processor, module, or system may determine, store or otherwise process the qualification information and perform steps 8604-8608, and accordingly, step 8602 need not be performed.

Step 8604 may include the processing equipment scaling one or more predefined templates based on the qualification information. The predefined templates may include asymmetrical pulses without a dicrotic notch, asymmetrical pulses with a dicrotic notch, approximately symmetrical pulses without a dicrotic notch, pulses of any other classification, any other suitable type of template, or any combination thereof. In some embodiments, the predefined templates may be derived from a subject's PPG signals. In some embodiments, the predefined templates may be mathematical functions, mathematical approximations to a PPG signal, any other suitable mathematical formulation, or any combination thereof. In some embodiments, scaling a predefined template may include stretching or compressing the template in the time domain (or corresponding sample number domain) to match a characteristic time scale of the template to that associated with the qualification information. For example, if an correlation lag value corresponds to a physiological rate of 1 Hz, a predefined template may be scaled to correspond to 1 Hz. The period associated with the lag will be referred to herein as "P", and may be used for qualification. Scaled templates may be referred to herein as "reference waveforms."

Step 8606 may include the processing equipment performing a cross-correlation of the scaled template(s) of step 8604 and the physiological signal. The physiological signal may be conditioned before being used in the cross-correlation. The signal conditioning may include removing DC components, low frequency components, or both, from the signal. In some embodiments, a varying baseline may be removed from the signal (i.e., de-trending) to constrain the data average to zero. The signal may also be normalized so that the amplitude of the signal is one. The cross-correlation may be performed using any suitable algorithm. The output of step 8606 may be a cross-correlation output, which may include a series of cross-correlation values taken for a corresponding series of time lags (or sample number lags) between the predefined template and the physiological signal.

Step 8608 may include the processing equipment analyzing the cross-correlation output(s) of step 8606 to qualify or disqualify the correlation lag value. A conditioned cross-correlation output of step 8606 may include one or more peaks, indicative of high correlation between the physiological signal and a predefined template. In some embodiments, step 8608 may include analyzing one or more peaks. In some embodiments, step 8608 may include analyzing one or more segments of the cross-correlation output. For example, tests described herein below such as the Symmetry Test, Radius Test, Angle Test, Area Test, Area Similarity Test, and Statistical Property Test, or any other suitable test, or combination thereof, may be performed at step 8608 to analyze the one or more cross-correlation outputs of step 8606. The processing equipment may perform any suitable analysis at step 8608 to qualify or disqualify lag values associated with the one or more cross-correlation outputs. In some embodiments, when a value is disqualified, the value may still be used although a rate filter may be modified. For example, a filter weight associated with the disqualified value may be reduced as a result of disqualification.

Figure 87:
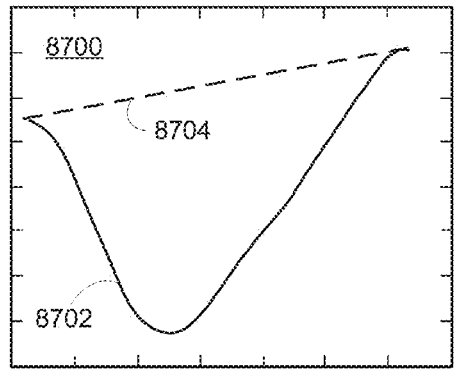
FIG. 87 is a plot of an illustrative PPG signal showing one pulse of a subject, in accordance with some embodiments of the present disclosure.

FIG. 87 is a plot 8700 of an illustrative PPG signal 8702 showing one pulse of a subject, in accordance with some embodiments of the present disclosure. The abscissa of plot 8700 is presented in arbitrary units, while the ordinate is also presented in arbitrary units. PPG signal 8702 exhibits non-zero baseline 8704, which may be, but need not be, a straight line. While PPG signal 8702 is relatively free of noise, sloped baseline 8704 indicates a relatively low frequency noise component. In some embodiments, PPG signal 8702 may be a raw PPG signal, a smoothed PPG signal, an ensemble averaged PPG signal, a filtered PPG signal, any other raw or processed PPG signal, or any combination thereof. In some embodiments, PPG signal 8702 may be approximated by a mathematical representation for further processing (e.g., step 8606, step 8608, or both, of flow diagram 8600).

Figure 88:
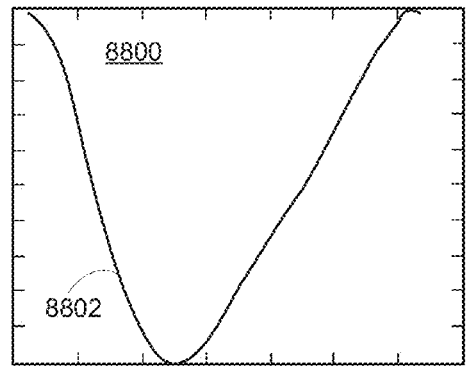
FIG. 88 is a plot of an illustrative template derived from the PPG signal of FIG. 87 with baseline removed, in accordance with some embodiments of the present disclosure.

FIG. 88 is a plot 8800 of a template 8802 derived from illustrative PPG signal 8702 of FIG. 87 with baseline 8704 removed (i.e., de-trended), in accordance with some embodiments of the present disclosure. The abscissa of plot 8800 is presented in arbitrary units, while the ordinate is also presented in arbitrary units. The conditioned signal derived from PPG signal 8702 is referred to as template 8802. De-trending, or other suitable conditioning, may be performed as part of step 8604 of flow diagram 8600. Although the ordinate of FIG. 88 is not numerated, template 8802 may be normalized or otherwise scaled along the ordinate of plot 8800 to range from $[-1,0]$, $[-1,1]$, $[0,1]$, or any other suitable range. For example, the mean of template 8802 may be set to zero.

Figure 89:
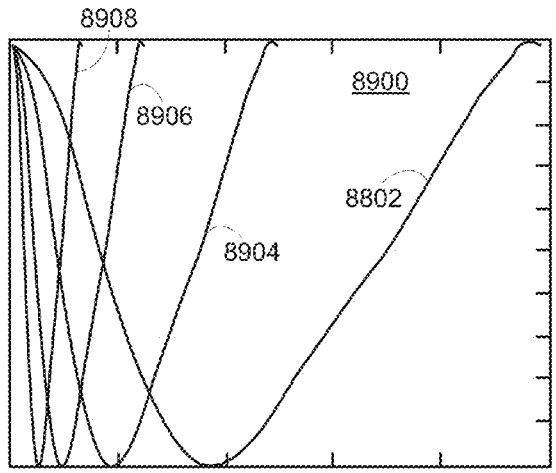
FIG. 89 is a plot of the illustrative template of FIG. 88 scaled to different sizes for use as templates in performing a cross-correlation, in accordance with some embodiments of the present disclosure.

FIG. 89 is a plot 8900 of illustrative template 8802 of FIG. 88 scaled to different sizes for use as templates in performing cross-correlations, in accordance with some embodiments of the present disclosure. The abscissa of plot 8900 is presented in arbitrary units, while the ordinate is also presented in arbitrary units. Illustrative scaled templates 8904, 8906, and 8908 are generated by scaling template 8802 by respective scale factors. In the illustrated example, with the abscissa beginning at zero, the pulse period is scaled by one-half, one-fourth, and one-eighth, to generate scaled templates 8904, 8906, and 8908, respectively.

The plots of FIGS. 87-89 illustrate one technique for creating templates for use in qualifying a correlation lag value. The starting pulse in FIG. 87 may be selected from the subject being monitored or may be selected offline from a library of stored PPG signals from subjects. In some embodiments, the starting pulse may be generated mathematically (e.g., based on one or more functions) or manually. In some embodiments, the processing equipment may generate the one or more templates for each qualification calculation. In some embodiments, a library of templates for one or more pulse shapes may be pre-generated and/or pre-stored in memory and the processing equipment may select the appropriate template or templates for use in the qualification based on the received qualification information. For example, 281 templates may be stored for each pulse shape, one for each BPM in the range of 20-300 BPM. This is merely illustrative and any suitable number of templates may be stored of any suitable BPM resolution and covering any suitable range of BPMs. The processing equipment may select an appropriate template based on rate information in the qualification information. In some embodiments, the pulse shape of the templates may vary as a function of BPM. For example, at low BPM values (e.g., less than about 60 BPM) the pulse shape may be asymmetrical with a dicrotic notch. However, as the BPM value increases, the pulse shape may become more symmetrical and the dicrotic notch may become relatively smaller and eventually not included in the pulse shape.

Figure 90:
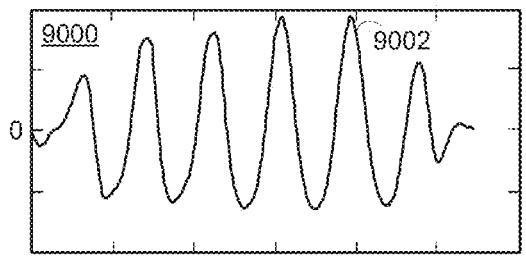
FIG. 90 is a plot of output of an illustrative cross-correlation between a photoplethysmograph signal or a signal derived thereof and a predefined template, in accordance with some embodiments of the present disclosure.

FIG. 90 is a plot 9000 of output 9002 of an illustrative cross-correlation between a PPG signal or a signal derived thereof and a predefined template, in accordance with some embodiments of the present disclosure. The abscissa of plot 9000 is presented in units of cross-correlation lag, while the ordinate is presented in arbitrary units, with zero notated. The shape of cross-correlation output 9002 indicates a relatively close match between the template and the PPG signal. In some embodiments, more than one cross-correlation output may be generated by using more than one scaled template. Accordingly, in some embodiments, cross-correlation outputs corresponding to multiple templates may be evaluated (e.g., using any of the cross-correlation analyses of the present disclosure) to determine which template most closely matches the PPG signal.

FIG. 91 is a flow diagram 9100 of illustrative steps for qualifying or disqualifying a value that may be indicative of a physiological rate based on an analysis of two segments of a cross-correlation, in accordance with some embodiments of the present disclosure. The illustrative steps of flow diagram 7900 may be referred to as the "Symmetry Test."

Step 9102 may include processing equipment receiving a cross-correlation signal (e.g., generated according to step 8606 of FIG. 86) as an input. In some embodiments, a cross-correlation signal may be a cross-correlation output (e.g., output of step 8606 of flow diagram 8600 of FIG. 86). In some embodiments, the cross-correlation signal may be generated by a cross-correlation module. In some embodiments the cross-correlation signal may be generated at an earlier time, and stored in suitable memory. Accordingly, in some embodiments, step 9102 may include recalling the stored cross-correlation signal from the memory. In some embodiments, a single processor, module, or system may perform the cross-correlation and steps 9104-9108, and accordingly, step 9102 need not be performed.

Step 9104 may include the processing equipment selecting any two suitable segments, having any suitable length (e.g., one full period, or more, or less), of the cross-correlation signal of step 9102. Period here refers to a period associated with a correlation lag value. The cross-correlation signal may include a series of data points exhibiting peaks and valleys. The two segments may be selected on either side of a peak or valley, in symmetric locations (e.g., see FIGS. 92-93 for a more detailed discussion of the segments' symmetry). For example, the segments may share a single point at the zenith of a peak or the nadir of a valley, and the segments may extend in opposite directions. In a further example, the segments need not share any points, and a gap may exist between the segments.

FIG. 92 is a plot 9200 of an illustrative cross-correlation signal 9202, showing several reference points for selecting two segments and generating a symmetry curve, in accordance with some embodiments of step 9104 of the present disclosure. As shown by Eqs. 45 and 46:

$$u_j = f(x_0 + \Delta x_j) \quad (45)$$

$$v_j = f(x_{00} - \Delta x_j) \quad (46)$$

the reference points may be used to generate a series of points $(u_j, v_j)$ in a Cartesian plane (or other suitable coordinate system), termed a "symmetry curve." Reference points $x_0$ and $x_{00}$ may be the same point located at a peak or valley (i.e., $x_0 = x_{00}$ as shown by point 9204 or point 9214), or points $x_0$ and $x_{00}$ may be different points, for example, symmetrical about a peak (or valley) of cross-correlation signal values $f(x)$ (e.g., as shown by points 9206 and 9208, or points 9210 and 9212). Note that x may include discrete values associated with a sampled signal. Shift $\Delta x_j$ may range from zero to any suitable number, generating two segments (i.e., the first and second segments, or vice versa) with data points at $(x_0+\Delta x_j)$ and $(x_{00}-\Delta x_j)$ for a suitable span of index j values. If the cross-correlation signal is symmetric (about the midpoint of $x_0$ and $x_{00}$), as shift $\Delta x_j$ increases, $u_j$ and $v_j$ will be equal numerically. The series of points $(u_j, v_j)$ will accordingly generate a straight line of unity slope through the origin. Any deviation between $u_j$ and $v_j$ may be attributed to asymmetry of the cross-correlation output, and will accordingly cause the series of points $(u_j, v_j)$ to not fall in a straight line of unity slope through the origin.

Step 9104 may include the processing equipment selecting any two suitable segments, of any suitable length (e.g., one full period, or more, or less), of a cross-correlation output (e.g., cross-correlation signal 9202). For example, the portion of cross-correlation signal 9202 between points 9208 and 9210 may be a first segment, with the second segment extending leftward from point 9206 to point 9220. In a further example, the portion of cross-correlation signal 9202 between points 9208 and 9210 may be a first segment, with a second segment extending rightward from point 9212 to point 9218. In a further example, the portion of cross-correlation signal 9202 between points 9204 and 9214 may be a first segment, and a second segment may extend from point 9214 to points 9216.

Step 9106 may include the processing equipment analyzing the two segments of step 9104. In some embodiments, step 9106 may include analyzing the symmetry of the two segments. For example, step 9106 may include the processing equipment generating a symmetry curve to analyze the symmetry between the first and second segments. FIG. 93 is a plot 9300 of an illustrative symmetry curve 9302 generated using two segments of a cross-correlation signal, in accordance with some embodiments of the present disclosure. The demarcations of the abscissa and ordinate of plot 9300 are scaled in arbitrary, but similar, units. Symmetry curve 9302 may be generated, for example, by tracing out a series of points $(u_j, v_j)$ in a Cartesian plane (or other suitable coordinate system), as shown by Eqs. 45 and 46. Symmetry curve 9302 is observed to pass roughly through the origin at (0,0) and have a slope of roughly one, with some relatively small deviation. Line 9304 shows the line through the origin with a slope of unity, for reference. In some circumstances, symmetry curve 9302 may be determined to be shaped sufficiently well (e.g., based on the analysis of step 9106 of flow diagram 9100), and a correlation lag value may be qualified.

In some embodiments, step 9106 may include comparing a symmetry curve to a reference curve (e.g., a line through the origin with a slope of unity). For example, a variability metric such as $V_1$ may be computed according to Eq. 47:

$$V_1 = \sum_{i=1}^{M} (S(x_i) - y(x_i))^2 \tag{47}$$

in which $S(x_i)$ is a symmetry curve value (e.g., a value of symmetry curve 9302) at point i of M data points, and $y(x_i)$ corresponds to a reference curve (e.g., line 9304 in which $y(x_i)=x_i$). Any suitable variability metric may be used to evaluate the symmetry curve, or otherwise the symmetry of the two segments.

In some embodiments, step 9106 may include comparing the two segments without first generating a symmetry curve or using a reference curve. For example, a variability metric such as $V_2$ may be computed according to Eq. 48:

$$V_2 = \sum_{j=1}^{M} (u_j - v_j)^2. \tag{48}$$

As a further example, a correlation coefficient between the two segments may be computed. Any suitable correlation coefficient computation may be used including, for example, Pearson's correlation coefficient.

In some embodiments, multiple pairs of first and second segments may be selected at step 9104 and analyzed at step 9106. For example, a first pair of segments sharing a single common point may each extend for a full pulse period, while a second pair of segments sharing the same common point may extend for a half pulse period. In a further example, different pairs of segments may be selected each referenced to different peaks or valleys of the cross-correlation signal.

Step 9108 may include the processing equipment qualifying, or disqualifying, one or more correlation lag values based on the analysis of step 9106. In some embodiments, one or more metric may be inputted into a classifier (e.g., a neural network). In some embodiments, qualification (or disqualification) may depend on a comparison between one or metrics computed at step 9106 and one or more threshold values. For example, a variability metric (e.g., $V_1$ of Eq. 47 or any other suitable metric) may be compared with a threshold, and if the variability metric does not exceed the threshold value, the associated correlation lag value may be qualified. Accordingly, if the variability metric exceeds the threshold value, the associated correlation lag value may be disqualified (and vice versa). In some embodiments, a disqualification at step 9108 may trigger steps 9104-9108 to repeat (i.e., two different segments may be selected from the same cross-correlation signal for analysis). In some embodiments, a disqualification at step 9108 may trigger steps 9102-9108 to repeat (i.e., two segments are selected from a different cross-correlation signal for analysis). In some embodiments, a disqualification at step 9108 may trigger an analysis different than that of flow diagram 9100 to be performed to either qualify or disqualify the correlation lag value associated with the cross-correlation signal.

Figure 94:
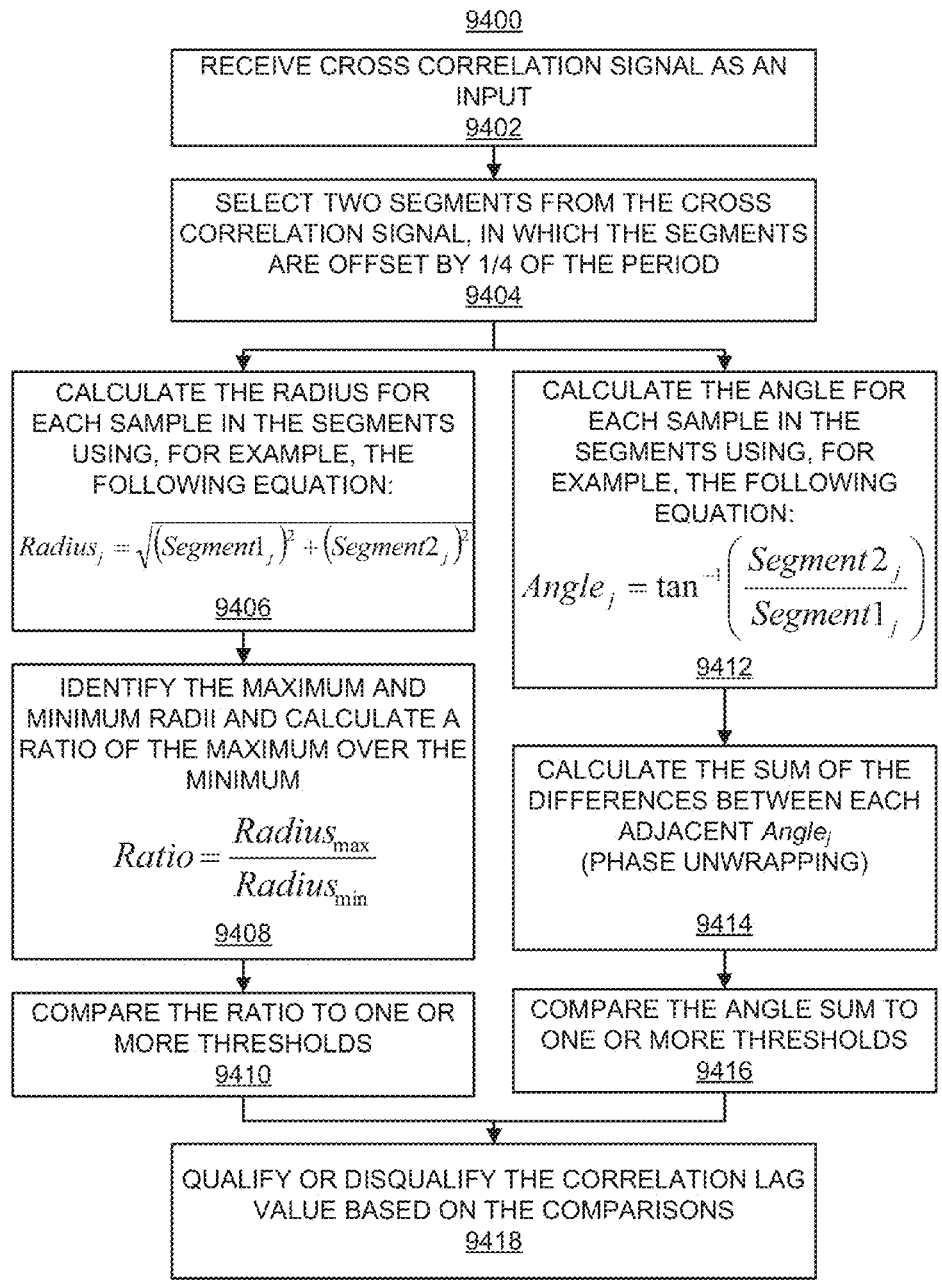
FIG. 94 is a flow diagram of illustrative steps for qualifying or disqualifying one or more values that may be indicative of a physiological rate based on an analysis of offset segments of a cross-correlation signal, in accordance with some embodiments of the present disclosure.

FIG. 94 is a flow diagram 9400 of illustrative steps for qualifying or disqualifying one or more values that may be indicative of a physiological rate based on an analysis of offset segments of a cross-correlation signal, in accordance with some embodiments of the present disclosure. In some embodiments, the illustrative steps of flow diagram 9400 aid in preventing a double-rate/half-period condition, or other condition in which period P is not indicative of a physiological rate.

Step 9402 may include processing equipment receiving a cross-correlation signal (e.g., generated according to step 8606 of FIG. 86) as an input. In some embodiments, the cross-correlation signal may be generated by a cross-correlation module. In some embodiments the cross-correlation signal may be generated at an earlier time, and stored in suitable memory. Accordingly, in some embodiments, step 9402 may include recalling the stored cross-correlation signal from the memory. In some embodiments, a single processor, module, or system may perform the cross-correlation and steps 9404-9418, and accordingly, step 9402 need not be performed.

Step 9404 may include the processing equipment selecting two segments of the cross-correlation signal of step 9402. The cross-correlation signal may include a series of data points exhibiting peaks and valleys. The two segments may be of equal length, offset by a quarter length of the period P associated with the correlation lag value. In some embodiments, the first and second segments may each have a length equal to period P, although they may be any suitable length as long as the segments are of approximately equal length. The two segments may be selected from any suitable portion of the cross-correlation signal. Note that the two segments will be referred to as Segment1 and Segment2, or the first segment and the second segment, although the designations are arbitrarily chosen for illustration purposes (e.g., the first and second segments may be interchanged in accordance with the present disclosure).

Following step 9404, the processing equipment may perform step 9406, 9412, or both (e.g., simultaneously or sequentially) in accordance with some embodiments of the present disclosure. In some embodiments, the "Radius Test" (i.e., steps 9406-9410) may be performed, and the "Angle Test" (i.e., steps 9412-9416) need not be performed. In some embodiments, the "Angle Test" may be performed, and the "Radius Test" need not be performed. In some embodiments, one of the "Radius Test" and the "Angle Test" may be performed initially, and depending upon the outcome of the test (e.g., qualify, disqualify) the other test may be performed.

step 9406 may include the processing equipment calculating the radius based on the two segments of step 9404, using Eq. 49. In Eq. 49, Segment1$_j$ and Segment2$_j$ are the cross-correlation output f(x) values of the first and second segments, respectively, evaluated for index j, which ranges from zero to N−1 for segments with N data points. Note that x may include discrete values associated with a sampled signal. With reference to Eqs. 50 and 51, Segment1 originates at point $x_0$ and extends rightward with index j in the Cartesian plane, and the origin of Segment2 is offset by a quarter period P relative to the first segment. Also note that $\Delta x_j$ may increase linearly with j. For example, $\Delta x_j$ may be given by Eq. 52, in which $\Delta x$ is the data point spacing in the domain.

$$\text{Radius}_j = \sqrt{\text{Segment1}_j^2 + \text{Segment2}_j^2} \tag{49}$$

$$\text{Segment1}_j = f(x_0 + \Delta x_j) \tag{50}$$

$$\text{Segment2}_j = f\left(x_0 + \frac{P}{4} + \Delta x_j\right) \tag{51}$$

$$\Delta x_j = j\Delta x \tag{52}$$

The radius of step 9406, as computed using Eq. 49, will be a constant if the period P identically matches the period of the cross-correlation output f(x), and has strictly sinusoidal character. Variations in the radius with index j may be attributed to the shape of the cross-correlation output, deviations between period P and the characteristic period of the cross-correlation signal, any other suitable characteristic of the cross-correlation signal, or any combination thereof.

Step 9408 may include the processing equipment identifying the maximum and minimum radii from step 9406, and calculating a ratio as shown, for example, by Eq. 53.

$$\text{Ratio} = \frac{\text{Radius}_{MAX}}{\text{Radius}_{MIN}} \tag{53}$$

The ratio of the maximum (Radius$_{MAX}$) and minimum (Radius$_{MIN}$) radii provides a variability metric, indicating variability in the calculated radii values. Note that if the radii values have low variability (i.e., are all substantially the same value), the ratio is near one. The presence of variability will necessarily cause the ratio to assume a value greater than one. In some embodiments, variability metrics other than the ratio of Eq. 53 may be calculated from the radii values. Any suitable variability metric may be used in accordance with the present disclosure.

Step 9410 may include the processing equipment comparing the ratio of step 9408 to one or more threshold values. In some embodiments, a fixed threshold may be used for comparison. In some embodiments, a variable threshold may be used. For example, threshold value(s) may be based on the value of the period P, subject information (e.g., subject history, medical history, medical procedure), segment length, any other suitable information, or any combination thereof. In some embodiments, the threshold value(s) may be stricter in an initial mode versus a subsequent mode. The stricter threshold(s) may prevent the algorithm from locking onto the wrong rate. Steps 9412-9416 may be performed in concert with, or in lieu of, steps 9406-9410, in accordance with some embodiments of the present disclosure.

Step 9412 may include the processing equipment calculating the angle for each index j of the two segments of step 9404, using Eq. 54. Each angle value, per index j, is the arctangent of the ratio of the first and second segment values, given by Eqs. 50 and 51, respectively.

$$\text{Angle}_j = \tan^{-1}\left(\frac{\text{Segment2}_j}{\text{Segment1}_j}\right) \tag{54}$$

Step 9414 may include the processing equipment calculating the sum of the differences between each adjacent angle of step 9412, also referred to as "phase unwrapping", as shown by Eq. 55:

$$\text{Sum}_{angle} = \sum_{j=1}^{N-1} (\text{Angle}_j - \text{Angle}_{j-1}). \tag{55}$$

The sum may be approximately proportional to the length of the segments. Segments of length equal to period P should give a sum of roughly 360°, the period P is approximately equal to the characteristic period of the cross-correlation signal. If the cross-correlation exhibits a period half that of period P, then the sum may tend towards 720° for segment lengths equal to period P. The sum will depend, however, on the length of the segments. For example, longer segments (in terms of period P) tend to provide larger sums.

Step 9416 may include the processing equipment comparing the sum of step 9414 to one or more threshold values, or range thereof. In some embodiments, the one or more thresholds may include an upper and lower limit. In some embodiments, a threshold value may be based on the segment length. For example, a sum may be compared to a threshold range of 300-420°, for segments having a length equal to period P. In a further example, larger threshold values may be used with segments having a length longer than period P. In some embodiments, for a given segment length, a threshold value may vary. For example, threshold value(s) may be based on the value of the period P, subject information (e.g., subject history, medical history, medical procedure), whether correlation lag values are being qualified, any other suitable information, or any combination thereof. In some embodiments, the threshold value(s) may be stricter in a particular Mode (e.g., Initialization Mode) versus another Mode (e.g., using a bandpass filter).

Step 9418 may include the processing equipment qualifying or disqualifying the associated correlation lag value based on the comparison of step 9410, the comparison of step 9416, or both. If the ratio, angle sum, or both, exceed the respective threshold value, the correlation lag value may be disqualified. If the ratio, angle sum, or both, do not exceed the threshold value, the correlation lag value may be qualified.

In some embodiments, the processing equipment may generate a metric based on a history of angle sum values stored in a buffer (e.g., angle sum values calculated using Eq. 55 for the previous 12 seconds, or any other suitable time interval). For example, the processing equipment may determine a metric M using an expression such as Eq. 56:

$$M = \sqrt{(SUM_{max} - SUM_{min})}(SUM_{mean})^{2-2*SUM_{mean}} \quad (56)$$

where $SUM_{max}$ is the maximum angle sum value stored in the buffer, $SUM_{min}$ is the minimum angle sum value stored in the buffer, and $SUM_{mean}$ is the mean angle sum value stored in the buffer. All of the SUM values shown in Eq. 56 are normalized by subtraction 360°, and then dividing by 360° to generate a non-dimensional angle sum variable. In some embodiments, the buffer may store normalized angle sum values in non-dimensional form. This metric analyzes the variability of the angle sum metric over time. In some situations, the angle metric may indicate a good angle even though the correlation lag value does not correspond to the physiological rate. However, in these situations, the angle metric may vary over time. Accordingly, metric M may be determined and compared to one more thresholds to qualify or disqualify a correlation lag value. Metric M may be used in addition to or in place of the Angle Test. It will be understood that Eq. 56 is merely illustrative and any suitable variation metric may be used. In some embodiments, the processing equipment may apply a variability metric such as an expression similar to Eq. 56 to any other suitable noise metric, de-trending metric, qualification metric, or other metric, to determine a variation over time of the metric.

Figure 95:
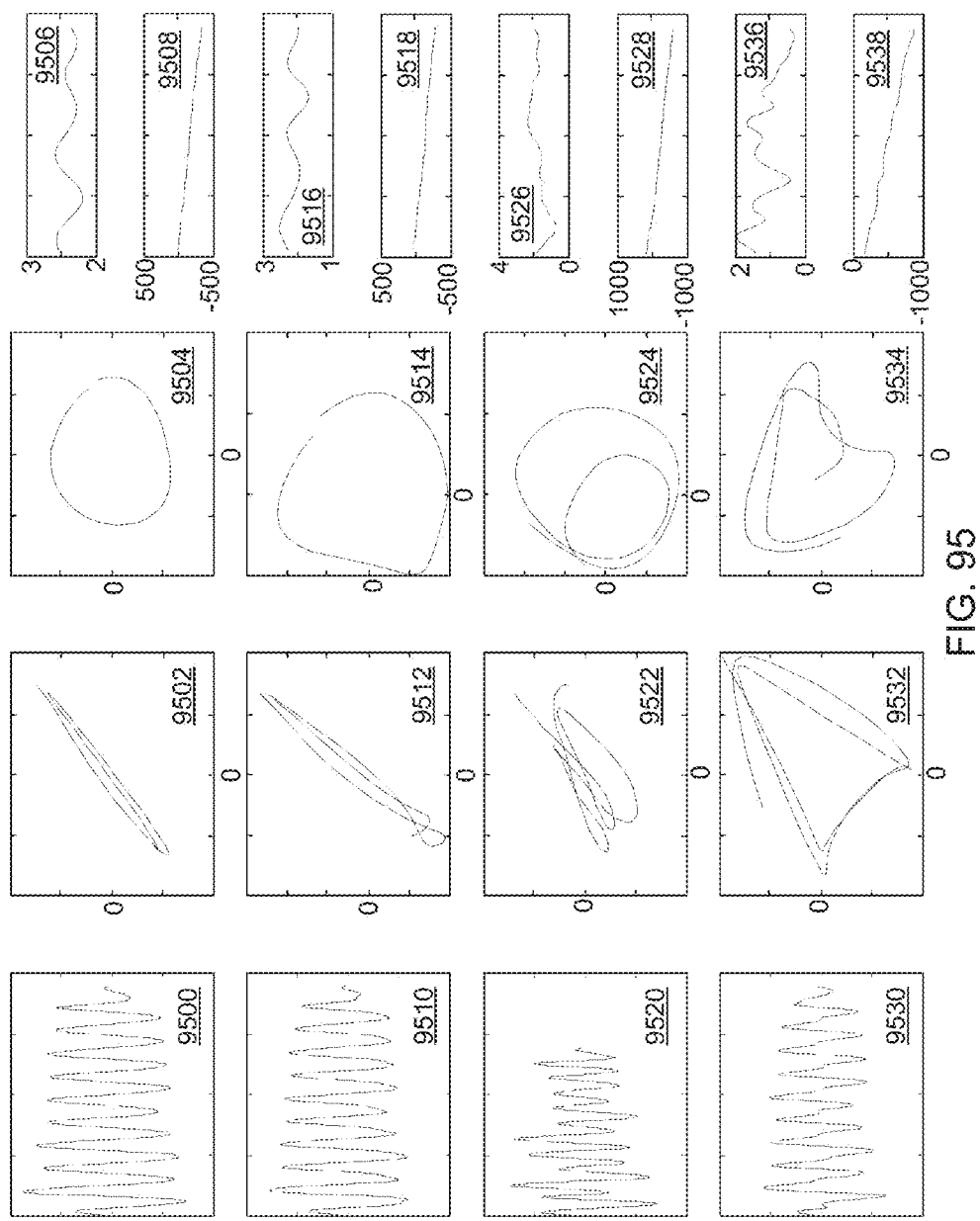
FIG. 95 shows four sets of plots of illustrative cross-correlation signals and corresponding symmetry curves, radial curves, radius calculations, and angle calculations, in accordance with some embodiments of the present disclosure.

FIG. 95 shows four sets of plots, arranged by row, of (from left to right) illustrative cross-correlation signals and corresponding symmetry curves, radial curves, radius calculations (top), and angle calculations (bottom), in accordance with some embodiments of the present disclosure.

Plots 9500, 9510, 9520, and 9530 show four respective, illustrative cross-correlation signals, in accordance with some embodiments of the present disclosure. The top two cross-correlation signals, of plots 9500 and 9510, do not exhibit notches and show relatively consistent periodic character. Plots 9502 and 9512 each show a symmetry curve, with lengths equal to 1.6 times period P, which corresponds to the cross-correlation signal of plots 9500 and 9510, respectively. The symmetry curves of plots 9502 and 9512 show substantially linear character, with respective slopes of nearly one, passing roughly through the origin. Accordingly, the peaks of the cross-correlation signals of plots 9500 and 9510 may be determined to be relatively symmetric, and an associated correlation lag value may be qualified based on the symmetry. Plots 9504 and 9514 each show a radial curve, using segment lengths equal to period P, which corresponds to the cross-correlation signal of plots 9500 and 9510, respectively. Plots 9506 and 9508 show respective radius and angle calculations based on the radial curve of plot 9504, while plots 9516 and 9518 show respective radius and angle calculations based on the radial curve of plot 9514. The radial curves of plots 9504 and 9514 are roughly circular, including a single loop. The radius calculations of plots 9506 and 9516 show some variation, with radius ratios (e.g., calculated using Eq. 53) of 1.18 and 1.54, respectively. The angle calculations of plots 9508 and 9518 give angle sums (e.g., calculated using Eq. 55) of 343.4° and 333.7°, respectively. The symmetry curves and radial curves associated with the cross-correlation results of plots 9500 and 9510, and calculations thereof, may indicate that the period P provides a relatively good estimate of the actual physiological period. Accordingly, under some circumstances, the correlation lag value associated with period P may be qualified.

The bottom two cross-correlation signals of FIG. 95, of plots 9520 and 9530, do not exhibit notches and show relatively consistent periodic character. Plots 9522 and 9532 each show a symmetry curve, with lengths equal to 1.6 times period P, which corresponds to the cross-correlation output of plots 9520 and 9530, respectively. The symmetry curves of plots 9522 and 9532 show substantially non-linear character, with varying slopes, and deviating relatively far from the origin. The peaks of the cross-correlation output of plot 9520 show varying amplitude, while the peaks of the cross-correlation signal of plot 9530 show an additional inflection likely caused by a dicrotic notch in the original physiological data. Accordingly, the peaks of the cross-correlation signals of plots 9520 and 9530 may be determined to be relatively asymmetric, and an associated correlation lag value may be disqualified based on the symmetry. Plots 9524 and 9534 each show a radial curve, using segment lengths equal to period P, which correspond to the cross-correlation signal of plots 9520 and 9530, respectively. Plots 9526 and 9528 show respective radius and angle calculations based on the radial curve of plot 9524, while plots 9536 and 9538 show respective radius and angle calculations based on the radial curve of plot 9534. The radial curve of plot 9524 shows two loops of substantially different radii, indicating that the period P may be roughly twice as long as the actual period of cross-correlation signal 9520. The radial curve of plot 9534 shows two non-circular loops, of varying radii, indicating that the period P may be roughly twice as long as the actual period of cross-correlation signal 9530. The radius calculations of plots 9526 and 9536 show significant variation, with radius ratios (e.g., calculated using Eq. 53) of 3.58 and 6.69, respectively. The angle calculations of plots 9528 and 9538 give angle sums (e.g., calculated using Eq. 55) of 757.6° and 703.9°, respectively. The symmetry curves and radial curves associated with the cross-correlation results of plots 9520 and 9530, and calculations thereof, may indicate that the period P provides a relatively poor estimate of the actual physiological period. In some embodiments, this may occur when the rate is locked onto low frequency noise or half the physiological rate or when correlation lag value identifies low frequency noise or half the physiological rate. Accordingly, under some circumstances, the correlation lag value associated with period P may be disqualified.

In some embodiments, flow diagram 9100 of FIG. 91 and flow diagram 9400 if FIG. 94 may operate directly on the physiological data (e.g., a de-trended physiological signal) instead of on a cross-correlation signal derived from the physiological signal.

Figure 96:
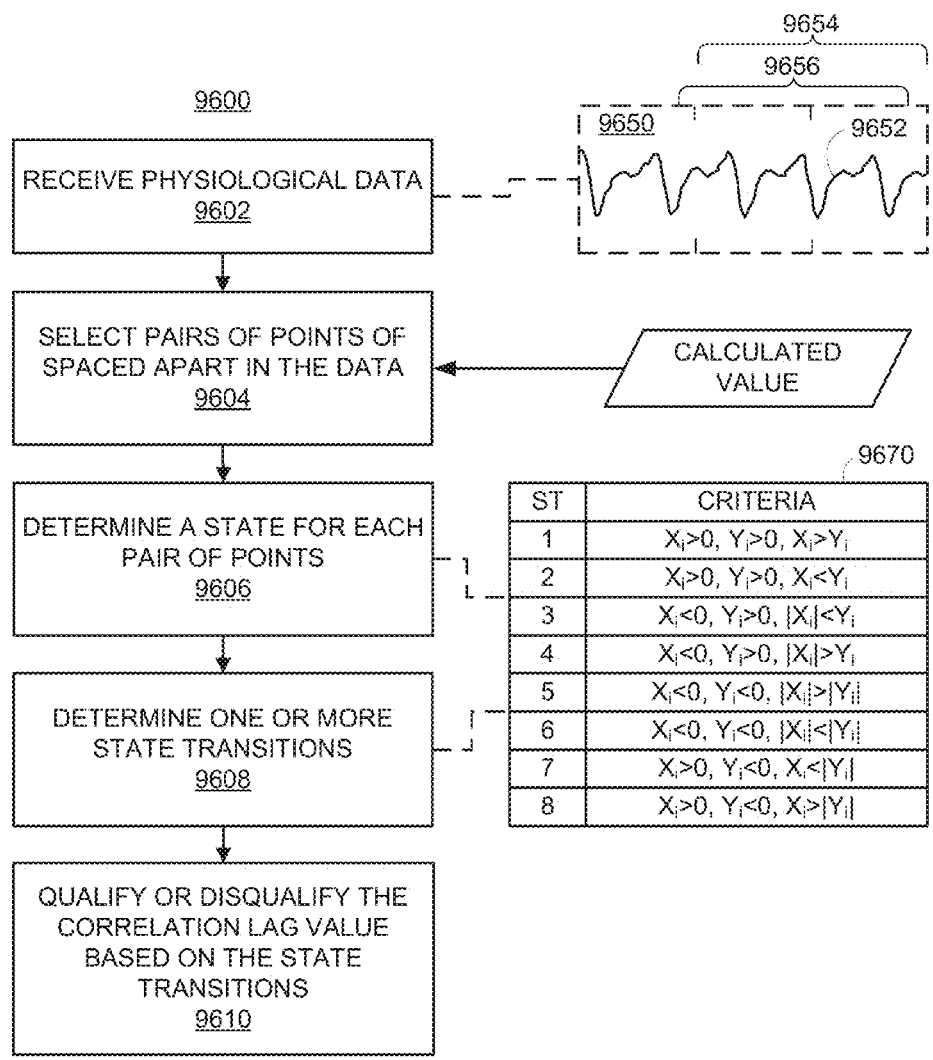
FIG. 96 is a flow diagram of illustrative steps for qualifying or disqualifying a value that may be indicative of a physiological rate based on a state transition, in accordance with some embodiments of the present disclosure.

In some embodiments, geometric properties or states of the physiological data (e.g., de-trended physiological data) may be analyzed to qualify or disqualify a correlation lag value. For example, states can be determined by analyzing the relationship of a sequence of paired values spaced apart in the physiological data and state transitions can be identified when the states change. FIG. 96 is a flow diagram 9600 of illustrative steps for qualifying or disqualifying a value that may be indicative of a physiological rate based on a state transition, in accordance with some embodiments of the present disclosure. The illustrative steps of flow diagram 9600 may be referred to as the "State Transition Test."

Step 9602 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 9602 may include recalling data from the memory for further processing.

Step 9604 may include the processing equipment selecting pairs of sample points of the physiological data, spaced apart in the physiological data. The spacing may be based on a calculated value indicative of a physiological rate of the subject. For example, the calculated value may be based on a correlation lag value, a rate corresponding to the correlation lag value, or any other calculated value indicative of a physiological rate of the subject. In some embodiments, a first portion of physiological data, including a particular number of sample points, may be point-wise paired with a second portion of the physiological data, including the same number of samples points as the first portion albeit shifted in time relative to the first portion. For example, as shown by panel 9650, the pairs may be generated by selecting corresponding points of portion 9654 and portion 9656 of physiological signal 9652. In some embodiments, selecting the pairs of points may include specifying indices of the points in the physiological data for reference.

Step 9606 may include the processing equipment determining a state for each pair of points of the plurality of pairs of step 9604. The state may be defined by a set of criteria such as, for example, logical operations, inequalities, and equalities. For example, referencing table 9670, for each pair of values $X_i$ and $Y_i$, an eight-state calculation may be performed using the inequality criteria in the second column of table 9670. The inequality criteria used in table 9670 include comparisons of the pair values each with zero and with each other. In a further example, a sixteen-state calculation can be performed by addition of one or more criteria such as that shown in Eq. 57:

$$CX_i > Y_i \text{ or } CX_i < Y_i \quad (57)$$

where C is a coefficient used to compare each pair of values $X_i$ and $Y_i$. The value, sign, or both of coefficient C can depend on other criteria such as the inequality criteria. Note that although illustrative Eq. 57 and illustrative table 9670 shows criteria including "greater than" and "less than" inequalities, the criteria may include "greater than or equal," or "less than or equal" inequalities. For example, in the case that $X_i = Y_i$, the "greater than or equal," or "less than or equal" inequalities still yield a state value. Any suitable number of states may be specified using any suitable number and type of criteria, in accordance with the present disclosure.

Step 9608 may include the processing equipment determining one or more state transitions based on the determined states of step 9606. In some embodiments, the processing equipment may index through the plurality of value pairs, in order (e.g., in the order of the data points in the first segment), determining the number of instances the state changes. For example, for a first segment size of 10 values, corresponding to 10 pairs, the states may be 1-1-1-2-2-3-4-5-5-5, for which there are five states, and four state transitions among states. As another example, for a segment size of 2 values, corresponding to 2 pairs, the states may be 1-3, for which there are two states, but the transition skipped a state. In this example, because state "2" was skipped, this may be counted as two state transitions. Step 9608 may include the processing equipment determining the total number of state transitions exhibited by the plurality of pairs. The total number of state transitions may be the total number of state transitions in one direction. For example, if there were eleven state transitions where the state increased and three state transitions where the state decreased, then the total number of state transitions may be determined to be eight. In some embodiments, step 9606 and 9608 may be performed sequentially. In some embodiments, step 9606 and 9608 may be performed substantially at the same time. For example, as each state determined for each point, the processing equipment may determine whether a state transition has occurred.

Step 9610 may include the processing equipment qualifying or disqualifying a correlation lag value, based on the determined state transitions of step 9608. In some embodiments, the processing equipment may determine the number of state transitions and compare the number of state transitions to one or more threshold values. For example, if the determined number of state transitions is between a lower threshold and an upper threshold, then the processing equipment may qualify the correlation lag value.

In an illustrative example, the processing equipment may receive physiological data, and select pairs of points in the data spaced by one fourth of the calculated value, which may be a previously calculated correlation lag value. The processing equipment may determine a state for each pair of points, and determine the number of state transitions. Referencing an eight-state calculation, if the processing equipment determines that seven, eight, or nine transitions have occurred, then the processing equipment may qualify the correlation lag value. If the processing equipment determines that less than six, or more than nine, transitions have occurred then the processing equipment may disqualify the correlation lag value. It will be understood that the illustrative numbers and thresholds described in this example are used to describe the technique, although any suitable number of states, and state transitions may be specified to qualify or disqualify a correlation lag value. In some embodiments, the processing equipment may output a one for a passed State Transition Test (e.g., qualified), and a zero for a failed State Transition Test (e.g., disqualified).

In some embodiments, the processing equipment may generate a metric based on a history of state transition values stored in a buffer (e.g., 12 number of state transitions values, calculated each second, for the previous 12 seconds). For example, the processing equipment may determine a metric M using an expression such as Eq. 58:

$$M = \sqrt{(NST_{max} - NST_{min})} (NST_{mean})^{2-K \cdot NST_{mean}} \quad (58)$$

where $NST_{max}$ is the maximum number of state transitions value stored in the buffer, $NST_{min}$ is the minimum number of state transitions value stored in the buffer, K is a constant, and $NST_{mean}$ is the mean number of state transitions value stored in the buffer. In some embodiments, the processing equipment may normalize the stored NST values to a predetermined range. This metric analyzes the variability of the number of state transitions metric over time. In some situations, the number of state transitions metric may indicate a good number of state transitions even though the correlation lag value does not correspond to the physiological rate. However, in these situations, the number of state transitions metric may vary over time. Accordingly, metric M may be determined and compared to one more thresholds to qualify or disqualify a correlation lag value. Metric M may be used in addition to or in place of the State Transition Test. It will be understood that Eq. 56 is merely illustrative and any suitable variability metric may be used. In some embodiments, the processing equipment may apply a variability metric such as an expression similar to Eq. 58 to any other suitable noise metric, de-trending metric, qualification metric, or other metric, to determine a variation over time of the metric.

Figure 97:
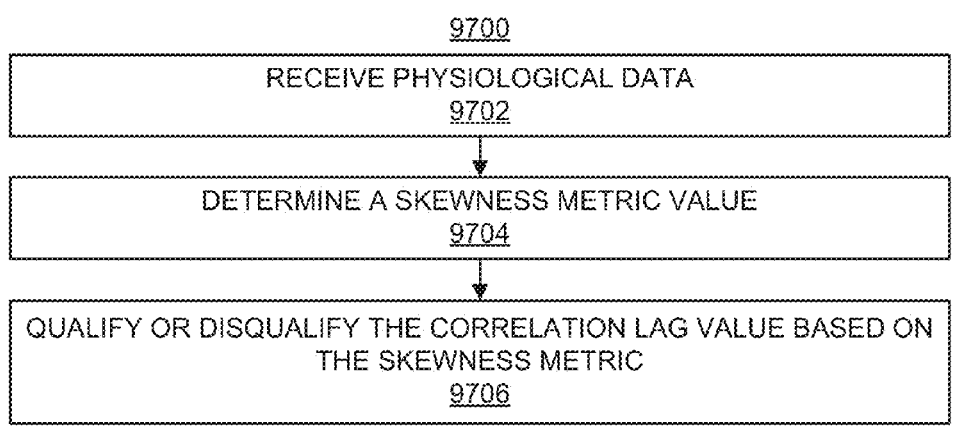
FIG. 97 is a flow diagram of illustrative steps for qualifying or disqualifying a value that may be indicative of a physiological rate based on a skew value, in accordance with some embodiments of the present disclosure.

FIG. 97 is a flow diagram 9700 of illustrative steps for qualifying or disqualifying a value that may be indicative of a physiological rate based on a skewness value, in accordance with some embodiments of the present disclosure. The illustrative steps of flow diagram 9700 may be referred to as the "Skewness Test."

Step 9702 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 9702 may include recalling data from the memory for further processing.

Step 9704 may include the processing equipment determining a skewness metric value based on the physiological data of step 9702. For example, the processing equipment may use an expression such as that shown in Eq. 16 to determine a skewness value. In a further example, the processing equipment may determine a skewness metric other than a third central moment of the data, such as an empirical skewness metric indicative of asymmetry of the a distribution of values of the physiological data.

Figure 98:
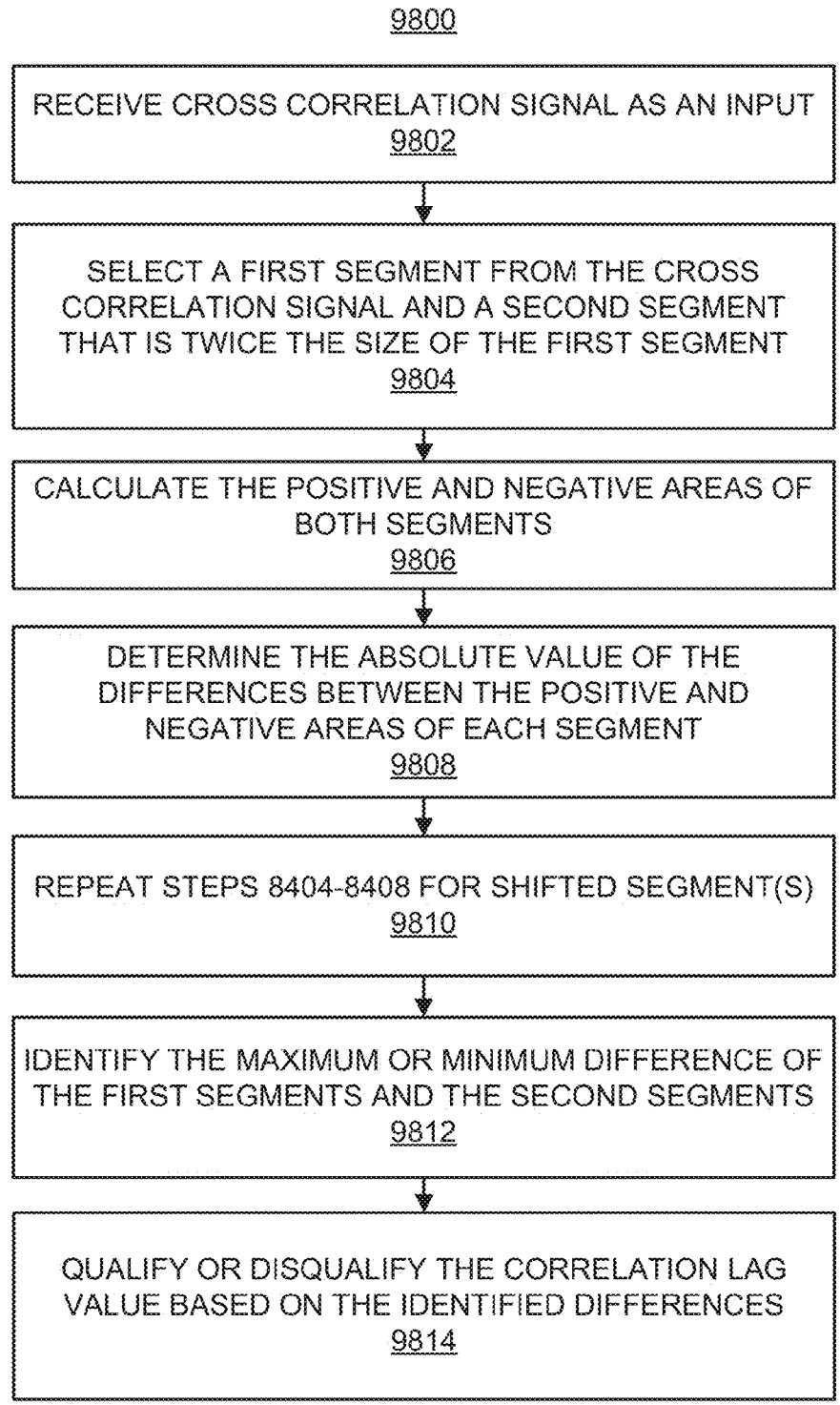
FIG. 98 is a flow diagram of illustrative steps for qualifying or disqualifying one or more values that may be indicative of a physiological rate based on an areas of positive and negative portions of segments of a cross-correlation output, in accordance with some embodiments of the present disclosure.

Step 9706 may include processing equipment qualifying or disqualifying a correlation lag value, based on the skewness metric value of step 9704. For example, referencing FIG. 22, the processing equipment may determine an expected correlation lag value, or range thereof, based on the skewness value and a reference look-up table, function, or other reference of related skewness values and expected correlation lag values. The processing equipment may compare the expected correlation lag value determined based on the skewness value of step 9704 to a correlation lag value calculated based on the physiological data. The comparison may include comparing the difference in determined and expected correlation lag values to a threshold. In a further example, the processing equipment may determine probabilities of particular correlation lag values, or ranges thereof, based on the determined skewness value and a reference relationship. If the determined correlation lag value corresponds to a relatively low probability (e.g., based on a predetermined threshold), the processing equipment may disqualify the determined correlation lag value. Alternatively, if the determined correlation lag value corresponds to a relatively high probability (e.g., based on a predetermined threshold), the processing equipment may qualify the determined correlation lag value. Similarly, in some embodiments, the processing equipment may determine an expected skewness value based on a correlation lag value calculated based on the physiological data, and compare the expected skewness value to the determined skewness value of step 9704. In some embodiments, the processing equipment may output a one for a passed Skewness Test (e.g., qualified), and a zero for a failed Skewness Test (e.g., disqualified). Typically, a particular sign of skewness value is expected for a PPG signal (depending on the signal conditioning and pre-processing), and the processing equipment may determine the sign of the skew as a Qualification Technique. For example, if the sign of the skewness metric value of step 9704 agrees with the expected sign the processing equipment may qualify a calculated correlation lag value, and if the sign of the skewness metric value does not agree with the expected sign the processing equipment may disqualify the calculated correlation lag value FIG. 98 is a flow diagram 9800 of illustrative steps for qualifying or disqualifying one or more values that may be indicative of a physiological rate based on areas of positive and negative portions of segments of a cross-correlation signal, in accordance with some embodiments of the present disclosure. In some embodiments, the illustrative steps of flow diagram 9800 aid in preventing a double-rate (half-period) condition, half-rate (double-period) condition, or other conditions in which period P is not indicative of a physiological rate. The illustrative steps of flow diagram 9800 may be referred to as the "Area Test."

Step 9802 may include processing equipment receiving a cross-correlation signal (e.g., generated according to step 8606 of FIG. 86) as an input. In some embodiments, the cross-correlation signal may be generated by a cross-correlation module. In some embodiments the cross-correlation signal may be generated at an earlier time, and stored in suitable memory. Accordingly, in some embodiments, step 9802 may include recalling the stored cross-correlation signal from the memory. In some embodiments, a single processor, module, or system may perform the cross-correlation and steps 9804-9814, and accordingly, step 9802 need not be performed.

Step 9804 may include the processing equipment selecting two signal segments of the cross-correlation signal of step 9802. The first segment may be half as large as the second segment. For example, the second segment may have a length equal to period P, while the first segment has a length equal to one half of period P and is included in the second segment. In a further example, the second segment may have a length equal to period 2P, while the first segment has a length equal to period P. The two segments may be selected from any suitable portion of the cross-correlation output.

Figure 99:
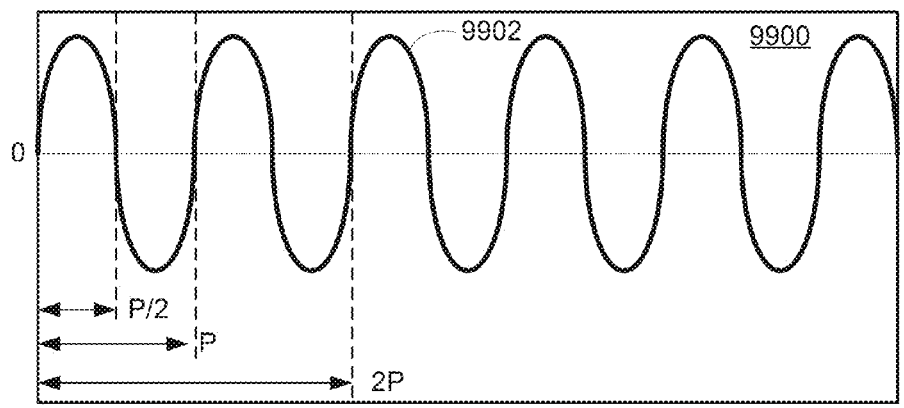
FIG. 99 is a plot of an illustrative cross-correlation output, centered about zero with a correctly determined correlation lag value, in accordance with some embodiments of the present disclosure.
Figure 100:
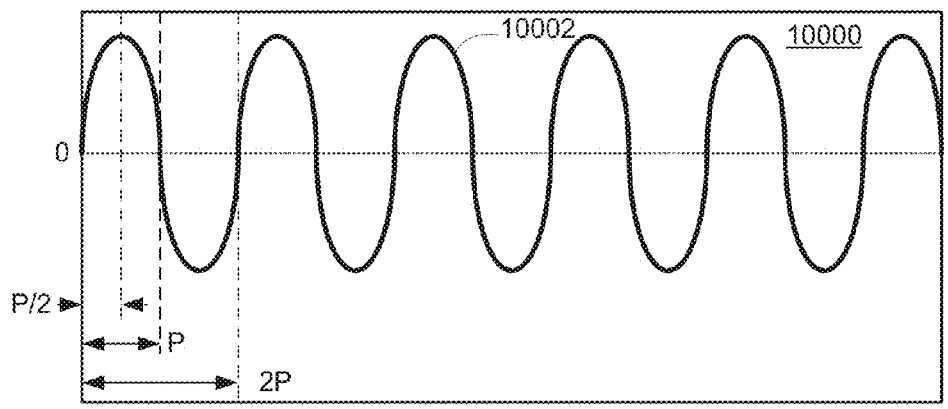
FIG. 100 is a plot of an illustrative cross-correlation output with a correlation lag value incorrectly determined to be double the correct rate, in accordance with some embodiments of the present disclosure.
Figure 101:
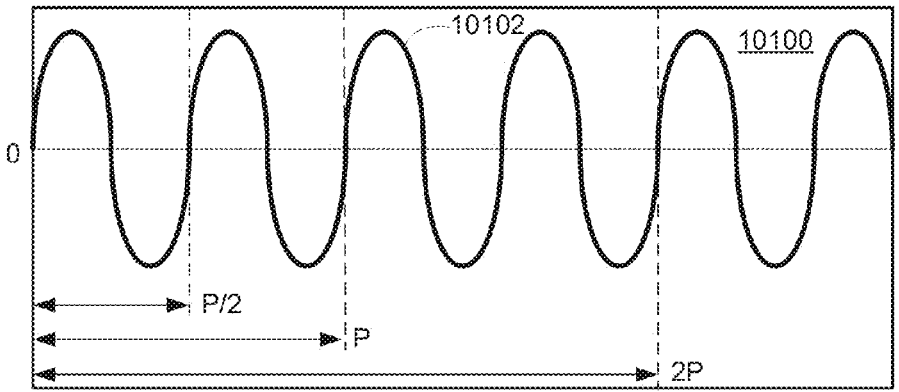
FIG. 101 is a plot of an illustrative cross-correlation output with the correlation lag value incorrectly determined to be half the correct rate, in accordance with some embodiments of the present disclosure.

Step 9806 may include the processing equipment calculating the positive and negative areas of both the first and second segments. Each segment may include one or more oscillations, or portions thereof, and accordingly may include positive and negative portions (e.g., FIGS. 99-101 provides further illustration). In some embodiments, step 9806 may include performing a summation of the positive data points, and a summation of the negative data points for each segment. In some embodiments, step 9806 may include performing a piecewise discrete integration (e.g., a piecewise numerical quadrature or any other suitable analytical or numerical technique) of the positive and negative portions of each of the two segments of the cross-correlation signal. In some embodiments, the area values of step 9806 may both be positive values, with the areas of a negative portion of a segment calculated by taking the absolute value of the integral of the negative portion. In some embodiments, either or both areas may be normalized by the associated segment length. This normalization may allow for a particular threshold to be used for segments having different lengths. For example, the areas of a segment of length P may both be divided by P or one. In a further example, the areas of a segment of length 2P may both be divided by 2P or two.

Step 9808 may include the processing equipment determining the absolute value of the difference between the positive and negative areas (which may both be positive values) for each segment. In some embodiments, the processing equipment may calculate the difference between the areas of the positive and negative portions of each segment by subtracting the area of the negative portion, which may be a positive value, from the area of the positive portion (or vice versa), and then calculating the absolute value of the difference.

Step 9810 may include the processing equipment repeating steps 9804-9808, for various shifts in the segments relative to one another, relative to a varying origin point with the segments' relative positions fixed, or any other suitable shift. In some embodiments, the first and second segments may always originate at the same point, which may be shifted along the cross-correlation output at step 9810 to define the different pairs of segments. In some embodiments, the first segment may remain fixed and the second segment may be shifted at step 9810. For example, the first segment, with a length equal to P/2, may remain fixed and the second segment, with a length equal to P, may be shifted by one or more degree measures and the difference may be calculated at each degree measure. In a further example, the second segment, with a length equal to P, may remain fixed and the first segment, with a length equal to P/2, may be shifted by one quarter of the period P, and the difference may be calculated at this new segment location. Either or both of the first and second segments may be shifted any suitable amount to generate one or more pairs of first and second segments. In some embodiments, step 9808, step 9810, or both, may include storing the one or more respective difference values of steps 9808 and 9810 in any suitable memory, using any suitable data-basing or filing protocol.

Step 9812 may include the processing equipment identifying maximum values, minimum values, or both, of the differences among both the first segments and the second segments. For example, in some embodiments, the processing equipment may identify the maximum difference of the first segment(s) and the minimum difference of the second segment(s). In some embodiments, the processing equipment may identify the maximum difference of the first segment(s) and the minimum difference of the second segment(s). Any suitable technique may be used to identify the respective maximum and minimum values. In some embodiments, step 9812 may be performed concurrent with steps 9808 and 9810. For example, initial maximum and minimum difference values may be calculated at step 9808 and stored. As subsequent difference values are calculated at step 9810, the stored values may be replaced as larger or smaller values, as appropriate, are calculated.

Step 9814 may include the processing equipment qualifying or disqualifying the correlation lag values, based on the identified maximum and minimum differences of step 9812.

In some embodiments, the processing equipment may calculate a difference between the maximum difference for the first segments and the minimum difference for the second segments. For example, one or more thresholds may be set based on the value of the minimum difference for the second segments (e.g., the threshold value may be equal to the minimum difference value or a scaling thereof). The maximum difference for the first segment may then be compared to the threshold. If the maximum difference is greater than the threshold, the processing equipment may qualify the correlation lag value. If the maximum difference is less than the threshold, the processing equipment may disqualify the correlation lag value. In some embodiments, the processing equipment may calculate a ratio of the maximum difference for the first segment to the minimum difference for the second segment. For example, one or more thresholds, which may be predetermined or may depend upon the difference values, may be set. The ratio may then be compared to the threshold. If the ratio is greater than the threshold, the processing equipment may qualify the correlation lag value. If the ratio is less than the threshold, the processing equipment may disqualify the correlation lag value. In some embodiments, the ratio may be calculated for each pair of first and second segments, and a maximum ratio value may be selected to be compared with one or more threshold values. In some embodiments, the areas, differences, or ratios may be normalized by dividing by a value corresponding to the segment length. In some embodiments, the thresholds may be scaled based on the segment lengths of the period P. In some embodiments, one or more metrics may inputted into a classifier.

In some embodiments, the illustrative steps of flow diagram 9800 may be performed using segments of length P/2 and P, which may provide particular benefits under some circumstances. In some embodiments, the illustrative steps of flow diagram 9800 may be performed using segments of length P and 2P, which may provide particular benefits under some circumstances. Any suitable first and second segments may be used to perform the Area Test. The following discussion, referencing FIGS. 99-101, provides further detail regarding flow diagram 9800, in accordance with some embodiments of the present disclosure. The abscissa of each of plots 9900, 10000, and 10100 of FIGS. 99-101, respectively, are presented in units proportional to cross-correlation lag, while the ordinate is presented in arbitrary units, with zero notated.

FIG. 99 is a plot 9900 of an illustrative cross-correlation output 9902, centered about zero with a correctly determined correlation lag value, in accordance with some embodiments of the present disclosure. The period P is close to the period exhibited by cross-correlation signal 9902. As shown in plot 9900, cross-correlation signal 9902 may include portions above the baseline (i.e., values greater than zero), and portions below the baseline (i.e., values less than zero). Depending on a how a segment of cross-correlation signal 9902 is selected, the areas of the positive and negative portions may change relative to one another.

Three illustrative segment lengths are shown in FIG. 99, including period P, one half of period P, and double period P. The difference in the areas of the positive and negative portions of segments of length P or 2P may be expected to be relatively small for any suitable shift because the segments approximately cover a complete period or double period exhibited by cross-correlation output 9902. The difference between the areas of the positive and negative portions of segments of length P/2 may be expected to range from small values (e.g., when a segment is centered near a zero of cross-correlation signal 9902) to relatively larger values (e.g., when the segment lies substantially between zeros of cross-correlation signal 9902).

In some cases, in which the correlation lag value is correctly determined, a first segment may have a length equal to P/2 and the second segment may have a length equal to period P. Differences in areas of positive and negative portions of cross-correlation signal 9902 may be calculated for multiple first and second segments, having constant respective lengths but varying shift. In some such cases, the maximum difference among first segments may be compared to the minimum difference among second segments, or a threshold derived thereof. For example, the maximum difference among first segments may be compared to a threshold equal to four times the minimum difference of the second segments. If the maximum difference among first segments is larger than the threshold, then the correlation lag value may be qualified.

In some cases, in which the correlation lag value is correctly determined, a first segment may have a length equal to P and the second segment may have a length equal to period 2P. Unlike the previously discussed cases, in which first and second segments had respective lengths of P/2 and P, the differences of the present cases are now both expected to be small values. Accordingly, in some such cases, the maximum difference among first segments may be compared to the minimum difference among second segments, or a threshold derived thereof. For example, the maximum difference among first segments may be compared to a threshold equal to two times the minimum difference of the second segments. If the maximum difference among first segments is smaller than the threshold, then the correlation lag value may be qualified.

FIG. 100 is a plot 10000 of an illustrative cross-correlation output 10002 with a correlation lag value incorrectly determined to be double the correct rate, in accordance with some embodiments of the present disclosure. The period P is close to one half of the period exhibited by cross-correlation signal 10002. Three illustrative segment lengths are shown in FIG. 100, including period P, one half of period P, and double period P. As illustrated, the difference in the areas of the positive and negative portions of segments of length 2P may be expected to be relatively small for any suitable shift. The difference in the areas of the positive and negative portions of segments of lengths P/2 or P may be expected to range from small values (e.g., when a segment is centered near a zero of cross-correlation signal 10002) to relatively larger values (e.g., when the segment lies substantially between zeros of cross-correlation signal 10002).

In some cases, in which the correlation lag value is incorrectly determined, a first segment may have a length equal to P/2 and the second segment may have a length equal to period P. Differences in areas of positive and negative portions of cross-correlation signal 10002 may be calculated for multiple first and second segments, having constant respective lengths but varying shift. In some such cases, the maximum difference among first segments may be relatively large compared to the minimum difference among second segments. Accordingly, under some circumstances, the use of first and second segments with respective lengths P/2 and P may allow a double-rate condition to qualify if similar threshold conditions are used as when the correlation lag value is correctly determined.

In some cases, in which the correlation lag value is incorrectly determined, a first segment may have a length equal to period P and the second segment may have a length equal to period 2P. In some such cases, the maximum difference of the first segment may be compared to the minimum difference of the second segment, or a threshold derived thereof. If the maximum difference among first segments is larger than a suitable threshold (e.g., the same threshold condition as used when the correlation lag value is correctly determined), as may be expected, then the correlation lag value may be disqualified. Accordingly, in some embodiments, the Area Test may provide techniques to disqualify a double-rate condition.

FIG. 101 is a plot 10100 of an illustrative cross-correlation signal 10102 with the correlation lag value incorrectly determined to be half the correct rate, in accordance with some embodiments of the present disclosure. The period P is close to twice the period exhibited by cross-correlation signal 10102. Three illustrative segment lengths are shown in FIG. 101, including period P, one half of period P, and double period P. As illustrated, the difference in the areas of the positive and negative portions of segments of length P/2, P, and 2P may be expected to be relatively small for any suitable shift. In some cases, any full period of cross-correlation signal 10102 may provide a relatively low difference value, regardless of shift.

In some cases, in which the correlation lag value is incorrectly determined to be one half the correct rate, a first segment may have a length equal to P/2 and the second segment may have a length equal to period P. Differences in areas of positive and negative portions of cross-correlation signal 10102 may be calculated for multiple first and second segments, having constant respective lengths but varying shift. In some such cases, the maximum difference among first segments may be comparable to the minimum difference among second segments. If the maximum difference among first segments is smaller than the threshold (e.g., the same threshold condition as used when the correlation lag value is correctly determined), then the correlation lag value may be disqualified. Accordingly, the Area Test may provide techniques to disqualify a half-rate condition.

In some cases, in which the correlation lag value is incorrectly determined to be one half the correct rate, a first segment may have a length equal to period P and the second segment may have a length equal to period 2P. In some such cases, the maximum difference of the first segment may be compared to the minimum difference of the second segment, or threshold derived thereof. If the maximum difference among first segments is smaller than a suitable threshold (e.g., the same threshold condition as used when the correlation lag value is correctly determined), as may be expected, then the correlation lag value may be qualified. Accordingly, under some circumstances, the use of first and second segments with respective lengths P and 2P may allow a half-rate condition to qualify if similar threshold conditions are used as when the correlation lag value is correctly determined.

In view of the foregoing, first and second segments with respective lengths P/2 and P may prevent qualification of a half-rate condition and first and second segment lengths of P and 2P may prevent qualification of a double-rate condition. Accordingly, in some embodiments, the Area Test may provide techniques to prevent qualification of double-rate, half-rate, or any other rate condition that is not indicative of a physiological rate.

Figure 102:
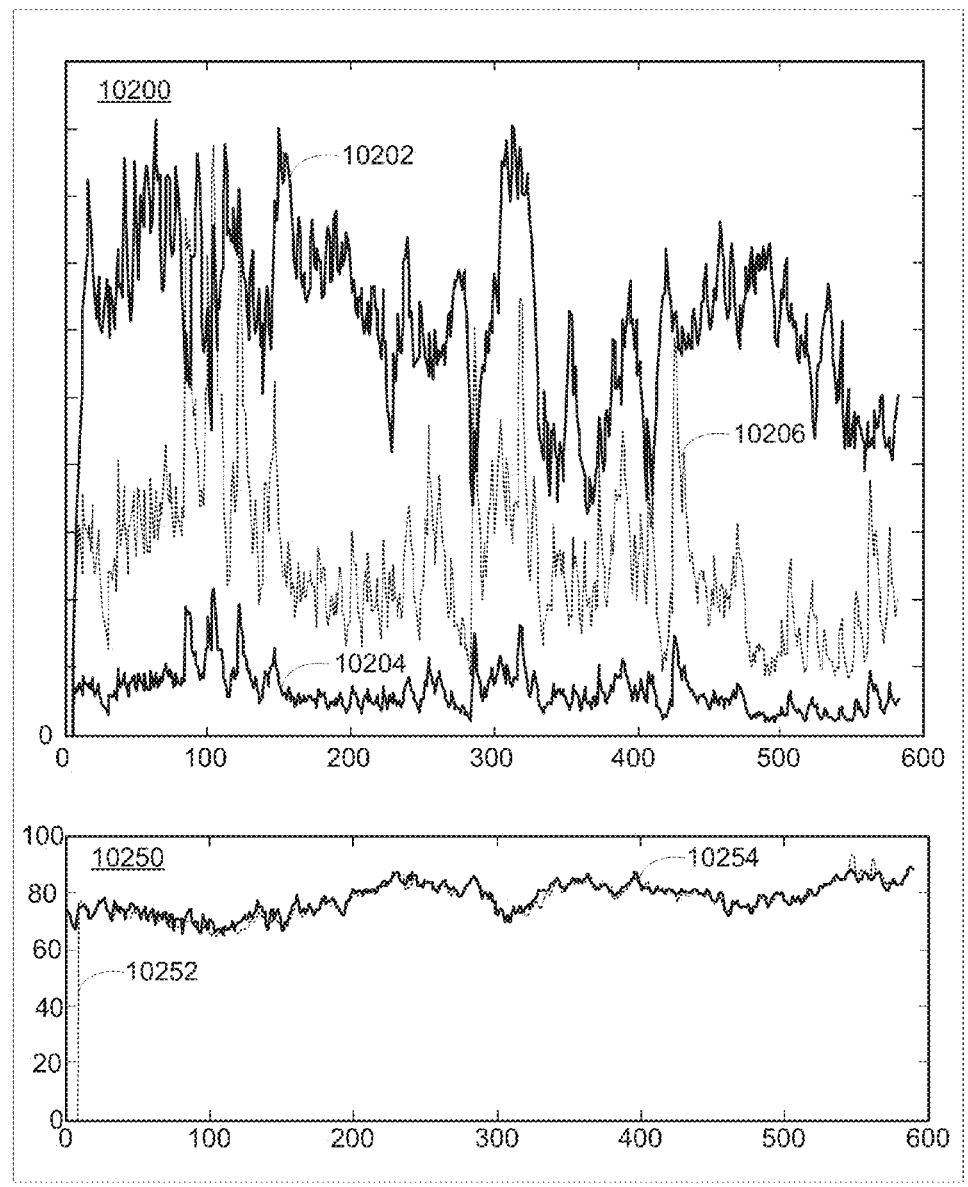
FIG. 102 is a plot of illustrative difference calculations of the Area Test, and a plot of illustrative calculated rates indicative of an actual physiological heart rate, in accordance with some embodiments of the present disclosure.

FIG. 102 is a plot 10200 of illustrative difference calculations of the Area Test with a correctly determined correlation lag value, and a plot 10250 of illustrative calculated rates indicative of an actual physiological heart rate, in accordance with some embodiments of the present disclosure. The abscissa of plot 10200 is presented in units of seconds, while the ordinate is presented in arbitrary units, with zero notated. Series 10202 is the maximum difference in first segments, with lengths equal to one half of period P. Series 10204 is the minimum difference in second segments, with lengths equal to period P. Threshold 10206 is an illustrative threshold equal to four times series 10204 (i.e., scaled from series 10204 by a multiplicative factor of four). As shown in FIG. 102, series 10202 lies above threshold 10206, indicating that the correlation lag value may be qualified. Plot 10250 illustrates calculated rates indicative of an actual physiological rate, in accordance with some embodiments of the present disclosure. The abscissa of plot 10250 is presented in units of seconds, while the ordinate is presented in units of BPM. Time series 10252 is the pulse rate (i.e., BPM) as calculated by a subject monitoring system tracking the actual rate, shown by time series 10254.

Figure 103:
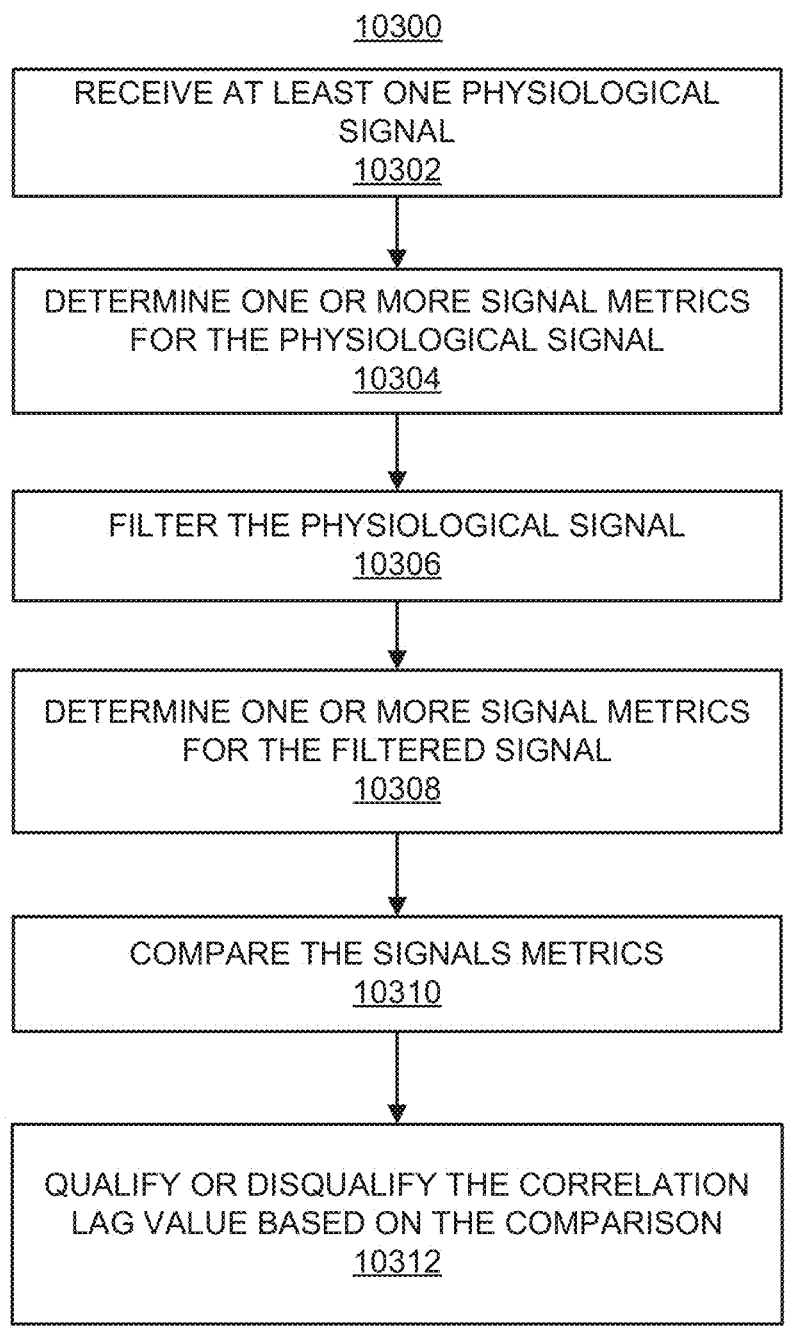
FIG. 103 is a flow diagram of illustrative steps for qualifying or disqualifying one or more values that may be indicative of a physiological rate based on a filtered physiological signal, in accordance with some embodiments of the present disclosure.

FIG. 103 is a flow diagram of illustrative steps for qualifying or disqualifying one or more values that may be indicative of a physiological rate based on a filtered physiological signal, in accordance with some embodiments of the present disclosure. In some embodiments, performance of the illustrative steps of flow diagram 10300 may provide an indication of the relative energy in a high frequency component of a physiological signal. Accordingly, in some circumstances, relatively large amounts of energy at rates much larger than the rate associated with the correlation lag value may indicate that low-frequency noise has been locked onto. The illustrative steps of flow diagram 10300 may be referred to as the "High Frequency Residual Test."

Step 10302 may include processing equipment receiving at least one physiological signal from a physiological sensor, memory, any other suitable source, or any combination thereof. For example, referring to system 300 of FIG. 3, processor 312 may receive a physiological signal from input signal generator 310. Sensor 318 of input signal generator 310 may be coupled to a subject, and may detect physiological activity such as, for example, RED and IR light attenuation by tissue, using a photodetector. In some embodiments, for example, physiological signals generated by input signal generator 310 may be stored in memory (e.g., memory of system 10 of FIGS. 1-2) after being pre-processed by pre-processor 320. In such cases, step 10302 may include recalling the signals from the memory for further processing. The physiological signal of step 10302 may include a PPG signal, which may include a sequence of pulse waves and may exhibit motion artifacts, noise from ambient light, electronic noise, system noise, any other suitable signal component, or any combination thereof. Step 10302 may include receiving a particular time interval or corresponding number of samples of the physiological signal. In some embodiments, step 10302 may include receiving a digitized, sampled, and pre-processed physiological signal.

Step 10304 may include the processing equipment determining one or more signal metrics for the physiological signal of step 10302. Signal metrics may include a standard deviation of the physiological signal, an RMS of the physiological signal, an amplitude of the physiological signal, a sum or integral of the physiological signal over time or samples, any other suitable metric indicative of a magnitude of a signal or change thereof, or any combination thereof. In some embodiments, the processing equipment may compute the standard deviation of the physiological signal, which may indicate the relative amplitude of excursions in the signal about the mean. In a further example, the processing equipment may take an absolute value of a physiological signal with zero mean, and then integrate the resulting signal over time or sample number to provide an indication of the magnitude of signal excursions about the mean (e.g., zero).

Step 10306 may include the processing equipment filtering the physiological signal of step 10302. In some embodiments, the processing equipment may apply a high-pass filter to the physiological signal of step 10302. For example, the processing equipment may apply a high-pass filter (e.g., having any suitable order and spectral characteristics) having a cutoff at double the rate associated with the one or more correlation lag values. In some embodiments, the processing equipment may apply a notch filter to the physiological signal of step 10302. For example, the processing equipment may apply a notch filter (e.g., having any suitable spectral characteristics) having a notch centered at double the rate associated with the one or more correlation lag values. In some embodiments, the processing equipment may apply a high-pass filter and a notch filter to the physiological signal of step 10302. For example, the processing equipment may apply a high-pass filter having a cutoff at double the rate associated with the correlation lag value, and a notch filter having a notch centered at double the rate associated with the one or more correlation lag values. The resulting high frequency (HF) signal may be further analyzed at step 10308. It will be understood that the physiological signal may undergo additional filtering before or after step 10306. Accordingly, the "filtered signal" of step 10306 refers to the filtering performed at step 10306, and not any previous or subsequent filtering.

Step 10308 may include the processing equipment determining one or more signal metrics for the filtered signal of step 10306. Signal metrics may include a standard deviation of the filtered signal, an RMS of the filtered signal, an amplitude of the filtered signal, a sum or integral of the filtered signal over time or samples, any other suitable metric indicative of a magnitude of a signal or change thereof, or any combination thereof. In some embodiments, the processing equipment may compute the standard deviation of the filtered signal, which may indicate the relative amplitude of excursions in the signal about the mean. In a further example, the processing equipment may take an absolute value of a filtered signal with zero mean, and then integrate the resulting signal over time or sample number to provide an indication of the magnitude of signal excursions about the mean (e.g., zero).

Step 10310 may include the processing equipment comparing the one or more signal metrics for the physiological signal of step 10302 with the one or more signal metrics for the filtered signal of step 10306. In some embodiments, the processing equipment may determine a comparison metric. In some embodiments, the processing equipment may determine the ratio of the signal metric(s) for the filtered signal to the signal metric(s) for the physiological signal. For example, the processing equipment may calculate the ratio of standard deviations of the filtered signal to the physiological signal. In some embodiments, the processing equipment may determine the difference between the signal metric(s) for the filtered signal and the signal metric(s) for the physiological signal.

Step 10312 may include the processing equipment qualifying or disqualifying correlation lag values based on the comparison of step 10310. In some embodiments, the processing equipment may compare the comparison metric of step 10310 with one or more threshold values. For example, the processing equipment may compare the ratio of standard deviations of the filtered signal to the physiological signal to a ratio threshold. The ratio threshold may be any suitable fixed or adjustable value. For example, the ratio threshold may depend on the correlation lag value. If the ratio is larger than the ratio threshold, the processing equipment may disqualify the correlation lag value. If the ratio is smaller than the ratio threshold, the processing equipment may qualify the correlation lag value. Accordingly, the processing equipment may use the High Frequency Residual Test to determine conditions having relatively large amounts of signal energy at rates significantly larger than the rate associated with one or more correlation lag values.

Figures 104, 105:
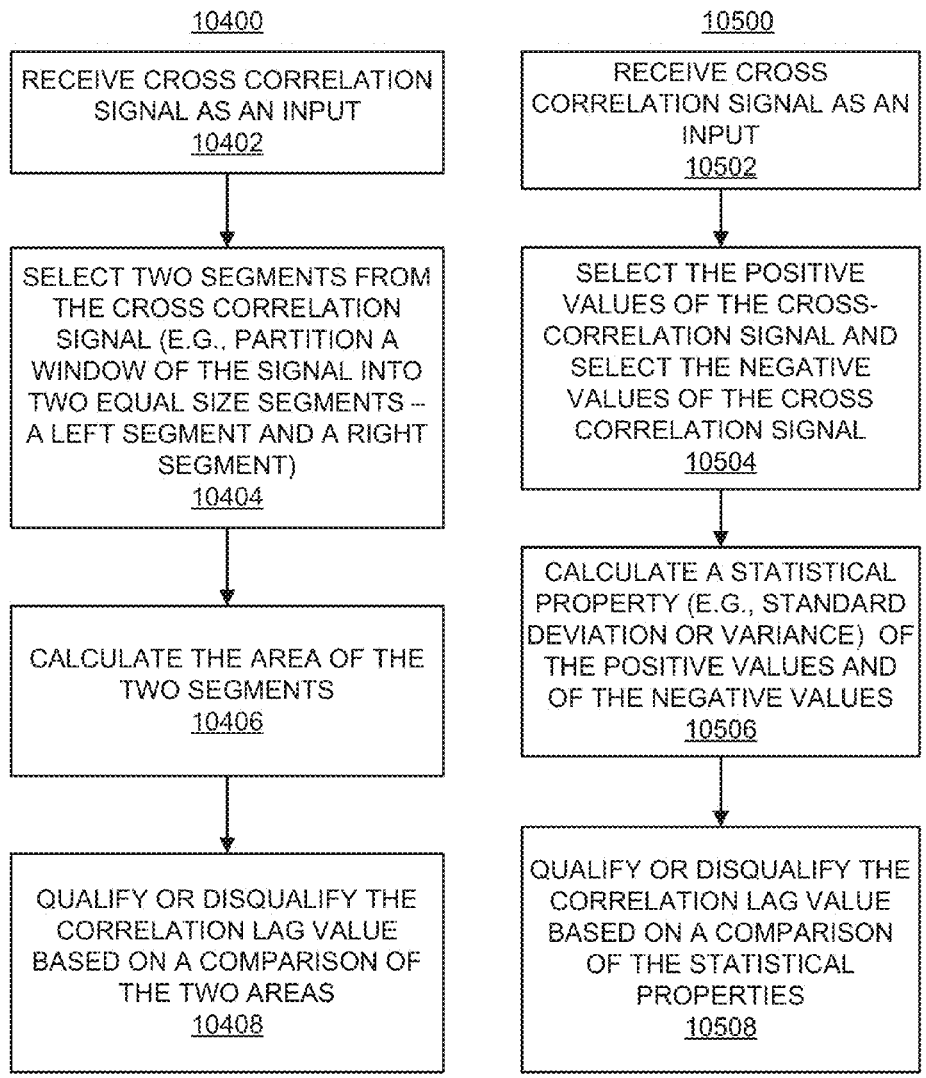
FIG. 104 is a flow diagram of illustrative steps for qualifying or disqualifying one or more values that may be indicative of a physiological rate based on a comparison of areas of two segments of a cross-correlation signal, in accordance with some embodiments of the present disclosure.
FIG. 105 is a flow diagram of illustrative steps for qualifying or disqualifying a value that may be indicative of a physiological rate based on statistical properties of a cross-correlation output, in accordance with some embodiments of the present disclosure.

FIGS. 104 and 105 are illustrative flow diagrams of techniques that may also be used to qualify or disqualify one or more correlation lag values. In some embodiments, the illustrative steps of flow diagrams 10400 and 10500 of FIGS. 104 and 105, respectively, may be performed based on a correlation lag value. In some embodiments, the illustrative steps of flow diagrams 10400 and 10500 of FIGS. 104 and 105, respectively, may be performed independent of a correlation lag value (e.g., to quantify noise and/or consistency in a buffered signal).

FIG. 104 is a flow diagram 10400 of illustrative steps for qualifying or disqualifying one or more values that may be indicative of a physiological rate based on a comparison of areas of two segments of a cross-correlation signal, in accordance with some embodiments of the present disclosure. In some embodiments, performance of the illustrative steps of flow diagram 10400 may provide an indication of the similarity between different segments of a cross-correlation signal. The illustrative steps of flow diagram 10400 may be referred to as the "Area Similarity Test."

Step 10402 may include processing equipment receiving a cross-correlation signal (e.g., generated according to step 8606 of FIG. 86) as an input. In some embodiments, the cross-correlation signal may be generated by a cross-correlation module. In some embodiments the cross-correlation signal may be generated at an earlier time, and stored in suitable memory. Accordingly, in some embodiments, step 10402 may include recalling the stored cross-correlation signal from the memory. In some embodiments, a single processor, module, or system may perform the cross-correlation and steps 10404-10408, and accordingly, step 10402 need not be performed.

Step 10404 may include the processing equipment selecting two segments of the cross-correlation signal of step 10402. In some embodiments, the two segments may be of equal length. In some such embodiments, the cross-correlation signal may be equi-partitioned into a right segment and a left segment. For example, if the cross-correlation signal is six seconds in length, the left segment may be the left three seconds and the right segment may be adjacent right three seconds of the signal. In a further example, the first and second segments may each have a length equal to period P. Any suitable segments may be selected in accordance with the present disclosure. Note that the two segments will be referred to as Segment1 and Segment2, or the first segment and the second segment, although the designations are arbitrarily assigned for illustration purposes (e.g., the first and second segments may be interchanged in accordance with the present disclosure).

Step 10406 may include the processing equipment calculating the area of each of the first and second segments of step 10404. In some embodiments, step 10406 may include calculating an integral (e.g., a quadrature or any other suitable analytical or numerical technique), sum, or both, of the first and second segments. In some embodiments, the calculated area may be additive among the positive and negative areas. For example, the area of positive portions and the absolute value of the area of negative portions may be summed, resulting in a positive result. In some embodiments, the calculated area may be subtractive, in which the area of positive portions and negative portions of each segment are respective positive and negative numbers (e.g., integral of the segment values in which negative portions contribute negative integrals), and a resulting sum may be positive or negative.

Step 10408 may include the processing equipment qualifying or disqualifying a correlation lag value based on a comparison of the calculated areas of step 10406. Any suitable comparison technique, including the calculation of any suitable comparison metric (e.g., difference, ratio), may be used to compare the areas of the two segments. In some embodiments, the processing equipment may calculate a difference between the area of the first segment and the area of the second segment (or vice versa). In some embodiments, the processing equipment may calculate a ratio of the area of the first segment to the area of the second segment (or vice versa). In some embodiments, qualification or disqualification may include comparing a comparison metric to a threshold value. For example, the difference between (or ratio of) the areas of the two segments may be calculated and if above a threshold value, the correlation lag value may be disqualified. Using suitable segment selection, the areas of the two segments may be expected to be similar, if period P provides a relatively accurate indication of a physiological pulse period.

In some embodiments, step 10408 need not be performed with steps 10402-10406. In some embodiments, steps 10402-10406 may be performed independent of a correlation lag value. For example, a cross-correlation signal of a buffered window of data may be analyzed using steps 10402-10406. The areas of two segments (e.g., fixed length segments) of the cross-correlation signal may be compared using a comparison metric, and under some circumstances the buffered data may be qualified or disqualified (e.g., based on a comparison of the comparison metric with a threshold). This may be particularly useful when the physiological signal is relatively noise free and then noise suddenly appears in the signal. This may also be particularly useful when strong non-periodic noise is present in the signal.

FIG. 105 is a flow diagram 10500 of illustrative steps for qualifying or disqualifying a value that may be indicative of a physiological rate based on statistical properties of a cross-correlation signal, in accordance with some embodiments of the present disclosure. In some embodiments, performance of the illustrative steps of flow diagram 10500 may provide an indication of the similarity between positive and negative portions of a cross-correlation signal. The illustrative steps of flow diagram 10500 may be referred to as the "Statistical Property Test."

Step 10502 may include processing equipment receiving a cross-correlation signal (e.g., generated according to step 8606 of FIG. 86) as an input. In some embodiments, the cross-correlation signal may be generated by a cross-correlation module. In some embodiments the cross-correlation signal may be generated at an earlier time, and stored in suitable memory. Accordingly, in some embodiments, step 10502 may include recalling the stored cross-correlation signal from the memory. In some embodiments, a single processor, module, or system may perform the cross-correlation and steps 10504-10508, and accordingly, step 10502 need not be performed.

Step 10504 may include the processing equipment selecting the positive values of the cross-correlation signal, and selecting the negative values of the cross-correlation signal. For example, the processing equipment may compare each value of the cross-correlation signal to zero, and use the comparison to select positive and/or negative values.

Step 10506 may include the processing equipment calculating a statistical property of the positive values and of the negative values of step 10504. The statistical property may include a mean, standard deviation, variance, root-mean-square (RMS) deviation (e.g., relative to zero), any other suitable statistical property, or any combination thereof. In some embodiments, the positive values and negative values may be processed separately at step 10506.

Step 10508 may include the processing equipment qualifying or disqualifying the one or more correlation lag values based on a comparison of the statistical properties of step 10506. Any suitable comparison technique, including the calculation of any suitable comparison metric (e.g., difference, ratio), may be used to compare the statistical properties of the positive and negative values. In some embodiments, the processing equipment may calculate a difference between the statistical properties of the positive and negative values (or vice versa). In some embodiments, the processing equipment may calculate a ratio of the statistical properties of the positive and negative values (or vice versa). In some embodiments, qualification or disqualification may include comparing a comparison metric to a threshold value. For example, the difference between (or ratio of) the statistical properties of the positive and negative values may be calculated and if above a threshold value, the correlation lag value may be disqualified.

In some embodiments, step 10508 need not be performed with steps 10502-10506. In some embodiments, steps 10502-10506 may be performed independent of a correlation lag value. For example, a cross-correlation signal of a buffered window of data may be analyzed using steps 10502-10506. The statistical properties of the positive and negative values of the cross-correlation output may be compared using a comparison metric, and under some circumstances the buffered data may be qualified or disqualified (e.g., based on a comparison of the comparison metric with a threshold).

Figure 106:
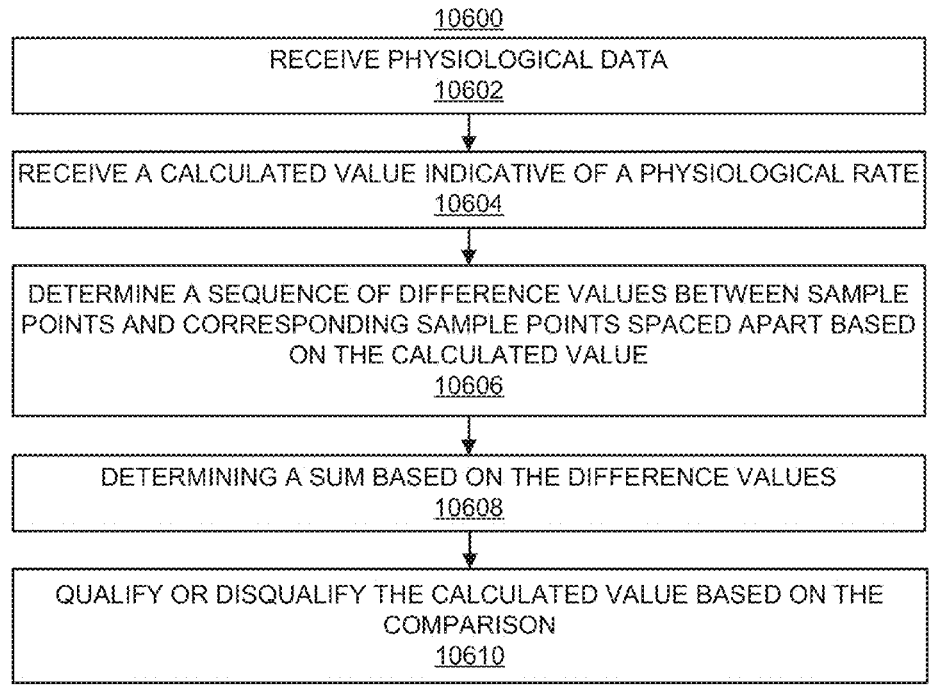
FIG. 106 is a flow diagram of illustrative steps for qualifying or disqualifying a value that may be indicative of a physiological rate based on differences of a physiological signal, in accordance with some embodiments of the present disclosure.

FIG. 106 is a flow diagram 10600 of illustrative steps for qualifying or disqualifying a value that may be indicative of a physiological rate based on differences of a physiological signal, in accordance with some embodiments of the present disclosure. The illustrative steps of flow diagram 10600 may be referred to as the "Integral Test."

Step 10602 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 10602 may include recalling data from the memory for further processing.

Step 10604 may include the processing equipment receiving a calculated value indicative of a physiological rate of the subject. For example, the calculated value may be based on a correlation lag value, a rate corresponding to the correlation lag value, or any other calculated value indicative of a physiological rate of the subject. In some embodiments, step 10604 may include recalling the calculated value from memory for further processing.

Step 10606 may include the processing equipment determining a sequence of difference values between samples points and corresponding sample points spaced apart based on the calculated value of step 10604. For example, the processing equipment may specify a segment of the physiological data, and determine the difference between each value of the segment and a corresponding sample point of the physiological data spaced by a shift. The calculated value may be a calculated correlation lag value, and the shift may be equal to the correlation lag value. The processing equipment may use an expression such as, for example, Eq. 59:

$$D_i = X_i - X_{i-N} \qquad (59)$$

to determine the sequence of difference values $D_i$, indexed by i, where $X_i$ is a sample point and $X_{i-N}$ is a sample point spaced by N points (e.g., where N corresponds to the correlation lag value). In some embodiments, the processing equipment may determine absolute values of the sequence of differences, thus resulting in positive values of the differences.

Step 10608 may include the processing equipment determining a sum based on the sequence of differences of step 10606. In some embodiments, the processing equipment may sum the sequence of difference values to obtain a single summation value. In some embodiments, the processing equipment may perform steps 10606 and 10608 by determining a root-mean-square (RMS) difference between the sample values and corresponding sample values. The sum may include any suitable mathematical combination of the collective differences of the sample points and corresponding sample points, and may be optionally normalized (e.g., by the number of sample points).

Step 10610 may include processing equipment qualifying or disqualifying the correlation lag value of step 10606, based on the sum of step 10608. In some embodiments, the sum may be compared to a threshold. If the sum is greater than the threshold, the processing equipment may disqualify the correlation lag value, while if the sum is less than the threshold, the processing equipment may qualify the correlation lag value. Accordingly, the sum may be expected to be relatively low when the physiological data is relatively more periodic, typically indicating a segment of data is relatively more similar to a segment spaced by a period corresponding to a physiological rate.

Figure 107:
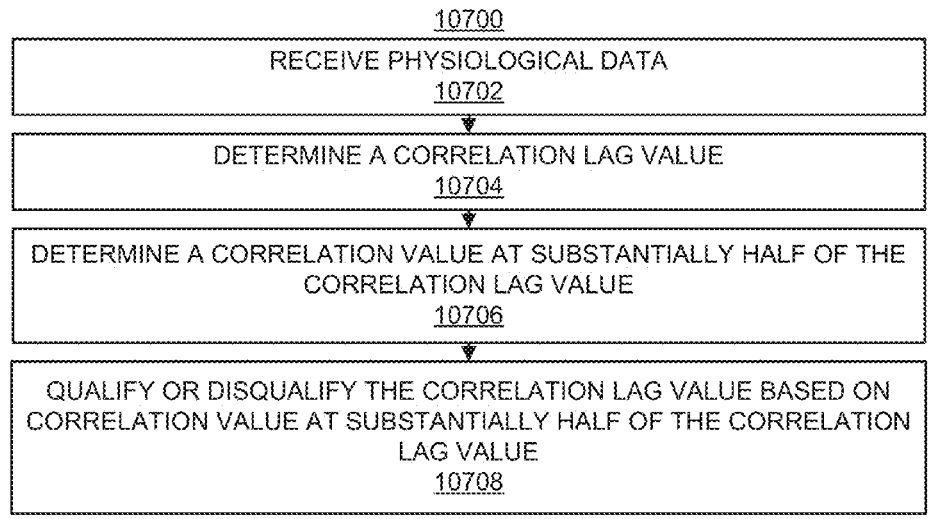
FIG. 107 is a flow diagram of illustrative steps for qualifying or disqualifying a value that may be indicative of a physiological rate based on a half lag analysis, in accordance with some embodiments of the present disclosure.

FIG. 107 is a flow diagram 10700 of illustrative steps for qualifying or disqualifying a value that may be indicative of a physiological rate based on a half lag analysis, in accordance with some embodiments of the present disclosure. The illustrative steps of flow diagram 10700 may be referred to as the "Half Lag Test."

Step 10702 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 10702 may include recalling data from the memory for further processing.

Step 10704 may include the processing equipment determining a correlation lag value of the physiological data of step 10702. In some embodiments, the processing equipment may generate a correlation sequence. The correlation sequence may include a sequence of correlation values corresponding to different lag values. In some embodiments, the processing equipment may generate the correlation sequence by multiplying values of a first segment of the physiological segment with corresponding values of a second segment of the physiological data, shifted in time by a particular lag, for multiple lag values. Any suitable technique in may be used to determine the correlation lag value such as, for example, the illustrative techniques discussed in the context of FIGS. 62-85, or any other suitable technique or combination of techniques thereof. For example, the processing equipment may identify a peak in the correlation sequence, and may determine the correlation lag value based on the identified peak.

Step 10706 may include the processing equipment determining a correlation value at a lag of substantially one half of the determined correlation lag value of step 10704. In some embodiments, the processing equipment may generate a correlation sequence at step 10704, and select the half lag value at step 10706. In some embodiments, the processing equipment may perform a correlation calculation at the half lag value to determine the correlation value.

Step 10708 may include processing equipment qualifying or disqualifying the correlation lag value of step 10706, based on the correlation value at a lag of substantially one half of the determined correlation lag value of step 10704. In some embodiments the correlation at the half lag value may be compared with a threshold, and if the correlation at lag exceeds the threshold, the correlation lag value is disqualified. In some embodiments, the correlation at the half lag value may be compared with the correlation value at the correlation lag value, and if the difference is greater than a threshold, the correlation lag value may be qualified. The correlation at the half lag value may be expected to be relatively less than the correlation value at the correlation lag value, and may be expected to be less than zero in some circumstances.

Figure 108:
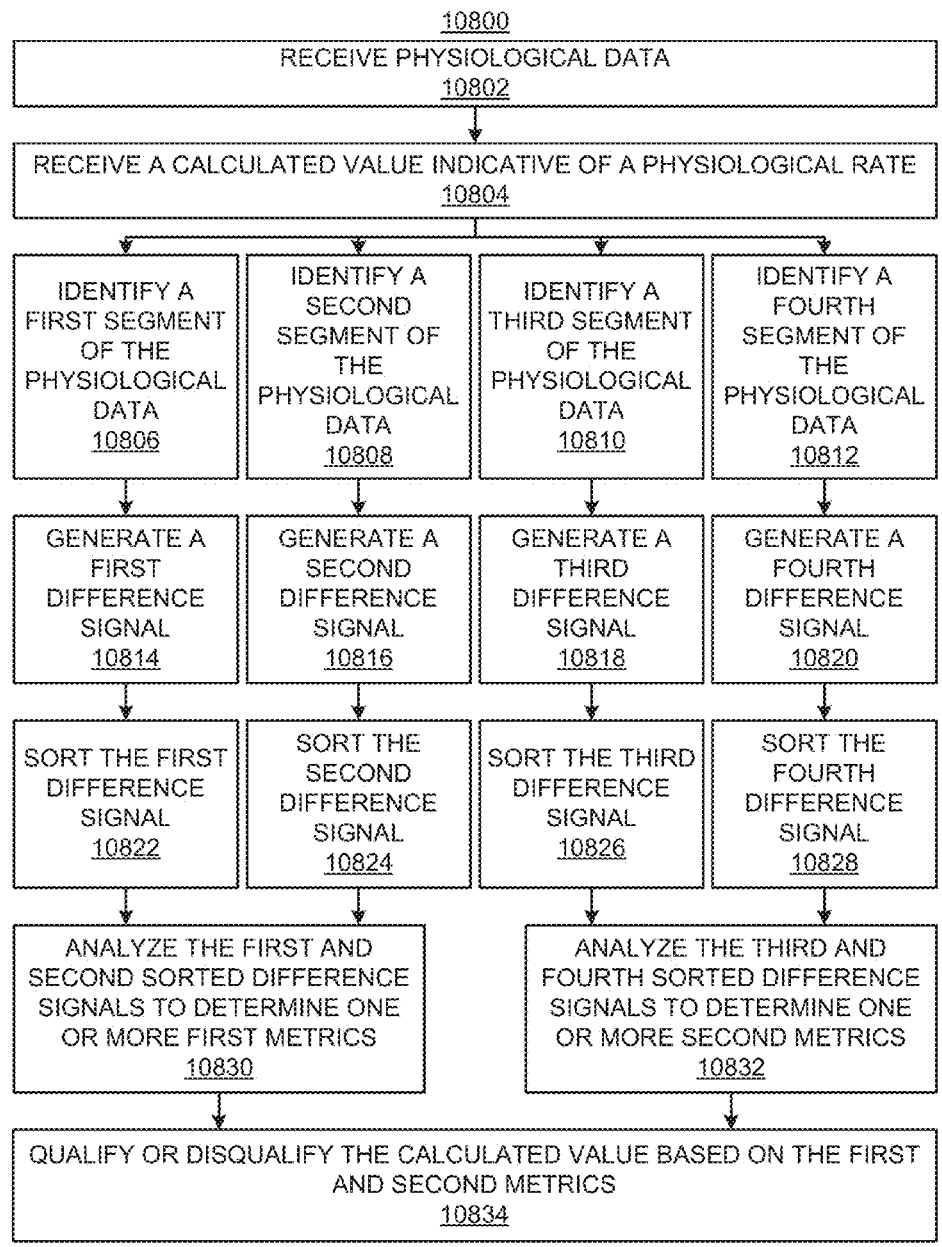
FIG. 108 is a flow diagram of illustrative steps for qualifying or disqualifying a value that may be indicative of a physiological rate based on a sorted difference signal, in accordance with some embodiments of the present disclosure.

FIG. 108 is a flow diagram 10800 of illustrative steps for qualifying or disqualifying a value that may be indicative of a physiological rate based on a sorted difference signal, in accordance with some embodiments of the present disclosure. The illustrative steps of flow diagram 10800 may be referred to as the "Ordered Statistic Test." The Ordered Statistic Test (OS Test) uses up to four segments of physiological data to determine whether to qualify a correlation lag value. The OS Test compares segments of data to determine if the correlation lag value is correct, if the window of physiological data is valid, or both. For example, the OS Test may analyze a left half and a right half of a window of data. Further to this example, the OS Test may analyze a segment of the left half of a size equal to a calculated correlation lag value and a segment of the right half of a size equal to a calculated correlation lag value. Each analysis may include determining one or more metrics based on the physiological data, generating a sorted difference signals and determining one or metrics based on the sorted difference signals, pairing the sorted difference signals and determining one or more metrics based on the value pairs, or any other suitable analyses. If the calculated correlation lag value substantially corresponds to a period of the physiological rate, and the physiological data does not exhibit significant noise or artifacts, the analysis of the left and right halves and the analysis of the two segments should produce similar results (e.g., metric values) when the OS Test is applied. Analysis of the left and right halves may provide an indication of the noise level in the physiological data (e.g., as described in the discussion of FIG. 37), for example. Analysis of the two segments of size equal to the period associated with the physiological rate, and/or comparison to the analysis of the halves, may provide an indication of whether the calculated correlation lag value is correct, for example.

Step 10802 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 10802 may include recalling data from the memory for further processing.

Step 10804 may include the processing equipment receiving a calculated value indicative of a physiological rate of the subject. For example, the calculated value may be based on a correlation lag value, a rate corresponding to the correlation lag value, or any other calculated value indicative of a physiological rate of the subject. In some embodiments, step 10804 may include recalling the calculated value from memory for further processing.

Figure 109:
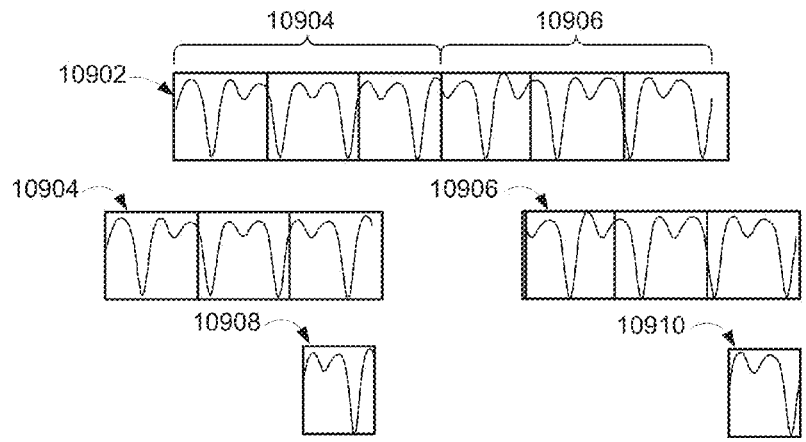
FIG. 109 is a block diagram of illustrative physiological data and four identified segments, in accordance with some embodiments of the present disclosure.

Steps 10806, 10808, 10810, and 10812 may include the processing equipment identifying a first segment of the physiological data, a second segment of the physiological data, a third segment of the physiological data, and a fourth segment of the physiological data, respectively. The first and second segments may be the same size (e.g., the same number of sample points), and the third and fourth segments may be the same size (e.g., the same number of sample points), not necessarily the same as the size of the first and second segments. In some embodiments, the processing equipment may identify a segment by identify indices of a sequence of physiological data points. In some embodiments, the processing equipment may identify the first segment, and then identify the second, third, and fourth segments relative to the first segment. In some embodiments, the processing equipment may identify the first segment and the third segment, and then identify the second segment and the fourth segment relative to the first segment and the second segment, respectively. For example, the processing equipment may receive a six second window of data at step 10802, and partition the data into two three-second segments as the first and second segments. Further to this example, the processing equipment may identify a smaller segment (e.g., having a size corresponding to the calculated value of step 10804) from the first segment as the third segment, identify a smaller segment (e.g., having a size corresponding to the calculated value of step 10804) from the second segment as the fourth segment. To illustrate the previous example, FIG. 109 is a block diagram of illustrative physiological data 10902 (e.g., from a PPG signal) and four identified segments 10904, 10906, 10908, and 10910, in accordance with some embodiments of the present disclosure. Segments 10904 and 10906 are the first and second segments, while segments 10908 and 10910 are the third and fourth segments.

Steps 10814, 10816, 10818, and 10820 may include the processing equipment generating a first difference signal based on the first segment, a second difference signal based on the second segment, a third difference signal based on the third segment, and a fourth difference signal based on the fourth segment, respectively. In some embodiments, the processing equipment may perform a subtraction between values of adjacent samples of a segment to generate the respective difference signal. In some embodiments, the processing equipment may calculate differences by calculating a first derivative of the respective segment. For example, the processing equipment may compute forward differences, backward differences, or central differences between each pair of adjacent points to generate a difference signal. In a further example, the processing equipment may compute a numerical derivative at each point in the segment, generating a difference signal. Any suitable difference technique may be used by the processing equipment to generate the difference signals.

Steps 10822, 10824, 10826, and 10828 may include processing equipment sorting the difference values of each difference signal of steps 10814, 10816, 10818, and 10820, respectively. The processing equipment may sort the values in ascending or descending order, either of which causes the negative and positive values to be separated. Referencing sorted values in ascending order, the most negative values come first followed by less negative values, positive values, and finally larger positive values. The output of steps 10822, 10824, 10826, and 10828 may be a first sorted difference signal, a second sorted difference signal, a third sorted difference signal, and a fourth sorted difference signal, respectively.

Figure 110:
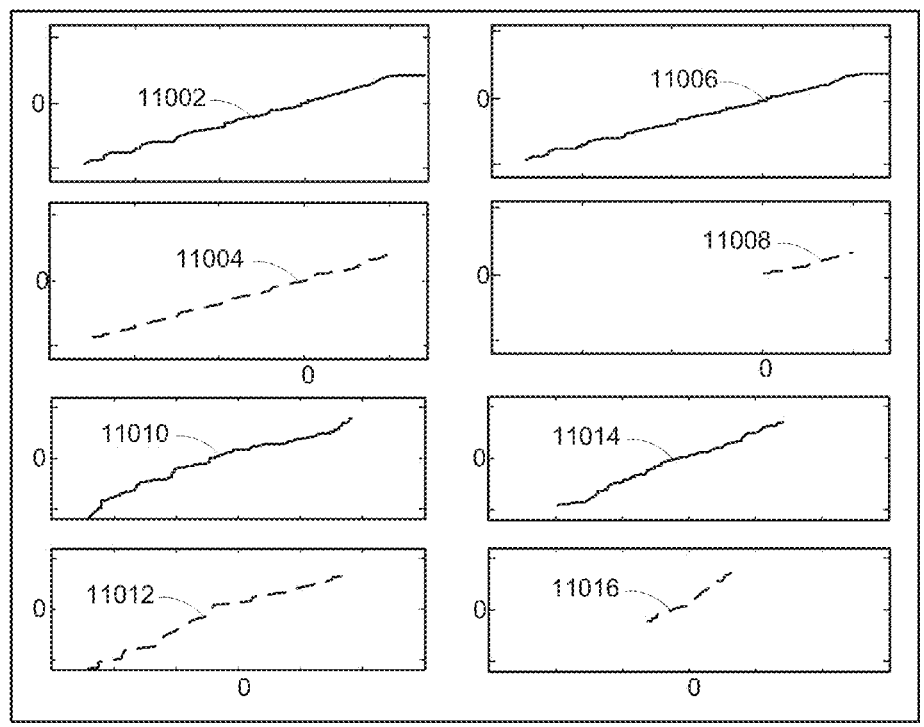
FIG. 110 is a panel of illustrative plots showing paired sorted difference signals, in accordance with some embodiments of the present disclosure.

In an illustrative example of the sorted difference signals of steps 10822, 10824, 10826, and 10828, FIG. 110 is a panel of illustrative plots showing paired sorted difference signals 11002, 11004, 11006, 11008, 11010, 11012, 11014, and 11016, in accordance with some embodiments of the present disclosure. Paired sorted difference signals 11002 and 11004 represent value pairs of first and second sorted difference signals, and value pairs third and fourth sorted difference signals, respectively, derived from physiological data exhibiting a dicrotic notch. The value pairs are generated by pairing corresponding points of the respective segments of the same size. First and second segment size of 3 seconds, and third and fourth segment sizes of 1 second (e.g., a correlation lag value corresponding to a physiological rate of 60 BPM) are used to generate paired sorted difference signals 11002 and 11004. Paired sorted difference signals 11006 and 11008 represent value pairs of first and second sorted difference signals, and value pairs third and fourth sorted difference signals, respectively, derived from physiological data exhibiting a dicrotic notch. First and second segment size of 3 seconds, and third and fourth segment sizes of one half a correlation lag value are used to generate paired sorted difference signals 11006 and 11008. It can be seen that if the processing equipment mistakenly posts a half lag, the paired sorted difference signals for the first and second segments, and the third and fourth segments, may have different characteristics. For example, the endpoints and curve lengths of paired sorted difference signals 11006 and 11008 are distinguishable. Paired sorted difference signals 11010 and 11012 represent value pairs of first and second sorted difference signals, and value pairs third and fourth sorted difference signals, respectively, derived from physiological data of a neonate. First and second segment size of 3 seconds, and third and fourth segment sizes of 1 second (e.g., a correlation lag value corresponding to a physiological rate of 60 BPM) are used to generate paired sorted difference signals 11010 and 11012. Paired sorted difference signals 11014 and 11016 represent value pairs of first and second sorted difference signals, and value pairs third and fourth sorted difference signals, respectively, derived from relatively noisier physiological data of a neonate. First and second segment size of 3 seconds, and third and fourth segment sizes of one half a correlation lag value are used to generate paired sorted difference signals 11014 and 11016. It can be seen that if the processing equipment mistakenly posts a half lag, the paired sorted difference signals for the first and second segments, and the third and fourth segments, may have different characteristics. For example, the endpoints and curve lengths of paired sorted difference signals 11014 and 11016 are distinguishable.

Step 10830 may include the processing equipment analyzing the first and second sorted difference signals to determine one or more first metrics. The one or more first metrics may include a correlation coefficient between the first and second sorted difference signals, slopes of the first and second sorted difference signals, lengths of the first and second sorted difference signals, corresponding values of the first and second difference signals, any other suitable metrics, any differences between metrics of the first and second segments thereof, or any combination thereof.

Step 10832 may include the processing equipment analyzing the third and fourth sorted difference signals to determine one or more second metrics. The one or more second metrics may include a correlation coefficient between the third and fourth sorted difference signals, slopes of the third and fourth sorted difference signals, lengths of the third and fourth sorted difference signals, corresponding values of the third and fourth difference signals, any other suitable metrics, any differences between metrics of the third and fourth segments thereof, or any combination thereof.

In an illustrative example, the processing equipment may determine any of the metrics shown in Eqs. 60-67 as the first and second metrics:

$$M_1 = \frac{\sum_{1}^{N}(X_i - \overline{X})(Y_i - \overline{Y})}{\sqrt{\sum_{1}^{N}(X_i - \overline{X})^2}\sqrt{\sum_{1}^{N}(Y_i - \overline{Y})^2}} \quad (60)$$

$$M_2 = \hat{b}(2, 1), \text{ where } \hat{b} = (\hat{X}^T\hat{X})^{-1}(\hat{X}^T\hat{y}) \quad (61)$$

$$M_3 = (1 - M_1)(1 - M_2) \quad (62)$$

$$M_4 = 10 * \log_{10}M_3 \quad (63)$$

$$M_5 = \sum_{1}^{N}\sqrt{\Delta X_i^2 + \Delta Y_i^2} \quad (64)$$

$$M_6 = \frac{|M_{2,2} - M_{2,1}|}{M_{2,1}} \quad (65)$$

$$M_7 = \frac{|M_{5,1} - M_{5,2}|}{M_{5,2}} \quad (66)$$

$$M_8 = [0.5*(X_1 + Y_1); 0.5*(X_N + Y_N)] \quad (67)$$

where:
$X_i$ and $Y_i$ are the first and second sorted difference signal values, or the third and fourth sorted difference signal values (sorted in ascending order for illustration);
$\Delta X_i$ and $\Delta Y_i$ are difference values of the first and second sorted difference signal values, or the third and fourth sorted difference signal values, where $\Delta X_i = X_i - X_{i-1}$, for example;
$\hat{X}$ is a N×2 matrix in which the first column is ones and the second column are the $X_i$ values;
$\hat{X}^T$ is a transpose of matrix $\hat{X}$;
$\hat{y}$ is a N×1 matrix of the $Y_i$ values;
$\hat{b}$ is a 2×2 matrix;
$M_{2,2}$ is $M_2$ evaluated for the third and fourth sorted difference signal;
$M_{2,1}$ is $M_2$ evaluated for the first and second sorted difference signal;
$M_{5,2}$ is $M_2$ evaluated for the third and fourth sorted difference signal; and
$M_{5,1}$ is $M_2$ evaluated for the first and second sorted difference signal.

In some embodiments, metric $M_1$ may be calculated for the first and second sorted difference signals, the third and fourth sorted difference signals, or both. Metric $M_1$, which is a correlation coefficient, is indicative of how well the sorted difference signals are correlated with each other. A value near one indicates good correlation, while a value near negative one indicates anti-correlation, with values near zero indicating no correlation. In some embodiments, the processing equipment may compare metric $M_1$ to a threshold as a qualification test.

In some embodiments, metric $M_2$ may be calculated for the first and second sorted difference signals, the third and fourth sorted difference signals, or both. Metric $M_2$ may be indicative of the slope of the value pairs generated from the two segments. A value near one may indicate good correlation, while a value near negative one may indicate anti-correlation. In some embodiments, the processing equipment may compare metric $M_2$ to a threshold, or to the same metric generated for the other two segments, as a qualification test. For pairs of segments exhibiting good correlation, metric $M_2$ values for the first/second segments, and third/fourth segments, are expected to be similar.

In some embodiments, metric $M_3$ may be calculated for the first and second sorted difference signals, the third and fourth difference signals, or both. Metric $M_3$ may be indicative of the combined slope and correlation of the value pairs generated from the two segments. In some embodiments, the processing equipment may compare metric $M_3$ to a threshold, or to the same metric generated for the other two segments, as a qualification test. For pairs of segment exhibiting good correlation, metric $M_3$ values for the first/second segments, and third/fourth segments, are expected to be similar and near zero. This is because, for good correlation, the slope and correlation coefficient are expected to each have a value of near one.

In some embodiments, metric $M_4$ may be calculated for the first and second sorted difference signals, the third and fourth difference signals, or both. Metric $M_4$ is a logarithmic scaling of metric $M_3$, which may be indicative of the combined slope and correlation of the value pairs generated from the two segments.

In some embodiments, metric $M_5$ may be calculated for the first and second sorted difference signals, the third and fourth difference signals, or both. Metric $M_5$ is indicative of the length of a particular paired sorted difference signal generated. For example, value pairs may be generated from corresponding values of the first and second, or third and fourth, sorted difference signals and in a graphical interpretation, metric $M_5$ represents the length of the resulting curve. In some embodiments, the processing equipment may compare metric $M_5$ to a threshold, or to the same metric generated for the other two segments, as a qualification test. For pairs of segments exhibiting good correlation, metric $M_5$ values for the first/second segments, and third/fourth segments, are expected to be similar. This is because, for good correlation, the four sorted difference signals are all expected to exhibit a similar shape.

In some embodiments, metric $M_6$ may be calculated for the first, second, third and fourth difference signals. Metric $M_6$ is a normalized comparison of slope of the value pairs of the first and second segments with the slope of the value pairs of the third and fourth segments. In some embodiments, the processing equipment may compare metric $M_6$ to a threshold as a qualification test. For pairs of segments exhibiting good correlation, the metric $M_6$ value is expected to be near zero because the slopes should have similar values near one.

In some embodiments, metric $M_7$ may be calculated for the first, second, third and fourth difference signals. Metric $M_7$ is a normalized comparison of curve length of the value pairs of the first and second segments with the curve length of the value pairs of the third and fourth segments. In some embodiments, the processing equipment may compare metric $M_7$ to a threshold as a qualification test. For pairs of segments exhibiting good correlation, the metric $M_7$ value is expected to be near zero because the curve lengths should be similar.

In some embodiments, metric $M_8$ may be calculated for the first and second sorted difference signals, the third and fourth difference signals, or both. Metric $M_8$ includes two values (e.g., averaged endpoint coordinates in a geometrical interpretation), indicative of the endpoint values of a set of value pairs generated from paired sorted difference signals. For example, value pairs may be generated from corresponding values of the first and second, or third and fourth, sorted difference signals and in a graphical interpretation, metric $M_8$ represents how well the endpoints of the sorted difference signals agree. In some embodiments, the processing equipment may compare the values of metric $M_8$ to a threshold, or to the same metric generated for the other two segments, as a qualification test. For pairs of segments exhibiting good correlation, metric $M_8$ values for the first/second segments, and third/fourth segments, are expected to be similar. This is because, for good correlation, the four sorted difference signals are all expected to exhibit a similar shape with similar endpoints. If any of the segments included large amounts of noise, for example, the corresponding sorted difference signal may have more extreme endpoints due to the noise. In a further example, if the endpoints of the sorted difference signals in a pair to not agree with the other pair, the calculated correlation lag value may be incorrect (e.g., a shown by paired sorted difference signals 11014 and 11016 of FIG. 110.

The illustrative metrics shown in Eqs. 60-67 and described above are provided as examples, and any suitable metrics, or combinations thereof, may be used to analyze two or more segments.

Step 10834 may include processing equipment qualifying or disqualifying the correlation lag value of step 10804, based on the first metrics of step 10830, the second metrics of step 10832, or both. In some embodiments, the processing equipment may compare a metric value to a threshold to determine whether to qualify or disqualify the correlation lag value. In some embodiments, the processing equipment may compare metric values to one another to determine whether to qualify or disqualify the correlation lag value. For example, the processing equipment may determine a percent difference between metric values calculated for the first and second sorted differences signals, and the third and fourth sorted difference signals.

Figure 111:
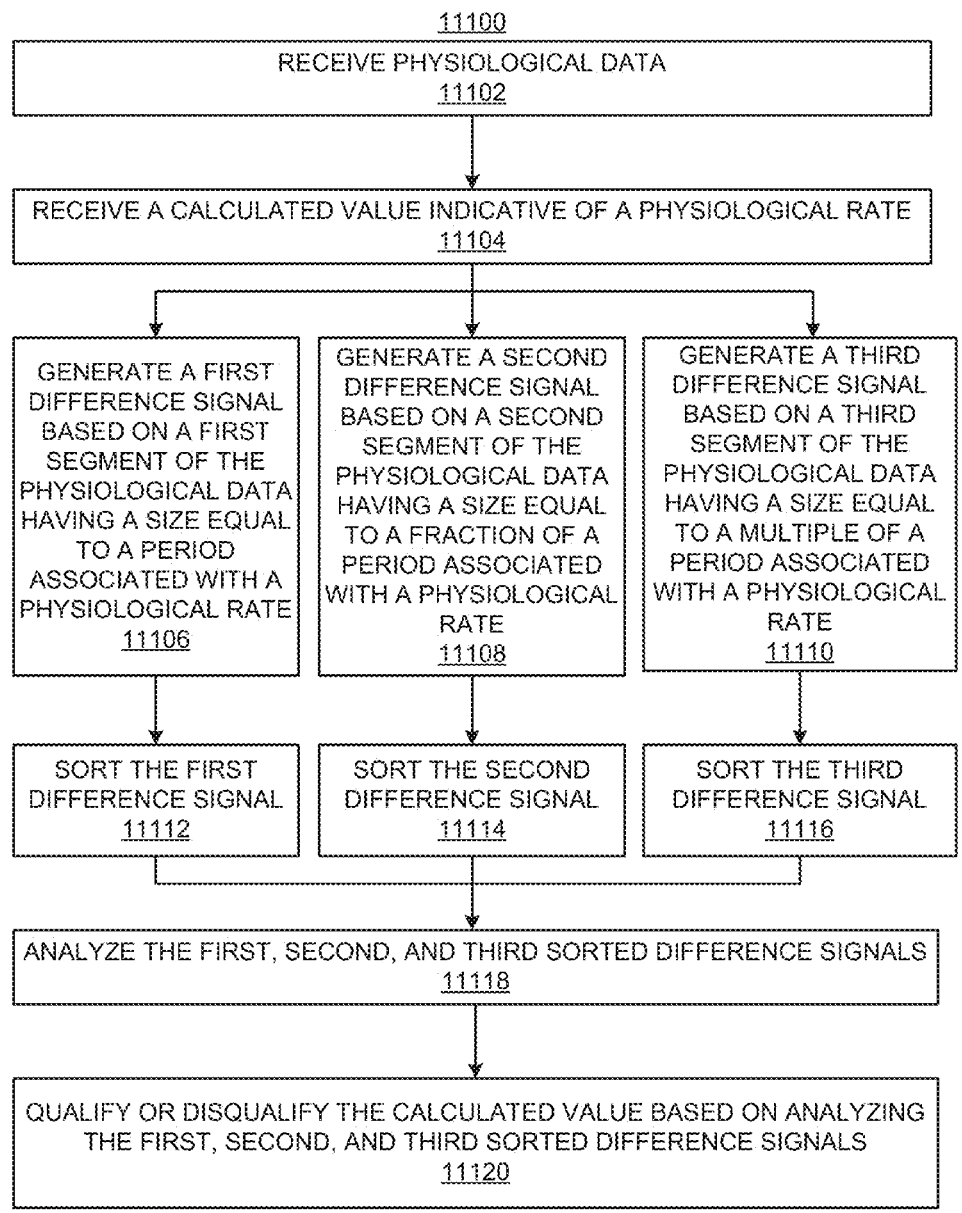
FIG. 111 is a flow diagram of illustrative steps for qualifying or disqualifying a value that may be indicative of a physiological rate based on analyzing harmonic sorted difference signals, in accordance with some embodiments of the present disclosure.
Figure 112:
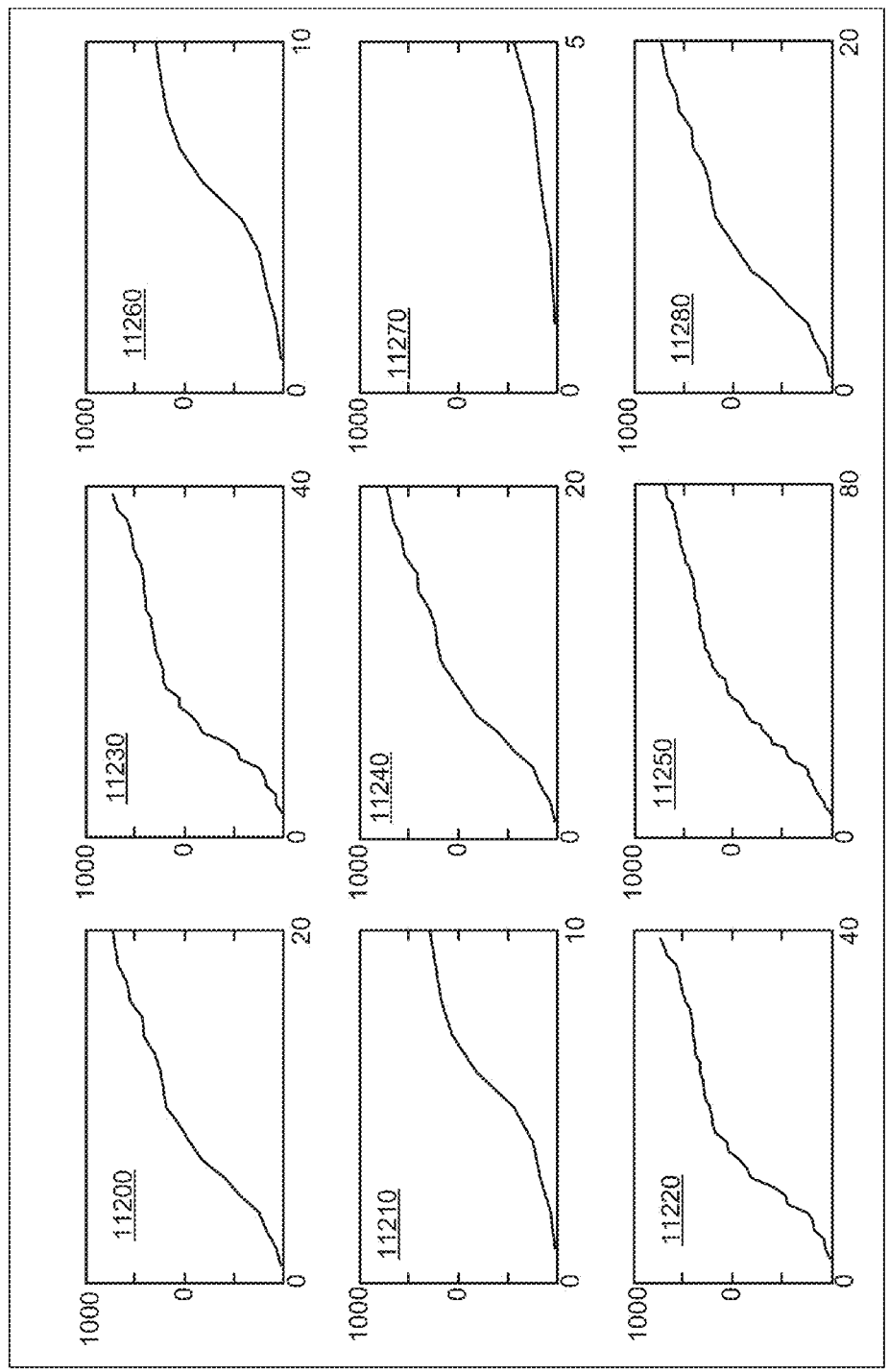
FIG. 112 is a panel of illustrative plots showing sorted difference signals for a lag, half lag, and double lag segment of physiological data, in accordance with some embodiments of the present disclosure.
Figure 113:
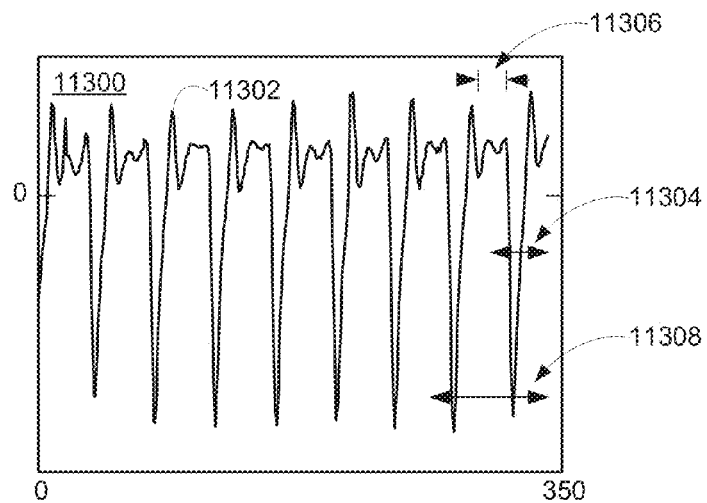
FIG. 113 is a panel of illustrative plots showing physiological data and three selected segments, in accordance with some embodiments of the present disclosure.
Figure 114:
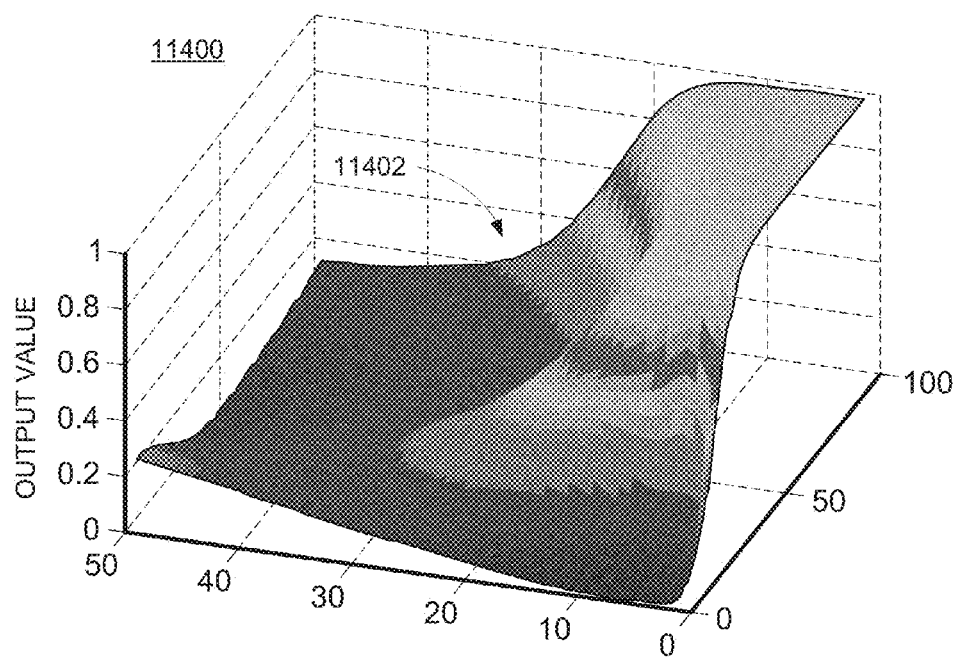
FIG. 114 is an illustrative plot showing a contour plot representation of a look-up table for qualifying or disqualifying a correlation lag value based on analyzing harmonic sorted difference signals, in accordance with some embodiments of the present disclosure.

FIG. 111 is a flow diagram 11100 of illustrative steps for qualifying or disqualifying a value that may be indicative of a physiological rate based on analyzing harmonic sorted difference signals, in accordance with some embodiments of the present disclosure. The illustrative steps of flow diagram 11100 may be referred to as a "Harmonic Rejection Test." FIGS. 112-114 are discussed in the context of flow diagram 11100.

Step 11102 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 11102 may include recalling data from the memory for further processing.

Step 11104 may include the processing equipment receiving a calculated value indicative of a physiological rate of the subject. For example, the calculated value may be based on a correlation lag value (e.g., a period associated with a physiological rate), a rate corresponding to the correlation lag value, or any other calculated value indicative of a physiological rate of the subject. In some embodiments, step 11104 may include recalling the calculated value from memory for further processing.

Steps 11106, 11116, 11108, and 11110 may include the processing equipment generating a first difference signal based on the first segment of physiological data having a size equal to the correlation lag value, a second difference signal based on the second segment of physiological data having a size equal to a fraction of the correlation lag value, and a third difference signal based on the third segment of physiological data having a size equal to an integer multiple of the correlation lag value, respectively. In some embodiments, the processing equipment may perform a subtraction between values of adjacent samples of a segment to generate the respective difference signal. In some embodiments, the processing equipment may calculate differences by calculating a first derivative of the respective segment. For example, the processing equipment may compute forward differences, backward differences, or central differences between each pair of adjacent points to generate a difference signal. In a further example, the processing equipment may compute a numerical derivative at each point in the segment, generating a difference signal. Any suitable difference technique may be used by the processing equipment to generate the difference signals. In some embodiments, the fraction of the period of step 11108 may be one half, and the integer multiple of step 11110 may be two.

Steps 11112, 11114, and 11116 may include the processing equipment sorting the difference values of each difference signal of steps 11106, 11108, and 11110, respectively. The processing equipment may sort the values in ascending or descending order, either of which causes the negative and positive values to be separated. Referencing sorted values in ascending order, the most negative values come first followed by less negative values, positive values, and finally larger positive values. The output of steps 11112, 11114, and 11116 may be a first sorted difference signal, a second sorted difference signal, and a third sorted difference signal, respectively.

To illustrate aspects of steps 11102, 11106, 11116, 11108, 11110, 11112, 11114, and 11116, FIG. 113 is a panel of illustrative plots showing physiological data and three selected segments, in accordance with some embodiments of the present disclosure. In some embodiments, the processing equipment may select the first, second and third segments from physiological data 11302 as shown in plot 11300. For example, first segment 11304 may be selected as the most recent data having a size equal to a calculated correlation lag value (e.g., indicative of a period associated with a physiological rate). In a further example, third segment 11308 may be selected as the most recent data having a size equal to twice a calculated correlation lag value (e.g., indicative of twice a period associated with a physiological rate). Selection of the second segment 11306 may include determining, within third segment 11308, the segment having a size equal to one half of a calculated correlation lag value (e.g., indicative of half a period associated with a physiological rate) having particular properties. For example, the segment of size equal to one half of a calculated correlation lag value having a minimum standard deviation may correspond to a relatively flat portion of physiological data (e.g., not substantially including the most extreme difference values), increasing the probability that the second segment differs from the first segment in shape. Plot 11310 shows a sorted difference signal corresponding to first segment 11304. Plot 11320 shows a sorted difference signal corresponding to second segment 11306. Plot 11330 shows a sorted difference signal corresponding to third segment 11308.

Step 11118 may include the processing equipment analyzing the first sorted difference signal, the second sorted difference signal, and the third sorted difference signal to determine one or more first metrics. In some embodiments, the analysis may include determining and comparing shape metrics for the sorted difference signals. Shape metrics may include a best fit slope, end points of a sorted difference signal, length of a sorted difference signal, any other suitable shape or geometrical metric, or any combination thereof. In some embodiments, the processing equipment may perform a KS test, comparing the sorted difference signal to a predetermined function. In some embodiments, the analysis may include determining a standard error between any two sorted difference signals of the three sorted difference signals. For example, FIG. 112 is a panel of illustrative plots showing sorted difference signals for a lag, half lag, and double lag segment of physiological data, in accordance with some embodiments of the present disclosure. Plots 11200, 11210, and 11220 show three sorted difference signals, corresponding to one lag, one half lag, and double lag segments (e.g., where the lag is a calculated value), respectively, for which the lag is indicative of a period of a physiological rate. Plots 11230, 11240, and 11250 show three sorted difference signals, corresponding to one lag, one half lag, and double lag segments (e.g., where the lag is a calculated value), respectively, for which the lag is indicative of double a period of a physiological rate. Plots 11260, 11270, and 11280 show three sorted difference signals, corresponding to one lag, one half lag, and double lag segments (e.g., where the lag is a calculated value), respectively, for which the lag is indicative of one half of a period of a physiological rate. Accordingly, the processing equipment may distinguish between conditions when a calculated lag value is a harmonic of the lag value associated with a physiological rate. For example, when the correct lag value is calculated, the lag and double lag sorted difference signals are similar in shape, while the half lag sorted difference signal has a different profile because it includes only a portion of a period of physiological data. In a further example, when double the correct lag value is calculated, the lag, double lag, and half lag sorted difference signals are all similar in shape, because all include at least one full period of physiological data. In a further example, when one half of the correct lag value is calculated, the lag, double lag, and half lag sorted difference signals are all different in shape, because they include a half period, a full period, and a quarter period, respectively of physiological data.

Step 11120 may include processing equipment qualifying or disqualifying the correlation lag value of step 11104, based on the analysis of step 11118. For example, if the processing equipment determines that the first and second sorted difference signals are not similar, the processing equipment may qualify the correlation lag value, while if the first and second sorted difference signals are determined to be similar, the processing equipment may disqualify the correlation lag value. In a further example, if the processing equipment determines that the first and third sorted difference signals are not similar, the processing equipment may disqualify the correlation lag value, while if the first and third sorted difference signals are determined to be similar, the processing equipment may qualify the correlation lag value.

FIG. 114 is an illustrative plot 11400 showing a contour 11402 representing a look-up table for qualifying or disqualifying a correlation lag value based on analyzing harmonic sorted difference signals, in accordance with some embodiments of the present disclosure. Contour 11402 shows table output values for input values of a half-lag KS Test metric and the log of a double-lag KS Test metric. The KS Test may include comparing the respective sorted difference signal to a reference distribution, and determining a KS metric value. The KS metric indicates how well the sorted difference signal and reference distribution match, assuming a value of one for a perfect match and a relatively lower value if the values are less well matched. In some embodiments, the look-up table represented by contour 11402 may be generated using a neural network classifier technique. For example, the look-up table may be generated prior to physiological monitoring (e.g., generated "offline"), based on a reference set of physiological data, and may then be used in lieu of a neural network calculation during physiological monitoring. While contour 11402 is indicative of data calculated using a KS Test, any suitable test may be used to generate a look-up table for qualifying or disqualifying a correlation lag value as part of the Harmonic Rejection Test.

Figure 115:
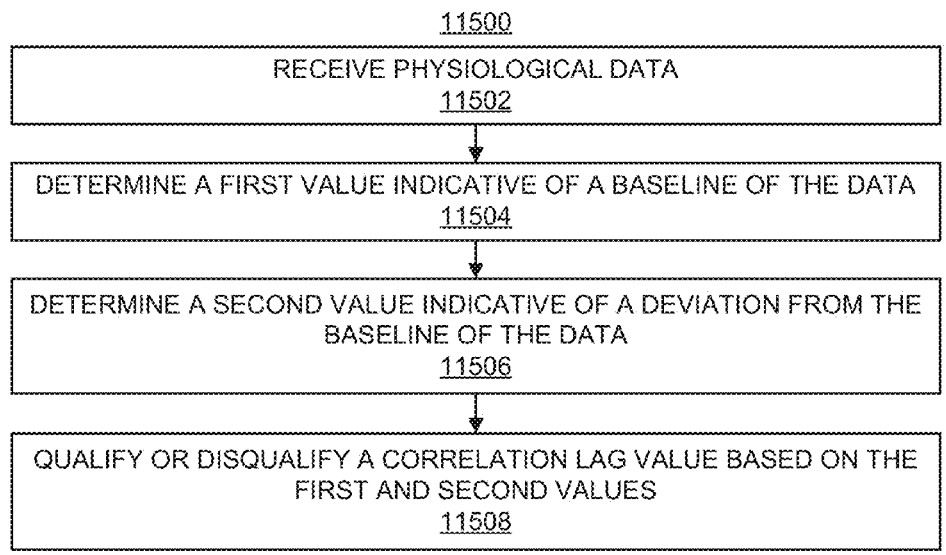
FIG. 115 is a flow diagram of illustrative steps for qualifying or disqualifying a value that may be indicative of a physiological rate based on a standard deviation ratio (SDR) metric, in accordance with some embodiments of the present disclosure.

FIG. 115 is a flow diagram 11500 of illustrative steps for qualifying or disqualifying a value that may be indicative of a physiological rate based on a standard deviation ratio (SDR) metric, in accordance with some embodiments of the present disclosure. The illustrative steps of flow diagram 11500 may be referred to as a "SDR Test." FIG. 117, which illustrates a SDR signal, is discussed in the context of flow diagram 11500. The SDR test determines a standard deviation, or a metric indicative of standard deviation, and normalized the deviation to a baseline value of the physiological data to generate an SDR metric. The SDR metric may be compared to an expected range that corresponds to physiological activity, and accordingly if the SDR metric is outside of that range the correlation lag value may be disqualified.

Step 11502 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 11502 may include recalling data from the memory for further processing.

Step 11504 may include the processing equipment determining a first value indicative of a baseline of the physiological data. The first value may include a minimum value, mean value, median value, any other suitable value indicative of a baseline, or any combination thereof. In some embodiments, the processing equipment may determine a trend-line or other varying baseline, defined for each sample point of the physiological data. For example, in some embodiments, the baseline may be a best fit line or a best fit parabola, having a defined value corresponding to each sample point. In some embodiments, the processing equipment may subtract the determined baseline from the physiological data, resulting in modified data having a baseline value of zero.

Step 11506 may include the processing equipment determining a second value indicative of a deviation from the baseline of the physiological data determined at step 11504. The second value may include a standard deviation, an RMS value, a maximum value minus minimum value calculation, any other suitable value indicative of deviation from a baseline, or any combination thereof. In some embodiments, the processing equipment may perform signal conditioning on the physiological data prior to determining the second value. For example, the processing equipment may determine the first value of the physiological data, de-trend the physiological data, and then determine the second value based on the de-trended physiological data.

Step 11508 may include processing equipment qualifying or disqualifying a correlation lag value, based on the first value and the second value. In some embodiments, the processing equipment may determine an SDR metric using an expression such as Eq. 68:

$$SDR = \frac{S}{M} \tag{68}$$

where S is a standard deviation value determined at step 11506, and M is a baseline value determined at step 11504, equal to the median value of the physiological data, for example. Changes in the SDR value over time may, for example, indicate a change in the noise level, a change in a physiological rate of the subject, or both. In some embodiments, the processing equipment may determine an SDR metric, using Eq. 68 or some other formulation (e.g., a scaled version), and compare the SDR metric with a threshold to determine whether to qualify or disqualify the correlation lag value.

Figure 116:
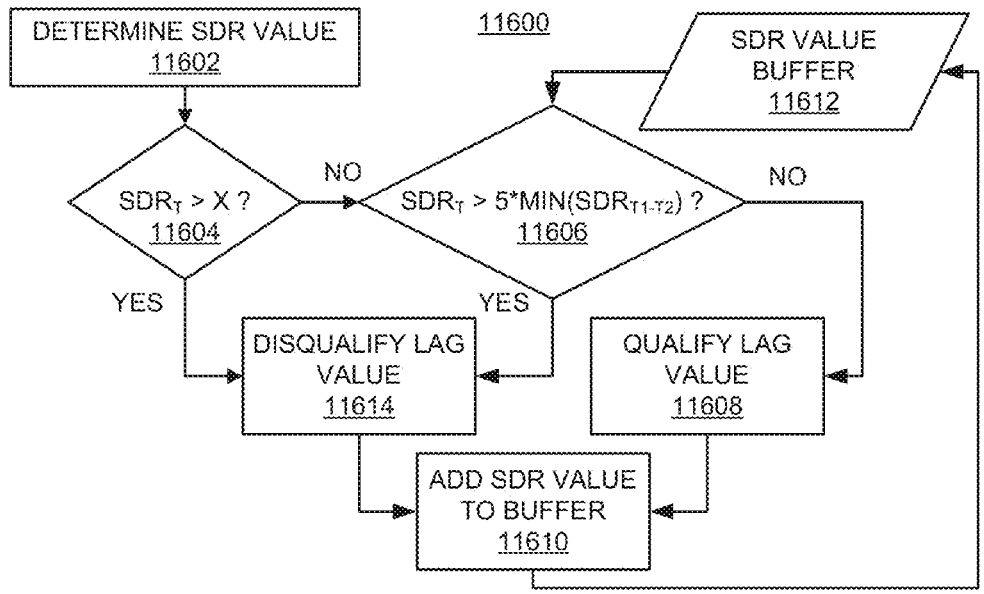
FIG. 116 is a flow diagram of illustrative steps for implementing a standard deviation ratio (SDR) technique, in accordance with some embodiments of the present disclosure.

In an illustrative example, FIG. 116 is a flow diagram of illustrative steps for implementing a standard deviation ratio (SDR) technique, in accordance with some embodiments of the present disclosure. Step 11602 may include determining an SDR metric value at current time T based on physiological data. Step 11604 may include comparing the SDR metric value to a threshold X, which may be any suitable value (e.g., X may be 0.28 in some embodiments). If the SDR metric value exceeds the threshold, the processing equipment may disqualify the currently calculated correlation lag value at step 11614. If the SDR metric value does not exceed the threshold, the processing equipment may then compare the SDR metric value with the minimum SDR metric value of a set of previous SDR values at step 11606. As illustrated, the SDR metric is compared with five times the minimum SDR metric value in a time interval from $T_1$ to $T_2$, which may be, for example, the last 30 seconds worth of calculated SDR values stored in a buffer 11612. This threshold is exemplary. The threshold may be any suitable fixed or variable value. Typically, the SDR metric is not expected to increase significantly over relatively short time scales (e.g., 30 seconds). The presence of noise typically increases the SDR metric value. Accordingly, by comparing the current SDR metric with the minimum SDR metric value from the history of values, the processing equipment may determine if the current physiological data is relatively noisy. If the SDR metric value exceeds the threshold of step 11606, the processing equipment may disqualify the currently calculated correlation lag value at step 11614. If the SDR metric value does not exceed the threshold of step 11606, the processing equipment may qualify the SDR metric value at step 11608. Whether qualified or disqualified, the current SDR metric value is added to buffer 11612 at step 11610, and the processing equipment may return to step 11602.

Figure 117:
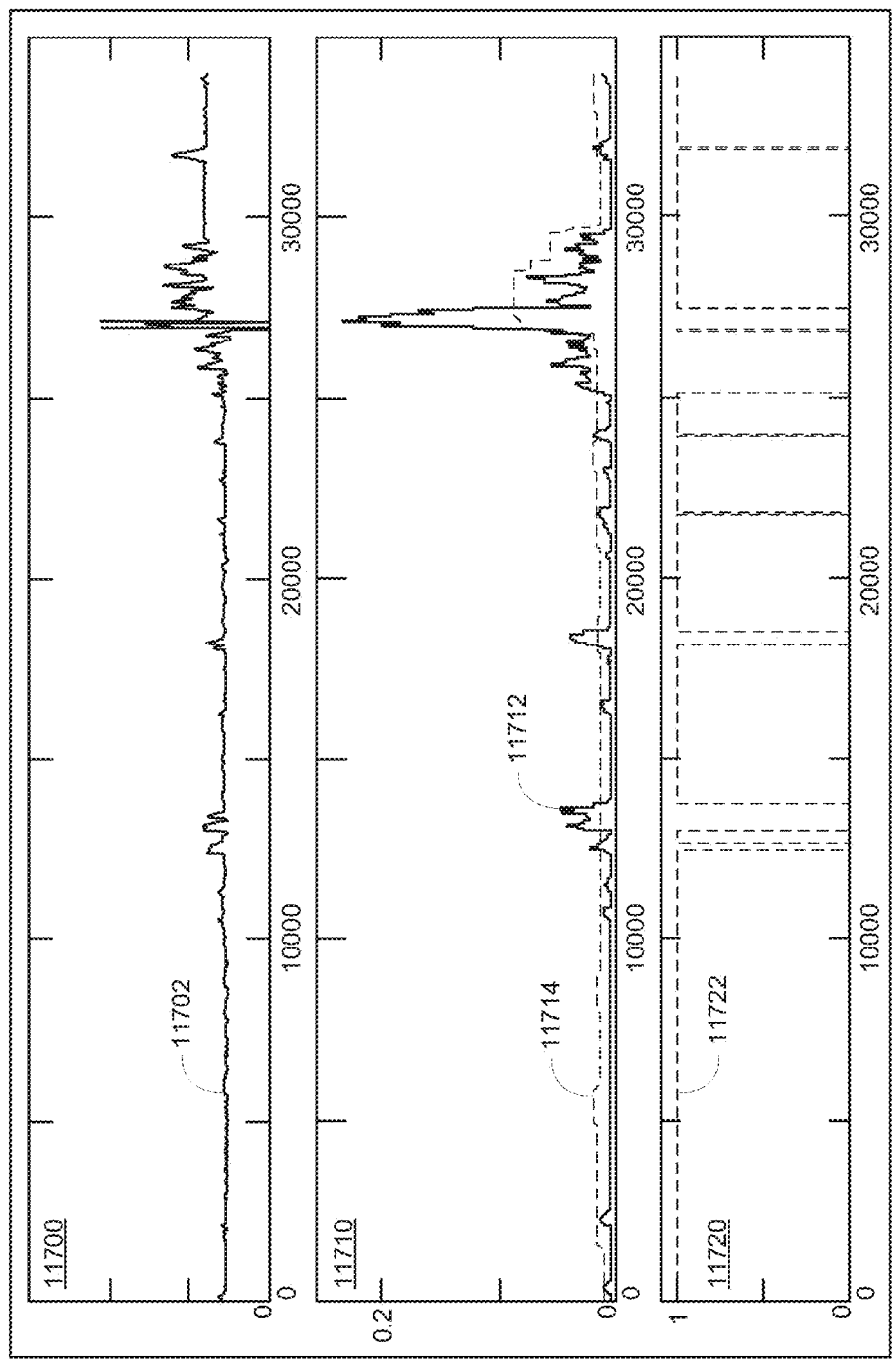
FIG. 117 is a panel of illustrative plots showing a physiological signal, an SDR signal, an SDR threshold, and a test outcome signal, in accordance with some embodiments of the present disclosure.

FIG. 117 is a panel of illustrative plots showing a physiological signal, an SDR signal, an SDR threshold, and a test outcome signal, in accordance with some embodiments of the present disclosure. The abscissa of plots 11700, 11710, and 11720 are in units of sample number, while the ordinates are shown in arbitrary units. Plot 11700 shows IR intensity signal 11702. Plot 11710 shows a calculated SDR signal 11712, and a threshold signal 11714 calculated as five times the minimum SDR value of the previous 30 seconds of IR intensity signal 11702. Plot 11720 shows SDR test outcome signal 11722 which assumes a value of one when SDR signal 11712 does not exceed threshold signal 11714, and a value of zero when SDR signal 11712 exceeds threshold signal 11714. Accordingly, the presence of significant noise (e.g., illustrated by IR intensity signal 11702 between abscissa values of 25000 and 30000 in plot 11700) may cause the SDR Test to fail.

Figure 118:
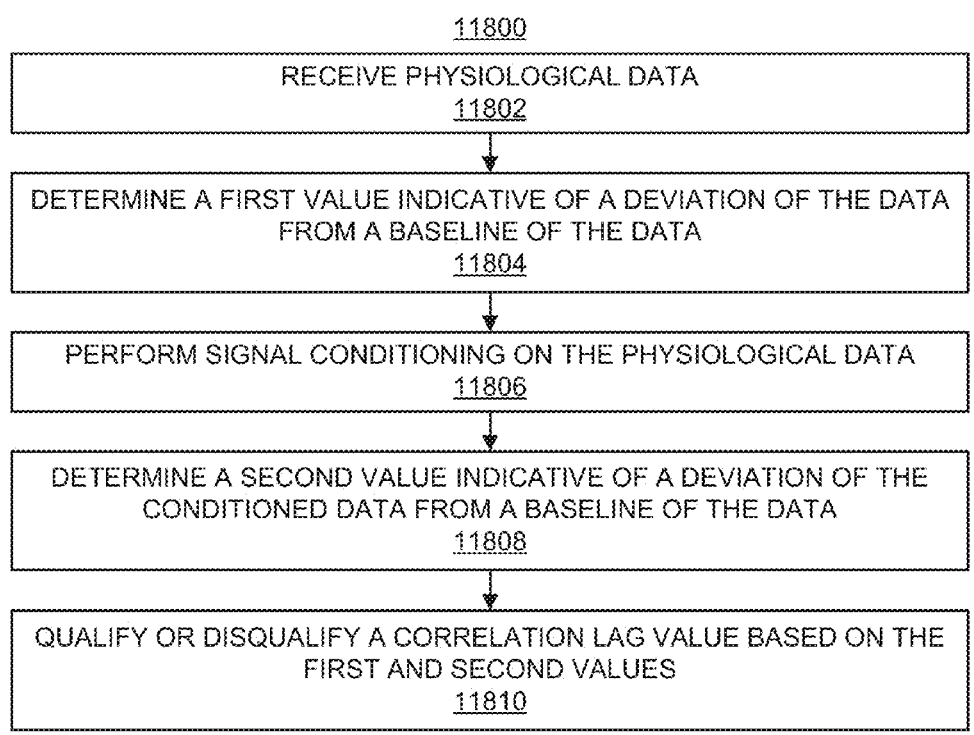
FIG. 118 is a flow diagram of illustrative steps for qualifying or disqualifying a value that may be indicative of a physiological rate based on a standard deviation ratio (SDR) metric, in accordance with some embodiments of the present disclosure.

FIG. 118 is a flow diagram of illustrative steps for qualifying or disqualifying a value that may be indicative of a physiological rate based on a different standard deviation ratio ($SDR_{II}$) metric, in accordance with some embodiments of the present disclosure. The illustrative steps of flow diagram 11800 may be referred to as a "SDR II Test." In some instances, physiological data may include multiple components, which may include the desired physiological component and an undesired component. The $SDR_{II}$ metric may be indicative of signal energy before and after signal conditioning (e.g., a ratio of standard deviation values before and after conditioning), which may be indicative of the amount of signal content removed during conditioning. For example, if the $SDR_{II}$ metric indicates that a large percentage of signal energy was removed during signal conditioning, then the processing equipment may determine the remaining signal energy is likely noise. If the level of noise in the physiological data is relatively low, the $SDR_{II}$ metric is expected to be within a particular range. In some embodiments, the $SDR_{II}$ metric may be compared to a threshold. For example, if the metric exceeds the threshold, the processing equipment may disqualify the correlation lag value, and if the metric does not exceed the threshold, the processing equipment may qualify the correlation lag value.

Step 11802 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 11802 may include recalling data from the memory for further processing.

Step 11804 may include the processing equipment determining a first value indicative of a deviation from a baseline of the physiological data determined at step 11802. The first value may include a standard deviation, an RMS value, any other suitable value indicative of deviation from a baseline, or any combination thereof.

Step 11806 may include the processing equipment performing signal conditioning on the physiological data of step 11802. Any suitable Signal Conditioning Technique may be applied to the physiological data such as, for example, application of a bandpass filter, de-trending, or other techniques. The output of step 11806 may be conditioned data, which may be stored in a buffer or other memory allocation.

Step 11808 may include the processing equipment determining a second value indicative of a deviation from a baseline of the conditioned data of step 11806. The second value may include a standard deviation, an RMS value, any other suitable value indicative of a deviation from a baseline in the conditioned data, or any combination thereof.

Step 11810 may include processing equipment qualifying or disqualifying a correlation lag value, based on the first value and the second value. In some embodiments, the processing equipment may determine an $SDR_{II}$ metric using an expression such as Eq. 69:

$$SDR_{II} = \frac{S_1}{S_2} \qquad (69)$$

where $S_1$ is a standard deviation value determined at step 11804, and $S_2$ is a standard deviation value determined at step 11808, for example. Changes in the $SDR_{II}$ value over time may, for example, indicate a change in the noise level, a change in a physiological rate of the subject, or both. In some embodiments, the processing equipment may determine an $SDR_{II}$ metric, using Eq. 69 or some other formulation, and compare the $SDR_{II}$ metric with a threshold to determine whether to qualify or disqualify the correlation lag value.

Figure 119:
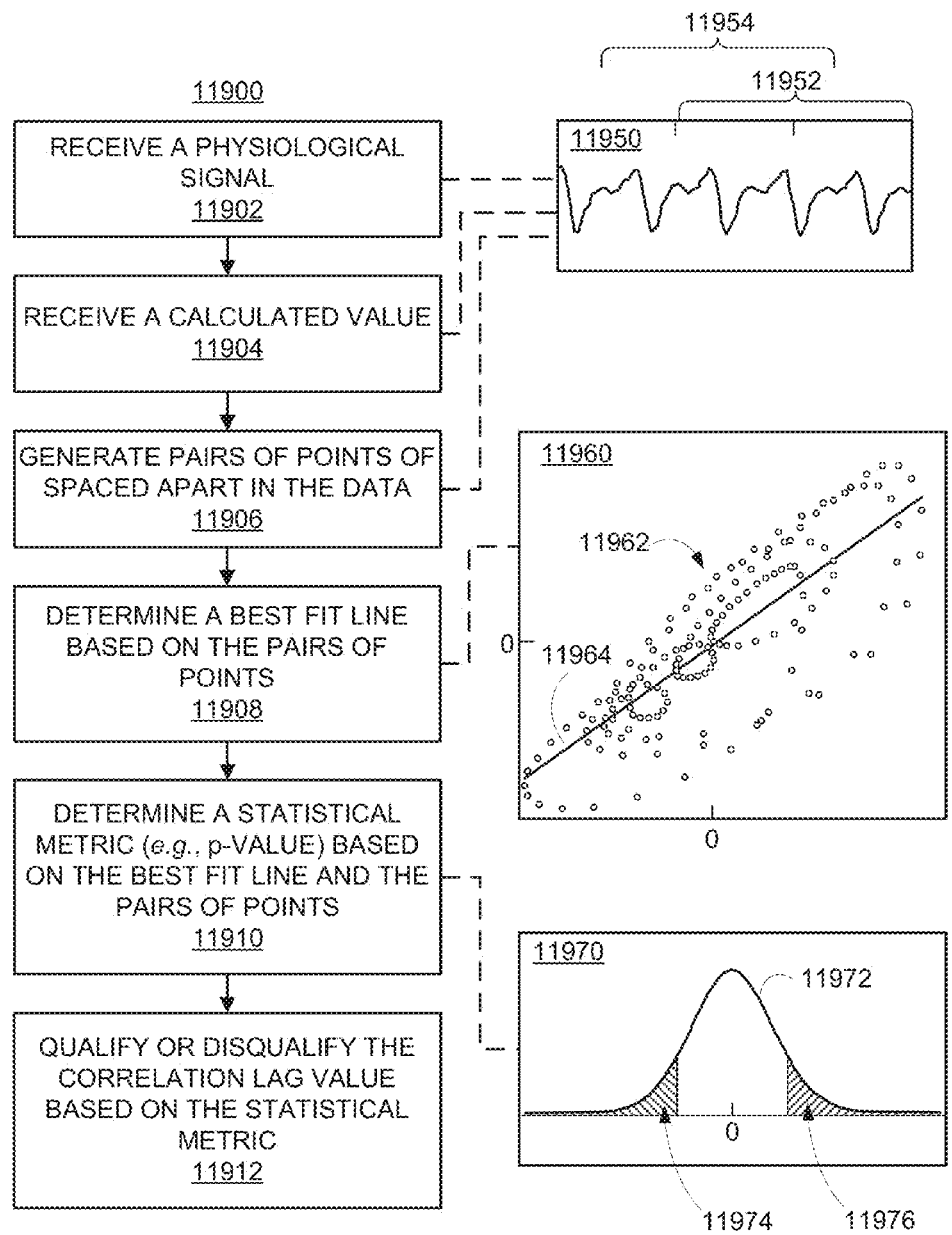

FIG. 119 is a flow diagram 11900 of illustrative steps for qualifying or disqualifying a value that may be indicative of a physiological rate based on a statistical metric such as a p-value, in accordance with some embodiments of the present disclosure. The illustrative steps of flow diagram 11900 may be referred to as the "p-Value Test." The statistical metric may be indicative of the probability that a property of a set of value pairs would be obtained due to chance.

Step 11902 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 11902 may include recalling data from the memory for further processing.

Step 11904 may include the processing equipment receiving a calculated value indicative of a potential physiological rate of the subject. For example, the calculated value may be based on a correlation lag value, a rate corresponding to the correlation lag value, or any other calculated value indicative of a physiological rate of the subject. In some embodiments, step 11904 may include recalling the calculated value from memory for further processing.

Step 11906 may include the processing equipment generating pairs of sample points of the physiological data, spaced apart in the physiological data. The spacing may be based on the calculated value indicative of a physiological rate of the subject. For example, the calculated value may be based on a correlation lag value, a rate corresponding to the correlation lag value, or any other calculated value indicative of a physiological rate of the subject. In some embodiments, as illustrated by panel 11950, a first portion of physiological data 11952, including a particular number of sample points, may be point-wise paired with a second portion of the physiological data 11954, including the same number of samples points as the first portion albeit shifted in time relative to the first portion. In some embodiments, generating the pairs of points may include specifying indices of the points in the physiological data for reference.

Step 11908 may include the processing equipment determining a best fit line based on the pairs of points of step 11906. In some embodiments, the processing equipment may apply a linear regression to the pairs of points. In some embodiments, the processing equipment may apply a constrained best line fit to the pairs of points such as, for example, constraining the best fit line to include the point (0,0). Panel 11960 graphically illustrates pairs of points 11962, and corresponding best fit line 11964. In some embodiments, the output of step 11908 may be a slope value (e.g., corresponding to a line including point 0,0), or an intercept and slope value (e.g., corresponding to a y=mx+b formulation).

Step 11910 may include the processing equipment determining a statistical metric based on the best fit line and the pairs of points. In some embodiments, the processing equipment may use an expression such as that shown in Eq. 70:

$$SE = \frac{\sqrt{\frac{1}{N-2}\sum (y_i - \hat{y}_i)^2}}{\sqrt{\sum (x_i - \bar{x})^2}} \quad (70)$$

to determine a standard error value SE, where N is the number of pairs, $x_i$ are the first values of the pairs, $y_i$ are the second values of the pairs, $\hat{x}$ is the average of the first values, and $\hat{y}_i$ is the best fit line value corresponding to $x_i$. In some embodiments, the processing equipment may determine a t-statistic metric t based on the standard error SE and the best fit line using Eq. 71:

$$t = \frac{m}{SE} \quad (71)$$

where m is the slope of the best fit line of step 11908. The processing equipment may then access a look-up table of one-sided or two-sided probabilities that a t-statistic greater than or equal to the determined value would be obtained due to chance (e.g., the p-value). To illustrate, panel 11970 shows an illustrative probability distribution 11972, with regions 11974 and 11976 indicating the two-sided probabilities of more extreme t-statistic values. The degrees of freedom of the calculation may be calculated as N−1, and a standard look-up table of Student-t distribution probabilities may be used. In some embodiments, the processing equipment may calculate probabilities (e.g., p-values) based on t-statistics for a series of correlation lag values. For example, the processing equipment may calculate probabilities for the correlation lag value indicative of the physiological rate, and the three adjacent smaller lags values, and three adjacent larger lag values.

Step 11912 may include processing equipment qualifying or disqualifying the calculated value of step 11904, based on the determined statistical metric of step 11910. In some embodiments, the processing equipment may use an inequality as a qualifying or a disqualifying criterion. For example, the processing equipment may calculate probabilities for the correlation lag value indicative of the physiological rate, and the three adjacent smaller lags values, and three adjacent larger lag values. Further, the processing equipment may use an expression such as Eq. 72:

$$\sum_{-3}^{3} p(l+i) < 4*0.05 \quad (72)$$

where l is the correlation lag value indicative of a physiological rate, i is an index, and p(l+i) is the probability value determined based on Eq. 71 and the look-up table of p-values for the indexed correlation lag value l+i. If the inequality of Eq. 72 is true, the processing equipment may qualify the correlation lag value of step 11904, while if the inequality is false, the processing equipment may disqualify the correlation lag value of step 11904. In a further example, the processing equipment may determine a p-value for the correlation lag value of step 11904, and compare the p-value with a threshold. If the p-value exceeds the threshold, the processing equipment may disqualify the correlation lag value, and if the p-value does not exceed the threshold, the processing equipment may qualify the correlation lag value.

Figure 120:
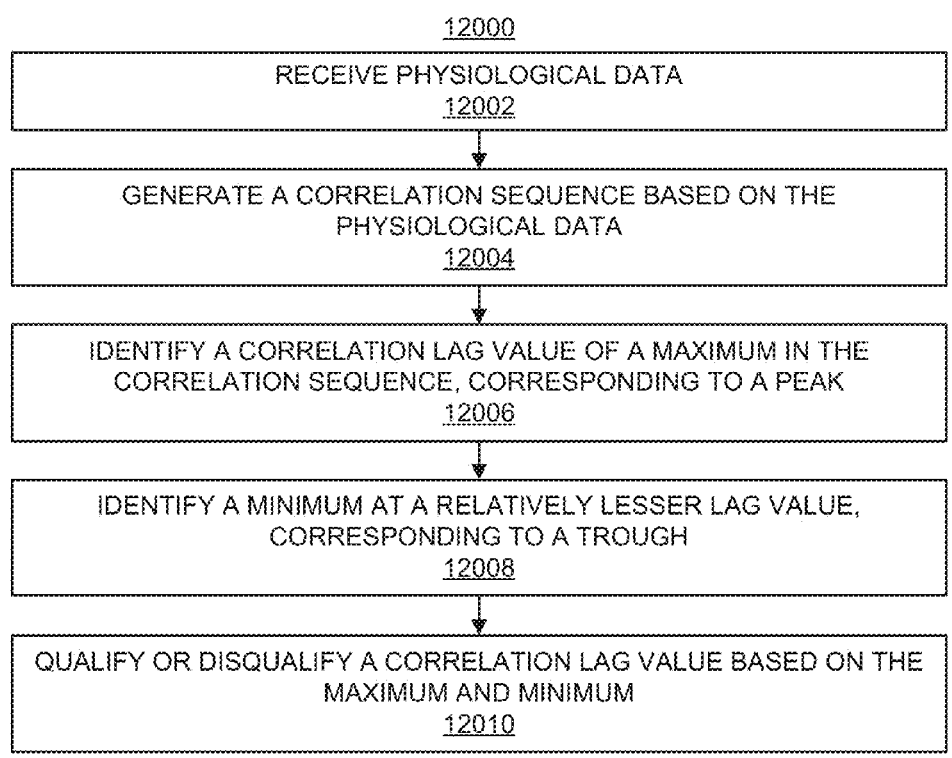

FIG. 120 is a flow diagram of illustrative steps for qualifying or disqualifying a value that may be indicative of a physiological rate based on a maximum and minimum of a correlation sequence, in accordance with some embodiments of the present disclosure. The illustrative steps of flow diagram 12000 may be referred to as a "Correlation Max-Min Test."

Step 12002 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 12002 may include recalling data from the memory for further processing.

Step 12004 may include processing equipment generating a correlation sequence based on the physiological data. In some embodiments, the processing equipment may generate the correlation sequence by multiplying corresponding values of two segments of the physiological data at a particular lag, for a sequence of lag values. Step 12004 may include the processing equipment normalizing the physiological data of step 12002. In some embodiments, the processing equipment may use any suitable signal conditioning technique (e.g., de-trending and/or normalization techniques, scaling, shifting, or any other suitable operation) to condition the physiological data before generating the correlation sequence.

Step 12006 may include processing equipment identifying a correlation lag value of a maximum in the correlation sequence, corresponding to a peak in the correlation sequence of step 12004. The identified correlation lag value may be identified using any of the illustrative techniques described in FIGS. 66, 67, 68, and 70. In some embodiments, step 12006 may include generating the threshold. The threshold may be generated using a predetermined value, a predetermined function, a value based on a previously calculated rate, a value based on the current operating Mode, a value based one or more metrics derived from the physiological data (e.g., detrending metrics, noise metrics), using any other suitable technique, or any combination thereof. The processing equipment may identify threshold crossings by comparing all or some of the correlation output to the threshold. The processing equipment may use any suitable peak finding techniques to identify the peak such as, for example, identifying a maximum, identifying an upstroke (i.e., positive slope) and downstroke (i.e., negative slope), applying a threshold, comparing one or more peaks to identify a particular peak (e.g., a largest peak, a peak occurring first in terms of lag), any other suitable peak finding technique, or any combination thereof. The processing equipment may identify the correlation lag value of the maximum value, lag values associated with the peak, or a combination thereof.

Step 12008 may include processing equipment identifying a relatively lesser lag value of a minimum in the correlation sequence, corresponding to a trough in the correlation sequence of step 12004. In some embodiments, the minimum corresponds to the nearest adjacent trough having a relatively lesser lag value than the peak. For example, referencing plot 6500 of FIG. 65, the processing equipment may identify the maximum associated with the peak located at a lag value of approximately 70 in units of sample point, and identify the minimum associated with the trough at a lag value of approximately 35 in units of sample point. In some embodiments, the processing equipment may only identify a lesser lag value at least a particular number of samples from the maximum value. For example, the processing equipment may only consider lesser lag values at least 10 samples before the lag value corresponding to the maximum. In a further example, the particular number of samples may be a function of a calculated physiological rate or a calculated correlation lag value (e.g., at larger calculated correlation lag values, the number of samples between the min and max may be larger).

Step 12010 may include processing equipment qualifying or disqualifying the correlation lag value of step 12006, based on the maximum and minimum of steps 12006 and 12008, respectively. In some embodiments, the processing equipment may determine a difference between the maximum correlation value of step 12006 and the minimum correlation value from step 12008 in order to determine whether to qualify the correlation lag value. For example, the processing equipment may determine the difference between a maximum correlation value and a minimum correlation value, and compare the difference to a threshold. If the difference is above the threshold, the processing equipment may qualify the correlation lag value associated with the maximum. If the normalized difference is below the threshold, the processing equipment may disqualify the correlation lag value associated with the maximum.

Figure 121:
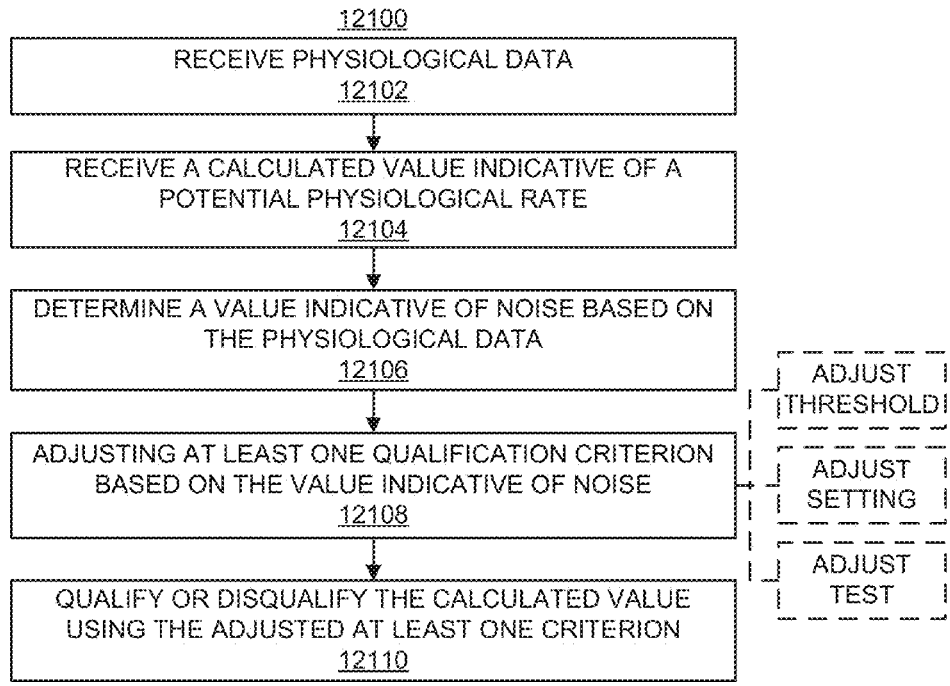

FIG. 121 is a flow diagram 12100 of illustrative steps for adjusting a qualification or disqualification criterion based on noise, in accordance with some embodiments of the present disclosure.

Step 12102 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 12102 may include recalling data from the memory for further processing.

Step 12104 may include the processing equipment receiving a calculated value indicative of a potential physiological rate of the subject. For example, the calculated value may be based on a correlation lag value, a rate corresponding to the correlation lag value, or any other calculated value indicative of a physiological rate of the subject. In some embodiments, step 12104 may include recalling the calculated value from memory for further processing.

Step 12106 may include processing equipment determining a value indicative of noise (e.g., a noise metric) using any of the techniques disclosed herein, or any combination thereof. For example, the processing equipment may determine a metric value using any of the techniques discussed in the context of FIGS. 11-41. In some embodiments, the processing equipment may determine multiple noise metric values, and then select a single value, generate a combined value using a suitable technique (e.g., an average, a weighted average, a product, or some other combination), determine a noise metric based on a lookup table using one or more noise metrics as an input, perform any other suitable calculation of a noise metric, or any combination thereof.

Step 12108 may include processing equipment adjusting at least one qualification criterion based on the value indicative of noise of step 12106. Adjusting the at least one criterion may include, for example, adjusting a threshold used in a qualification test, adjusting a metric calculated in a qualification test, adjusting a setting of a qualification test, adjusting which qualification test or combination of tests are used, or any combination thereof. For example, in some embodiments, the processing equipment may loosen one or more thresholds to lessen the probability of disqualification under relatively noisy conditions. Further, in some embodiments, the processing equipment may tighten one or more thresholds to increase the probability of disqualification under relatively less noisy conditions. Accordingly, when physiological data exhibits less noise, the processing equipment may apply more strict qualification tests, or settings of tests, to increase the confidence in qualified values.

Step 12110 may include processing equipment qualifying or disqualifying the calculated value of step 12104, based on the adjusted qualification criterion of step 12108. In some embodiments, the processing equipment may apply the adjusted qualification criterion to the physiological data to determine whether to qualify or disqualify the calculated value.

Figure 122:
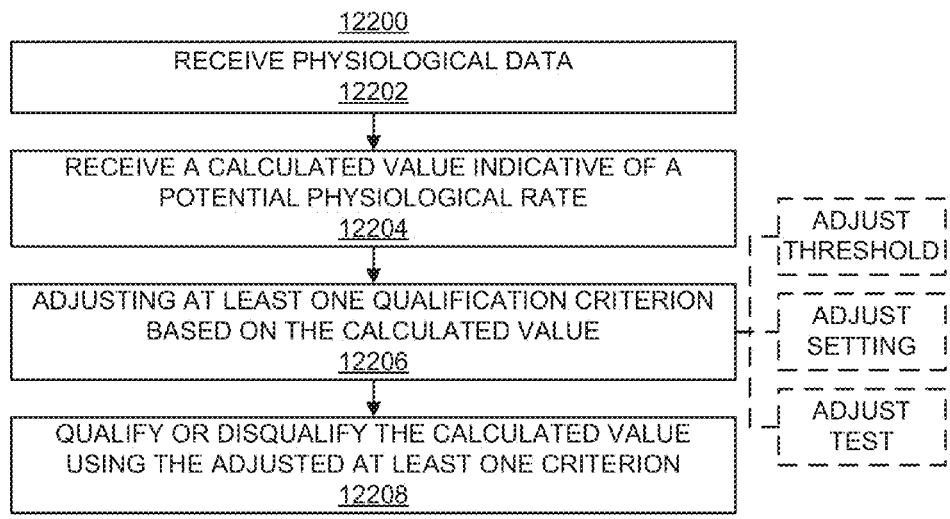

FIG. 122 is a flow diagram 12200 of illustrative steps for adjusting a qualification or disqualification criterion based on a value indicative of a physiological rate, in accordance with some embodiments of the present disclosure.

Step 12202 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 12202 may include recalling data from the memory for further processing.

Step 12204 may include the processing equipment receiving a calculated value indicative of a potential physiological rate of the subject. For example, the calculated value may be based on a correlation lag value, a rate corresponding to the correlation lag value, or any other calculated value indicative of a physiological rate of the subject. In some embodiments, step 12204 may include recalling the calculated value from memory for further processing.

Step 12206 may include processing equipment adjusting at least one qualification criterion based on the value indicative of a physiological rate of step 12206. Adjusting the at least one criterion may include, for example, adjusting a threshold used in a qualification test, adjusting a metric calculated in a qualification test, adjusting a setting of a qualification test, adjusting which qualification test or combination of tests are used, or any combination thereof. In some embodiments, for example, the processing equipment may determine not to perform qualification tests that are directed to identifying a lock on a double rate when the calculated rate is lower than a predetermined value. For example, at calculated rates of 50 BPM or less, the processing equipment may refrain from perform qualifications tests that indicate a double rate lock condition. In a further example, when the rate is relatively low (e.g., 40 BPM or less), the processing equipment may perform qualification tests that indicate whether the rate algorithm is tracking low frequency noise.

Step 12208 may include processing equipment qualifying or disqualifying the calculated value of step 12204, based on the adjusted qualification criterion of step 12208. In some embodiments, the processing equipment may apply the adjusted qualification criterion to the physiological data to determine whether to qualify or disqualify the calculated value.

Figure 123A:
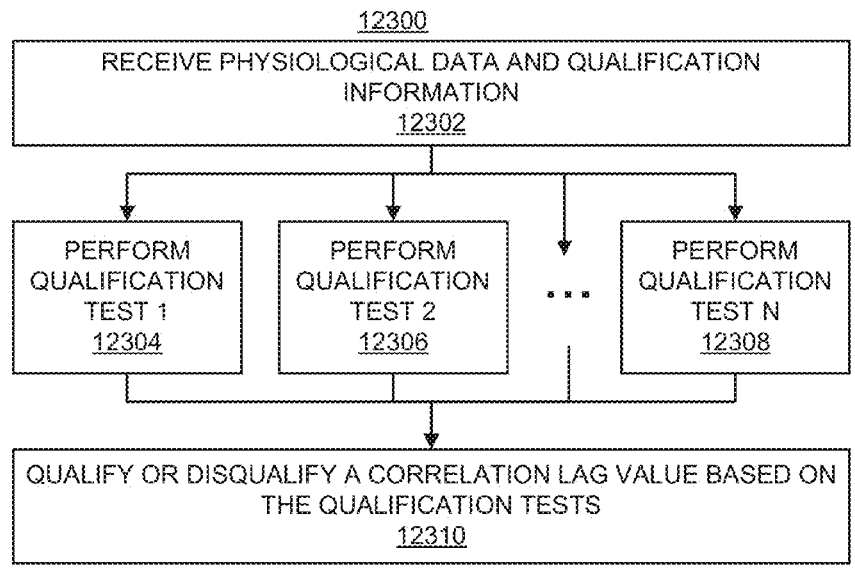

FIG. 123A is a flow diagram 12300 of illustrative steps for combining qualification tests, in accordance with some embodiments of the present disclosure.

Step 12302 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 12302 may include recalling data from the memory for further processing. Step 12302 may include processing equipment receiving qualification information such as a calculated correlation lag value, a calculated rate, any suitable algorithm settings used for qualification, any other suitable information, or any combination thereof.

Steps 12304, 12306, and 12308 may include processing equipment performing a first qualification test, a second qualification test, through an $N^{th}$ qualification test, respectively to qualify or disqualify a calculated correlation lag value based on the physiological data and the qualification information. Any suitable number of qualification tests may be performed, for example, using any of the illustrative Qualification Techniques discussed in the context of FIGS. 86-122. The qualification tests may be performed in parallel, in series, or a combination thereof.

Step 12310 may include processing equipment qualifying or disqualifying the correlation lag value based on the qualification tests of steps 12304, 12306, and 12308. In some embodiments, the processing equipment may average, sum, or otherwise combine one or more qualification metrics from the qualification tests. In some embodiments, the processing equipment may qualify the correlation lag value if all of the qualification tests are passed. In some embodiments, the processing equipment may qualify the correlation lag value if at least a particular percentage of the qualification tests are passed. For example, referencing flow diagram 12300, the processing equipment may sequentially apply qualification tests and disqualify the correlation lag value when a qualification test fails. In a further example, the processing equipment may pass the results of the qualification tests to a neural network calculation, to determine one or more output values (e.g., qualification pass or fail), as described below in the context of FIG. 123B.

Figure 123B:
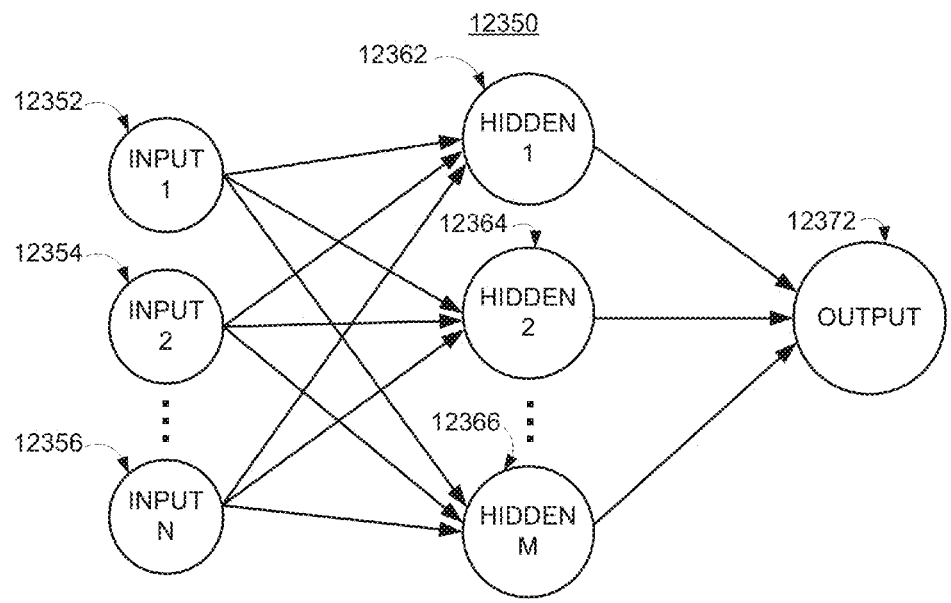
Figure 124:
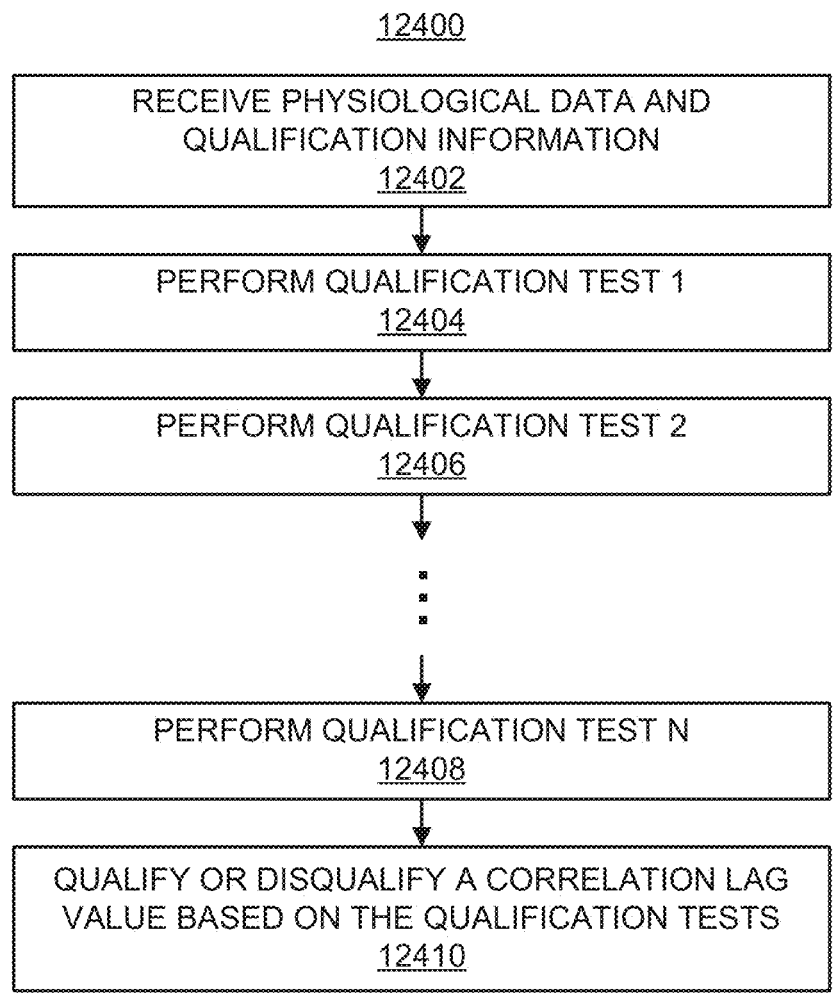

FIG. 123B is a block diagram of an illustrative neural network 12350 that may receive a combination of inputs, in accordance with some embodiments of the present disclosure. Neural network 12350 is an interconnected group of nodes graphically representing a calculation technique. In some embodiments, neural network 12350 may be trained using a set of training data to determine coefficients or other parameters, and then apply the coefficient or other parameters to current physiological data. In some embodiments, neural network 12350 may be adaptive, where the coefficients or other parameters are updated (e.g., neural network learning) as new physiological data is analyzed. For example, in some circumstances an electrocardiographic (EKG) probe may be used to provide accurate rate information of a subject, and the processing equipment may further train an adaptive neural network using recent physiological data and the EKG probe information. The interconnections between the nodes represent information flows. For example, the processing equipment may perform one or more qualification tests, using the same physiological data, as described in flow diagram 12300 of FIG. 123A. The results of each, such as a metric value (e.g., a number) or pass/fail value (e.g., zero or one, "pass" or "fail"), for example, may be used as inputs to input nodes 12352, 12354, and 12356 test (e.g., N input nodes where N is any suitable integer greater than or equal to two) of neural network 12350. In some embodiments, one or more metrics, such as those described in the context of FIGS. 11-41, may also be used as an input. In some embodiments, a calculated correlation lag value may also be used as an input. The input values (e.g., metric values or pass/fail values) may be passed to hidden nodes 12362, 12364, and 12366 (e.g., M hidden nodes where M is any suitable integer greater than or equal to two) of neural network 12350. The processing equipment may perform calculations at hidden nodes 12362, 12364, and 12366 on the input values from input nodes 12352, 12354, and 12356, using predetermined functions or other predetermined calculations. The outputs from hidden nodes 12362, 12364, and 12366 may be passed to output node 12372. The processing equipment may perform calculations at output node 12372 on the outputs from hidden nodes 12362, 12364, and 12366, using predetermined functions or other predetermined calculations. Output node 12372 may output information that may be used to qualify or disqualify a value that may be indicative of a physiological rate. For example, the output information may be a number (e.g., a number between 0 and 1, where a number greater than or equal to 0.5 may cause the value to be qualified), a text string such as "pass" or "fail," or both. In some embodiments, the number between 0 and 1 may be indicative of the probability or confidence that the value correctly indicates the physiological rate. For example, a low number may indicate low confidence and a high number may indicate high confidence. The processing equipment may qualify or disqualify a value, such as a correlation lag value, based on the output information of neural network 12350. For example, the processing equipment may compare the number to a threshold to determine whether or not to qualify the value FIG. 124 is a flow diagram 12400 of illustrative steps for combining qualification tests, in accordance with some embodiments of the present disclosure.

Step 12402 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 12402 may include recalling data from the memory for further processing. Step 12402 may include processing equipment receiving qualification information such as a calculated correlation lag value, a calculated rate, any suitable algorithm settings used for qualification, any other suitable information, or any combination thereof.

Steps 12404, 12406, and 12408 may include processing equipment performing a first qualification test, a second qualification test, through an $N^{th}$ qualification test, in sequence to qualify or disqualify a calculated correlation lag value based on the physiological data and the qualification information. Any suitable number of qualification tests may be performed, for example, using any of the illustrative Qualification Techniques discussed in the context of FIGS. 86-122. The qualification tests may be performed in series, for example, and if a disqualification occurs at any qualification test, the processing equipment may skip any remaining qualification tests and proceed to disqualification at step 12410.

Step 12410 may include processing equipment qualifying or disqualifying the correlation lag value based on the qualification tests of steps 12404, 12406, and 12408. In some embodiments, the processing equipment may qualify the correlation lag value if all of the qualification tests are passed. For example, referencing flow diagram 12400, the processing equipment may sequentially apply qualification tests and disqualify the correlation lag value when a qualification test fails.

Figure 125:
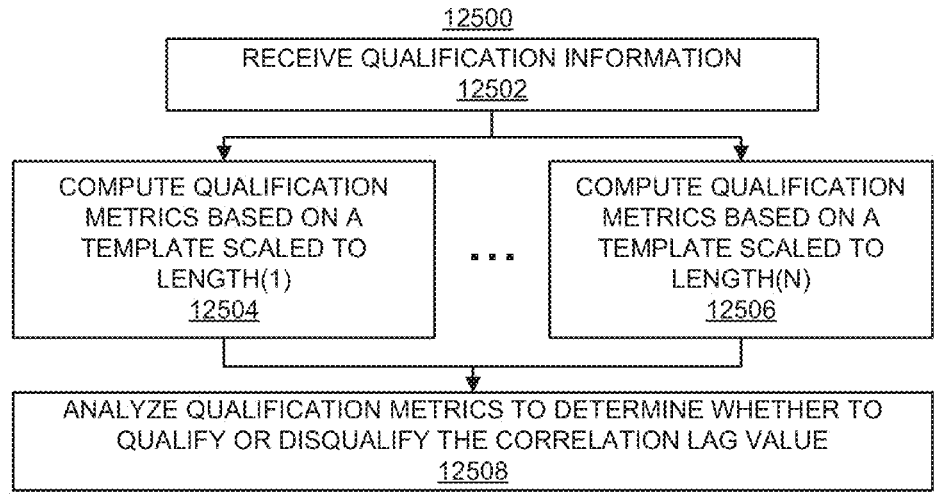
Figure 126:
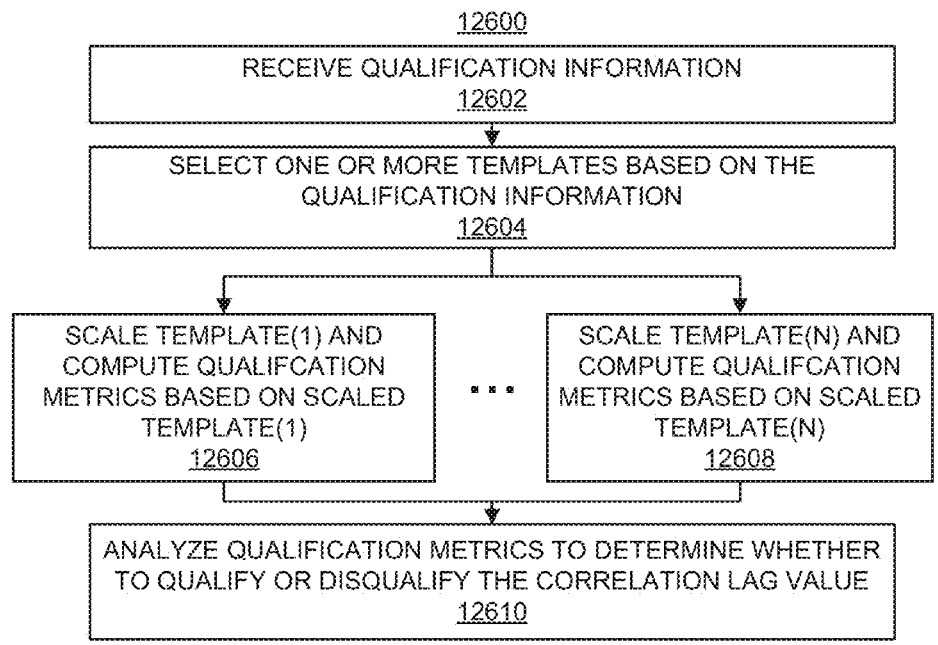

In some embodiments, the illustrative steps of flow diagrams 12500 and 12600 of FIGS. 125 and 126, respectively, may be performed to qualify or disqualify one or more correlation lag values based on a cross-correlation calculation using a cross-correlation template. In some embodiments, the illustrative analyses of flow diagrams 12500 and 12600 of FIGS. 125 and 126, respectively, may be performed to increase confidence in a qualified rate. In some embodiments, flow diagrams 12500 and 12600 of FIGS. 125 and 126, respectively, may use a combination of any or all of the previously discussed qualification techniques. For example, the steps of flow diagrams 12500 and 12600 of FIGS. 125 and 126 may be performed to further investigate whether correlation lag values correspond to a physiological rate of interest (e.g., pulse rate) by using multiple types of templates, multiple lengths of templates, or both.

FIG. 125 is a flow diagram 12500 of illustrative steps for analyzing qualification metrics based on scaled templates of different lengths, in accordance with some embodiments of the present disclosure. In some embodiments, performance of the illustrative steps of flow diagram 12500 may provide an evaluation of the qualification, or disqualification, of a correlation lag value. The illustrative steps of flow diagram 12500 may be referred to as "Qualification Analysis."

Step 12502 may include processing equipment receiving a correlation lag value, any other suitable qualification information, or any combination thereof. In some embodiments, step 12502 may include recalling the stored correlation lag value from suitable memory. In some embodiments, a single processor, module, or system may calculate, store, or both, the correlation lag value and perform steps 12504-12508, and accordingly, step 12502 need not be performed.

Step 12504 may include the processing equipment computing one or more qualification metrics based on a template scaled to a first length. In some embodiments, the scaled template may be used to generate a cross-correlation signal (e.g., using any suitable steps of flow diagram 8600 of FIG. 86), which may be analyzed according to any of the Qualification Techniques. In some embodiments, step 12504 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof. For example, a qualification metric may include a variability metric (e.g., calculated using Eq. 47 or 48), a radius value (e.g., calculated using Eq. 49), and angle sum value (e.g., calculated using Eq. 55), an area of a segment, a statistical property, any other suitable metric, any metric derived thereof, or any combination thereof.

Step 12506 may include the processing equipment computing one or more qualification metrics based on a template scaled to a particular length different than the length of step 12504. In some embodiments, step 12506 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof. Step 12506 may be performed any suitable number of times with templates of different lengths, as indicated by the ellipsis of flow diagram 12500.

In some embodiments, using templates scaled to different lengths at steps 12504-12506 may aid in determining whether the correlation lag value is the true physiological rate. In some embodiments, a template may be scaled to a first length, based on the correlation lag value or associated period (e.g., scaled to one half, one third, or double the rate). In some embodiments, the scaling used may be based on the correlation lag value. In a further example, a template may be scaled based on expected noise and physiological ranges. For example, if the calculated rate is 50 BPM, a template need not be scaled to the half-rate because 25 BPM is an unlikely physiological pulse rate. For relatively lower rates, templates scaled to higher rates may be used to determine if the correlation lag value is indicative of low-frequency noise. In a further example, for higher rates (e.g., 90 BPM and above) a template may be scaled to one half, one third, or other fraction of the calculated rate to determine if the correlation lag value corresponds to a harmonic of the physiological rate.

Step 12508 may include the processing equipment analyzing the qualification metrics of steps 12504 and 12506 to determine whether to qualify or disqualify the correlation lag value of step 12502. For example, the Angle Test may give a calculated angle sum of about 700° when a template is scaled to the calculated rate. If the Angle Test gives a calculated angle sum of about 360° when a template is scaled to one half of the period corresponding to the calculated rate, then the processing equipment may determine that there is a half-rate condition, and accordingly may qualify the half-rate and/or disqualify the correlation lag value. In a further example, two templates of the same length may be used at steps 12504 and 12506, one having a dicrotic notch and the other having no dicrotic notch. If the processing equipment qualifies at least one of the two templates, then correlation lag value may be qualified.

FIG. 126 is a flow diagram 12600 of illustrative steps for selecting one or more templates, and analyzing qualification metrics based on scaled templates, in accordance with some embodiments of the present disclosure. In some embodiments, performance of the illustrative steps of flow diagram 12600 may provide an evaluation of the qualification, or disqualification, of one or more correlation lag values.

Step 12602 may include processing equipment receiving a correlation lag value, any other suitable qualification information, or any combination thereof. In some embodiments, step 12602 may include recalling the stored correlation lag value from suitable memory. In some embodiments, a single processor, module, or system may calculate, store, or both, the correlation lag value and perform steps 12604-12610, and accordingly, step 12602 need not be performed.

Step 12604 may include the processing equipment selecting one or more templates based on the qualification information of step 12602. In some embodiments, a variety of template shapes may be available to the processing equipment (e.g., stored in suitable memory accessible to the processing equipment). For example, some templates may exhibit a dicrotic notch while others do not exhibit a dicrotic notch. In a further example, some templates may exhibit symmetric peaks, while others do not exhibit symmetric peaks. In some embodiments, the template type may depend on a representative rate or period, which may be associated with a correlation lag value. For example, in some embodiments, the processing equipment may select the one or more templates depending on the value of period P. For example, at relatively lower values of period P, a relatively more symmetrical template, without a dicrotic notch, may be selected. In some embodiments, a predefined number of templates may be used (e.g., all templates are always used), and accordingly, the selection of step 12604 need not be performed.

Step 12606 may include the processing equipment scaling a first template, of the one or more templates of step 12604, and calculating one or more qualification metrics based on the scaled first template. In some embodiments, the scaled first template may be used to generate a cross-correlation signal (e.g., using any suitable steps of flow diagram 8600 of FIG. 86), which may be analyzed according to any of the Qualification Techniques. In some embodiments, step 12606 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof.

Step 12608 may include the processing equipment scaling a second template, of the one or more templates of step 12604, and calculating one or more qualification metrics based on the scaled second template. In some embodiments, the scaled second template may be used to generate a cross-correlation signal (e.g., using any suitable steps of flow diagram 8600 of FIG. 86), which may be analyzed according to any of the Qualification Techniques. In some embodiments, step 12608 may include performing a Symmetry Test, performing a Radius Test, performing an Angle Test, performing an Area Test, performing an Area Similarity Test, performing a Statistical Property Test, performing a High Frequency Residual Test, performing any other suitable test, performing any portions thereof, or any combination thereof. Step 12608 may be performed any suitable number of times with different template shapes, as indicated by the ellipsis of flow diagram 12600.

Step 12610 may include the processing equipment analyzing the quantification metrics of steps 12606 and 12608 to determine whether to qualify or disqualify a correlation lag value. The use of templates having different shapes may allow for more confidence in the results of a qualification. For example, if a calculated rate is 120 BPM or higher, then a symmetric template may be used. Further, if the calculated rate is below 120 BPM, then four templates may be used (e.g., symmetric and asymmetric, both with and without a dicrotic notch) to determine which template provides the best results during qualification.

In some embodiments, any or all of the illustrative steps of flow diagrams 12500 and 12600 of FIGS. 125 and 126 may be suitably combined. The illustrative steps of flow diagrams 12500 and 12600 may be performed sequentially, simultaneously, alternately, or any other suitable combination. In some embodiments, variation in both the length and shape of a template may be used to aid in qualifying or disqualifying a correlation lag value. In some embodiments, the shape of a template may depend on the length of the template. For example, templates of shorter length (i.e., shorter period), may exhibit more symmetry than templates of longer length. In some embodiments, a set of templates may be used, which each may have a particular length and shape. For example, a coarse set of templates (e.g., spanning a relatively large range of lengths, shapes, or both) may be used initially to determine a region of interest among the lengths and shapes (e.g., which templates provide the best result). A more refined set of templates, selected based on the region of interest, may then be used to calculate the rate with more accuracy, confidence, or both.

In some embodiments, the processing equipment may use data interpolation to implement any of the Qualification Techniques disclosed herein (e.g., discussed in the context of FIGS. 86-126). At higher physiological rates, a single period of physiological data (e.g., a segment of data having a size equal to a correlation lag value corresponding to an identified peak) may include relatively less data points. For example, at a physiological rate of 240 BPM, the associated period is 0.25 seconds. For a sample rate of 57 Hz, this corresponds to about 14 sample points, which may be coarser than desired for analysis. In some such circumstances, the processing equipment may interpolate the data to generate additional data points in between the sampled data points. The interpolation may be linear, spline, or any other suitable interpolation technique. The interpolated data may include an increased number of data points, having a reduced spacing interval. Interpolation may, in some instances, aid implementation of one or more Qualification Techniques. In some embodiments, interpolation may be applied during signal conditioning. For example, interpolation may be applied before or after applying any of the techniques described in the context of FIGS. 42-61.

It will be understood that the Qualification Techniques disclosed herein are merely illustrative and any suitable variations may be implemented in accordance with the present disclosure. In some embodiments, the Qualification Techniques may be performed on signals other than cross-correlation signals. For example, the Qualification Techniques may be performed on any suitable physiological signal or any suitable signal derived thereof, such as a raw intensity signal, a conditioned intensity signal, and an autocorrelation signal. In some embodiments, it may be desired that the signal used in the Qualification Techniques includes a periodic component that corresponds to a physiological rate. It will also be understood that although plots of graphical representations of data are shown for illustration, the disclosed techniques need not require plotting data or generating graphical representations.

It will be understood that the templates used in the Qualification Techniques need not be scaled. In some embodiments, a library of templates may be stored in memory and accessible by the processing equipment. For each template, the library may store a complete range of desired template lengths (e.g., lengths corresponding to the range of 20-300 BPM, with a resolution of 1 BPM). Therefore, instead of scaling a template, the processing equipment may select a template with a desired length from the library. Regardless of how the template is selected or generated, the template may be referred to herein as a "reference waveform."

In some embodiments, the processing equipment may calculate a physiological rate based on a correlation lag value (e.g., as shown by steps 422 and 424 of flow diagram 400 of FIG. 4), and manage posting of the calculated rate. For example, a physiological rate may be calculated by qualifying a correlation lag value, and determining the rate that has a period corresponding to the calculated lag value (e.g., for a calculated correlation lag value of 1 second, the associated physiological rate would be 60 BPM). The processing equipment may also manage posting when a correlation lag value is not identified or when a correlation lag value is disqualified. Posting the rate may include storing the calculated value, displaying the calculated value to a user, any other suitable output functions, or any combination thereof. Some aspects of managing rate calculation and posting are described in the context of FIGS. 127-128, for example.

Figure 127:
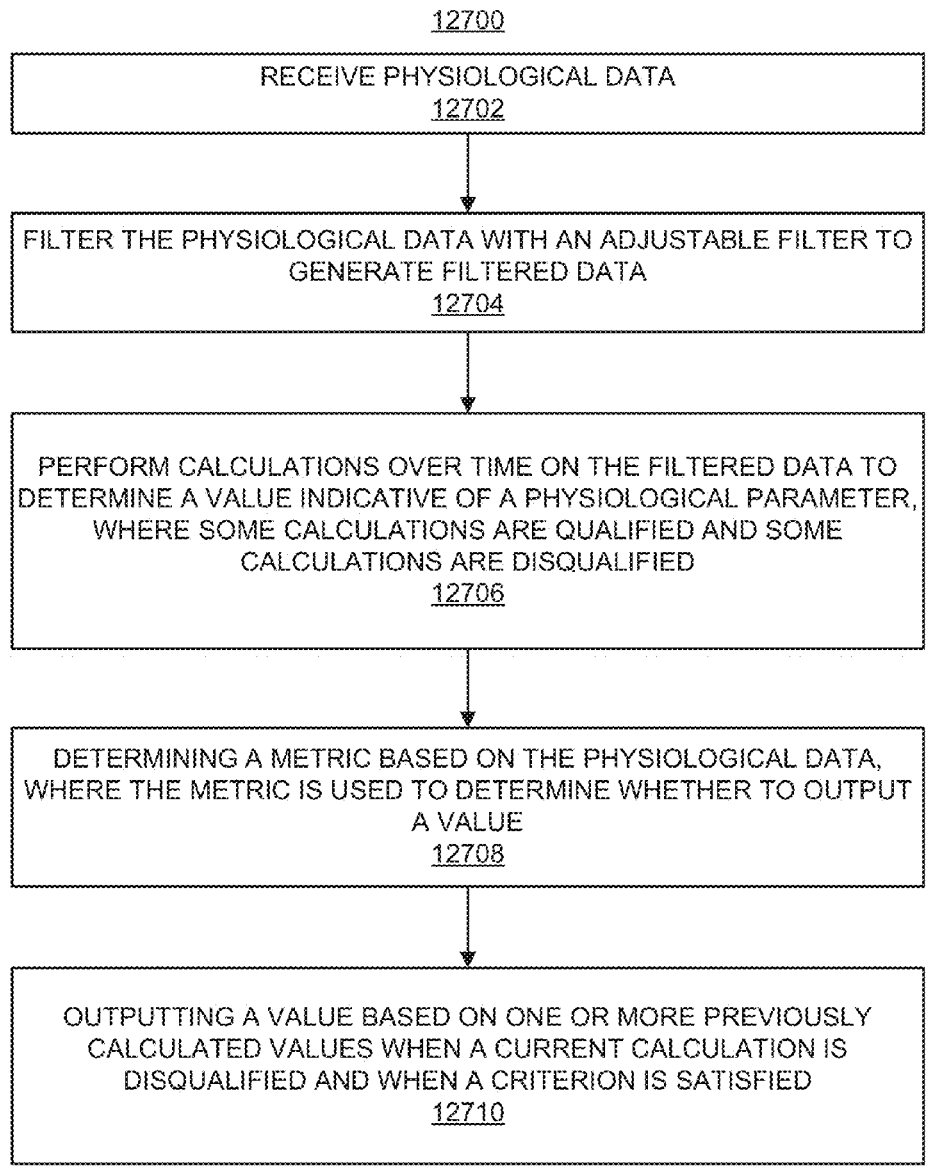

FIG. 127 is a flow diagram 12700 of illustrative steps for managing posting a value indicative of a physiological parameter, in accordance with some embodiments of the present disclosure.

Step 12702 may include processing equipment receiving physiological data from a physiological sensor, memory, any other suitable source, or any combination thereof. For example, referring to system 300 of FIG. 3, the processing equipment may receive a window of physiological data from input signal generator 310. Sensor 318 of input signal generator 310 may be coupled to a subject, and may detect physiological activity such as, for example, RED and/or IR light attenuation by tissue, using a photodetector. In some embodiments, physiological signals generated by input signal generator 310 may be stored in memory (e.g., RAM 54 of FIG. 2, QSM 72 and/or other suitable memory) after being pre-processed by pre-processor 320. In such cases, step 12702 may include recalling data from the memory for further processing.

Step 12704 may include processing equipment filtering the physiological data of step 12702 with an adjustable filter to generate filtered data. The adjustable filter may include one or more adjustable settings. For example, the filter may be a bandpass filter having an adjustable center frequency and an adjustable passband. In a further example, the filter may be either a lowpass filter or a highpass filter, having an adjustable cutoff frequency. In some embodiments, the filter may be adjusted based on a previously calculated metric of step 12708.

Step 12706 may include processing equipment performing calculations over time on the filtered data to determine a value indicative of a physiological parameter, where some of the calculations are qualified and some calculations are disqualified. For example, the processing equipment may perform a rate calculation over time based on the physiological data, for which some rate values may be qualified and posted while others are disqualified and accordingly not posted.

Step 12708 may include processing equipment determining a dropout metric based on the physiological data, where the dropout metric is used to determine whether to output a value indicative of a physiological parameter when a sufficient value is not determined at step 12706. The metric may be based on one or more noise metrics, one or more noise qualification metrics, calculation history (e.g., the number of consecutive calculations that did not result in sufficient values), current algorithm mode, or a combination thereof.

Step 12710 may include processing equipment outputting a value based on one or more previously calculated values when a current calculation is disqualified and a criterion is satisfied. In some embodiments, the processing equipment may maintain one or more counters. For example, the processing equipment may maintain a dropout counter that counts the number of dropout events (e.g., rate disqualifications) of the rate algorithm. The processing equipment may compare the dropout counter value to a predetermined threshold, or an adjustable threshold which may depend on a metric value (e.g., the metric value determined at step 12708). For example, the processing equipment may determine a threshold based on the noise metric, and output a calculated rate value based on one or more previously calculated rate values based on a comparison of the dropout counter value to the threshold.

In some embodiments, the processing equipment may manage rate posting to mitigate disruptions in the posted rate value due to noise. For example, when the noise level in the physiological data is relatively high and sufficient values are not being calculated, the rate algorithm may continue posting previous values to disregard the noise. However, when the noise level in the physiological is relatively low, the rate algorithm may dropout more quickly because the rate algorithm should be able to calculate a rate with higher accuracy. This behavior by the rate algorithm may be especially useful when the bandpass filter is filtering at the wrong rate (e.g., the central frequency is tuned to noise), and it is desirable to drop out and start posting values again corresponding to the correct rate. In some embodiments, this behavior may be implemented by using a dropout counter that counts up each time an insufficient value is calculated (and cleared or decremented every time a sufficient value is calculated). The counter can, for example, be compared against a threshold that is based on the dropout metric. Alternatively, the threshold may be fixed and the dropout metric may be used to scale or otherwise modify the dropout counter value.

Figure 128:
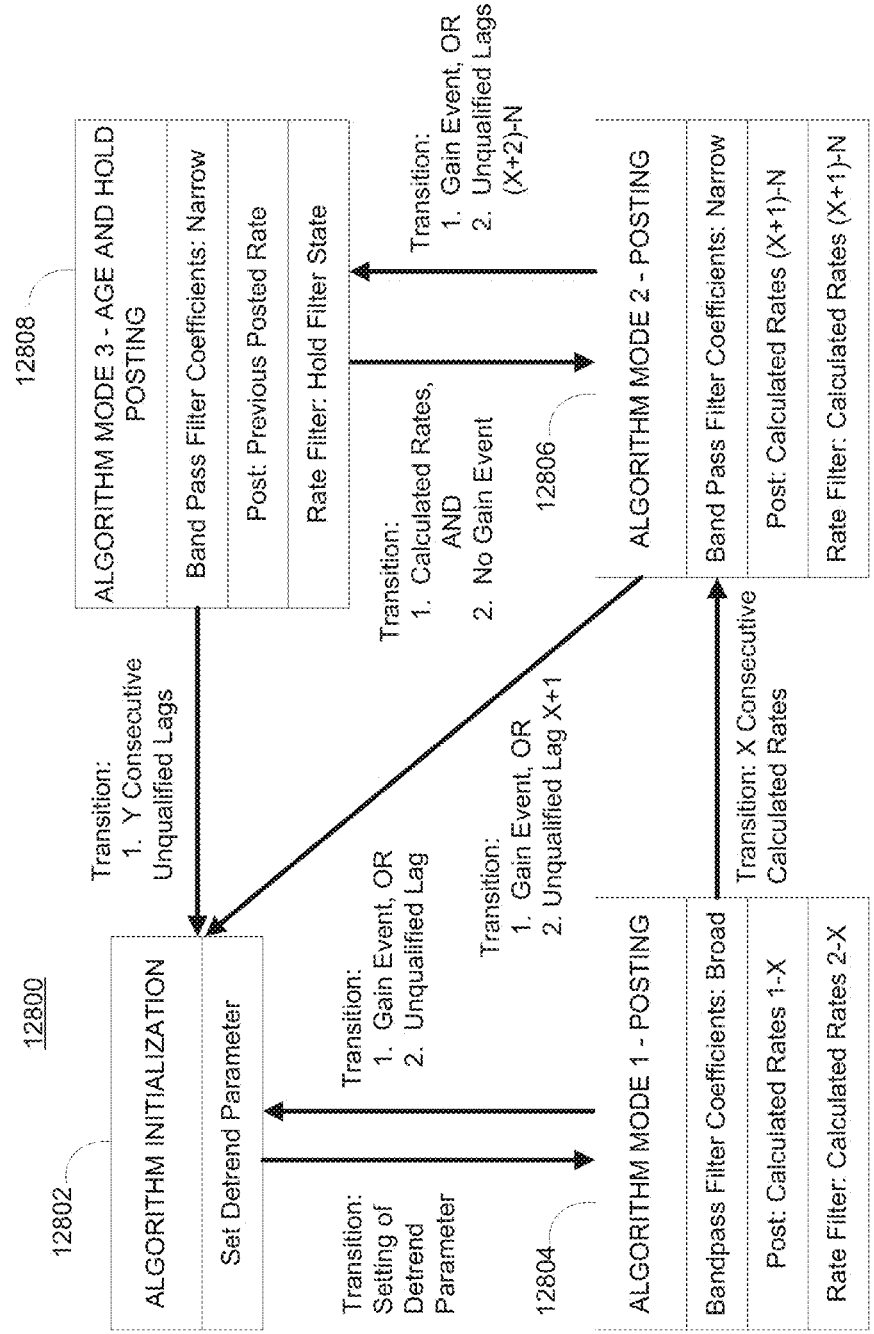

FIG. 128 is a block diagram 12800 of illustrative modes of a rate algorithm, in accordance with some embodiments of the present disclosure. Modes 12802, 12804, 12806, and 12808 may be implemented using hardware modules, software modules, modes of a single software algorithm, a single processing unit, or any combination thereof. In some embodiments, for example, the rate algorithm may implement any of the techniques described in the context of FIG. 127 as part of one or more modes.

Mode 12802 is an algorithm initialization mode. Mode 12802 may be performed during, for example, startup when a rate has not yet been calculated or after the rate algorithm starts over after failing to calculate a rate. Mode 12802 may set a de-trend parameter based on a predetermined setting or a de-trend metric determined based on physiological data. When the de-trend parameter has been set, the rate algorithm may transition from mode 12802 to mode 12804.

Mode 12804 is a first rate posting mode of the rate algorithm. Mode 12804 may be performed as long as there is no unqualified lag value or gain change event. Mode 12804 may use a broadly set bandpass filter to filter physiological data, or no bandpass filter. Mode 12804 may calculate rates for qualified lag values, including the first qualified lag value. Mode 12804 may post each of the calculated rates. In some embodiments, each of the calculated rates may be added to a rate filter to smooth the displayed rate, except for the first rate. If a disqualification occurs, or a gain change event occurs, mode 12804 may transition back to mode 12802. After "X" consecutive qualified lags, and no gain change event, mode 12804 may transition to mode 12806. "X" may be a fixed number or it may be adjustable based on one or more criteria or metrics. The transition to block 12806 may include selecting and storing narrowly set bandpass filter coefficients based on the last qualified lag value, posting the rate associated with the last qualified lag, and clearing the rate filter and any rate value buffers.

Mode 12806 is a second rate posting mode. Mode 12806 may be performed as long as there is no unqualified lag value, other than the first calculated value, or gain change event. Mode 12806 may use a narrowly set bandpass filter to filter physiological data. Mode 12806 may use a rate filter based on the qualified lag values. Mode 12806 may calculate rates for qualified lag values, including the first qualified lag value, and post the filtered rate. If the first lag value calculated by mode 12806 is disqualified, or if a gain change event occurs, mode 12806 may transition to mode 12802 to reinitialize. If a disqualification occurs after the first rate calculation of mode 12806, or a gain change event occurs, mode 12804 may transition to mode 12808 and post the previously posted rate. In some embodiments, the previous rate information may be retained when the rate algorithm transitions from mode 12804 to mode 12806. If the rate information is retained, the rate algorithm need not reinitialize when the first lag value is disqualified in mode 12806. Instead, the rate algorithm may transition to mode 12808 and post the previously posted rate.

Mode 12808 is a third rate posting mode. Mode 12808 may be performed until a lag value is qualified, and no gain change event occurs. Mode 12808 may use a narrowly set bandpass filter to filter physiological data. Mode 12808 may hold the rate filter based on the settings and values from mode 12806. Mode 12808 attempts to identify and qualify lag values, but posts the last rate from mode 12806, until a new lag value is identified and qualified. If "Y" consecutive lag values are disqualified by mode 12808, mode 12808 may transition to mode 12802 to reinitialize. "Y" may be a fixed number or it may be adjustable based on one or more criteria or metrics. The transition back to block 12802 may include posting the previously posted rate, clearing the rate filter, clearing any rate value buffers, and clearing the current de-trend parameter. If a lag value calculated by mode 12808 is qualified, and no gain change event occurs, mode 12808 may transition back to mode 12806. The transition back to mode 12806 may include adding the rate associated with the qualified lag value to the rate filter, and posting the rate associated with the qualified lag value.

Figure 129:
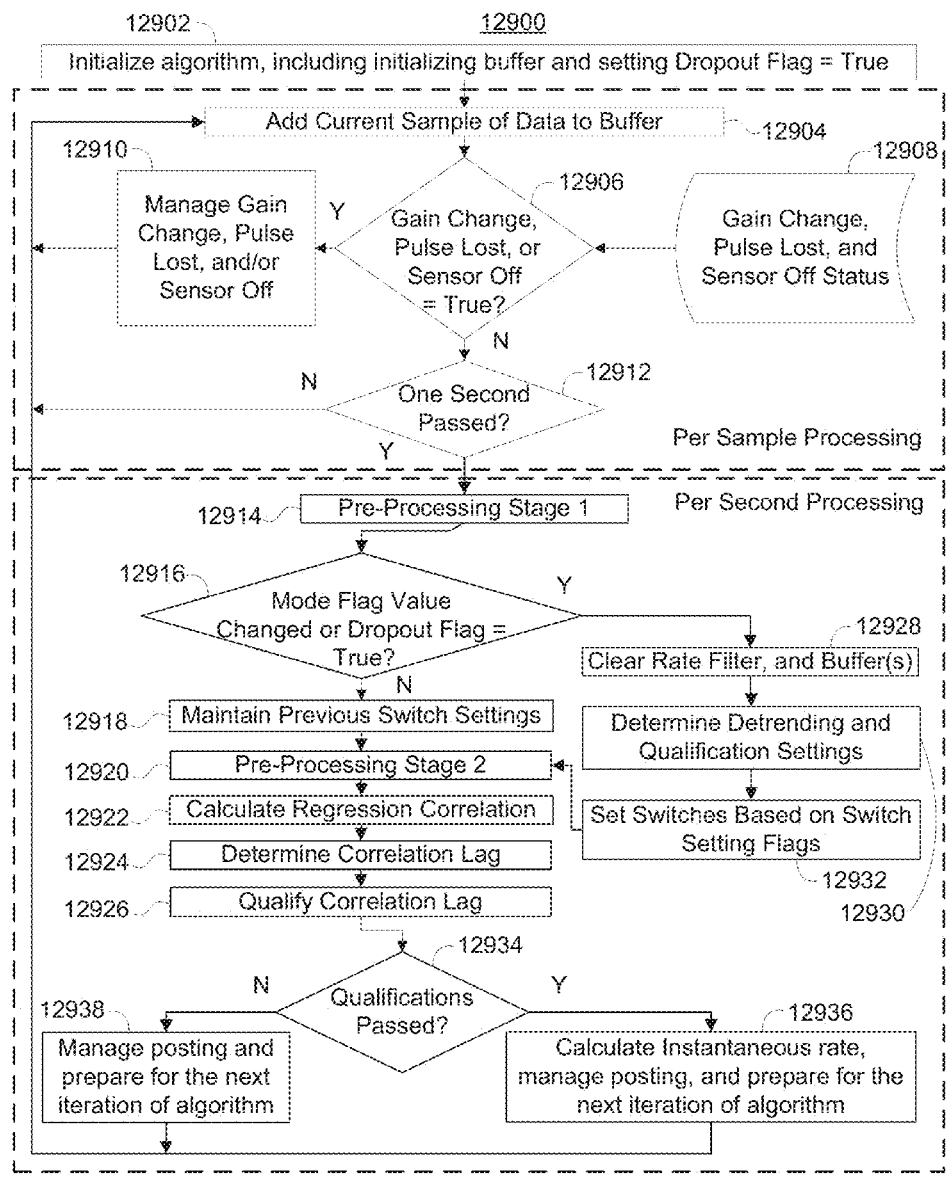

FIG. 129 is a flow diagram 12900 of illustrative steps for calculating and posting a physiological rate, in accordance with some embodiments of the present disclosure.

Step 12902 may include processing equipment initializing the rate algorithm. Initialization may include initializing the buffer (e.g., padding the buffer with initialization values), setting a Dropout Status Flag to "True," any other suitable processing functions, or any combination thereof. In some embodiments, the processing equipment may implement any of the illustrative techniques of step 402 of flow diagram 400 of FIG. 4, the illustrative techniques of flow diagram 500 of FIG. 5, the illustrative techniques of flow diagram 900 of FIG. 9, or any combination thereof.

After initialization at step 12902, the rate algorithm may perform "per sample processing" at steps 12904-12912, to fill the buffer with data samples from a physiological signal. Step 12904 may include processing equipment adding a current data sample to the buffer. Step 12906 may include determining whether a gain change event, pulse lost, or sensor off event, has occurred based on status flags 12908. If an event has occurred, the processing equipment may manage the event at step 12910. For example, managing the event may include holding a current state of the buffer, and not adding new data until the event has passes. In a further example, managing the event may include stopping the rate algorithm, and restarting when a sensor off event has ended. In a further example, managing the event may include performing any of the illustrative steps of flow diagram 800 of FIG. 8. If no event has occurred, the processing equipment may determine whether one second has passed since initialization or the last rate calculation. If one second has not passed, as determined at step 12912, the processing equipment may continue adding data samples to the buffer until a second has passed. If one second has passed, as determined at step 12912, the processing equipment may transition to "per second processing" at steps 12914-12938. It will be understood that the one second check in step 12912 is merely illustrative and any suitable calculation interval may be used.

Step 12914 may include processing equipment performing a first pre-processing of the physiological data (e.g., see FIG. 131 for further details). The first pre-processing may include de-trending, smoothing, any other suitable signal conditioning, or any combination thereof. For example, any of the illustrative techniques described in the context of FIGS. 42-61 may be used at step 12914.

Step 12916 may include processing equipment determining whether a Mode Status Flag value has changed, a Dropout Status Flag value has changed, or both. If either status flag has a value of "True," the processing equipment may clear the rate filter and data buffer at step 12928. The processing equipment may then determine de-trending settings at step 12930 (e.g., see FIG. 130 for further details), and set switches based on switch setting flags at step 12932, before proceeding to step 12920. If neither status flag has a value of "True," the processing equipment may maintain the previous switch settings at step 12918.

Step 12920 may include processing equipment performing a second pre-processing of the physiological data (e.g., see FIG. 132 for further details). The second pre-processing may include de-trending, applying a derivative limiter, applying a bandpass filter, performing mean subtraction, applying an FIR filter, any other suitable signal conditioning, or any combination thereof. For example, any of the illustrative techniques described in the context of FIGS. 42-61 may be used at step 12920.

Step 12922 may include processing equipment calculating a regression correlation using the pre-processed window of data of the buffer. The processing equipment may determine a correlation sequence at step 12922. Step 12924 may include the processing equipment determining a correlation lag value corresponding to a peak or maximum in the correlation sequence of step 12922. The processing equipment may, for example, apply any of the illustrative techniques described in the context of FIGS. 62-85, to calculate the regression correlation and determine the correlation lag value.

Step 12926 may include processing equipment applying one or more Qualification Techniques (e.g., see FIG. 133 for further details) to the correlation lag value of step 12924. The processing equipment may determine whether the one or more qualification tests are passed (e.g., the correlation lag value is qualified) at step 12934. If the correlation lag value is disqualified, the processing equipment may manage rate posting and prepare for the next iteration of the rate algorithm at step 12938 (e.g., see FIG. 134 for further details). If the correlation lag value is qualified, the processing equipment may calculate the instantaneous rate, manage posting, and prepare for the next iteration of the rate algorithm at step 12936 (e.g., see FIG. 135 for further details). The processing equipment may then continue to add data samples to the buffer and repeat per sample processing and per second processing as appropriate.

FIG. 130 is a flow diagram of illustrative steps for determining de-trending settings and qualification settings, corresponding to step 12930 of flow diagram 12900 of FIG. 129, in accordance with some embodiments of the present disclosure. Step 13002 may include processing equipment determining whether a Dropout Status Flag value is "True." If the Dropout Status Flag value is not "True," the processing equipment may proceed to step 12932 of flow diagram 12900 of FIG. 129. If the Dropout Status Flag value is "True," the processing equipment may calculate a de-trend metric at step 13004 based on one or more noise metrics 13006 (e.g., which may be calculated in a separate module). If the de-trend metric is greater than a predetermined value "X," as determined at step 13008, the processing equipment may set the De-trend Status Flag to "High," while if the de-trend metric less than "X," the processing equipment may set the De-trend Status Flag to "Low," as shown respectively by steps 13012 and 13010. Step 13014 may include the processing equipment setting the Dropout Status Flag to "False," setting the Mode Status Flag to "Mode 1," and setting a qualification threshold to "setting 1" (e.g., see FIG. 133 for further details). Step 13016 may include the processing equipment setting a Rate History counter to zero. The processing equipment may proceed to step 12932 of flow diagram 12900 of FIG. 129.

FIG. 131 is a flow diagram 13100 of illustrative steps for pre-processing physiological data, corresponding to step 12914 of flow diagram 12900 of FIG. 129, in accordance with some embodiments of the present disclosure. Step 3102 may include processing equipment applying quadratic and cubic de-trending to the physiological data as described, for example, in flow diagram 4300 of FIG. 43. Step 13104 may include the processing equipment applying a normalization technique to the pre-processed data from step 13102 such as, for example, that described in flow diagram 5600 of FIG. 56.

FIG. 132 is a flow diagram 13200 of illustrative steps for further pre-processing physiological data, corresponding to step 12920 of flow diagram 12900 of FIG. 129, in accordance with some embodiments of the present disclosure. Step 13202 may include processing equipment applying a derivative limiter to the physiological data from step 12918 of flow diagram 12900 of FIG. 129. The processing equipment may apply the derivative limiter using, for example, any of the illustrative techniques discussed in the context of FIGS. 50-55. Step 13204 may include processing equipment applying quadratic and cubic de-trending to the derivative limited physiological data as described, for example, in flow diagram 4300 of FIG. 43. Step 13206 may include processing equipment applying a broadly-set bandpass filter to the physiological data from step 13204. The bandpass filter may be set to pass the expected frequency range of physiological rates. Step 13208 may include the processing equipment applying a normalization technique to the bandpass filtered data from step 13206 such as, for example, that described in flow diagram 5600 of FIG. 56. Step 13210 may include the processing equipment applying a normalization technique to the data from step 13208 such as, for example, that described in flow diagram 5800 of FIG. 58. Step 13212 may include the processing equipment applying a normalization technique to the data from step 13210 such as, for example, that described in flow diagram 5600 of FIG. 56. The three normalization techniques applied at steps 13208, 13210, and 13212 may aid in further processing of the data by reducing baseline shifts and amplitude variations in the physiological data. The processing equipment may apply a filter switch at step 13214, in which "setting a" corresponds to no bandpass filter application, and "setting b" corresponds to application of a bandpass filter and mean subtraction. The bandpass filter may have one or more filter coefficients 13218, which may be based on a calculated rate, a noise metric, an operating mode, any other criterion, or any combination thereof. Whether the tracking bandpass filter is applied or not, the processing equipment may then proceed to step 13220, and clear the tracking bandpass filter coefficients from memory (e.g., future filter coefficients may be determined on subsequent calculated rates). The processing equipment may apply a de-trending switch at step 13222, in which "setting a" corresponds to a De-trend Status Flag value of "Low," and "setting b" corresponds to a De-trend Status Flag value of "High." If the processing equipment selects setting b at step 13222, the processing equipment may then proceed to step 13224. Step 13224 may include the processing equipment applying a FIR filter such as that described in flow diagram 6000 of FIG. 60 (e.g., using a weighted sum of the physiological data and a difference signal derived thereof), and also applying a mean subtraction. The processing equipment may then proceed to step 12922 of flow diagram 12900 of FIG. 129.

FIG. 133 is a flow diagram 13300 of illustrative steps for qualifying or disqualifying a correlation lag value, corresponding to step 12926 of flow diagram 12900 of FIG. 129, in accordance with some embodiments of the present disclosure. Step 13302 may include processing equipment determining whether a correlation lag value was identified at step 12924 of flow diagram 12900 of FIG. 129. If no correlation lag value was identified, the processing equipment may determine that qualification has failed at step 13330. If a correlation lag value was identified, the processing equipment may proceed to step 13304 and determine one or more lag metrics. Step 13306 may include the processing equipment calculating a dropout limit using, for example, a single equation, one or more lag metrics, one or more noise metrics, a correlation lag value, any other suitable information, or any combination thereof. In some embodiments, the lag metrics and drop out limit may be determined by processing one or more versions of the processed data. For example, the processed data can be the data at the end of preprocessing stage 1, before the first switch in preprocessing stage 2, at the end of stage 2, at any other intermediate stage or after any other suitable preprocessing. In some embodiments, the processing equipment may determine different metrics using different processed data. The processing equipment may apply a qualification switch at step 13308, in which "setting a" corresponds to a first qualification threshold, "setting b" corresponds to a second qualification threshold, through "setting c" which corresponds to a third qualification threshold, although any suitable number of settings may be used. For "setting a," the processing equipment may perform a sequence of qualification tests at steps 13310, 13312, through 13314. If any of the qualifications tests for "setting a" fail, the processing equipment may determine that qualification has failed at step 13330. For "setting b," the processing equipment may perform a sequence of qualification tests at steps 13316, 13318, through 13320. If any of the qualifications tests for "setting b" fail, the processing equipment may determine that qualification has failed at step 13330. For "setting c," the processing equipment may perform a sequence of qualification tests at steps 133122, 13324, through 13326. If any of the qualifications tests for "setting c" fail, the processing equipment may determine that qualification has failed at step 13330. For any setting, if each qualification test is passed, the processing equipment may determine that qualification has passed at step 13328. Steps 13310-13326 may include any suitable Qualification Techniques, having any suitable qualification settings. The processing equipment may proceed to step 12934 of flow diagram 12900 of FIG. 129 when the qualification tests are complete. The techniques of flow diagram 13300 are merely illustrative, and any single qualification test, or combination of qualification tests, may be applied using a calculated correlation lag value. In some embodiments, different qualification tests may be performed for each switch setting. For example, in some embodiments, one or more qualification tests may be run in parallel, series, or a combination thereof. In a further example, one or more neural network techniques, based on one or more metric values or other qualification results, may be used.

FIG. 134 is a flow diagram 13400 of illustrative steps for managing algorithm settings when a correlation lag value is disqualified, corresponding to step 12938 of flow diagram 12900 of FIG. 129, in accordance with some embodiments of the present disclosure. The processing equipment may determine which Mode the rate algorithm is operating in (e.g., the Mode Status Flag value) at steps 13402 and 13408. If the rate algorithm is operating in Mode 1, the processing equipment does not post a rate value, as shown by step 13404. The processing equipment may then set the Dropout Status Flag to "True" at step 13406. If the rate algorithm is operating in either of Modes 2 or 3, the processing equipment may determine whether the rate history (e.g., the iteration value with 1 being the first calculated rate in Mode 2, and Y being the first calculated rate in Mode 3) is either 1 or Y, which may indicate that the current rate is the first calculated rate in Mode 2 or Mode 3, respectively. For example, the value Y may be 9 seconds (i.e., 9 iterations for per second processing) in some implementations. If the rate history is 1 or Y, then the processing equipment may proceed to dropout, by not posting the rate at step 13424, and setting the Dropout Status Flag to "True" at step 13426. If the rate history is not 1 or Y, the processing equipment may compare a dropout counter to a dropout limit at step 13412. If the dropout counter exceeds the dropout limit, the processing equipment may proceed to dropout, by posting the previous rate at step 13420, and setting the Dropout Status Flag to "True" at step 13422. If the dropout counter does not exceed the dropout limit, the processing equipment may proceed to age and hold, by posting the previous rate at step 13414, incrementing the dropout counter (e.g., to indicate the qualification failure) at step 13416, and incrementing the rate history counter at step 13418. The processing equipment may proceed to per sample processing after completing the relevant illustrative steps of flow diagram 12900 of FIG. 129.

FIG. 135 is a flow diagram 13500 of illustrative steps for managing algorithm settings when a correlation lag value is qualified, corresponding to step 12936 of flow diagram 12900 of FIG. 129, in accordance with some embodiments of the present disclosure. Step 13502 may include processing equipment calculating an instantaneous rate value based on the qualified correlation lag value. For example, the rate may be determined as having a period equal to the qualified correlation lag value. Step 13504 may include processing equipment incrementing the rate history counter. The processing equipment may determine which Mode the rate algorithm is operating in (e.g., the Mode Status Flag value) at steps 13506, 13516, and 13530. If the rate algorithm is operating in Mode 1, as determined at step 13506, the processing equipment does not post a new rate value, as shown by step 13508. The processing equipment may then set the dropout counter value to zero at step 13510, clear the dropout counter limit at step 13512, and set the Mode Status Flag value to "Mode 2" and the qualification threshold to "setting 2" at step 13514. If the rate algorithm is operating in Mode 2, as determined at step 13516, the processing equipment may filter and post the calculated rate at step 13518. In some embodiments, the processing equipment may not add the first calculated rate to the filter. The processing equipment may then decrement the dropout counter value by 2, but not below zero, at step 13520. The processing equipment may determine at step 13522 if the rate history counter is greater than or equal to a value "X," which is the rate counter limit to transition to Mode 3. If the rate history counter is less than "X," the processing equipment may proceed to per sample processing of flow diagram 12900 of FIG. 129. If the rate history counter is greater than or equal to "X," the processing equipment may clear the dropout counter limit at step 13524, set the Mode Status Flag value to "Mode 3" and set the qualification threshold to "setting 3" at step 13526, and select bandpass filter coefficients based on the posted rate at step 13528 before proceeding to per sample processing of flow diagram 12900 of FIG. 129. If the rate algorithm is operating in Mode 3, as determined at step 13530, the processing equipment may determine if the rate history counter is equal to a value "Y," which is the first rate calculation performed in Mode 3, at step 13532. If the rate history counter is equal to "Y," the processing equipment may post the instantaneous rate but not add the rate to the rate filter, as shown by step 13534. If the rate history counter is not equal to "Y," the processing equipment may filter and post the calculated rate at step 13536. The processing equipment may then decrement the dropout counter value by 2, but not below zero, at step 13538. The processing equipment may then select bandpass filter coefficients based on the posted rate at step 13540 before proceeding to per sample processing of flow diagram 12900 of FIG. 129.

FIG. 136 is a flow diagram 13600 of illustrative steps for determining a physiological parameter using more than one algorithm mode in parallel, in accordance with some embodiments of the present disclosure.

Step 13602 may include processing equipment determining a physiological parameter using rate algorithm Mode 1. Step 13604 may include processing equipment determining a physiological parameter using rate algorithm Mode 2. Step 13606 may include processing equipment determining a physiological parameter using rate algorithm Mode N, which may be any suitable integer greater than one. Step 13608 may include determining a physiological parameter for outputting based on one or more of the rate algorithm Modes 1-N. The foregoing illustrative embodiments, shown in FIGS. 128-135, show a sequential transition between Modes over time based on rate qualifications and algorithm settings. In some embodiments, one or more Modes of the rate algorithm may be operated in parallel (e.g., simultaneously or sequentially on the same physiological data). For example, the rate algorithm may operate in Model for the first iteration, and once a correlation lag value is qualified, the rate algorithm may operate in Modes 1 and 2 in parallel. Further, once sufficient confidence is obtained, Mode 3 operation can be initiated, and the rate algorithm may operate in Modes 1, 2, and 3 in parallel. In some embodiments, more than three Modes may be used. For example, the rate algorithm may operate in two variations of Mode 3, using both high and low de-trending, respectively, or other setting variations. In some embodiments, the history of metric values (e.g., noise metrics, de-trending metrics, qualification metrics, or other metrics) and physiological parameter values from operation in the different Modes may be stored in memory and analyzed to determine which physiological parameter value should be outputted. For example, operation in a particular Mode using a tracking bandpass filter may start to track noise in the physiological data rather than the signal component corresponding to the true physiological rate. By analyzing the physiological data using multiple Modes (e.g., including Modes that do not use the tracking bandpass filter), the processing equipment may determine that the tracking filter mode is likely wrong. For example, if a calculated noise metric value is low and a majority of Modes indicate a calculated rate different than the calculated rate of the tracking bandpass filter Mode, then the processing equipment may ignore or reset the tracking bandpass filter Mode.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof which are within the spirit of the following claims.

What is claimed is:

1. A subject monitoring pulse oximetry system for determining physiological information of a subject, comprising:
   a pulse oximetry sensor configured to detect light attenuated by the subject and generate a photoplethysmographic (PPG) signal based on the detected attenuated light; and
   a pulse oximeter coupled to the pulse oximetry sensor, wherein the pulse oximeter is configured to:
      store a rate algorithm;
      determine a skew metric based on the PPG signal;
      determine an algorithm setting based on a reference relationship between the determined skew metric and a value indicative of a physiological rate;
      apply the algorithm setting to the rate algorithm stored by the pulse oximeter; and
      determine the physiological information of the subject using the rate algorithm and the PPG signal, wherein the physiological information comprises pulse rate of the subject.

2. The system of claim 1, wherein the reference relationship comprises a look-up table, wherein the pulse oximeter is further configured to:
   reference the look-up table using the skew metric as an input; and
   determine the value indicative of physiological rate based on the look-up table.

3. The system of claim 1, wherein the reference relationship comprises a function, wherein the pulse oximeter is further configured to:
   reference the function using the skew metric as an input; and
   determine the value indicative of physiological rate based on the function.

4. The system of claim 1, wherein the algorithm setting comprises a central frequency of a bandpass filter, and wherein the pulse oximeter is configured to determine the central frequency to be substantially equal to the value indicative of the physiological rate.

5. The system of claim 1, wherein the algorithm setting comprises a cutoff frequency of a lowpass filter, and wherein the pulse oximeter is configured to determine the cutoff frequency to be greater than the value indicative of the physiological rate.

6. The system of claim 1, wherein the algorithm setting comprises a cutoff frequency of a highpass filter, and wherein the pulse oximeter is configured to determine the cutoff frequency to be less than the value indicative of the physiological rate.

7. The system of claim 1, wherein the algorithm setting comprises a finite impulse response filter, and wherein the pulse oximeter is configured to determine whether to apply the finite impulse response filter based on the skew metric.

8. A pulse oximetry processing module for determining physiological information of a subject, wherein the pulse oximetry processing module comprises a non-transitory computer readable medium having instructions stored thereon, wherein the instructions comprise a rate algorithm, and wherein the instructions are configured to instruct the pulse oximetry processing module to:
   receive a photoplethysmographic (PPG) signal derived from a pulse oximetry sensor output, wherein the pulse oximetry sensor detects light attenuated by the subject and generates the PPG signal based on the detected attenuated light;
   determine a skew metric based on the PPG signal;
   determine an algorithm setting based on a reference relationship between the determined skew metric and a value indicative of a physiological rate;
   apply the algorithm setting to the rate algorithm stored by the pulse oximetry processing module; and
   determine the physiological information of the subject using the rate algorithm and the PPG signal, wherein the physiological information comprises pulse rate of the subject.

9. The pulse oximetry processing module of claim 8, wherein the reference relationship comprises a look-up table, wherein the instructions are further configured to instruct the pulse oximetry processing module to:
   reference the look-up table using the skew metric as an input; and
   determine the value indicative of physiological rate based on the look-up table.

10. The pulse oximetry processing module of claim 8, wherein the reference relationship comprises a function, wherein the instructions are further configured to instruct the pulse oximetry processing module to:

reference the function using the skew metric as an input; and determine the value indicative of physiological rate based on the function.

11. The pulse oximetry processing module of claim 8, wherein the algorithm setting comprises a central frequency of a bandpass filter, and wherein the instructions are configured to instruct the pulse oximetry processing module to determine the central frequency to be substantially equal to the value indicative of the physiological rate.

12. The pulse oximetry processing module of claim 8, wherein the algorithm setting comprises a cutoff frequency of a lowpass filter, and wherein the instructions are configured to instruct the pulse oximetry processing module to determine the cutoff frequency to be greater than the value indicative of the physiological rate.

13. The pulse oximetry processing module of claim 8, wherein the algorithm setting comprises a cutoff frequency of a highpass filter, and wherein the instructions are configured to instruct the pulse oximetry processing module to determine the cutoff frequency to be less than the value indicative of the physiological rate.

14. The pulse oximetry processing module of claim 8, wherein the algorithm setting comprises a finite impulse response filter, and wherein the instructions are configured to instruct the pulse oximetry processing module to determine whether to apply the finite impulse response filter based on the skew metric.

15. A method for determining physiological information of a subject, comprising:
   storing, using a pulse oximeter, a rate algorithm;
   receiving, using the pulse oximeter, a photoplethysmographic (PPG) signal derived from a pulse oximetry sensor output, wherein the pulse oximetry sensor detects light attenuated by the subject and generates the PPG signal based on the detected attenuated light;
   determining, using the pulse oximeter, a skew metric based on the PPG signal;
   determining, using the pulse oximeter, an algorithm setting based on a reference relationship between the determined skew metric and a value indicative of a physiological rate;
   applying, using the pulse oximeter, the algorithm setting to the stored rate algorithm; and
   determining, using the pulse oximeter, the physiological information of the subject using the rate algorithm and the PPG signal, wherein the physiological information comprises pulse rate of the subject.

16. The method of claim 15, wherein the reference relationship comprises a look-up table, the method further comprising:
   referencing the look-up table using the skew metric as an input; and
   determining the value indicative of physiological rate based on the look-up table.

17. The method of claim 15, wherein the reference relationship comprises a function, the method further comprising:
   referencing the function using the skew metric as an input; and
   determining the value indicative of physiological rate based on the function.

18. The method of claim 15, wherein the algorithm setting comprises a central frequency of a bandpass filter, and wherein determining the algorithm setting comprises determining the central frequency to be substantially equal to the value indicative of the physiological rate.

19. The method of claim 15, wherein the algorithm setting comprises a cutoff frequency of a lowpass filter, and wherein determining the algorithm setting comprises determining the cutoff frequency to be greater than the value indicative of the physiological rate.

20. The method of claim 15, wherein the algorithm setting comprises a cutoff frequency of a highpass filter, and wherein determining the algorithm setting comprises determining the cutoff frequency to be less than the value indicative of the physiological rate.

21. The method of claim 15, wherein the algorithm setting comprises a finite impulse response filter, and wherein determining the algorithm setting comprises determining whether to apply the finite impulse response filter based on the skew metric.

22. A non-transitory computer-readable medium for use in determining physiological information of a subject, the computer-readable medium comprising:
   computer program instructions recorded thereon for causing a pulse oximeter storing a rate algorithm to:
      receive a photoplethysmographic (PPG) signal derived from a pulse oximetry sensor output, wherein the pulse oximetry sensor detects light attenuated by the subject and generates the PPG signal based on the detected attenuated light;
      determine a skew metric based on the PPG signal;
      determine an algorithm setting based on a reference relationship between the determined skew metric and a value indicative of a physiological rate;
      apply the algorithm setting to the stored rate algorithm; and
      determine the physiological information of the subject using the rate algorithm and the PPG signal, wherein the physiological information comprises pulse rate of the subject.

23. The non-transitory computer-readable medium of claim 22, wherein the reference relationship comprises a look-up table, the computer-readable medium comprising further computer program instructions recorded thereon for causing the pulse oximeter to:
   reference the look-up table using the skew metric as an input; and
   determine the value indicative of physiological rate based on the look-up table.

24. The non-transitory computer-readable medium of claim 22, wherein the reference relationship comprises a function, the computer-readable medium comprising further computer program instructions recorded thereon for causing a pulse oximeter to:
   reference the function using the skew metric as an input; and
   determine the value indicative of physiological rate based on the function.

25. The non-transitory computer-readable medium of claim 22, wherein the algorithm setting comprises a central frequency of a bandpass filter, and wherein determining the algorithm setting comprises determining the central frequency to be substantially equal to the value indicative of the physiological rate.

26. The non-transitory computer-readable medium of claim 22, wherein the algorithm setting comprises a cutoff frequency of a lowpass filter, and wherein determining the algorithm setting comprises determining the cutoff frequency to be greater than the value indicative of the physiological rate.

27. The non-transitory computer-readable medium of claim 22, wherein the algorithm setting comprises a cutoff frequency of a highpass filter, and wherein determining the algorithm setting comprises determining the cutoff frequency to be less than the value indicative of the physiological rate.

28. The non-transitory computer-readable medium of claim 22, wherein the algorithm setting comprises a finite impulse response filter, and wherein determining the algorithm setting comprises determining whether to apply the finite impulse response filter based on the skew metric.

* * * * *